United States Patent
Dalmia

(10) Patent No.: US 10,914,713 B2
(45) Date of Patent: Feb. 9, 2021

(54) SYSTEMS AND METHODS FOR PESTICIDE DETECTION USING MASS SPECTROSCOPY

(71) Applicant: PerkinElmer Health Sciences, Inc., Waltham, MA (US)

(72) Inventor: Avinash Dalmia, Hamden, CT (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 0 days.

(21) Appl. No.: 16/254,795

(22) Filed: Jan. 23, 2019

(65) Prior Publication Data

US 2019/0227041 A1 Jul. 25, 2019

Related U.S. Application Data

(60) Provisional application No. 62/620,961, filed on Jan. 23, 2018, provisional application No. 62/637,350, filed on Mar. 1, 2018.

(51) Int. Cl.
| | |
|---|---|
| *H01J 49/10* | (2006.01) |
| *H01J 49/00* | (2006.01) |
| *G01N 33/68* | (2006.01) |
| *G01N 30/72* | (2006.01) |
| *G01N 30/88* | (2006.01) |
| *H01J 49/42* | (2006.01) |

(Continued)

(52) U.S. Cl.
CPC ......... *G01N 30/7266* (2013.01); *G01N 30/88* (2013.01); *G01N 33/6848* (2013.01); *G01N 33/94* (2013.01); *G01N 33/948* (2013.01); *H01J 49/004* (2013.01); *H01J 49/0045* (2013.01); *H01J 49/107* (2013.01); *H01J 49/4225* (2013.01); *G01N 2030/884* (2013.01); *G01N 2033/184* (2013.01); *H01J 49/145* (2013.01); *H01J 49/165* (2013.01); *H01J 49/168* (2013.01); *H01J 49/4215* (2013.01)

(58) Field of Classification Search
None
See application file for complete search history.

(56) References Cited

U.S. PATENT DOCUMENTS

| | | | |
|---|---|---|---|
| 2007/0164209 A1* | 7/2007 | Balogh | H01J 49/145 250/288 |
| 2012/0037798 A1* | 2/2012 | Amini | B01J 20/28033 250/282 |

(Continued)

OTHER PUBLICATIONS

Ren et al., "Determination of Multi-Class Mycotoxins in Tartary Buckwheat by Ultra-Fast Liquid Chromatography Coupled with Triple Quadrupole Mass Spectrometry" Toxins 10(1):28 (Jan. 4, 2018) (Year: 2018).*

(Continued)

*Primary Examiner* — James Choi
(74) *Attorney, Agent, or Firm* — Banner & Witcoff, Ltd.

(57) ABSTRACT

This disclosure provides quantitative, rapid, and reliable LC-MS/MS methods for analyzing panels of pesticides and mycotoxins in various samples, including very hydrophobic and chlorinated compounds normally analyzed on a GC-MS/MS system. The methods can be carried out using a single instrument and can detect and quantify levels of the pesticides and mycotoxins that are well below action limits specified by U.S. states (e.g., California) and other countries (e.g., Canada) for these compounds in *cannabis* products.

19 Claims, 167 Drawing Sheets

(51) Int. Cl.
*G01N 33/94* (2006.01)
*H01J 49/14* (2006.01)
*H01J 49/16* (2006.01)
*G01N 33/18* (2006.01)

(56) References Cited

U.S. PATENT DOCUMENTS

2013/0334415 A1* 12/2013 Sugawara ........... H01J 49/0009
  250/288
2017/0138953 A1* 5/2017 Young .................... G01N 33/64

OTHER PUBLICATIONS

Nakazawa et al., "Rapid and simultaneous analysis of dichlorvos, malathion, carbaryl, and 2,4-dichlorophenoxy acetic acid in citrus fruit by flow-injection ion spray ionization tandem mass spectrometry" Talanta 64 (2004) 899-905 (Year: 2004).*
Lacina et al. "Critical assessment of extraction methods for the simultaneous determination of pesticide residues and mycotoxins in fruits, cereals, spices and oil seeds employing ultra-high performance liquid chromatography-tandem mass spectrometry" Journal of Chromatography A, 1262 (2012) (Year: 2012).*
Mastovska et al. "Improved LC/MS/MS Pesticide Multiresidue Analysis Using Triggered MRM and Online Dilution" (2017) (Year: 2017).*
Baker et al. "Highly Polar Pesticide Multi-Residue Analysis in Food Safety by LC-MS/MS", Shimadzu LAAN-A-LM-E089 (2016) (Year: 2016).*
Koesukwiwat et al. "Fast, low-pressure gas chromatography triple quadrupole tandem mass spectrometry for analysis of 150 pesticide residues in fruits and vegetables" 1218 J. Chromatogr. A 7039 (2011) (Year: 2011).*
Yang et al. "Effects of introducing theanine or glutamic acid core to tralopyril onsystemicity and insecticidal activity" 141 Pesticide Biochemistry and Physiology 29 (2017) (Year: 2017).*
He et al. "QuEChERS Combined with an Agilent 7000 Series Triple Quadrupole GC/MS System for the Analysis of Over 200 Pesticide Residues in Leek and Garlic" Agilent Application Note (2015) (Year: 2015).*
Young et al. "Atmopsheric Presure Ionization Mass Spectrometry for GA (APGC-MS-MS)" ACS Poster (2014) (Year: 2014).*
Cuypers et al., "The use of pesticides in Belgian illicit indoor cannabis plantations," Forensic Science International 277, 59-65, 2017.
Golge & Kabak, "Determination of 115 pesticide residues in oranges by high-performance liquid chromatography-triple quadrupole mass spectrometry in combination with AuEChERS method," Food Chemistry 41, 86-97, 2015.
Golge & Kabak, "Evaluation of QuEChERS sample preparation and liquid chromatoography-triple-quadrupole mass spectrometry method for the determination of 109 pesticide residues in tomatoes," Food Chemistry 176, 319-32, available online Dec. 29, 2014.
Hernando et al., "Fast separation liquid chromatography-tandem mass spectrometry for the confirmation and quantitative analysis of avermectin residues in food," J. Chromatography A 1155, 62-73, 1155.
Hollosi et al., "Coupled Turbulent Flow Chromatography: LC-MS/MS Method for the Analysis of Pesticide Residues in Grapes, Baby Food and Wheat Flour Matrices," Chromatographia 75, 1377-93, 2012.
International Search Report and Written Opinion for PCT/US2019/014693, 18 pages, dated May 20, 2019.
Krogh et al., "Development of an analytical method to determine avermectins in water, sediments and soils using liquid chromatography-tandem mass spectrometry," J. Chromatography A 1211, 60-69, 2008.
Armstrong & Camagey, "Analysis of Pesticide Residues in Cannabis Regulated by Oregon State Using LC/MS/MS," PerkinElmer Application Note, 10 pages, 2017.
Dalmia et al., "LC-MS/MS with ESI and APCI Sources for Meeting California Cannabis Pesticide and Mycotoxin Residue Regulatory Requirements," Cannabis Science & Technology 1(3), 38-50, Sep. 21, 2018.
Dalmia, "Overcoming Challenges Associated with Pesticide & Mycotoxins Residue Analysis in Complex Cannabis matrix regulated by California and Oregon State using QSight LC-MS/MS," slides from webinar presentation Jun. 12, 2018, 73 pages.
Niessen et al., "Matrix Effects in Quantitative Pesticide Analysis Using Liquid Chromatography-Mass Spectrometry," Mass. Spec. Rev. 25, 881-99, 2006.
Carlton, "Pesticide Analysis in Cannabis: Choosing the Right Technique," Cannabis Science and Technology, dated Jan. 26, 2018 and available at cannabissciencetech.com/view/pesticide-analysis-cannabis-choosing-right-technique, 5 pages.

* cited by examiner

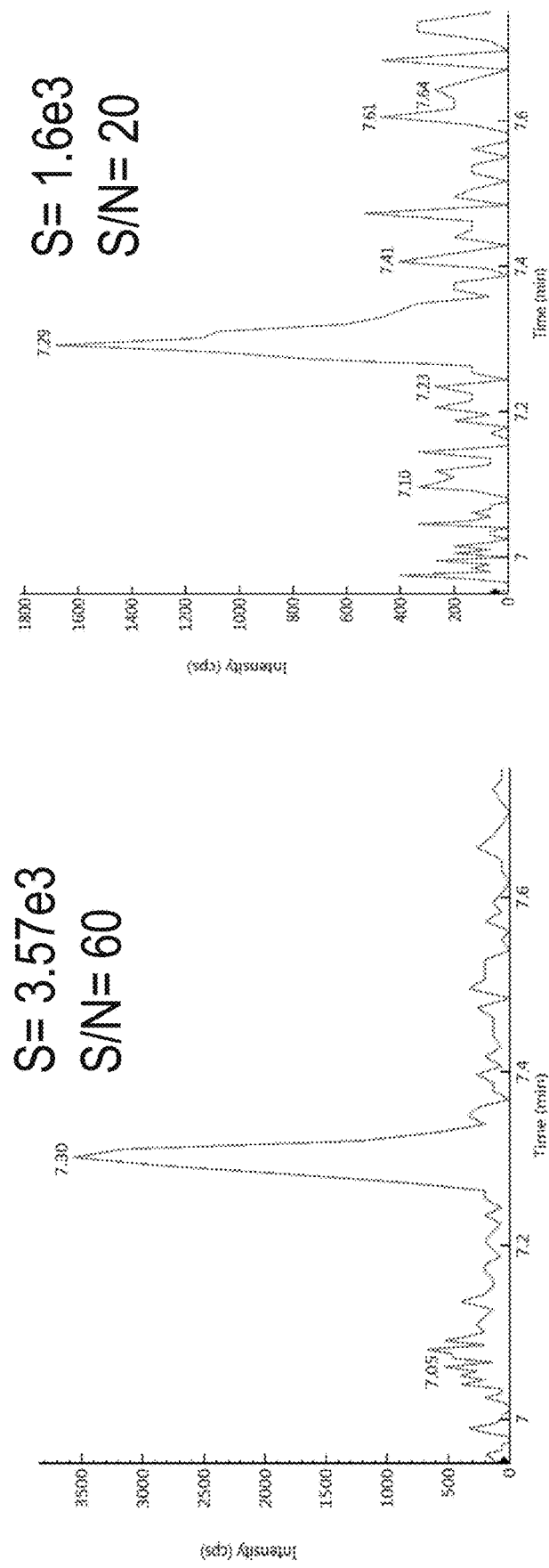
FIG. 16F
FIG. 16E

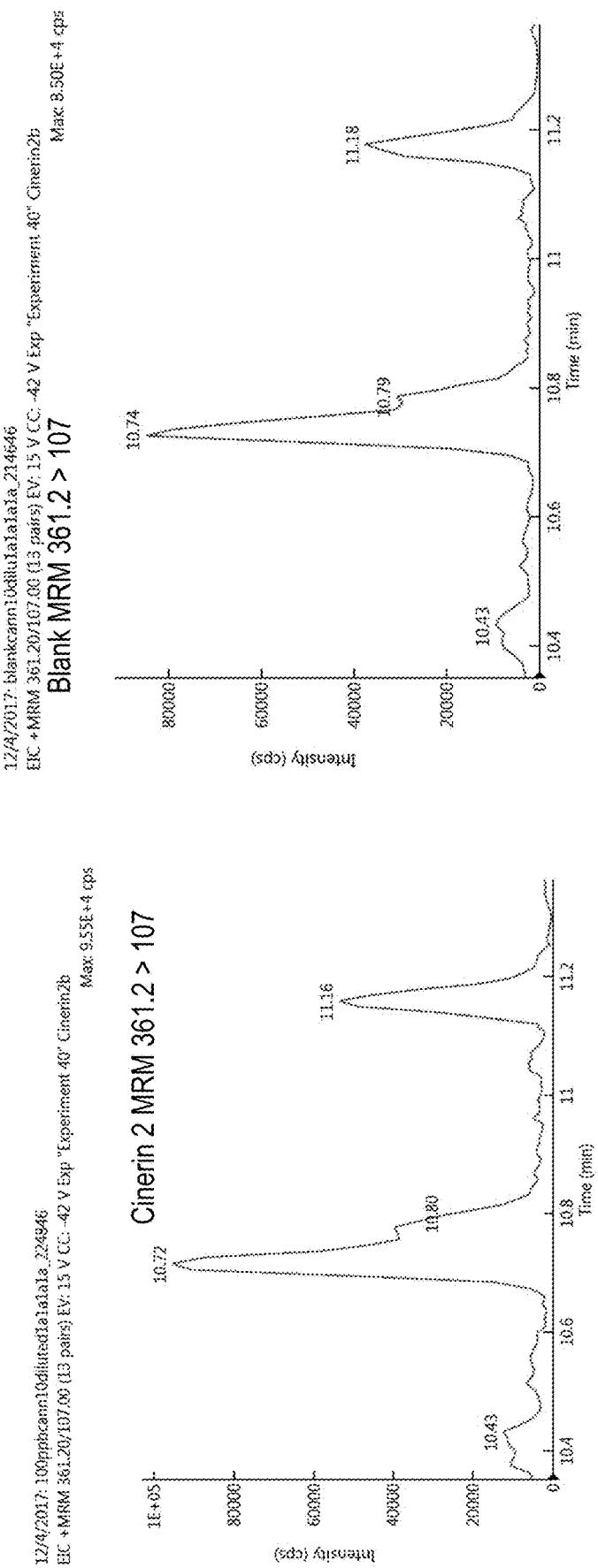

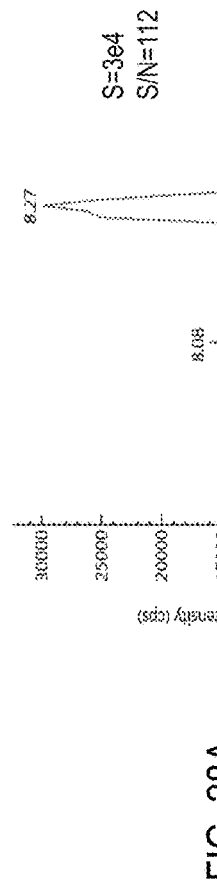
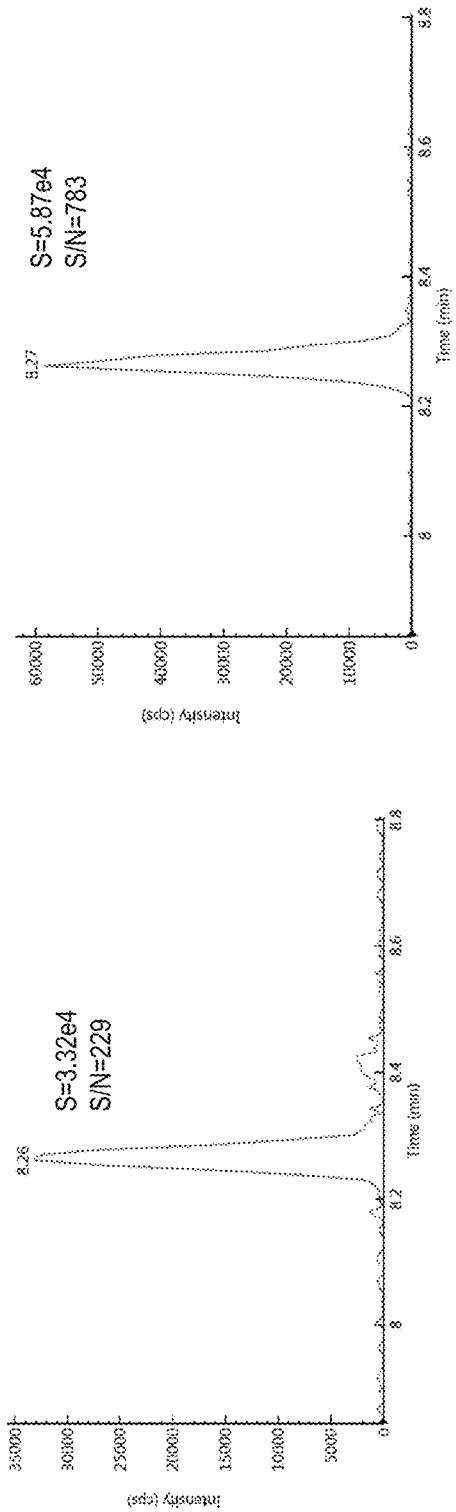
FIG. 28A
FIG. 28B
FIG. 28C

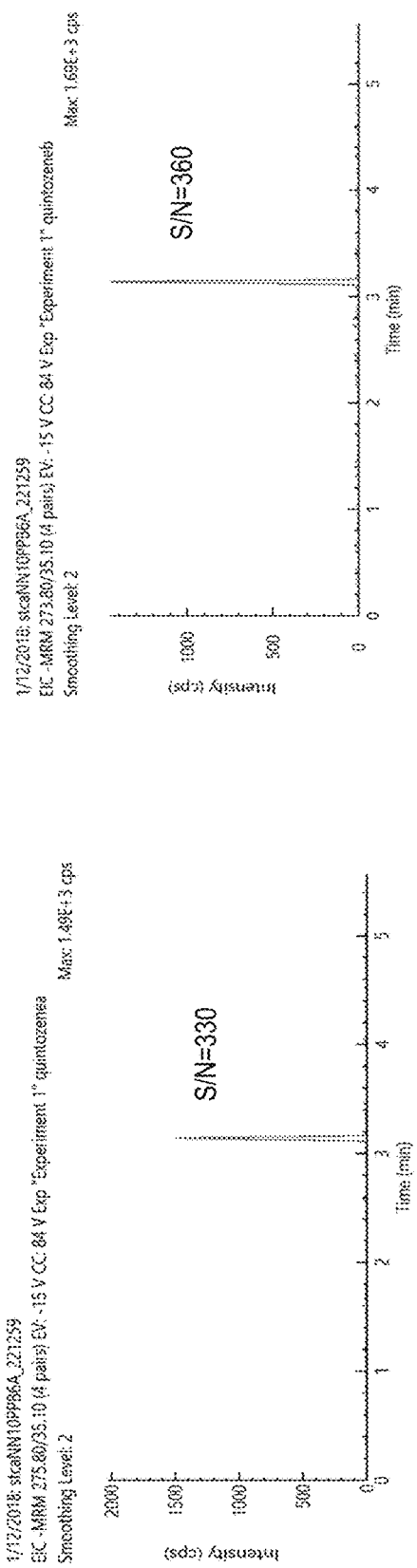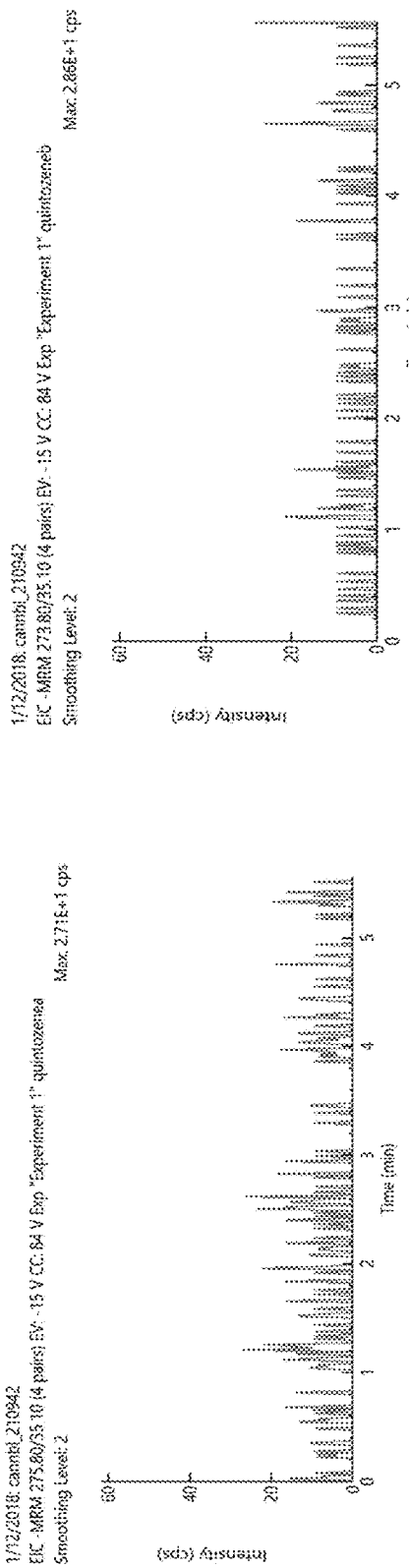
FIG. 37A
FIG. 37B
FIG. 37C
FIG. 37D

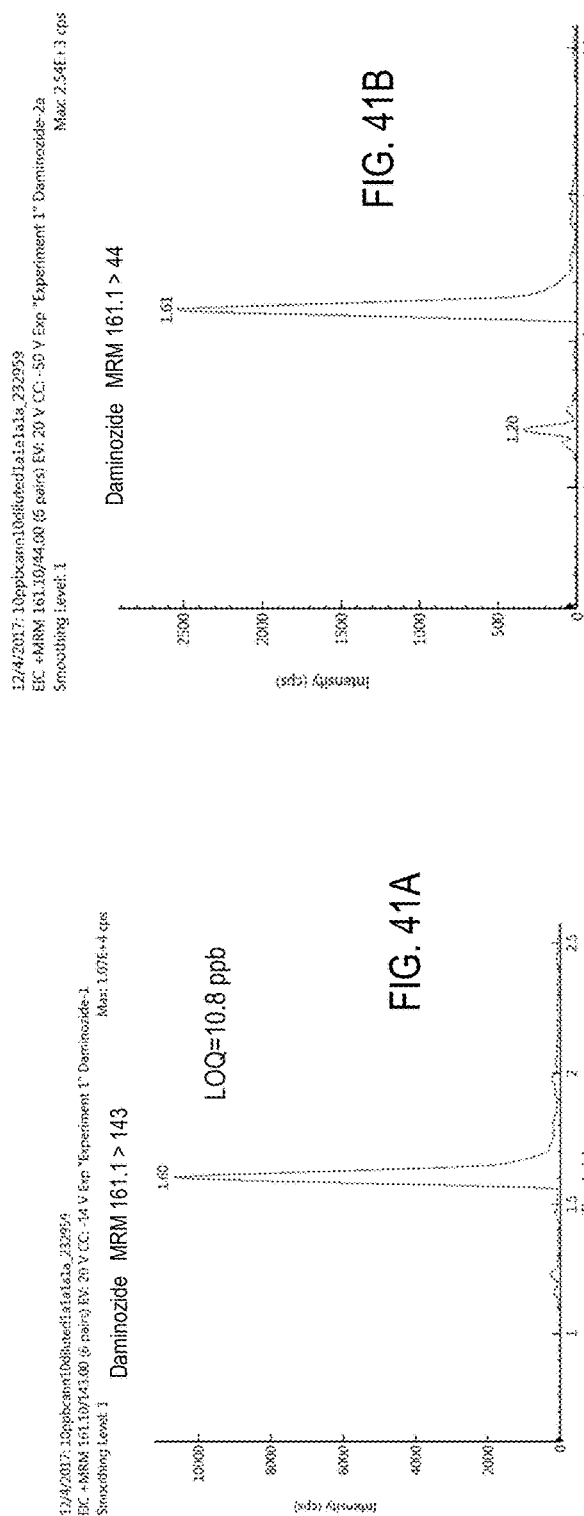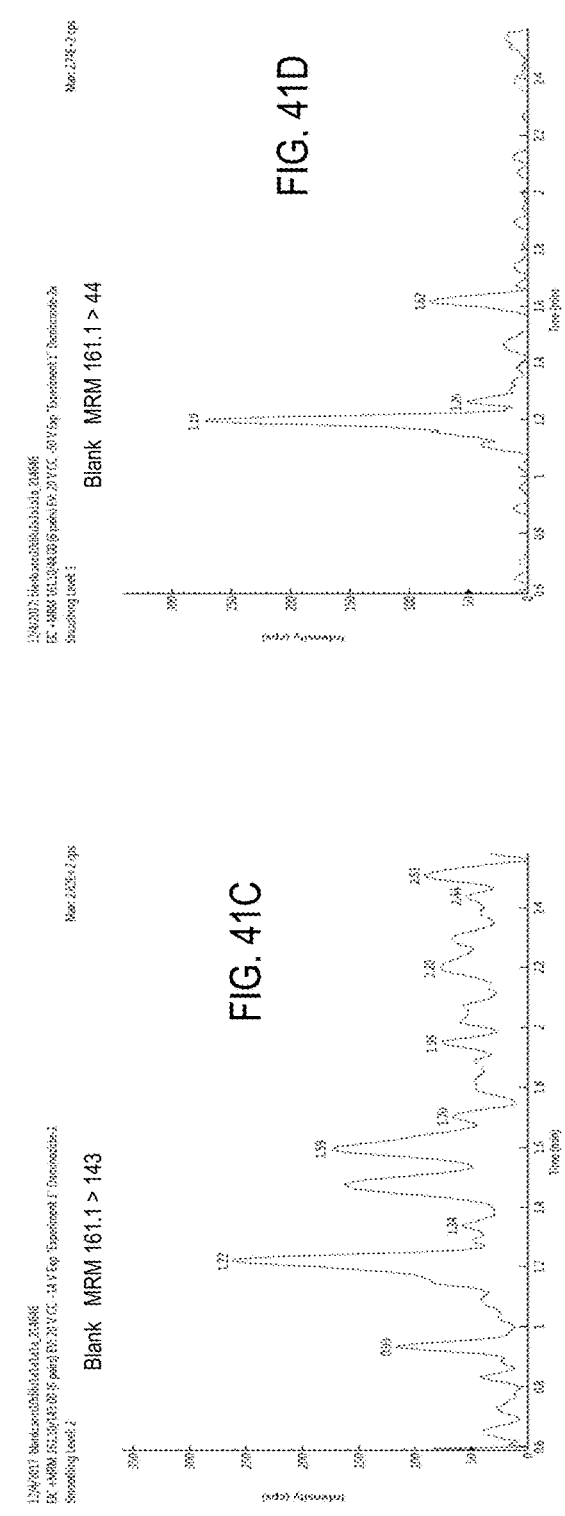
FIG. 41A
FIG. 41B
FIG. 41C
FIG. 41D

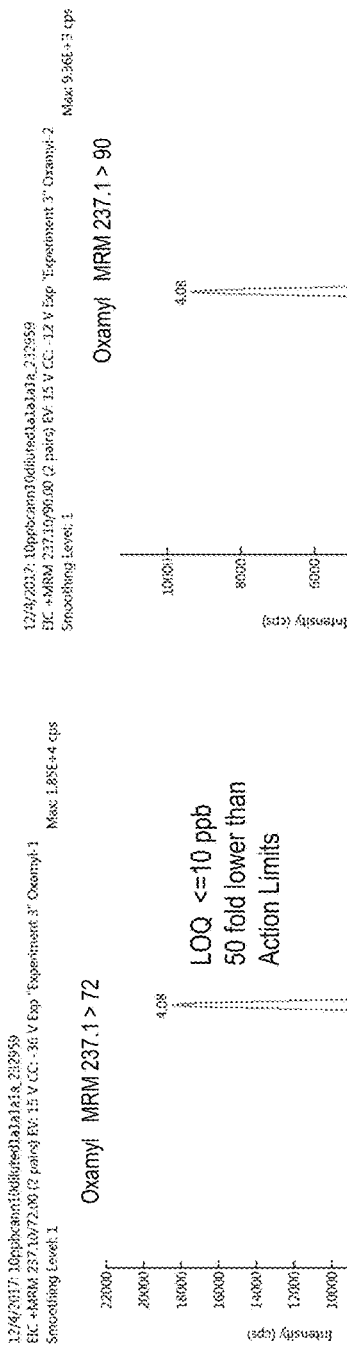
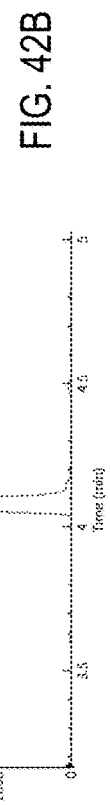
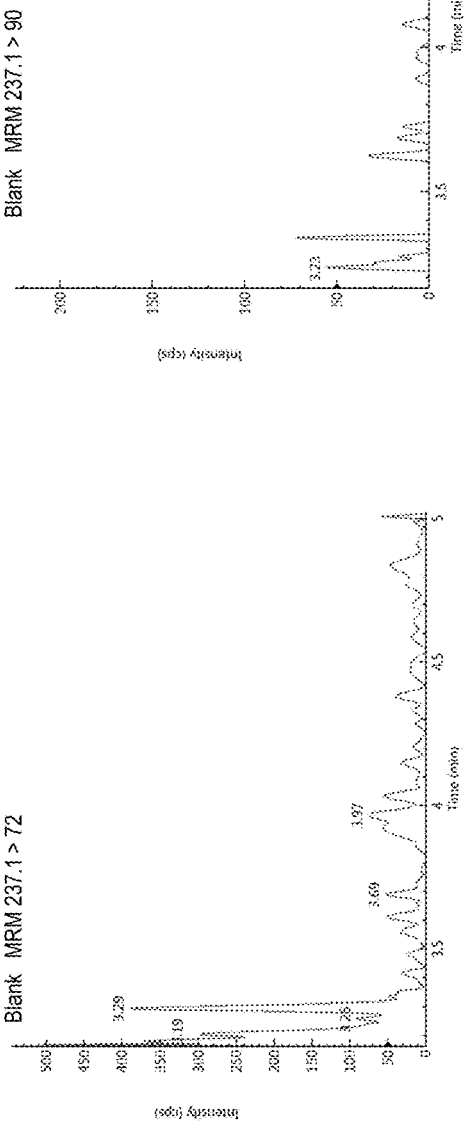
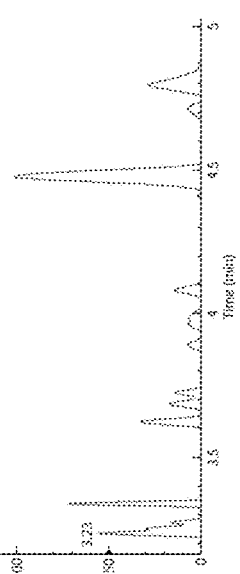
FIG. 42A
FIG. 42B
FIG. 42C
FIG. 42D

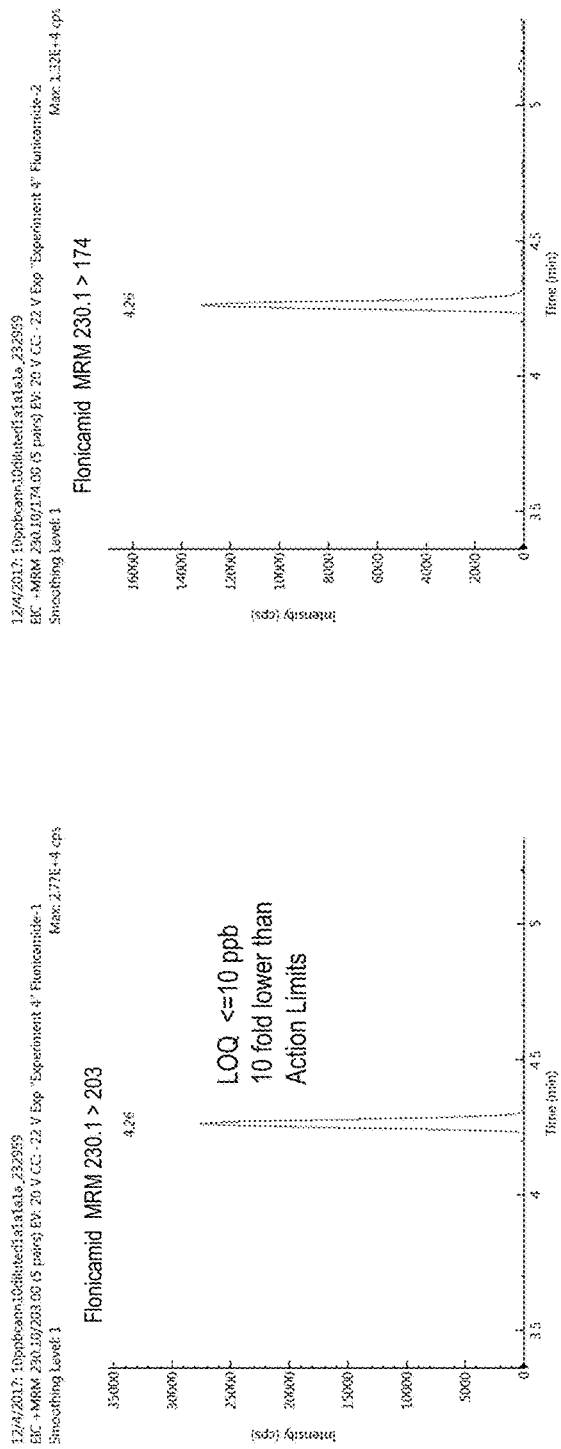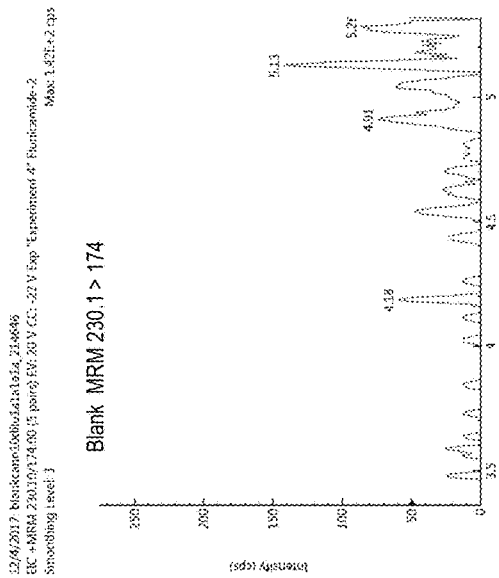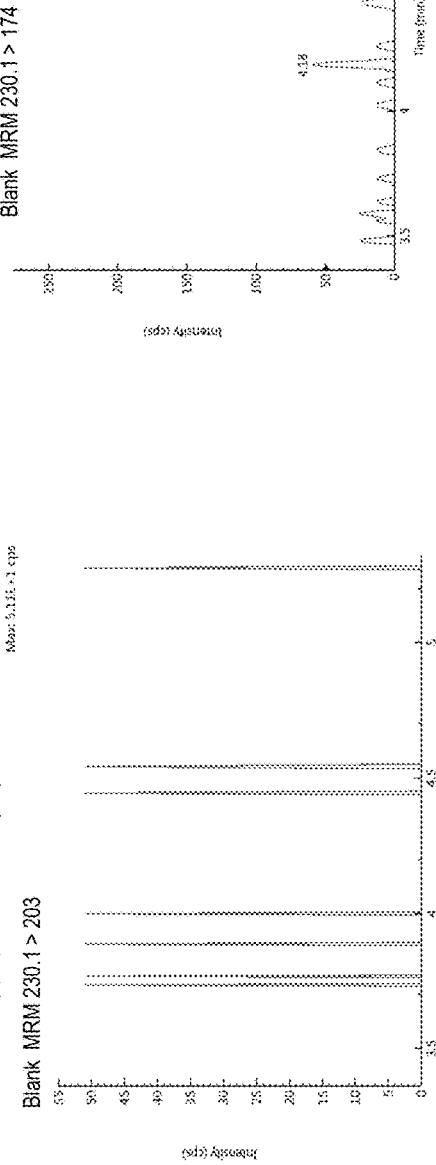
FIG. 43A FIG. 43B FIG. 43C FIG. 43D

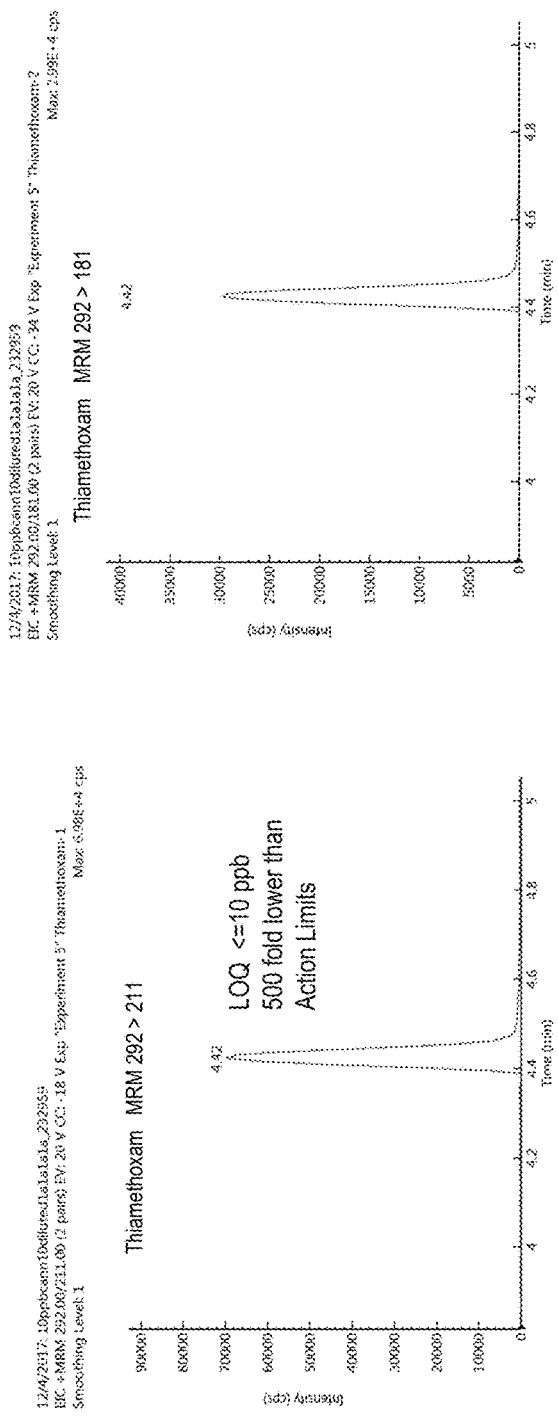
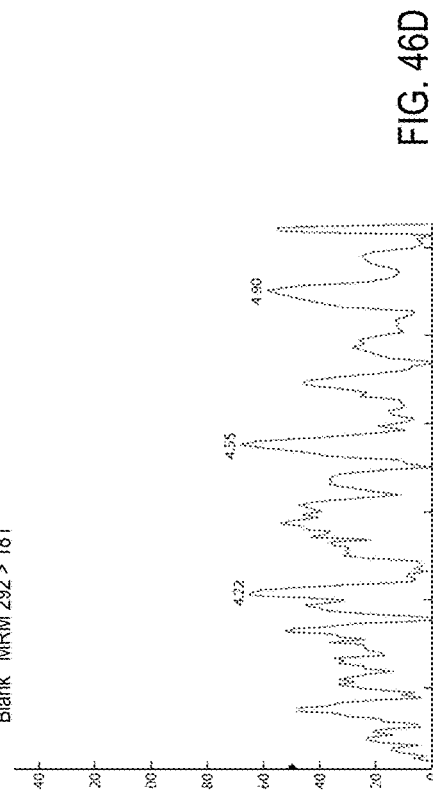
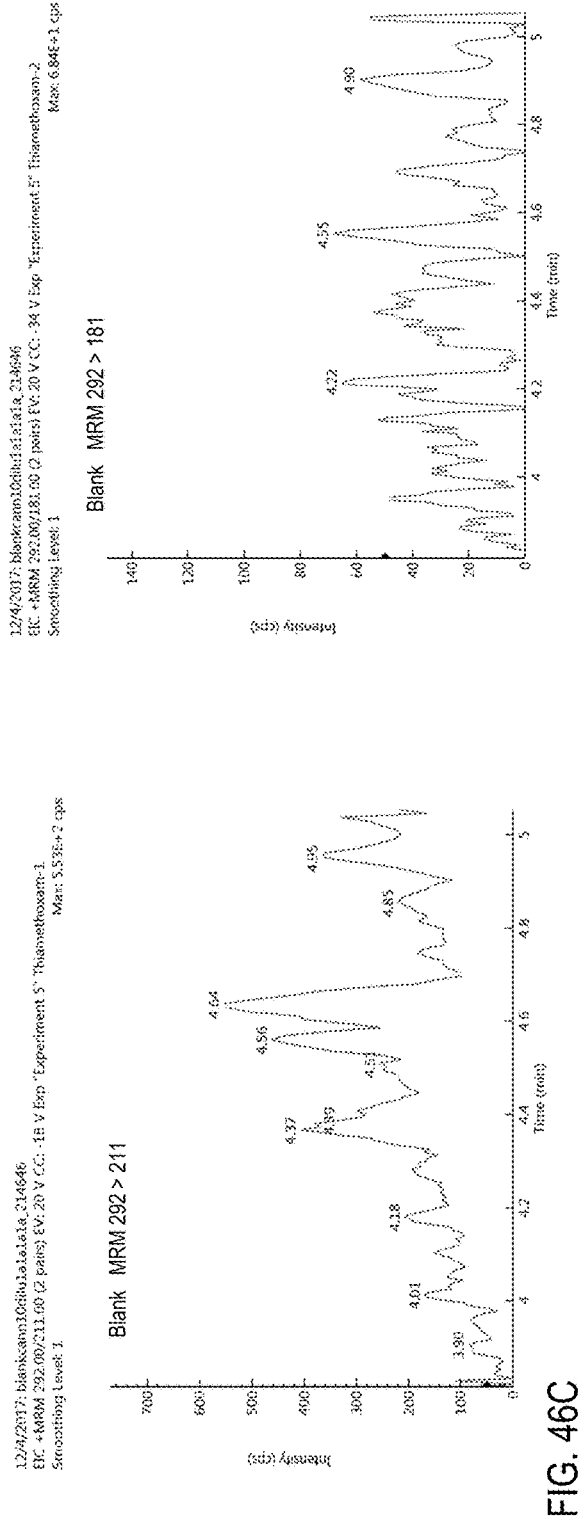
FIG. 46A
FIG. 46B
FIG. 46C
FIG. 46D

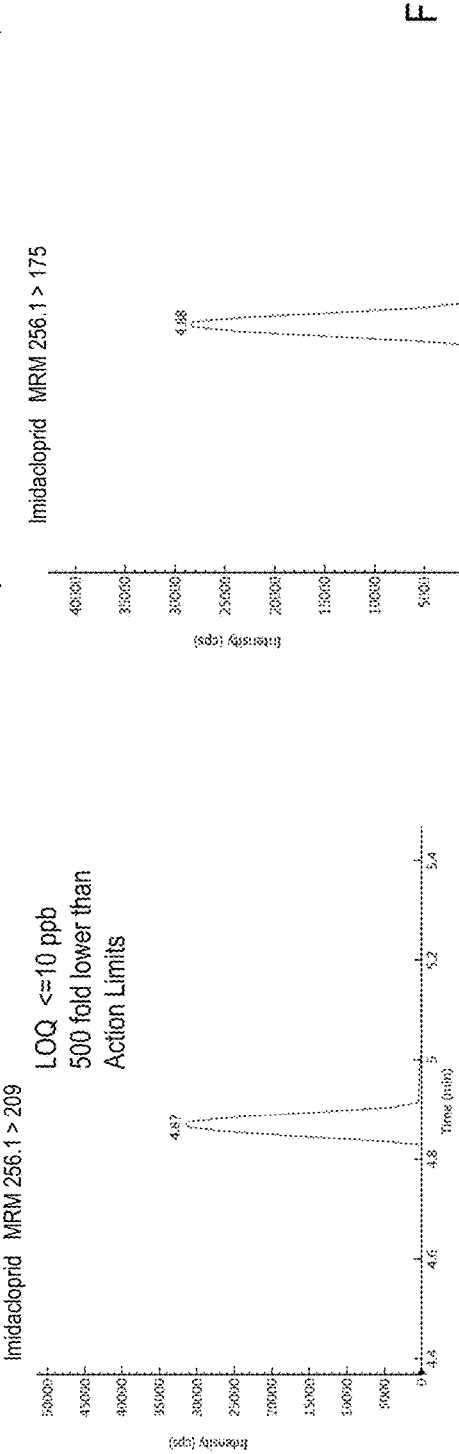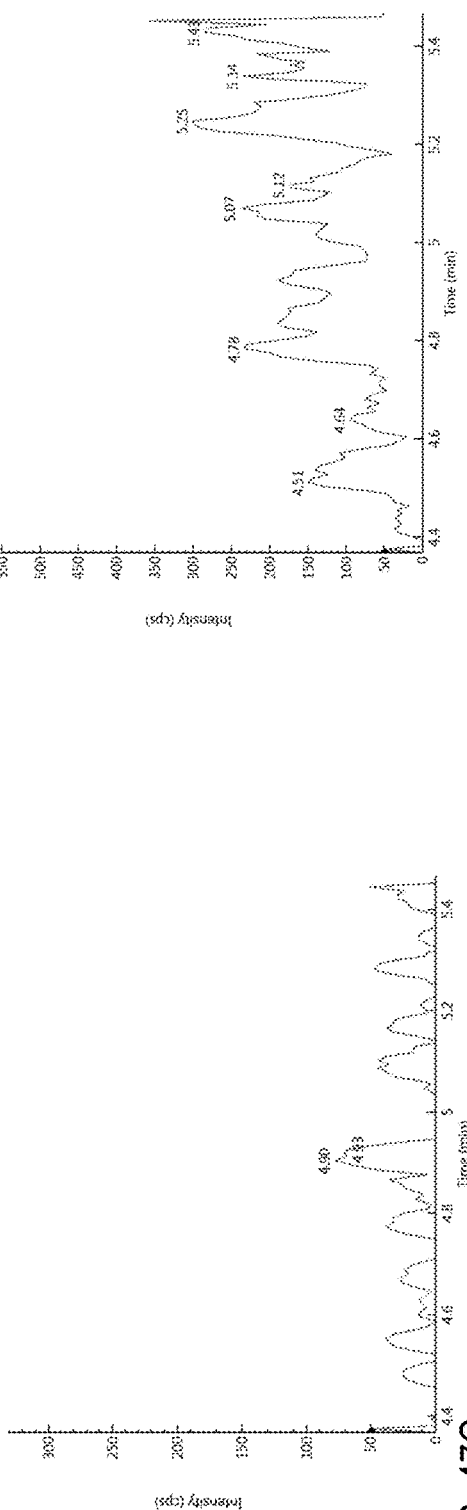
FIG. 47A
FIG. 47B
FIG. 47C
FIG. 47D

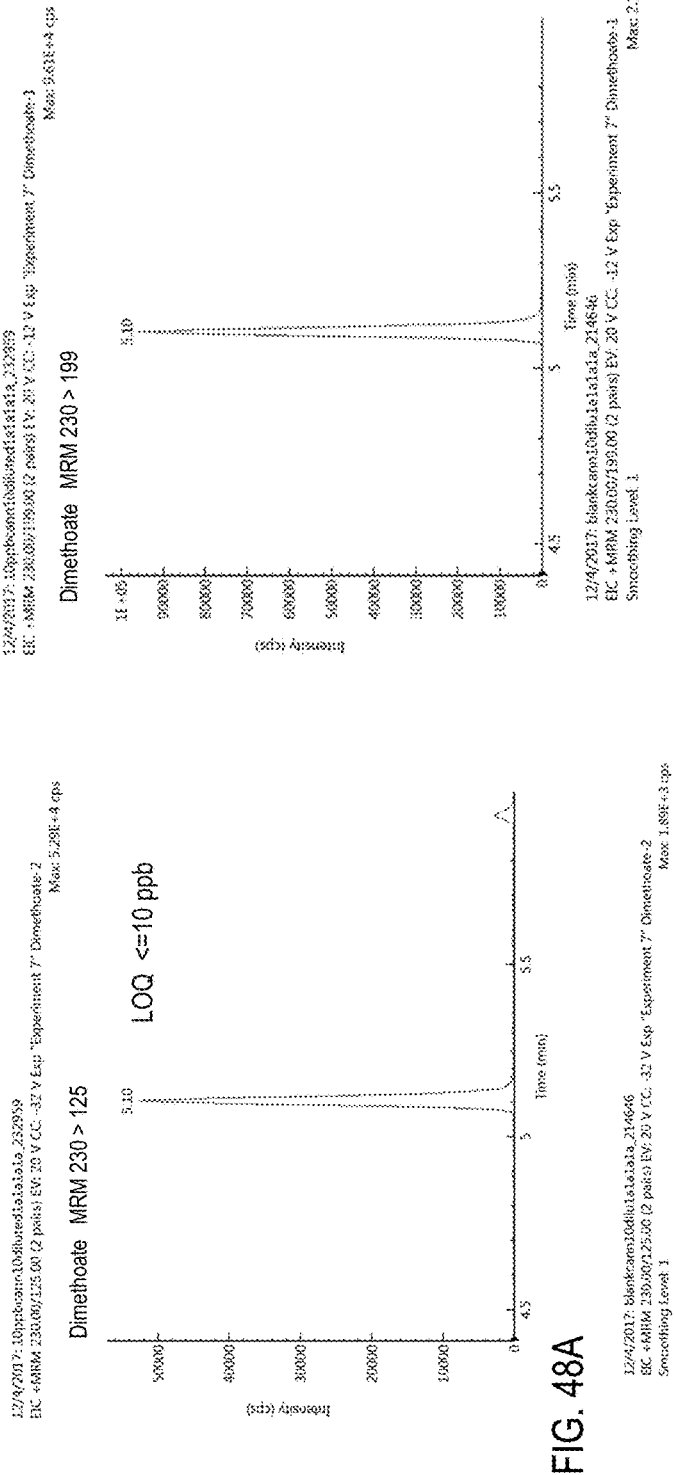
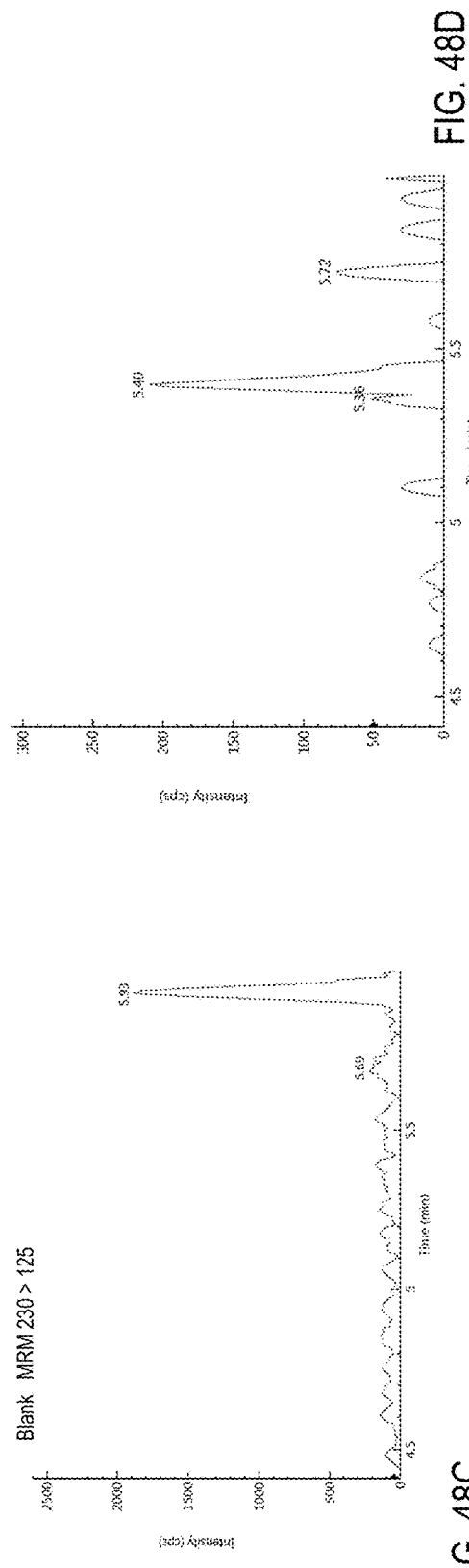
FIG. 48A
FIG. 48B
FIG. 48C
FIG. 48D

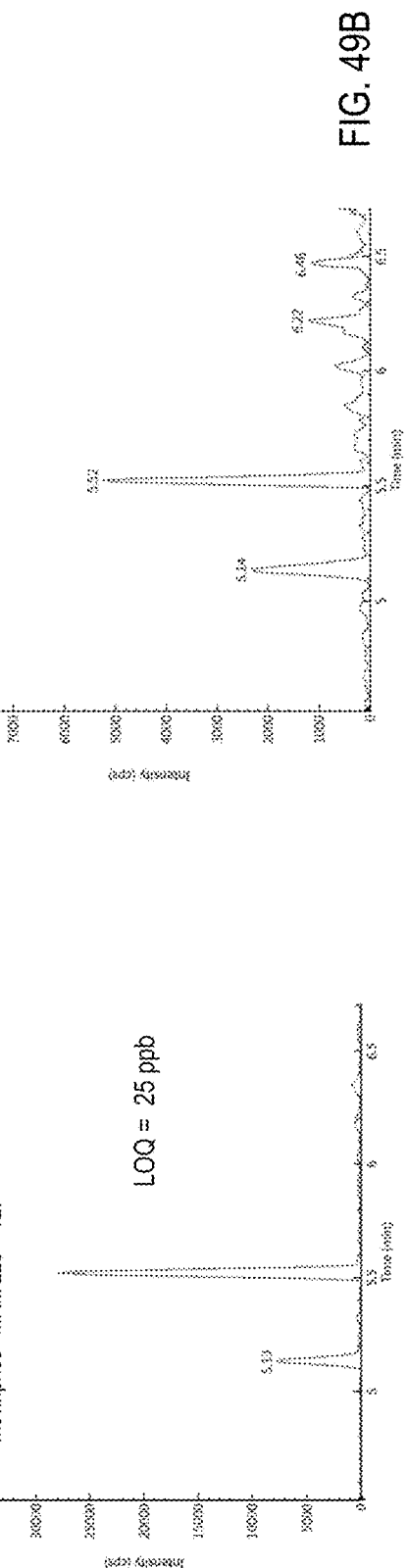
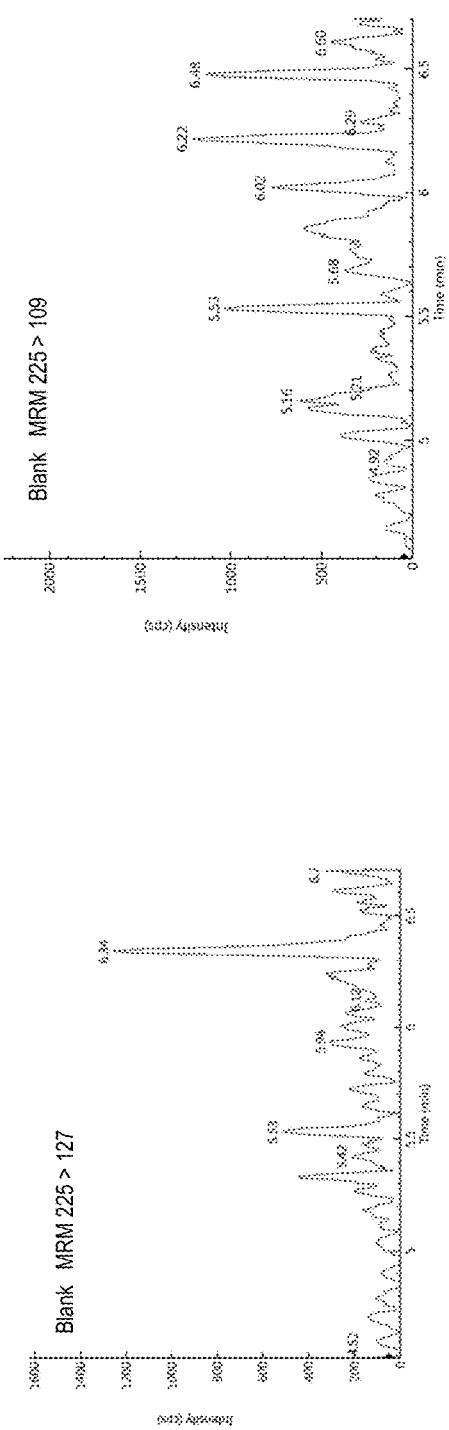
FIG. 49A
FIG. 49B
FIG. 49C
FIG. 49D

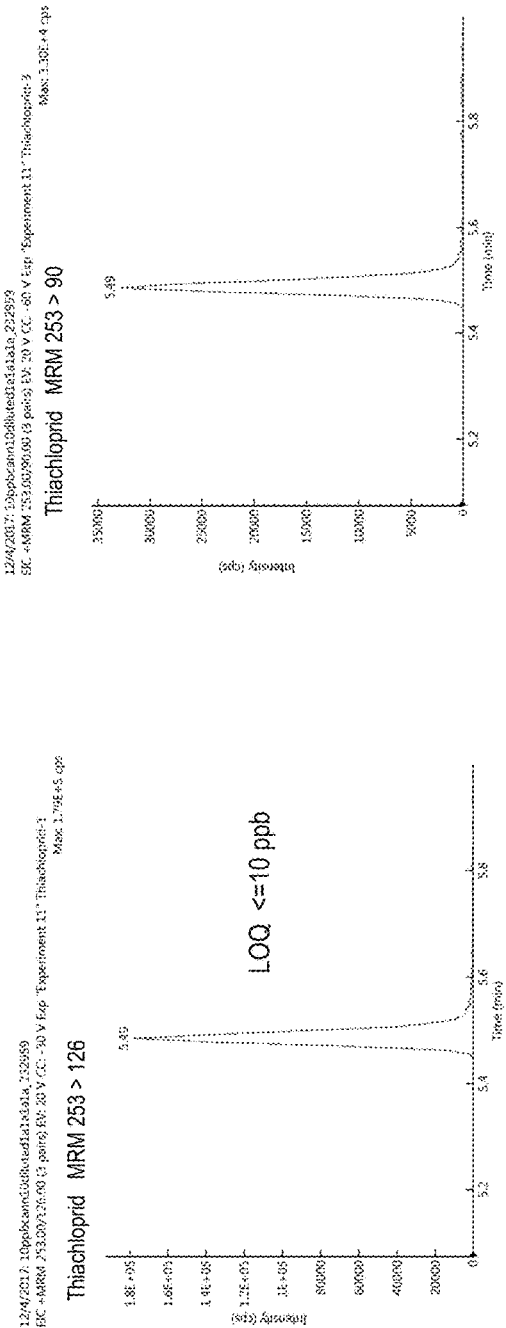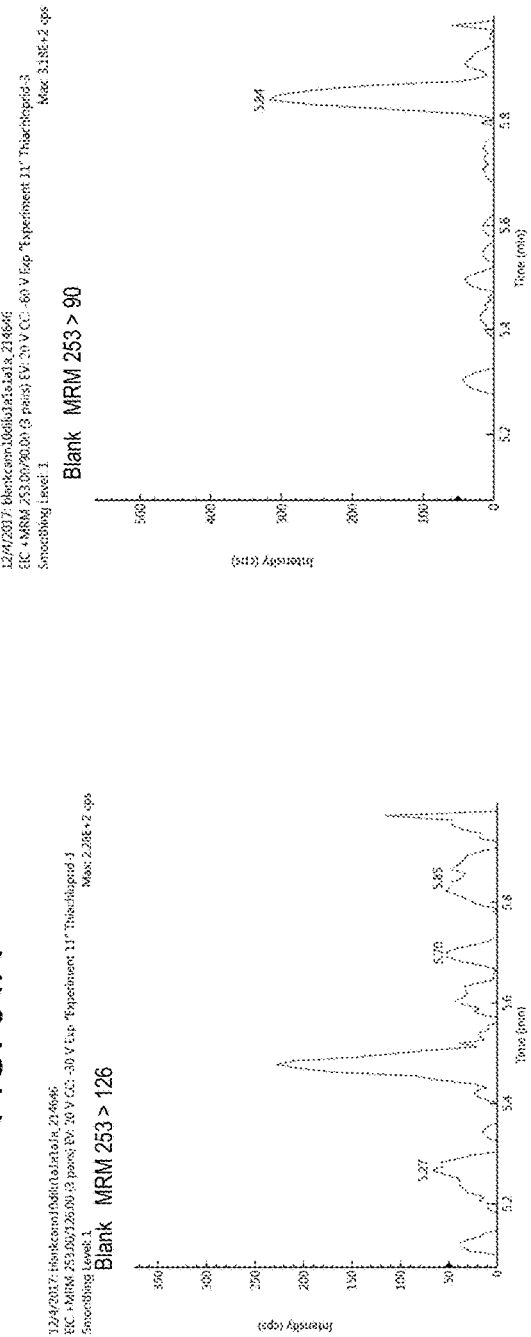

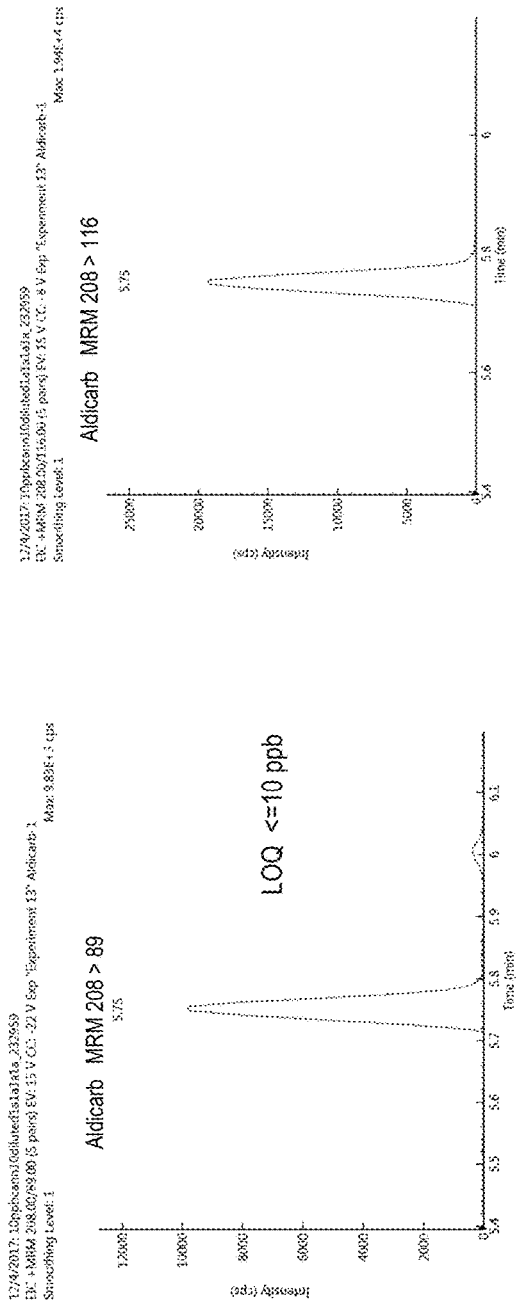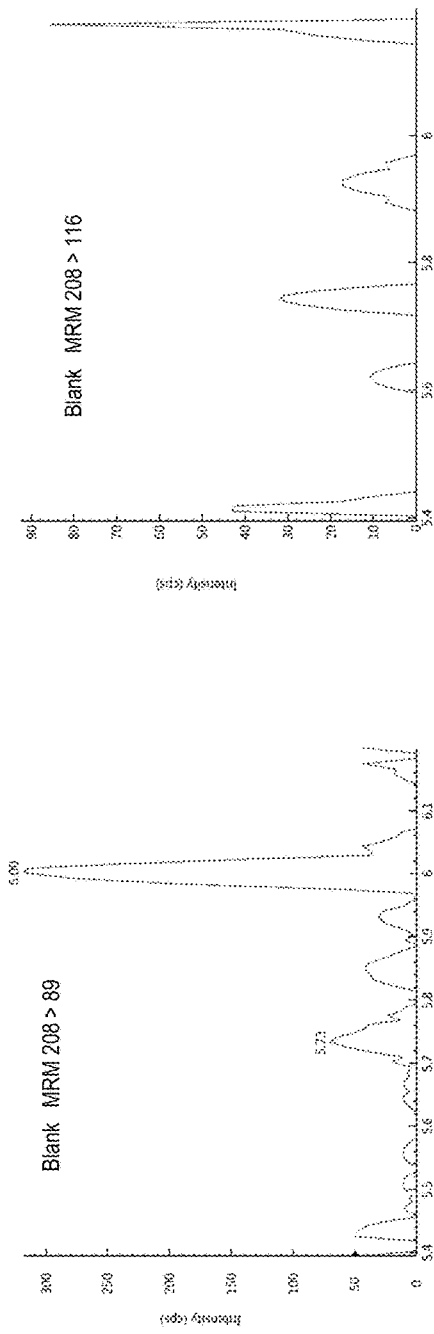
FIG. 54A
FIG. 54B
FIG. 54C
FIG. 54D

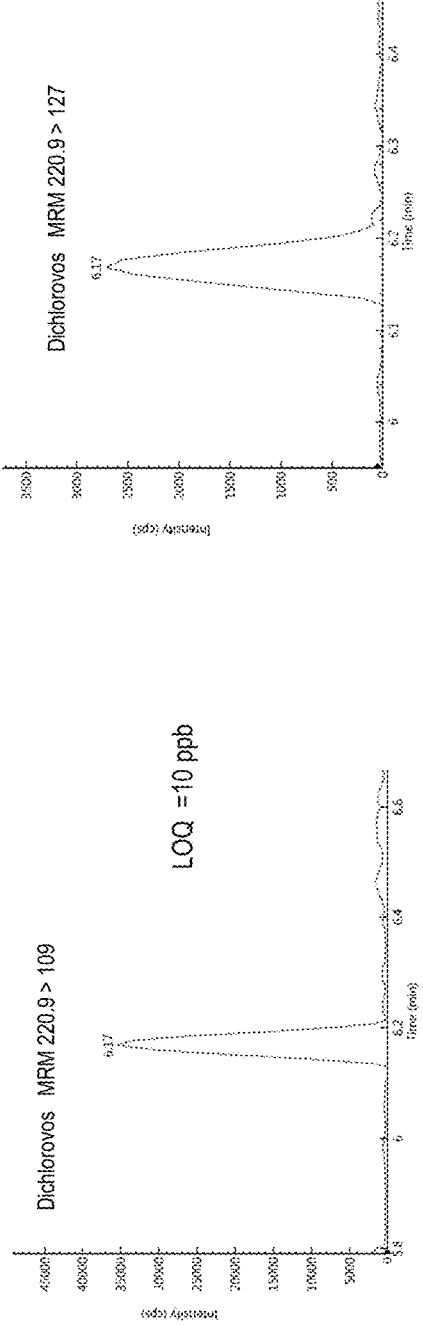
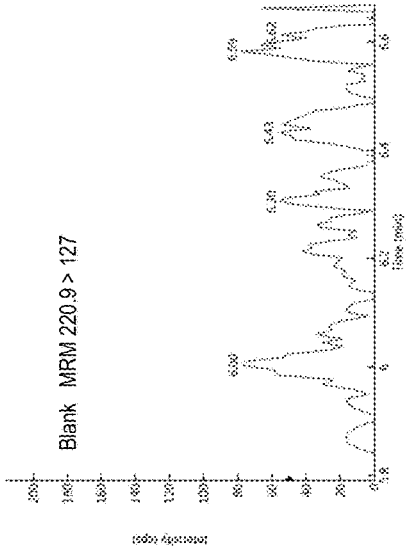
FIG. 56A
FIG. 56B
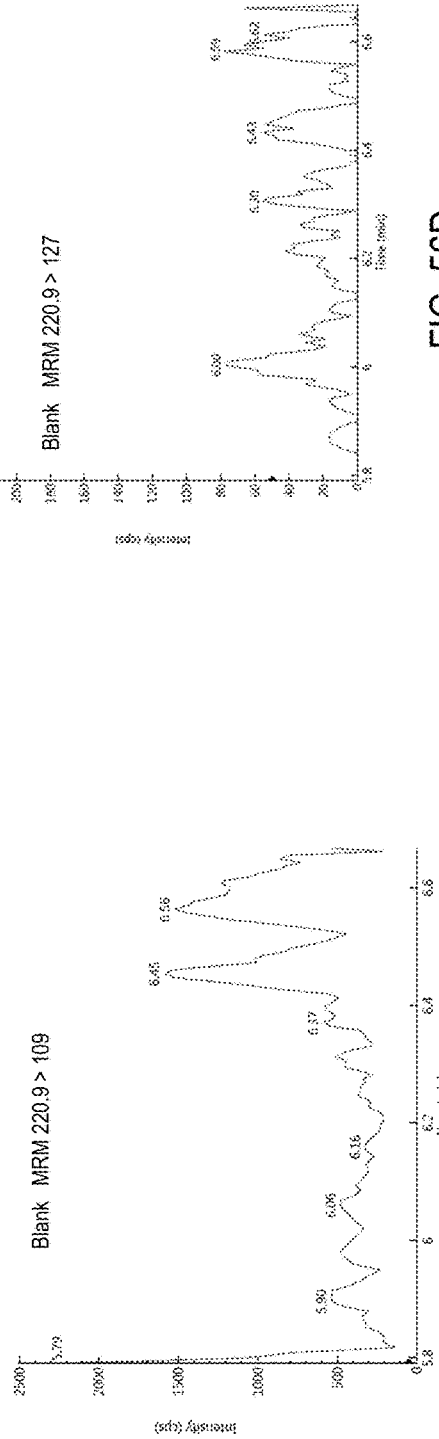
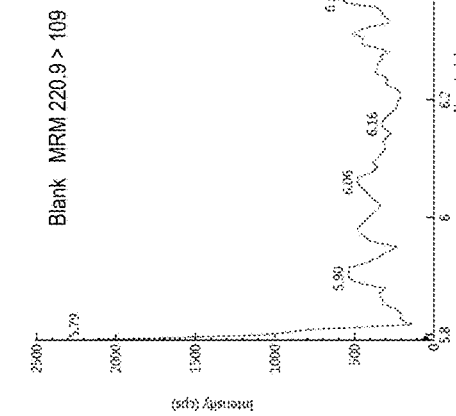
FIG. 56C
FIG. 56D

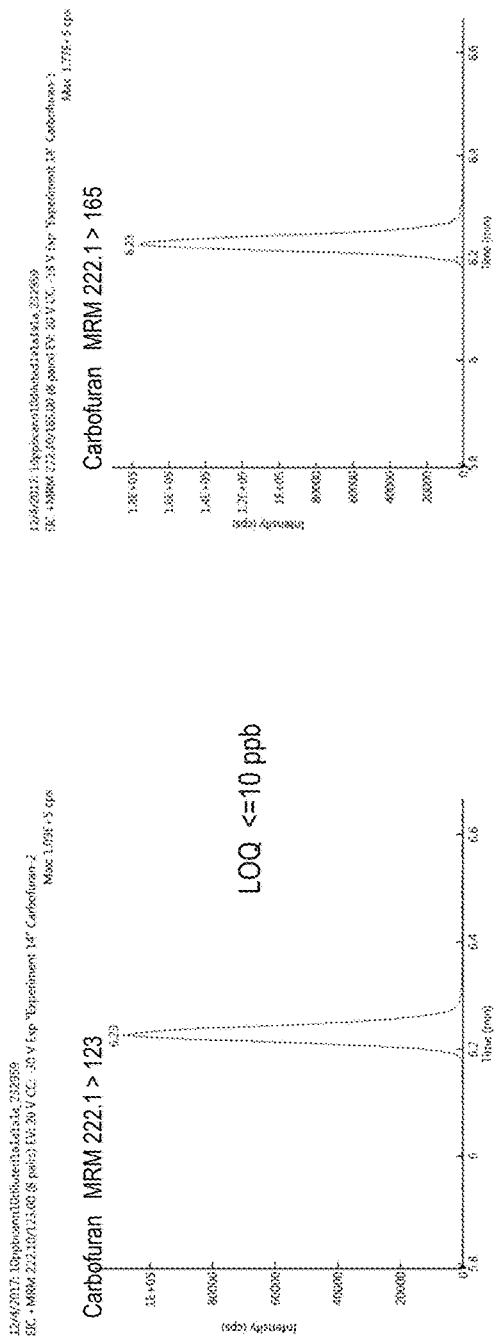
FIG. 57A
FIG. 57B
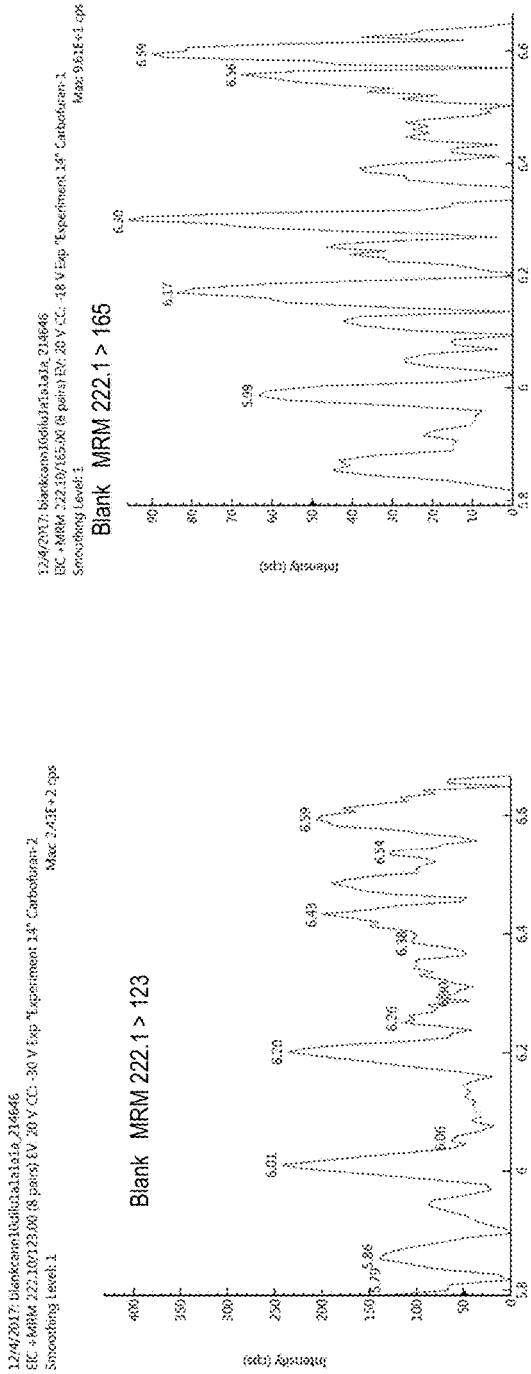
FIG. 57C
FIG. 57D

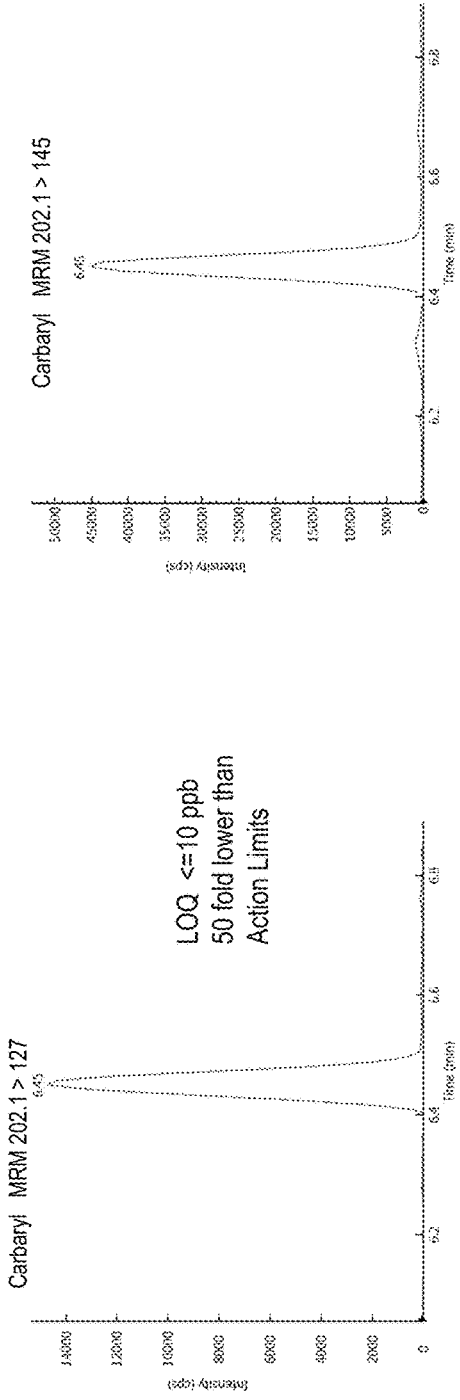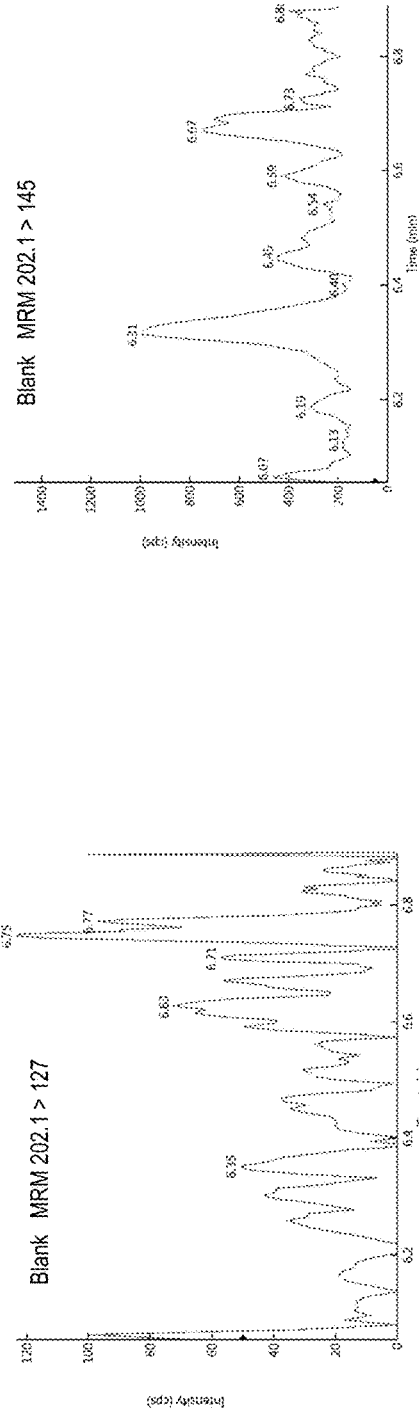
FIG. 58A
FIG. 58B
FIG. 58C
FIG. 58D

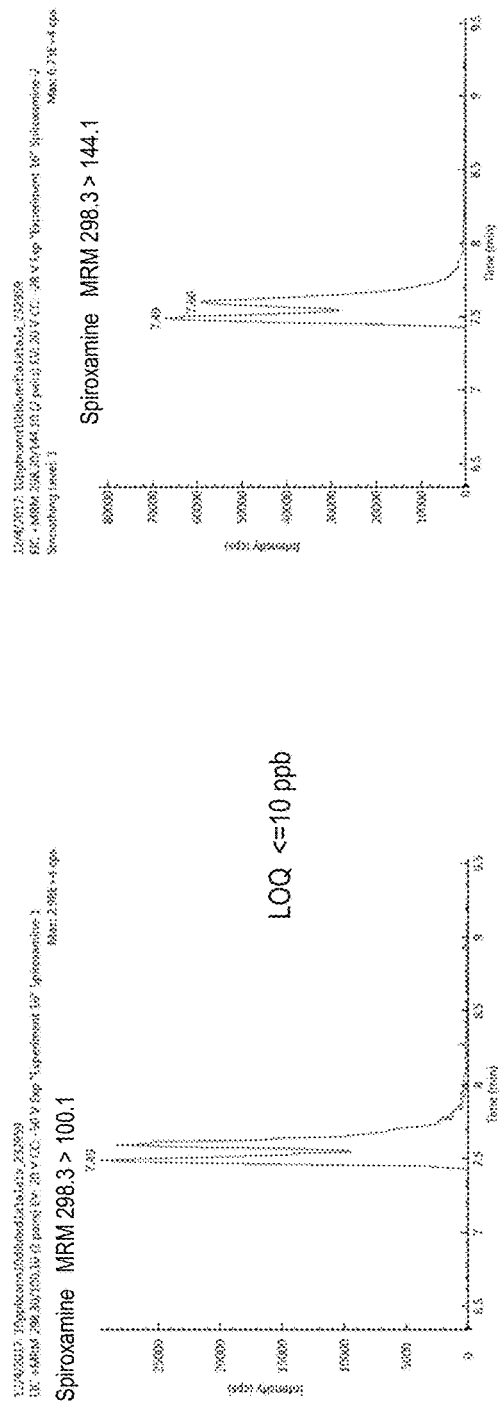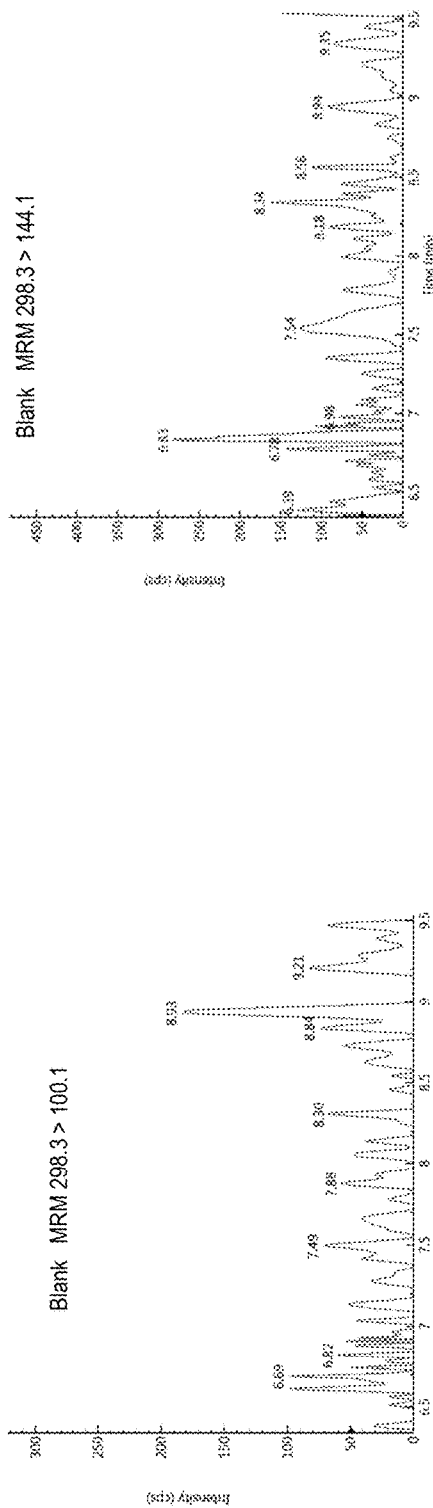
FIG. 59A
FIG. 59B
FIG. 59C
FIG. 59D

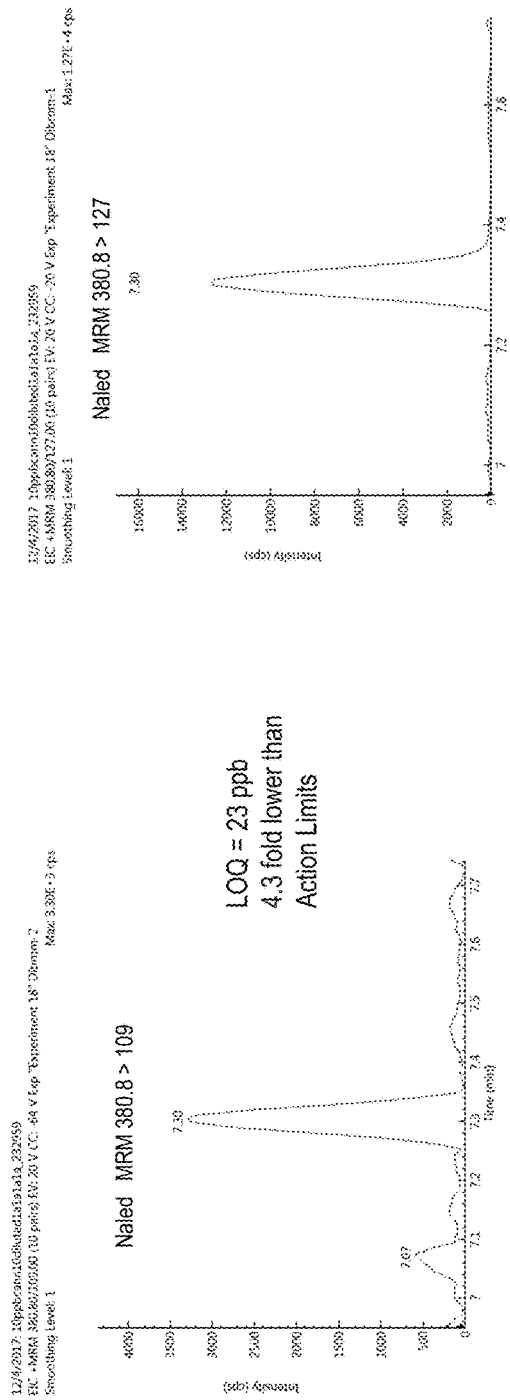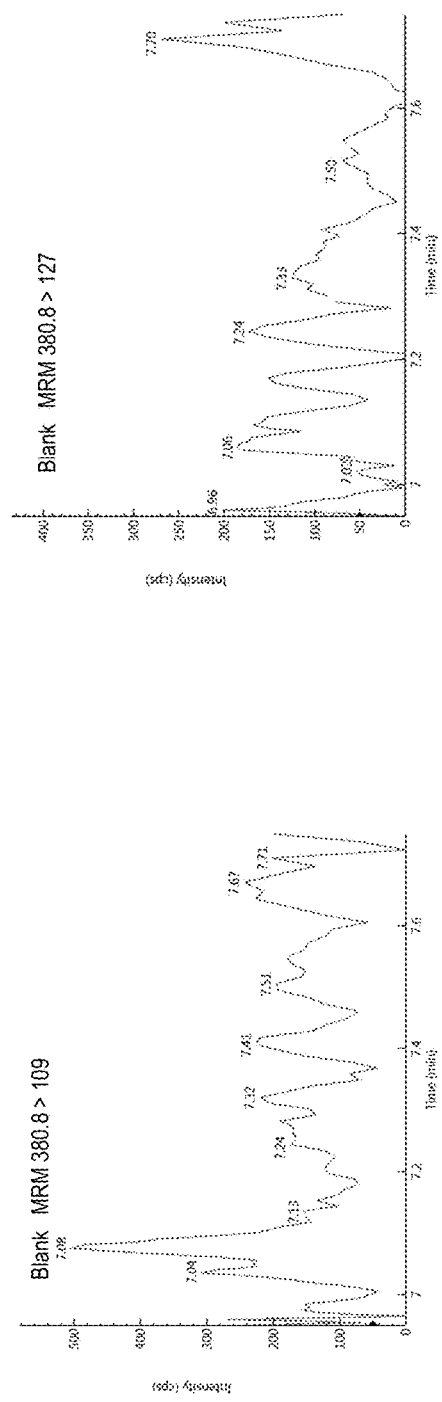

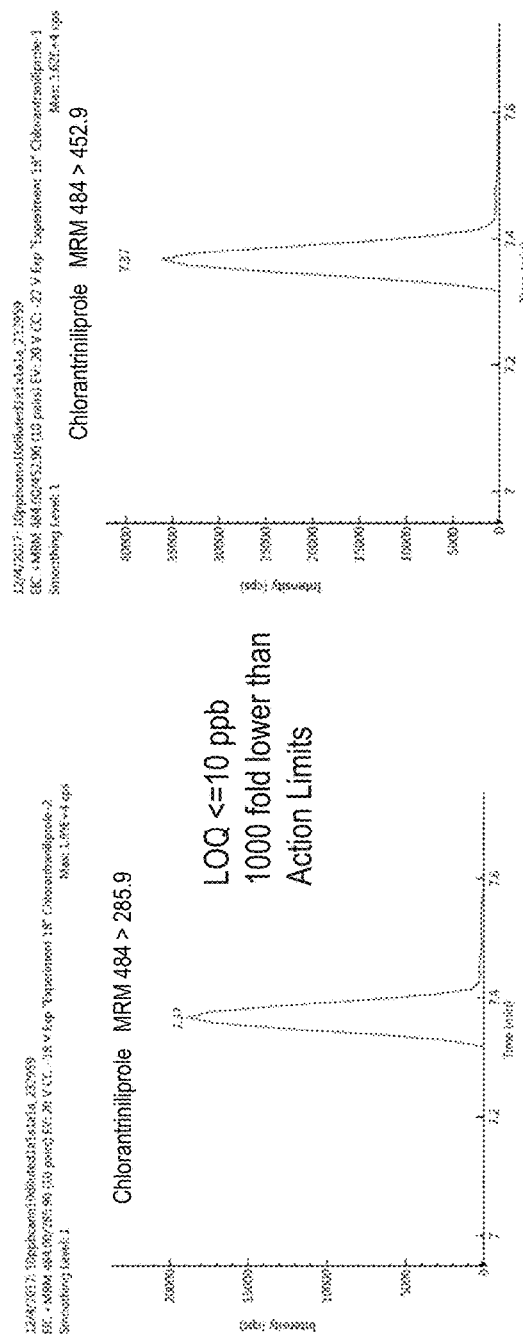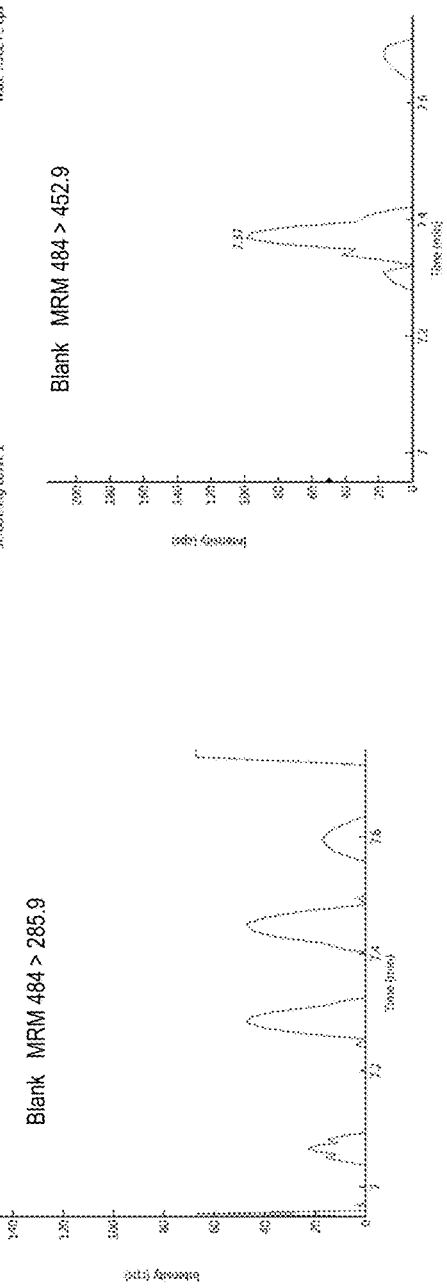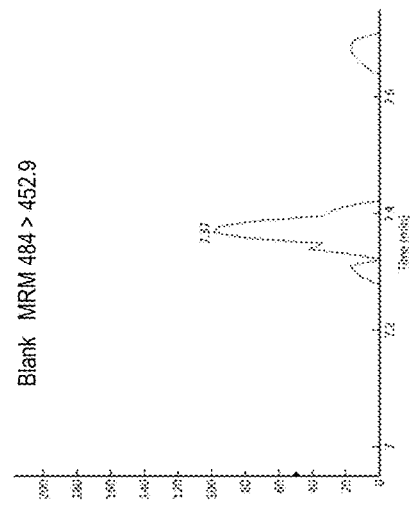
FIG. 62A  FIG. 62B  FIG. 62C  FIG. 62D
LOQ <=10 ppb
1000 fold lower than Action Limits

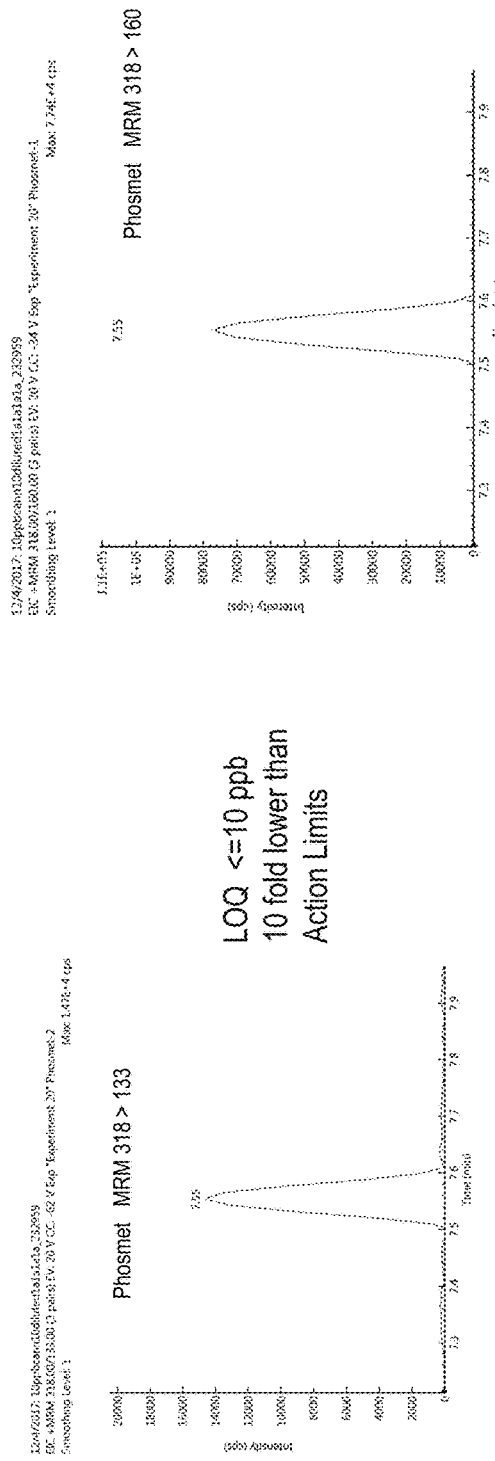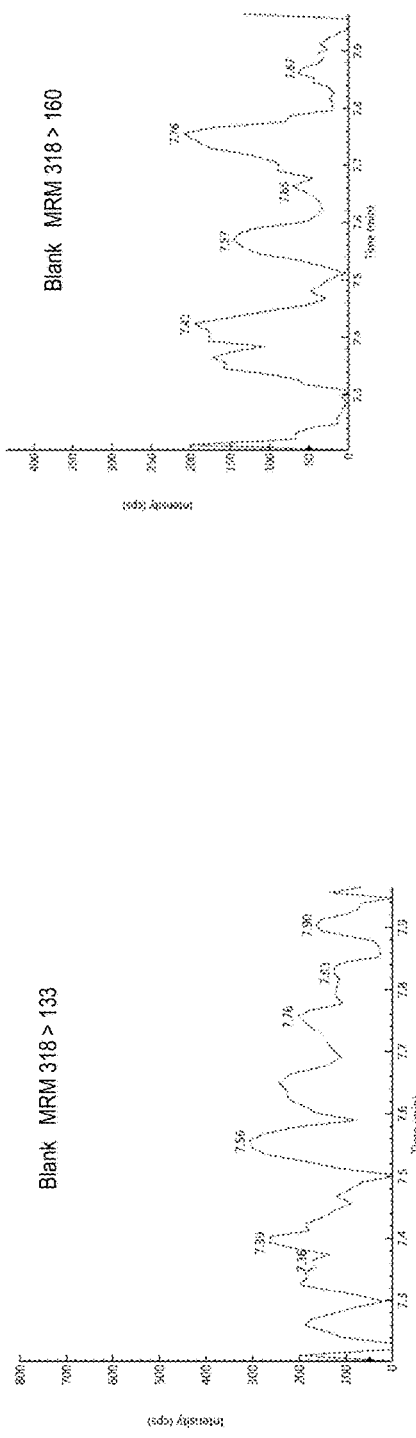
FIG. 63A  FIG. 63B  FIG. 63C  FIG. 63D
LOQ <=10 ppb
10 fold lower than
Action Limits

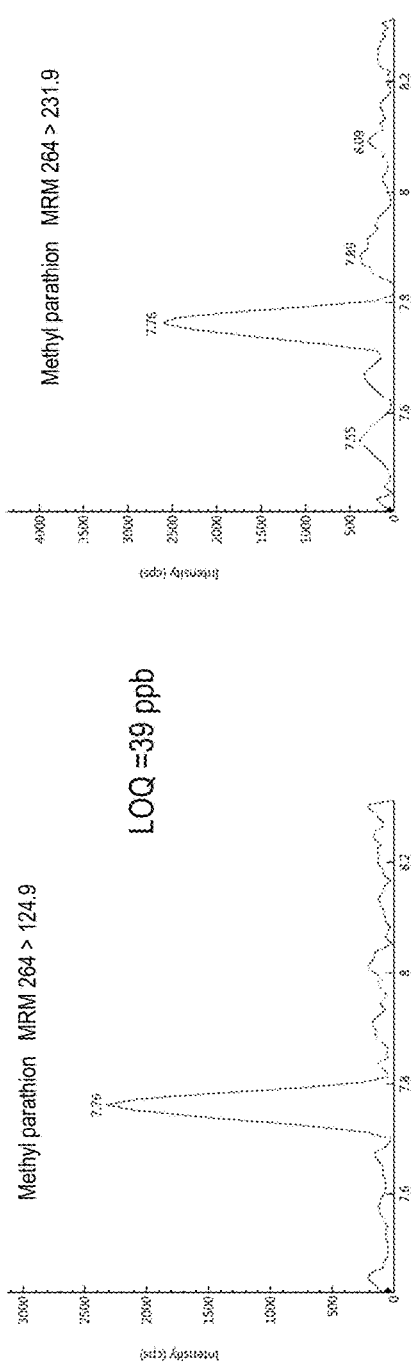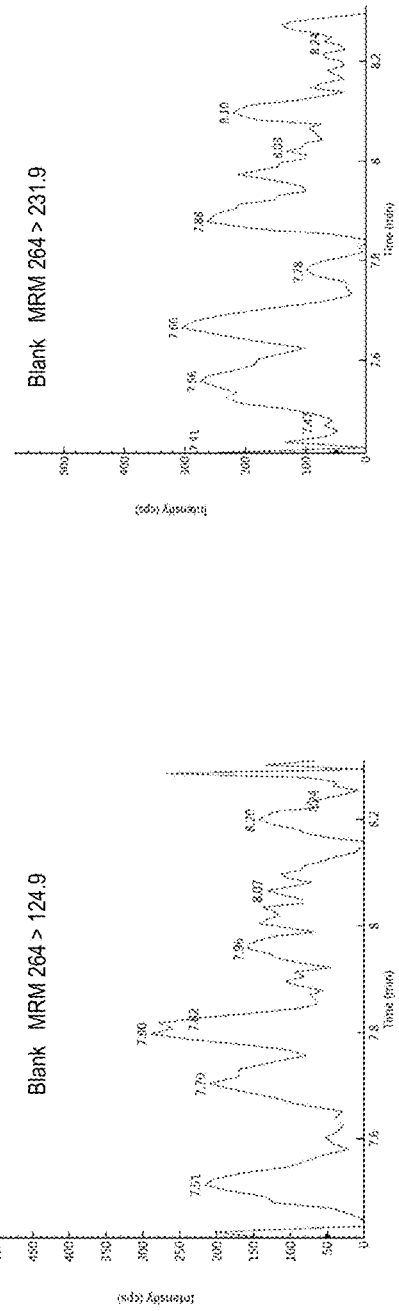

LOQ <=10 ppb
10 fold lower than
Action Limits

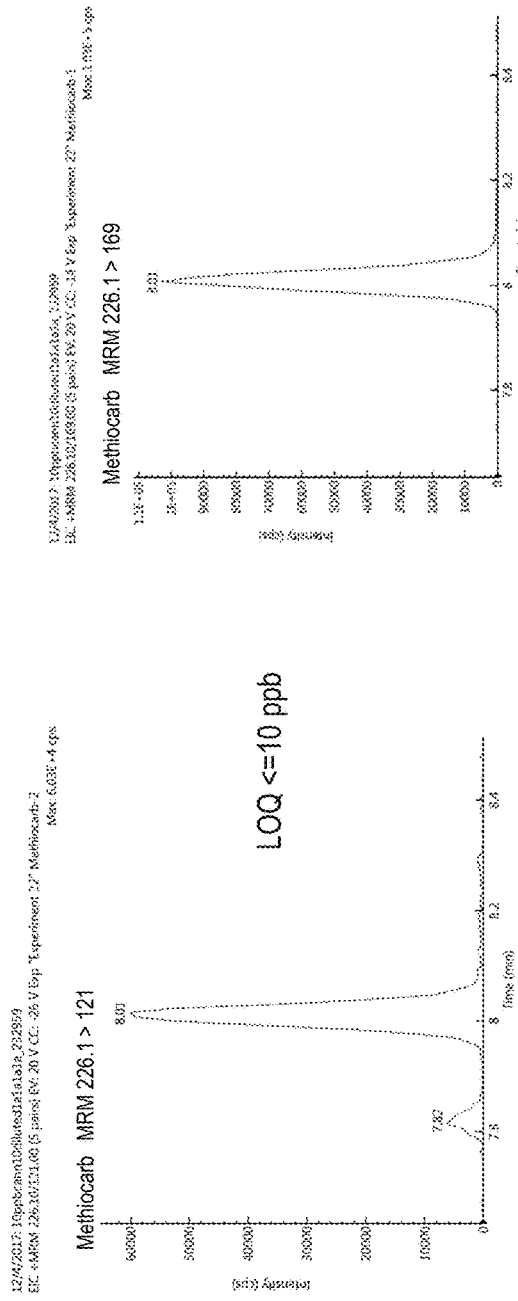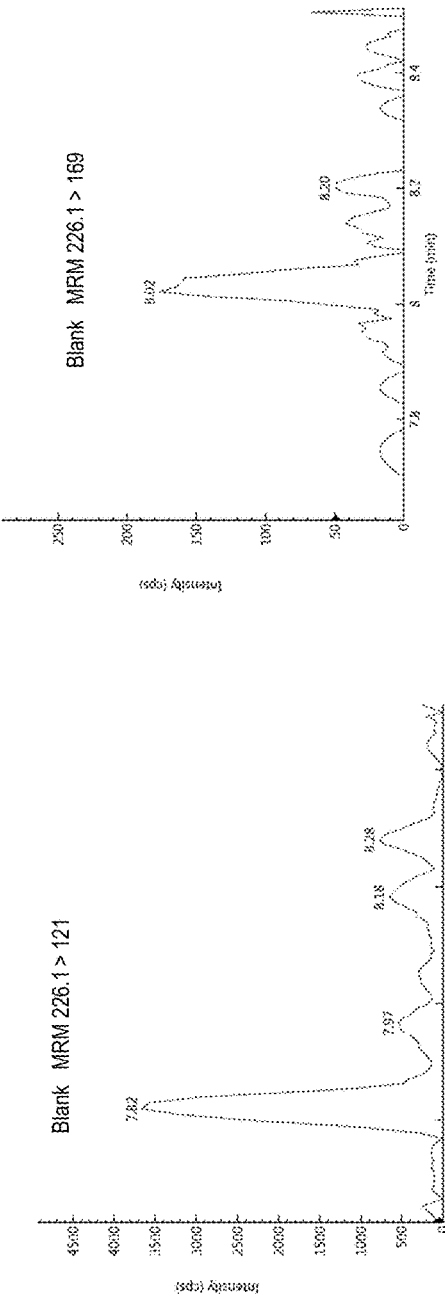

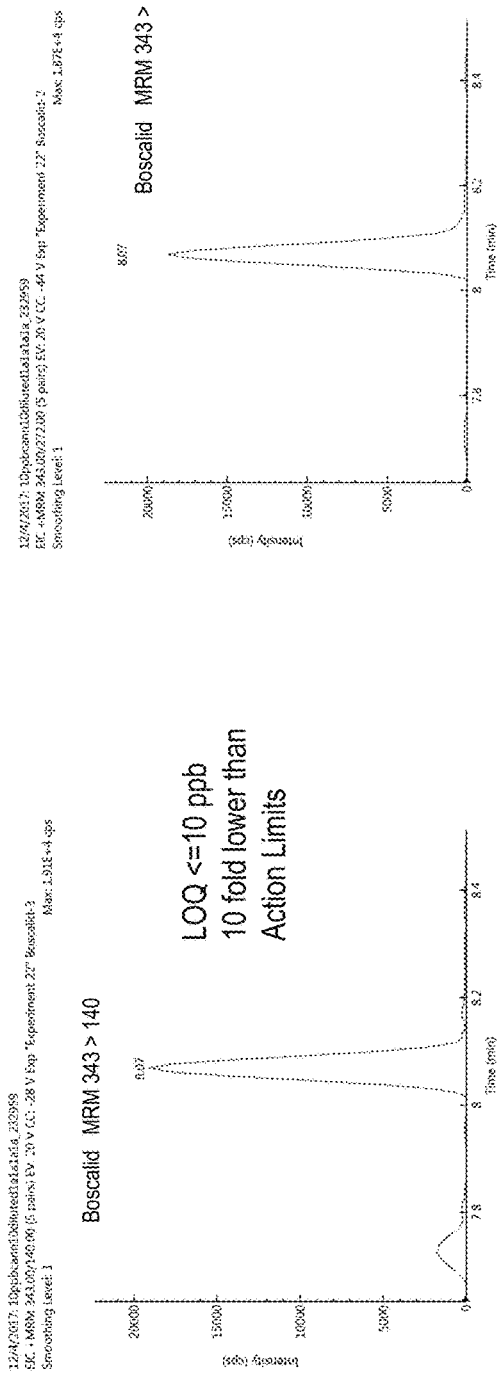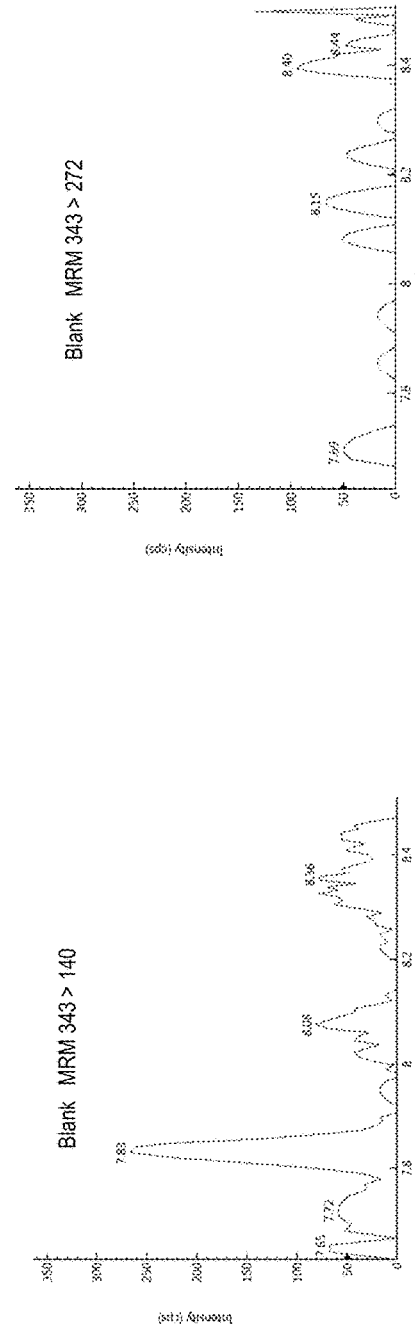
FIG. 68A  FIG. 68B  FIG. 68C  FIG. 68D

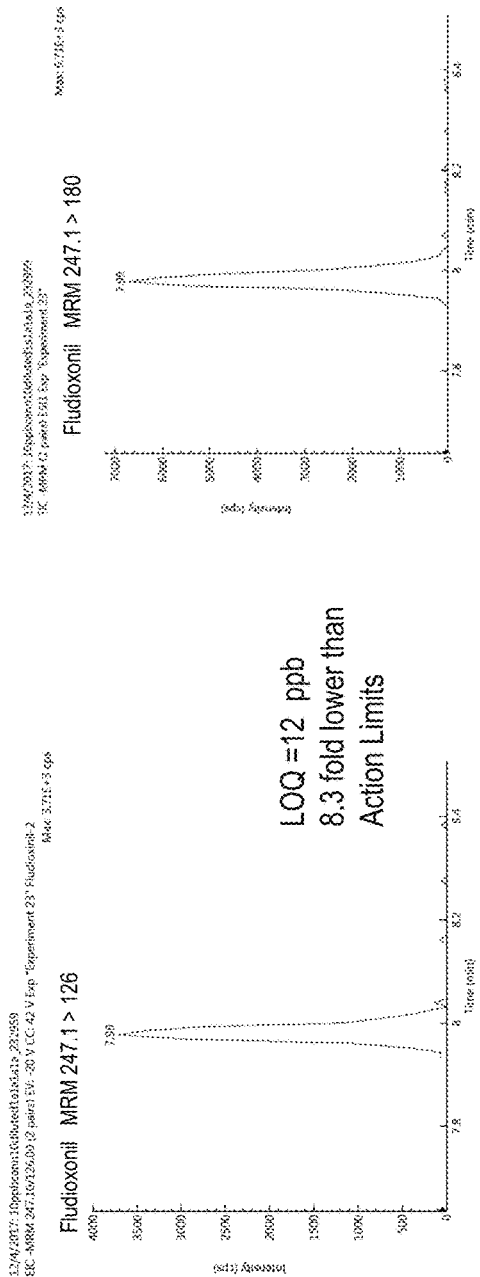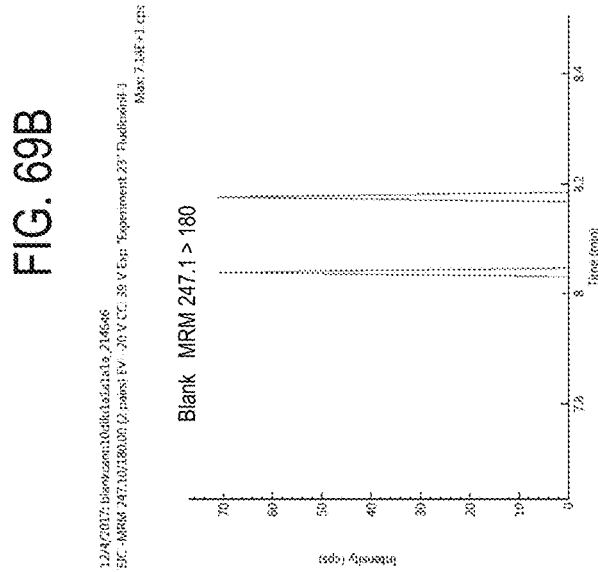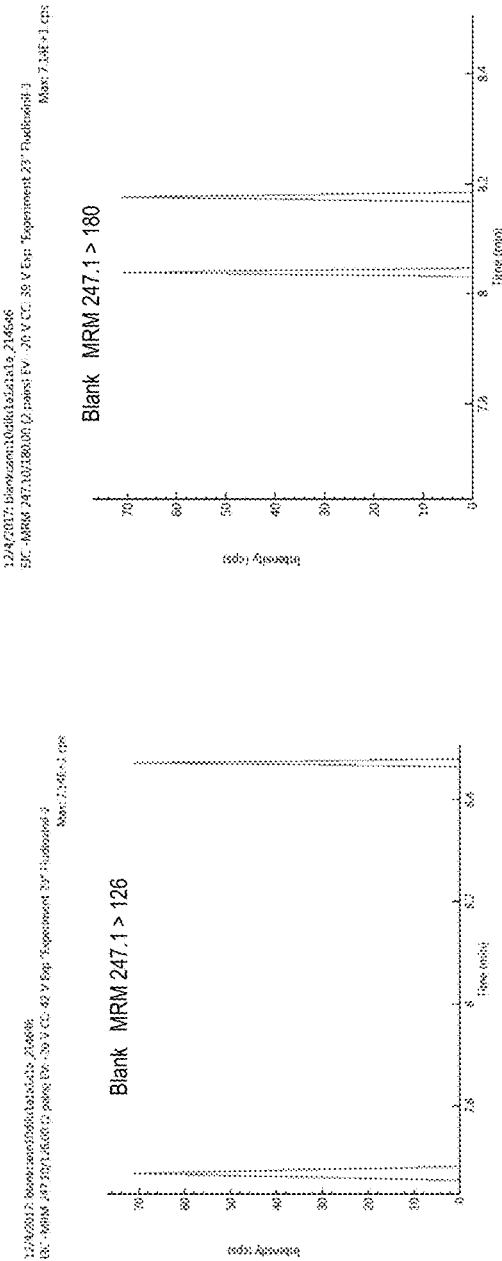
FIG. 69A
FIG. 69B
FIG. 69C
FIG. 69D

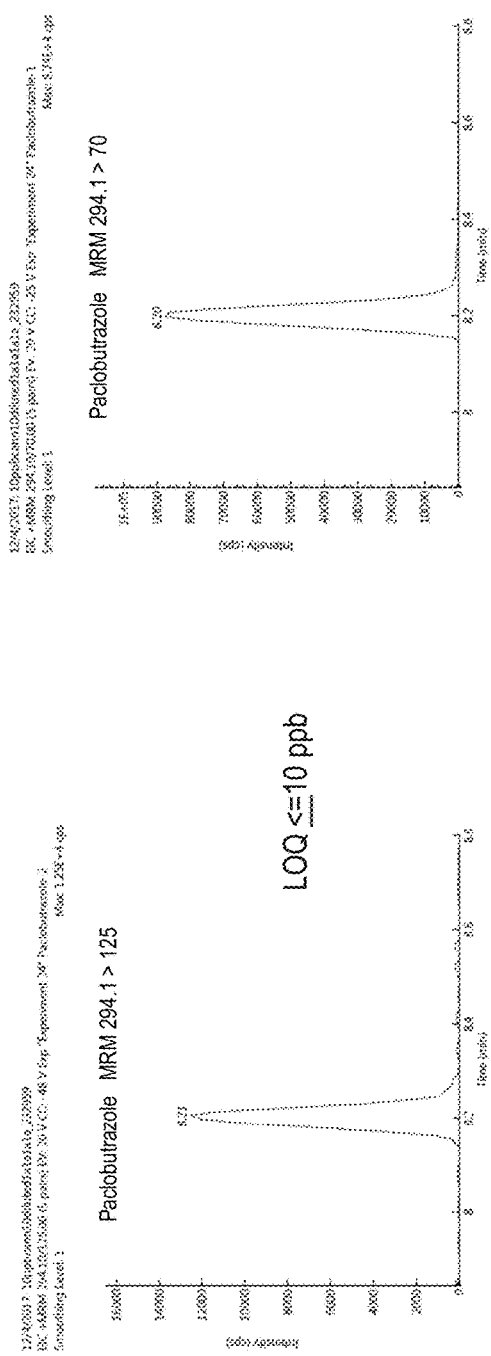
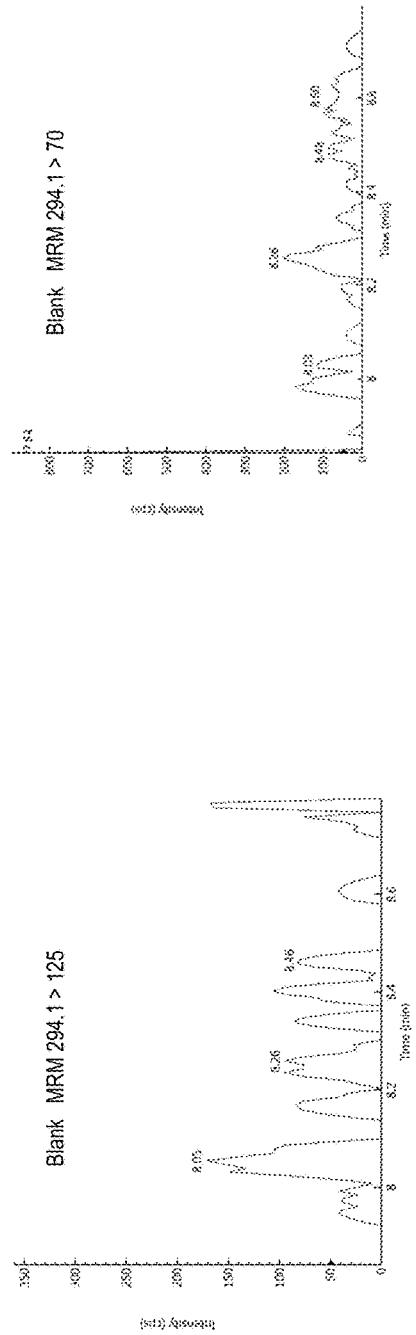
FIG. 70A
FIG. 70B
FIG. 70C
FIG. 70D

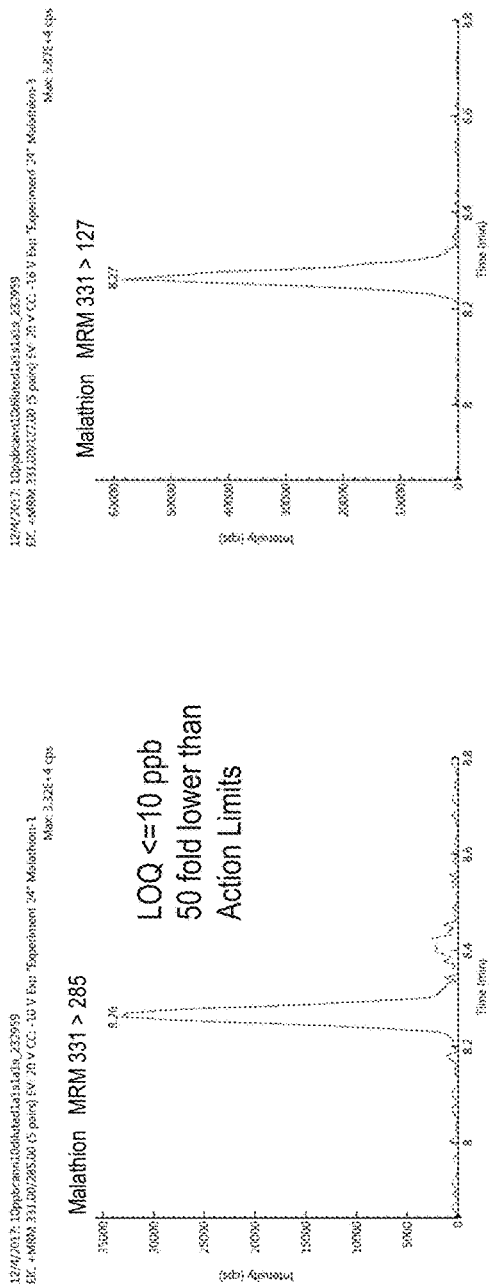
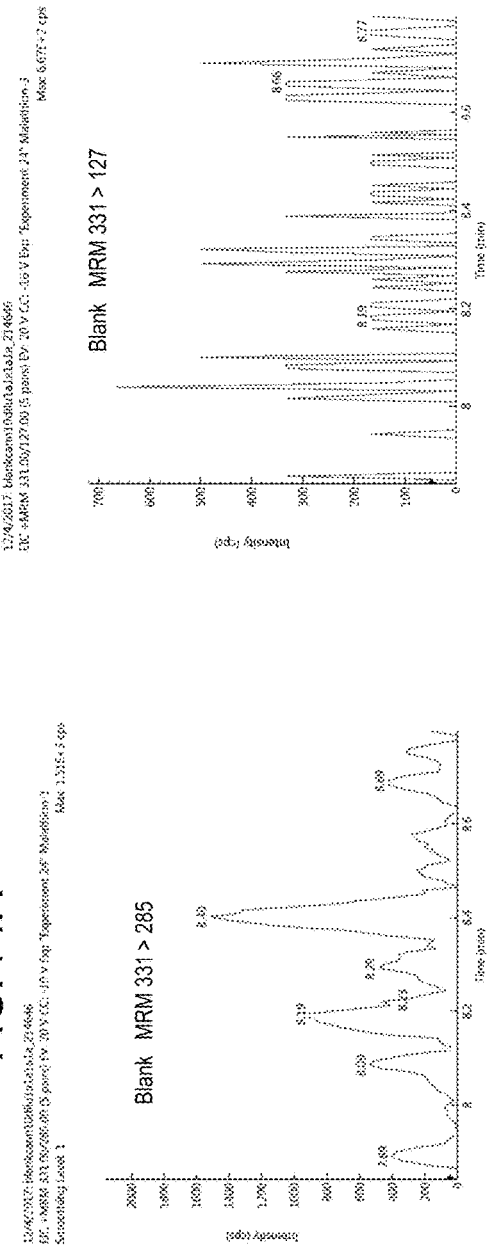
FIG. 71A
FIG. 71B
FIG. 71C
FIG. 71D

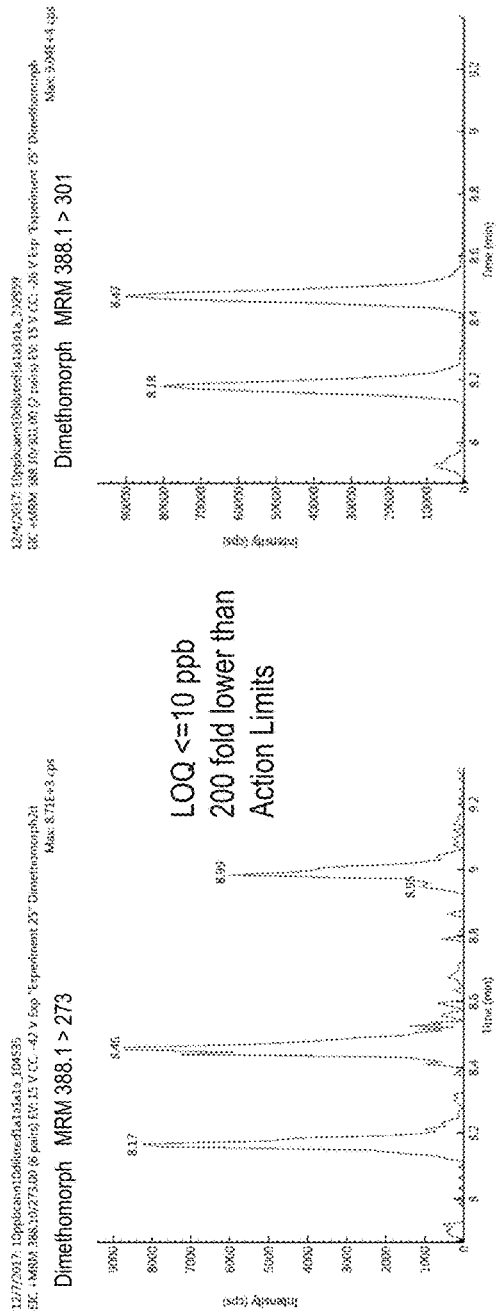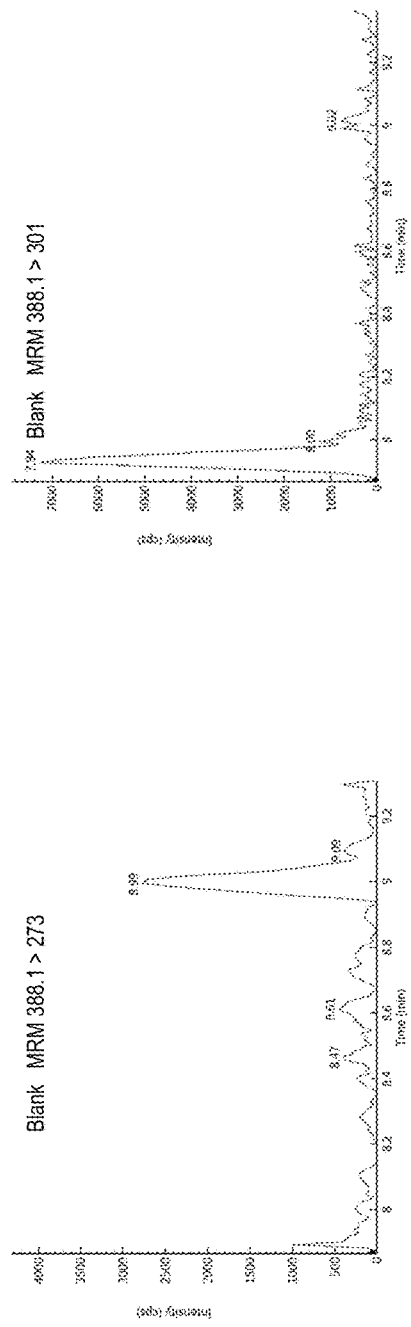
FIG. 72A  FIG. 72B  FIG. 72C  FIG. 72D
LOQ <=10 ppb
200 fold lower than
Action Limits

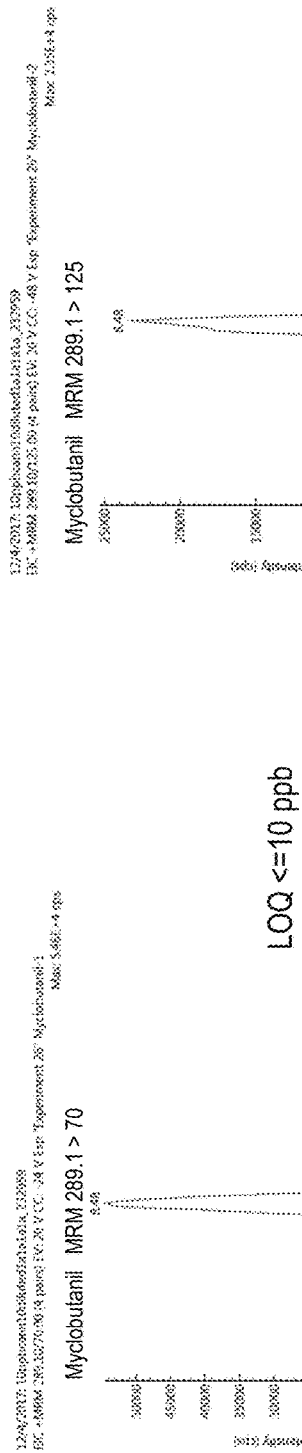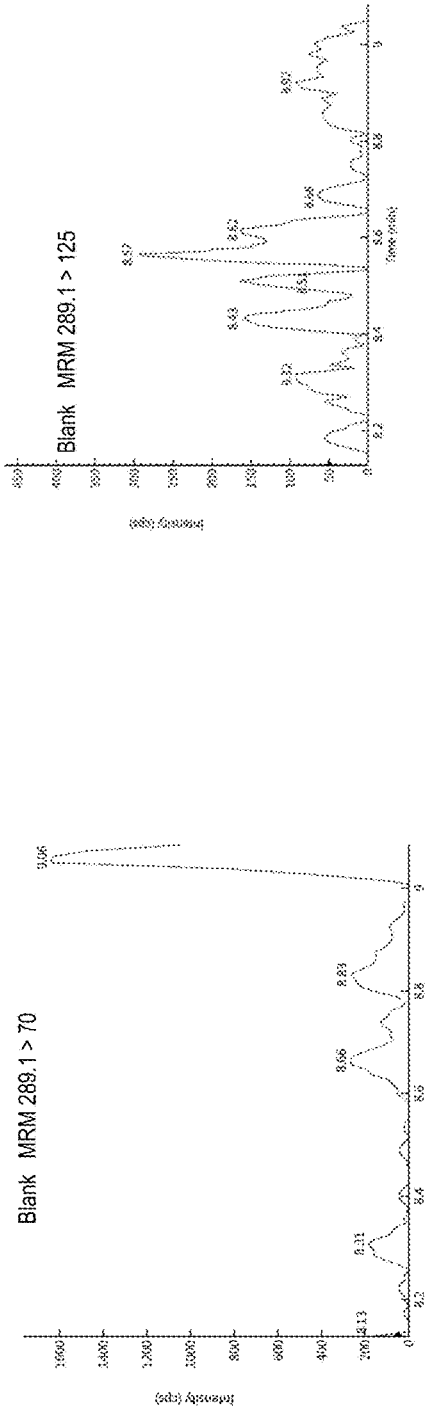
FIG. 73A
FIG. 73B
FIG. 73C
FIG. 73D

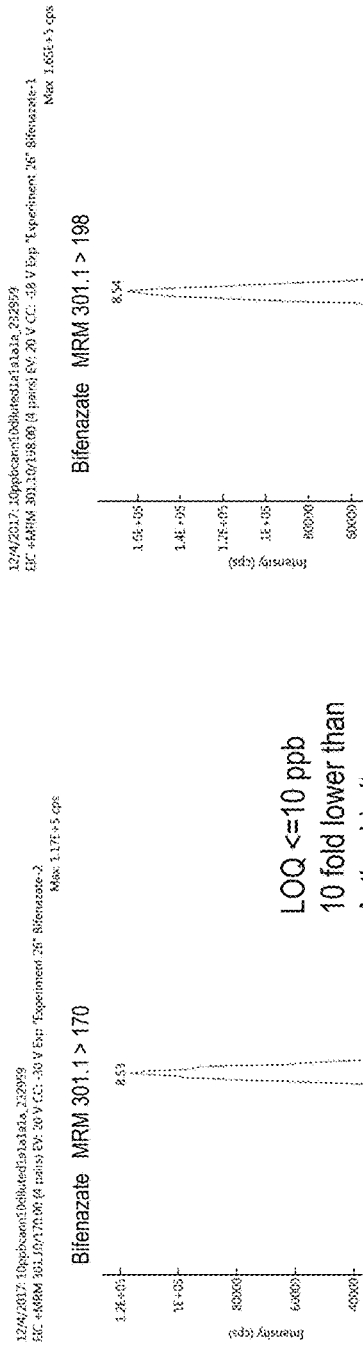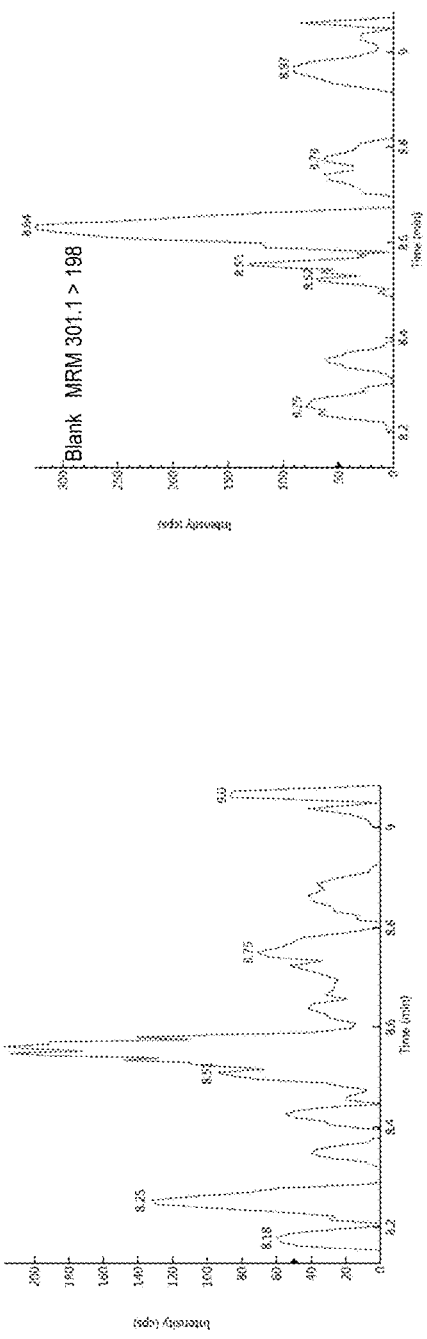
FIG. 74A  FIG. 74B  FIG. 74C  FIG. 74D

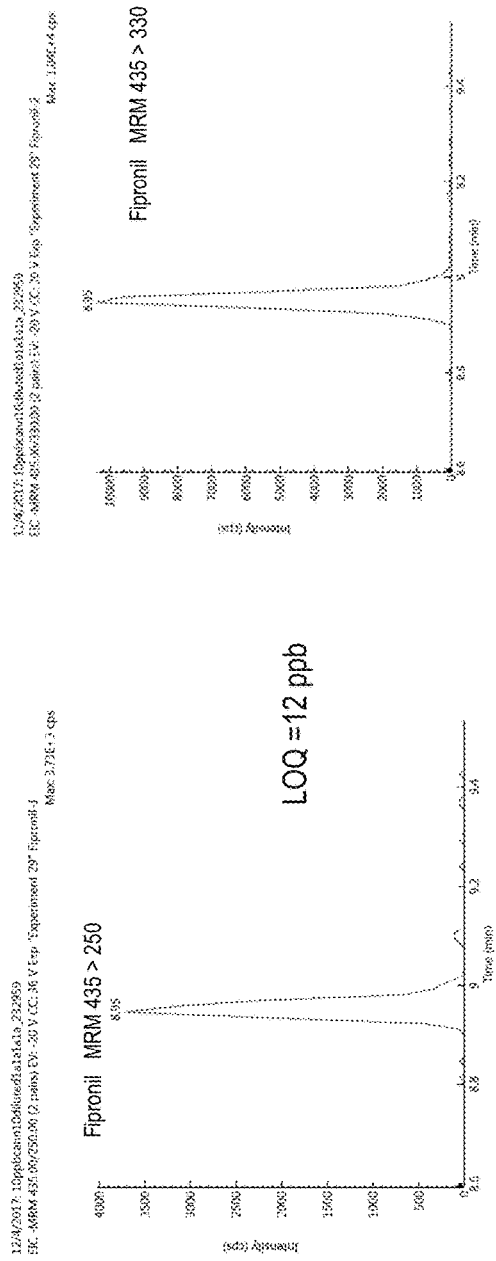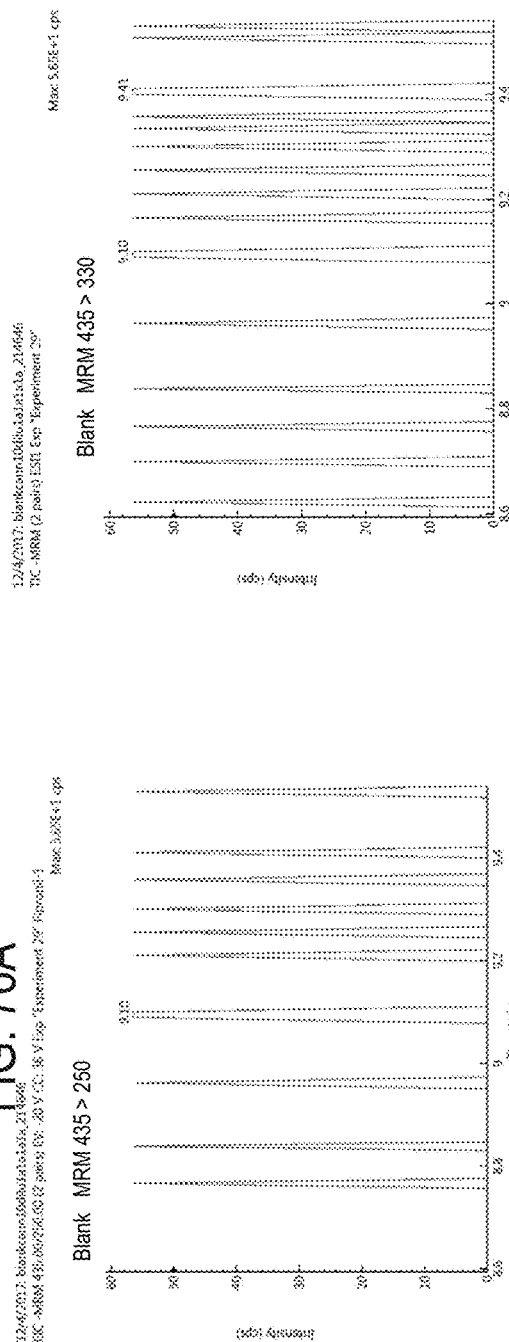

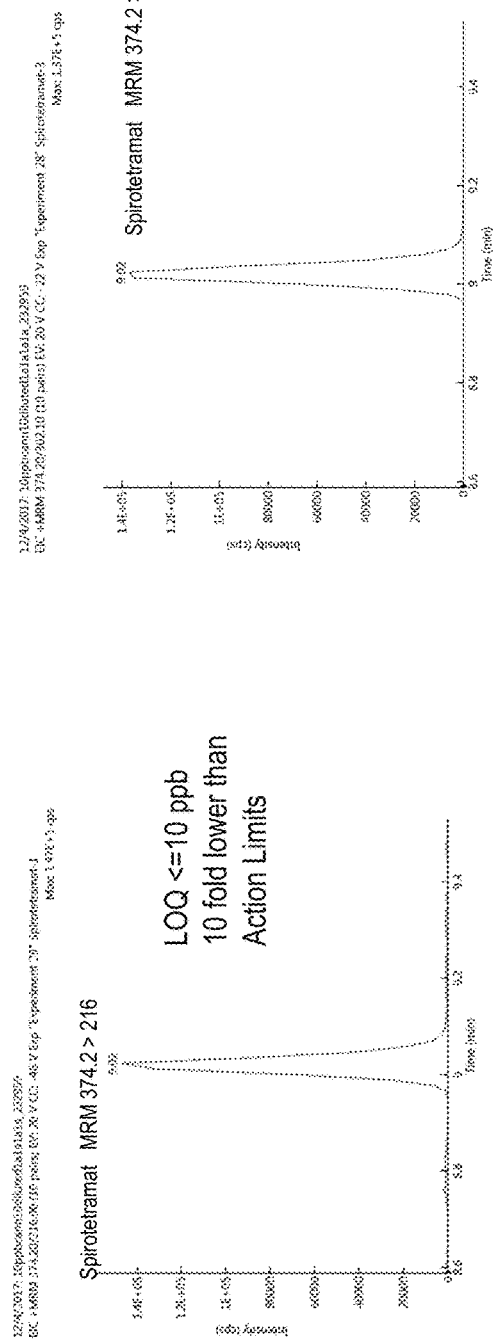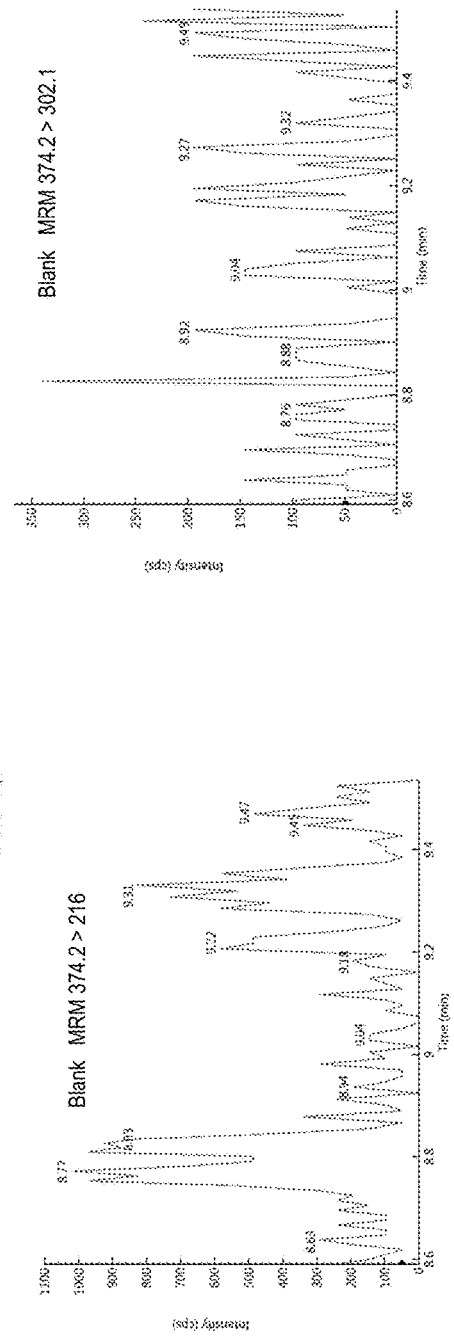
FIG. 77A
FIG. 77B
FIG. 77C
FIG. 77D

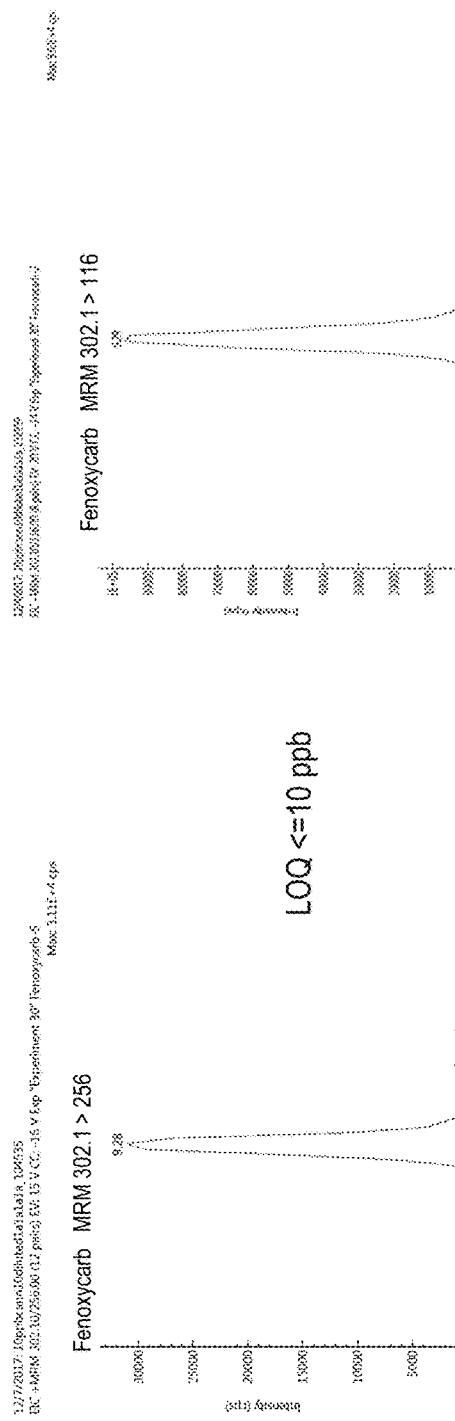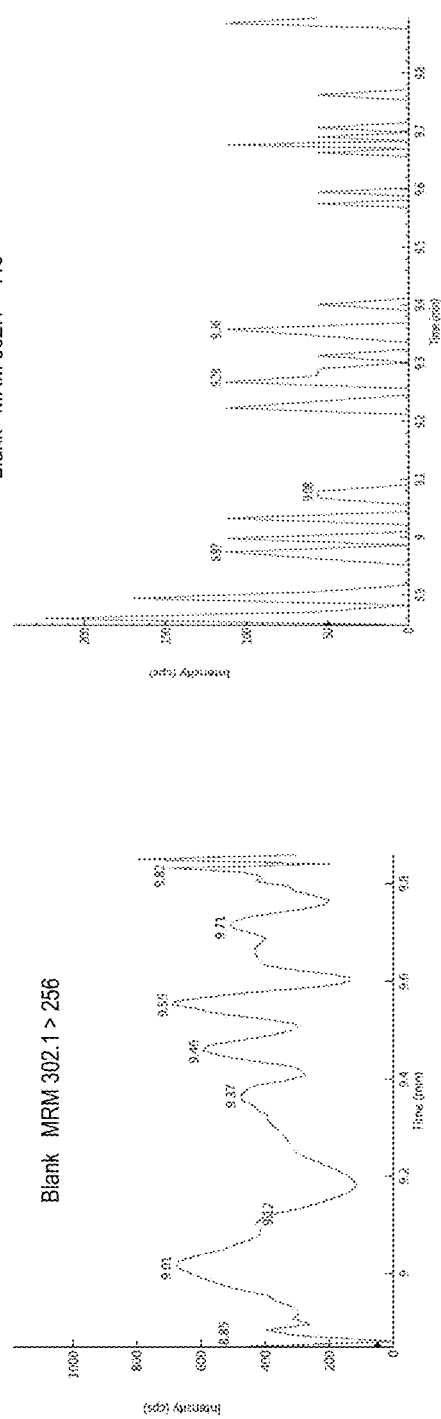
FIG. 79A FIG. 79B FIG. 79C FIG. 79D

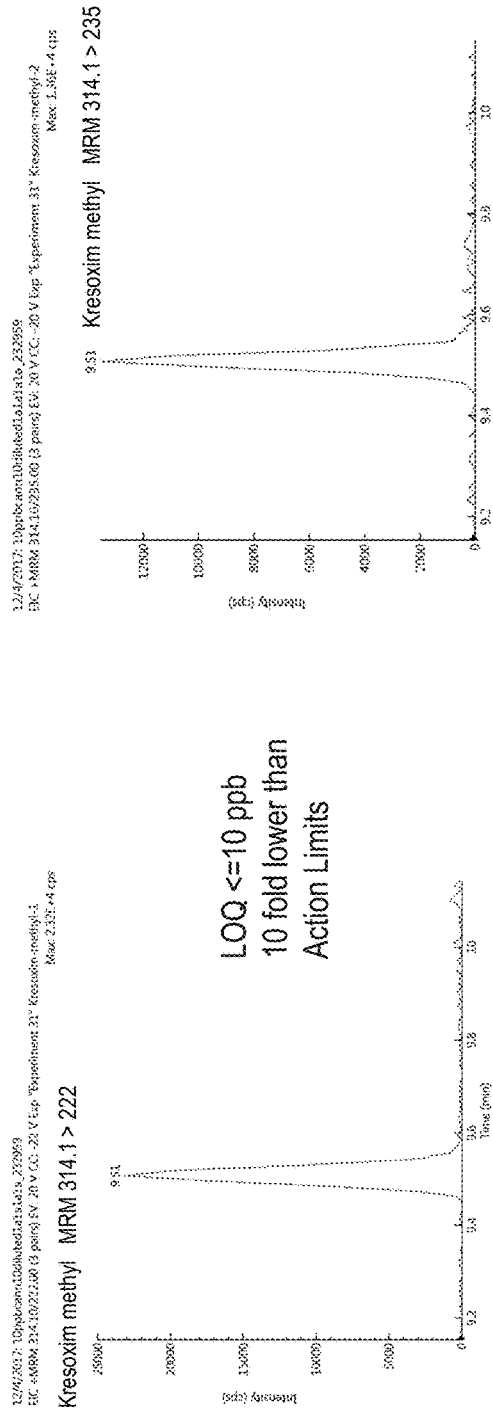
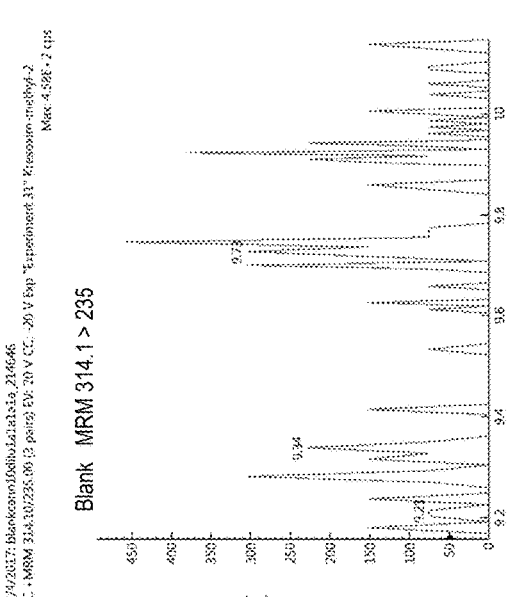
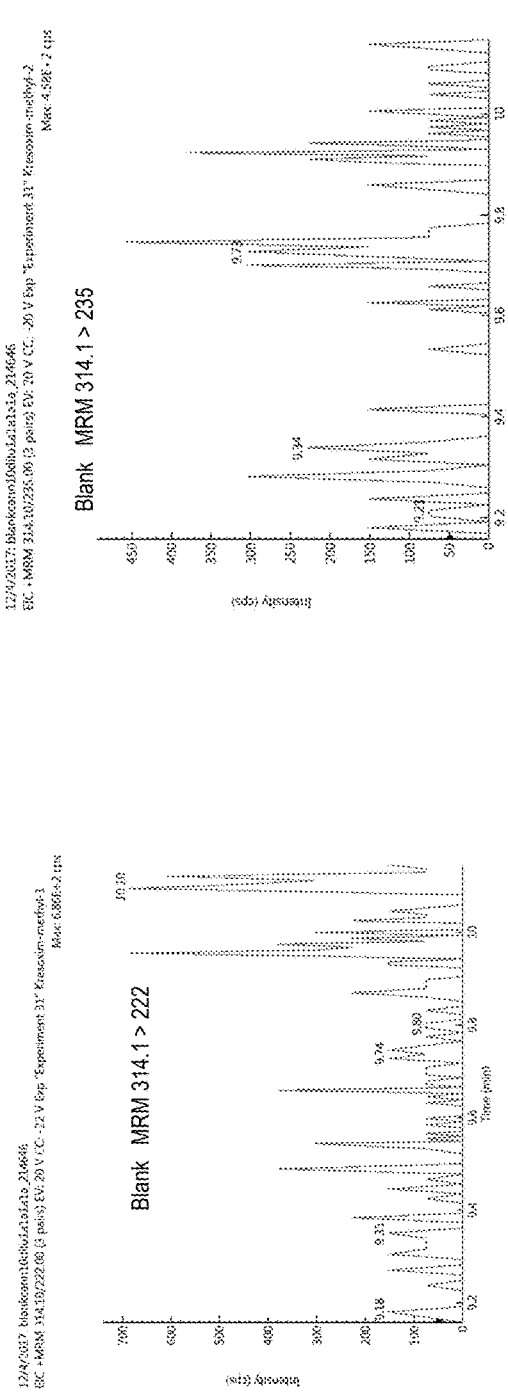
FIG. 80A
FIG. 80B
FIG. 80C
FIG. 80D
LOQ <=10 ppb
10 fold lower than
Action Limits

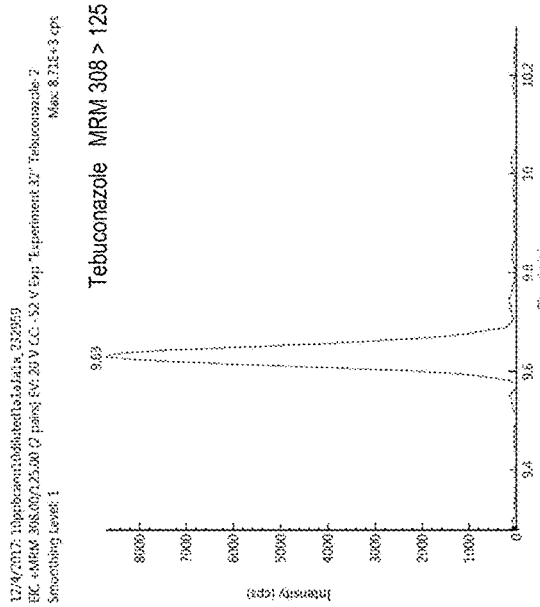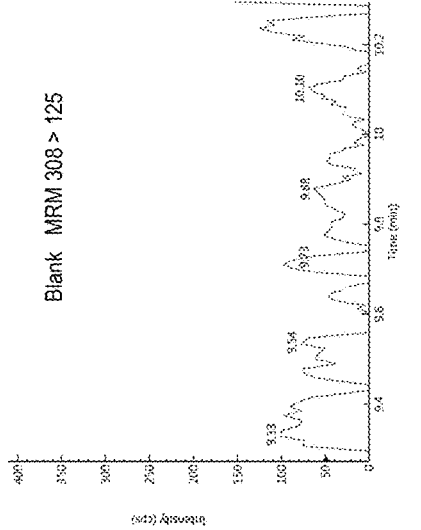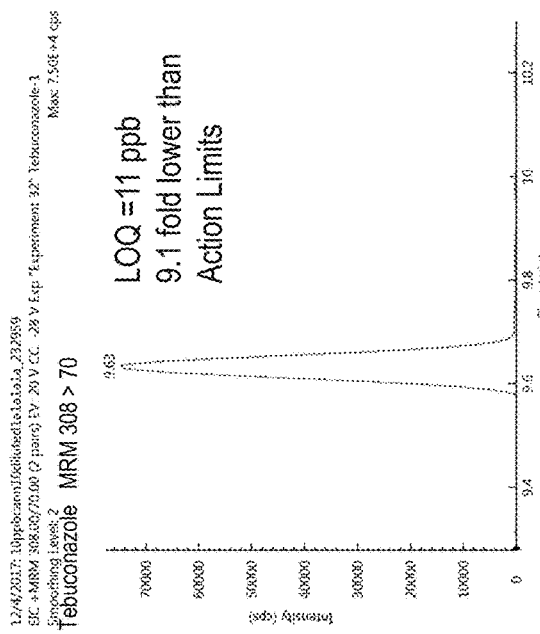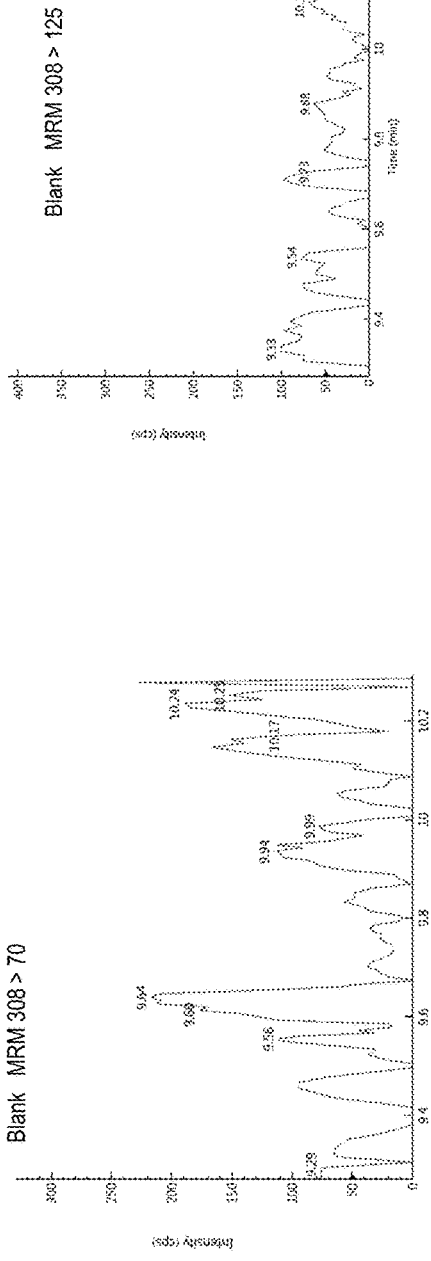

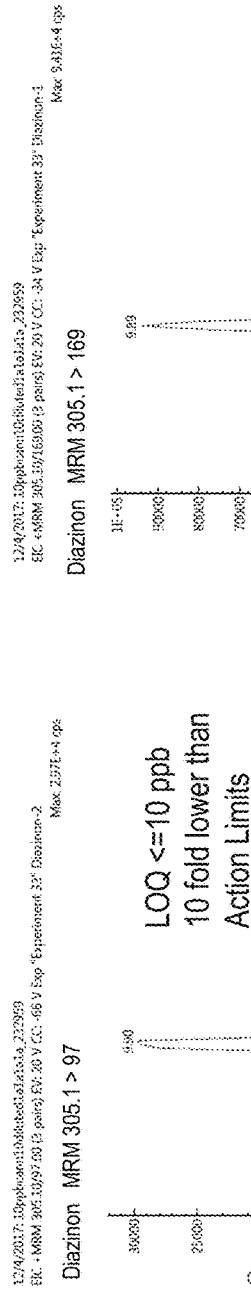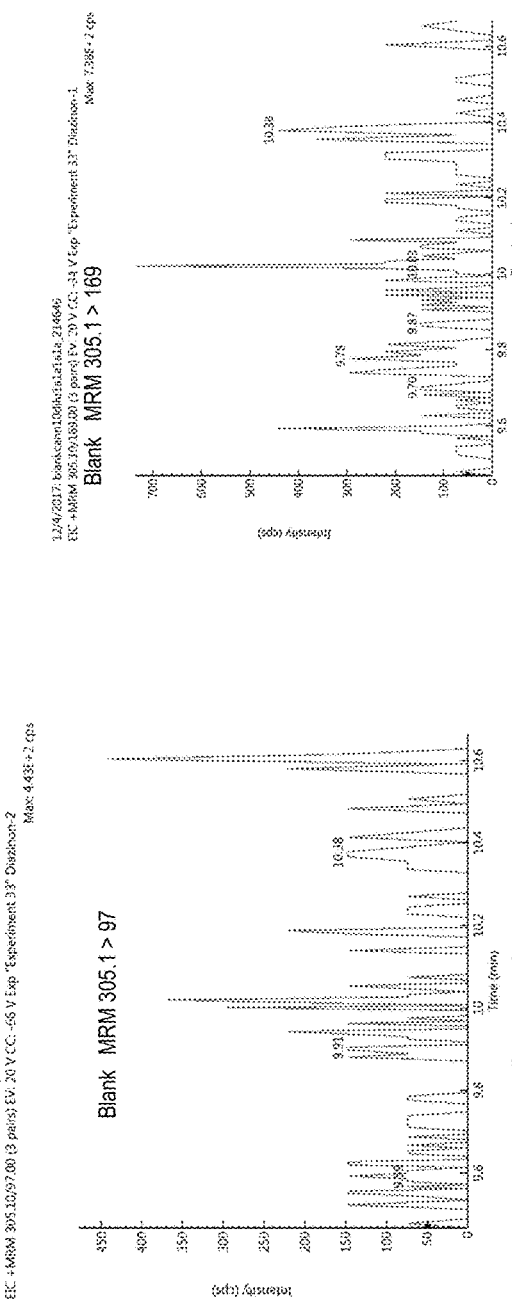
FIG. 82A
FIG. 82B
FIG. 82C
FIG. 82D

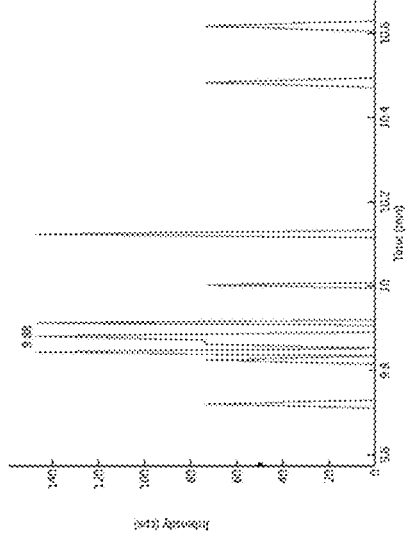
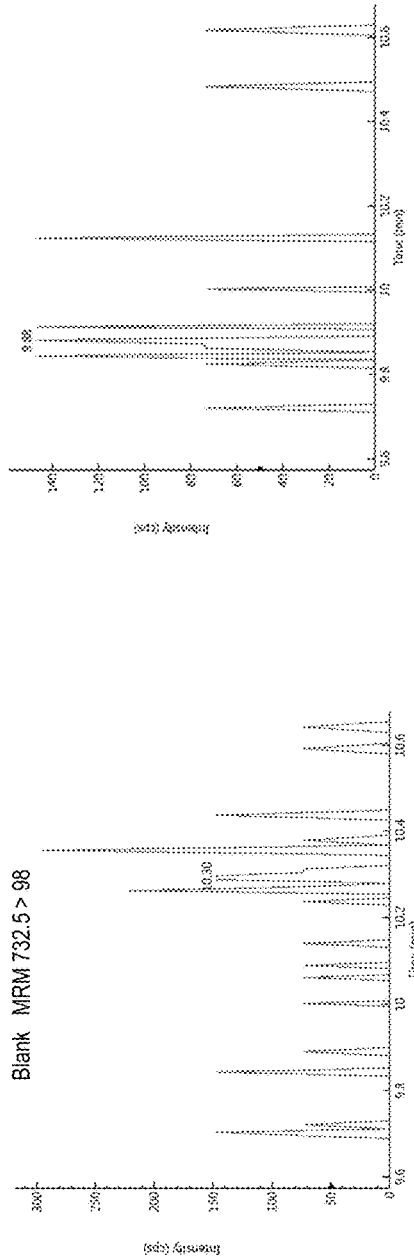
FIG. 83A
FIG. 83B
FIG. 83C
FIG. 83D

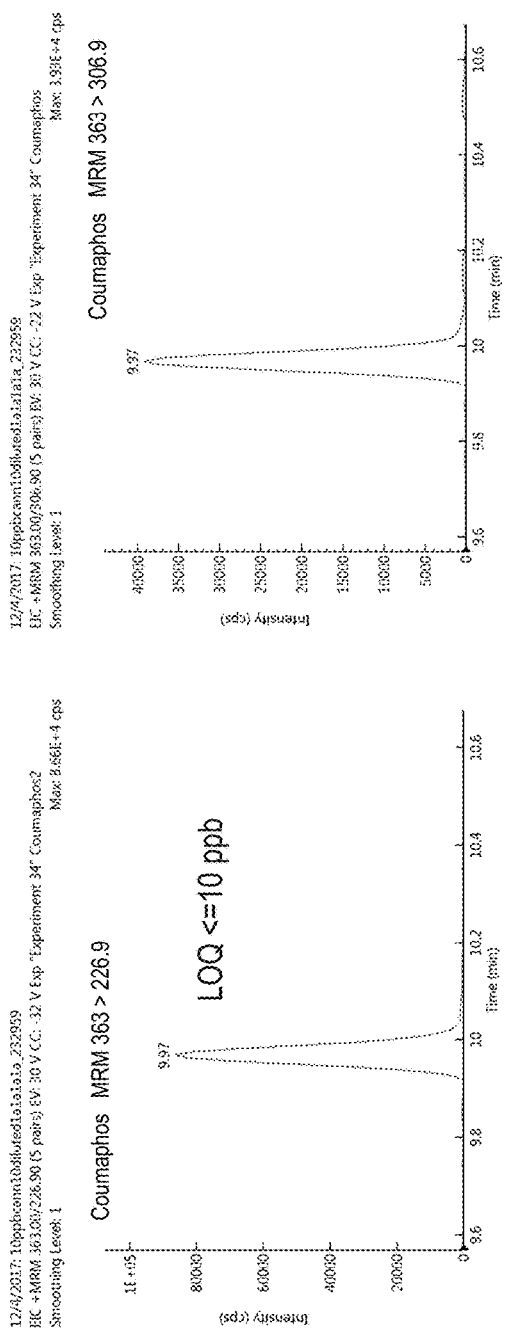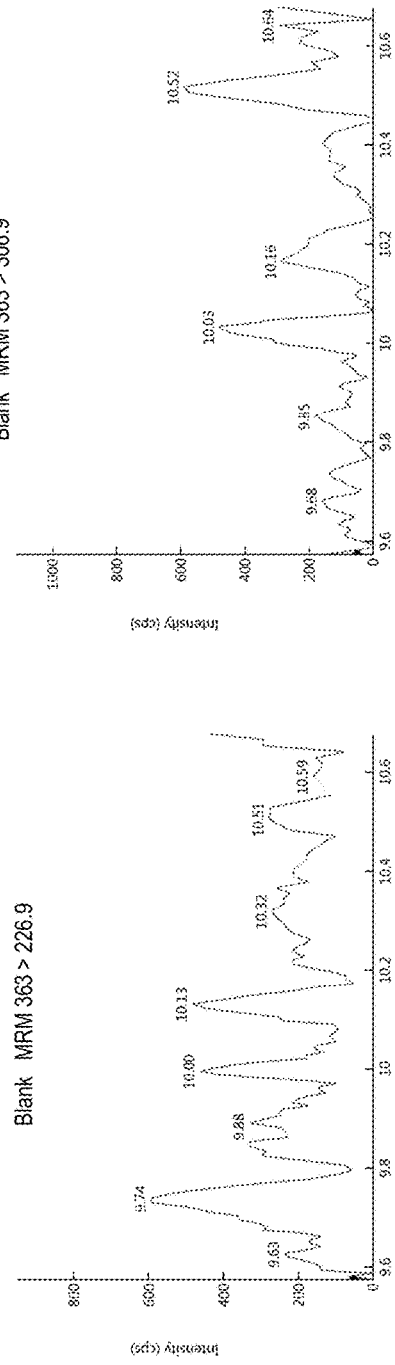

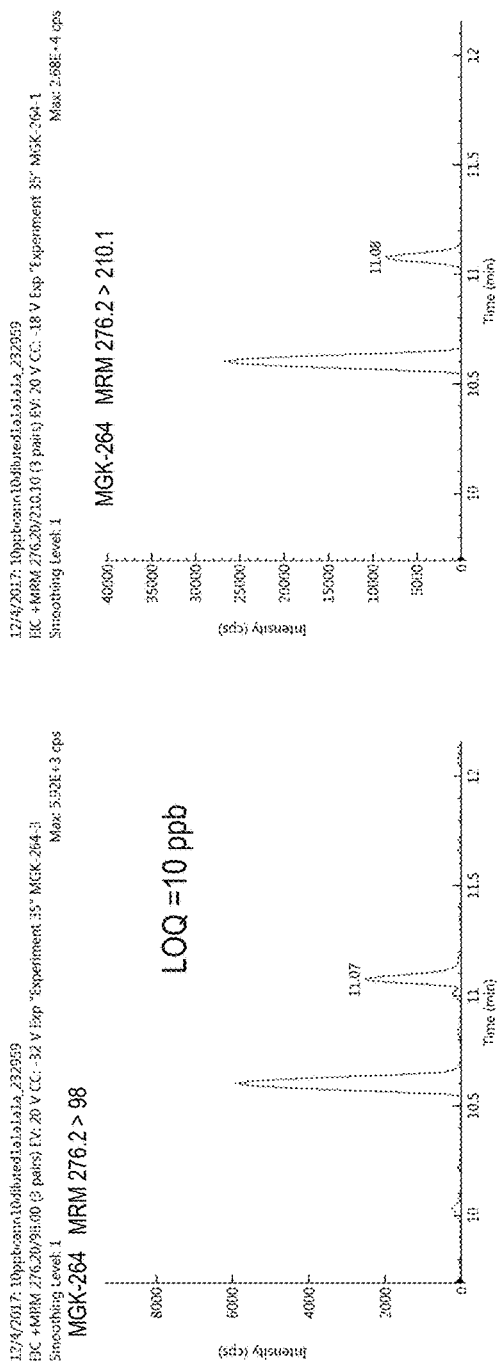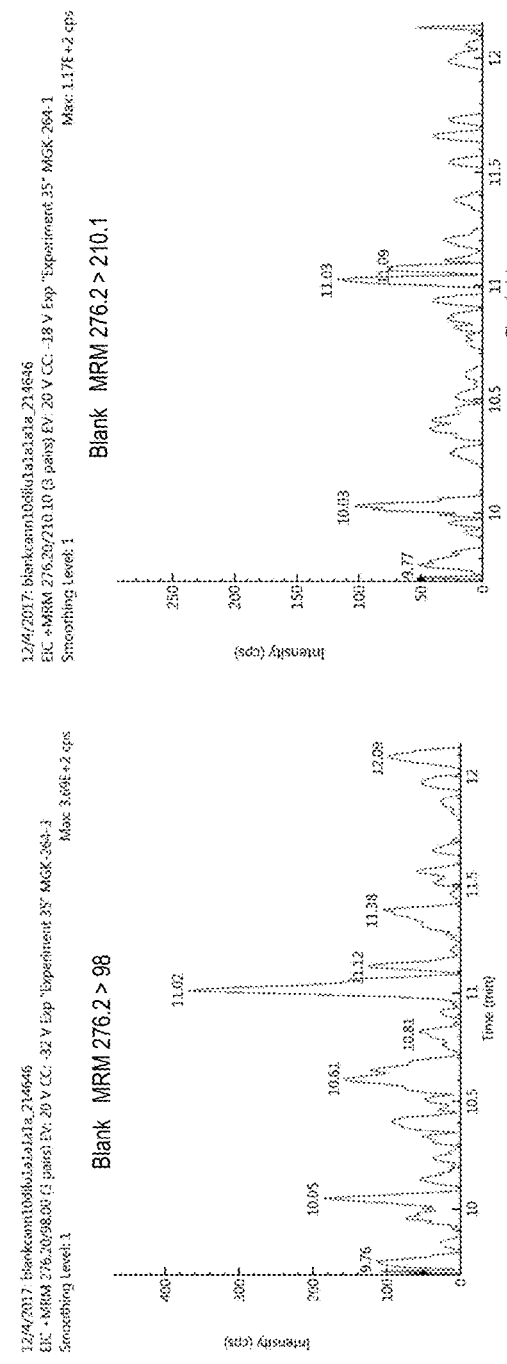

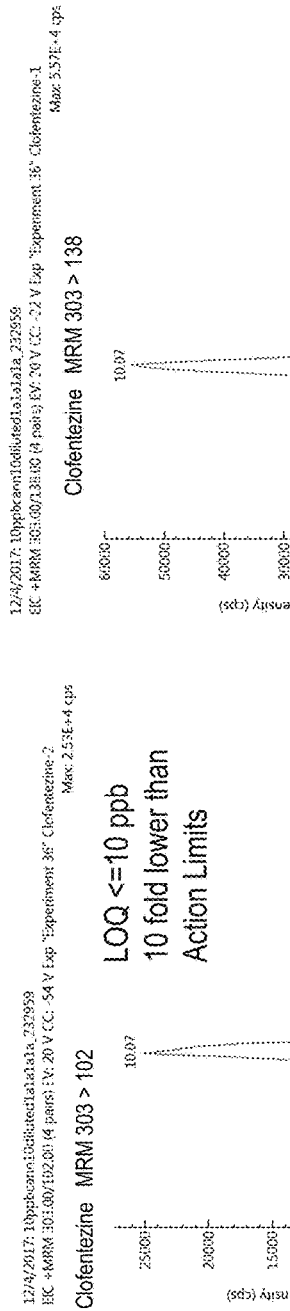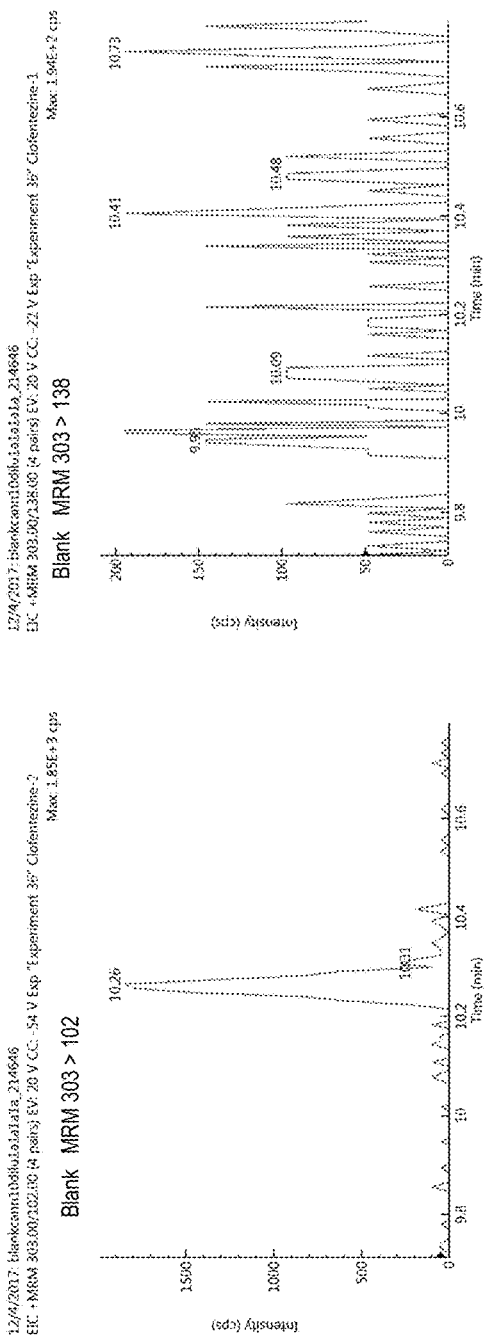
FIG. 86A
FIG. 86B
FIG. 86C
FIG. 86D

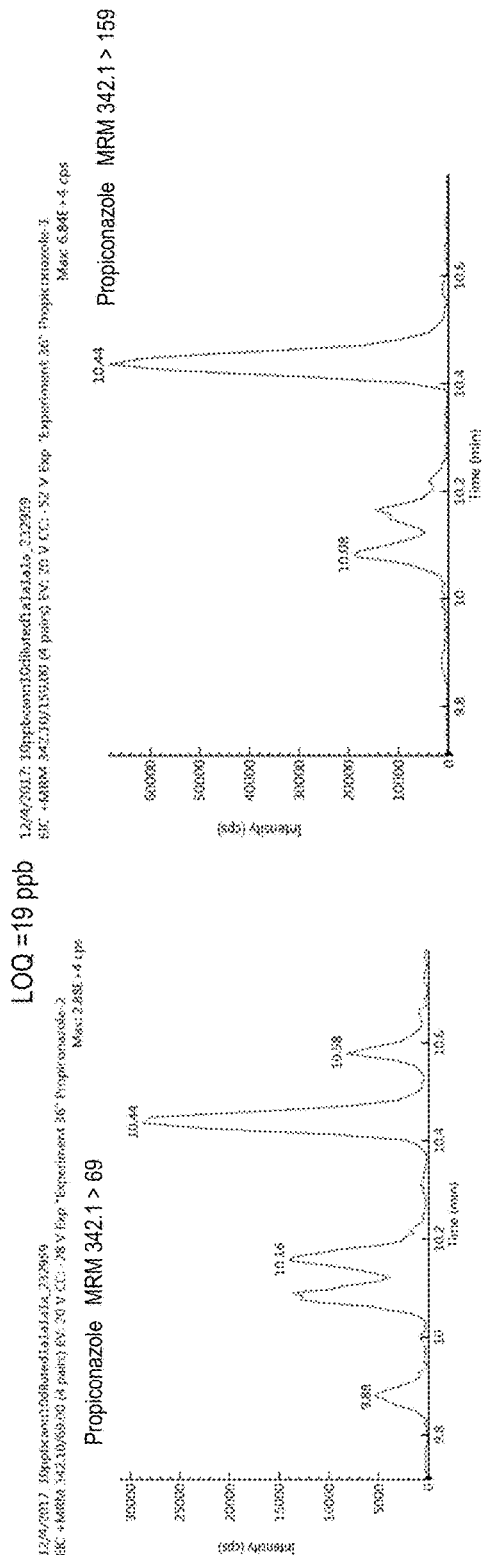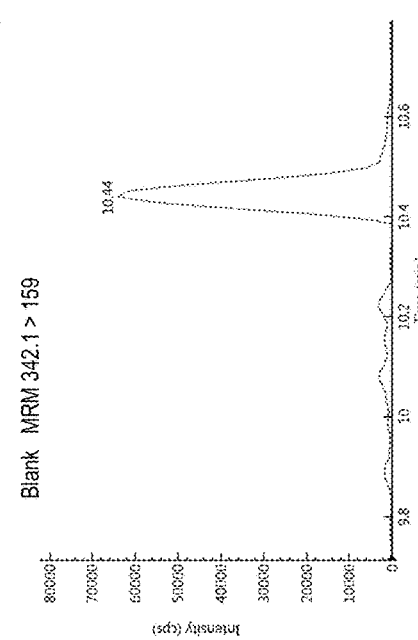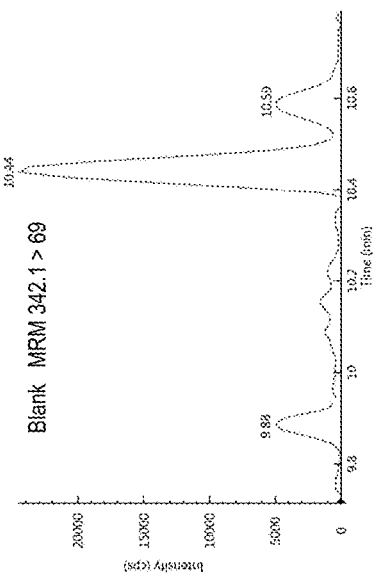
FIG. 87A
FIG. 87B
FIG. 87C
FIG. 87D

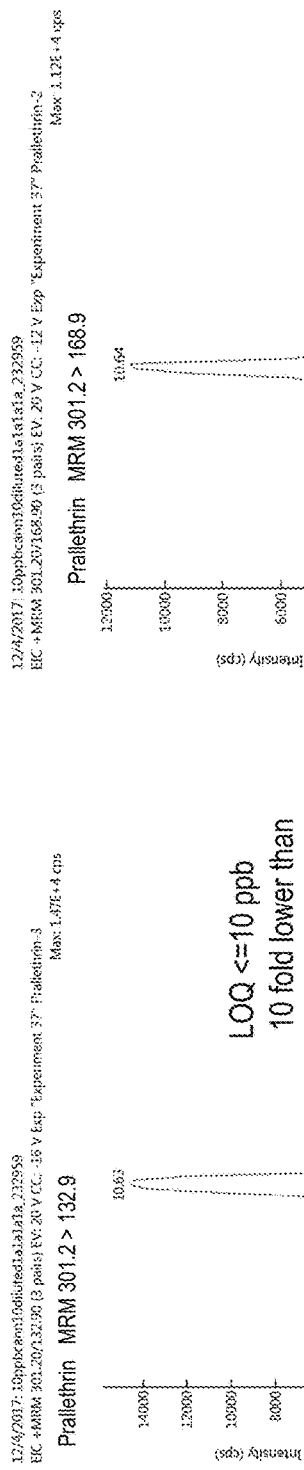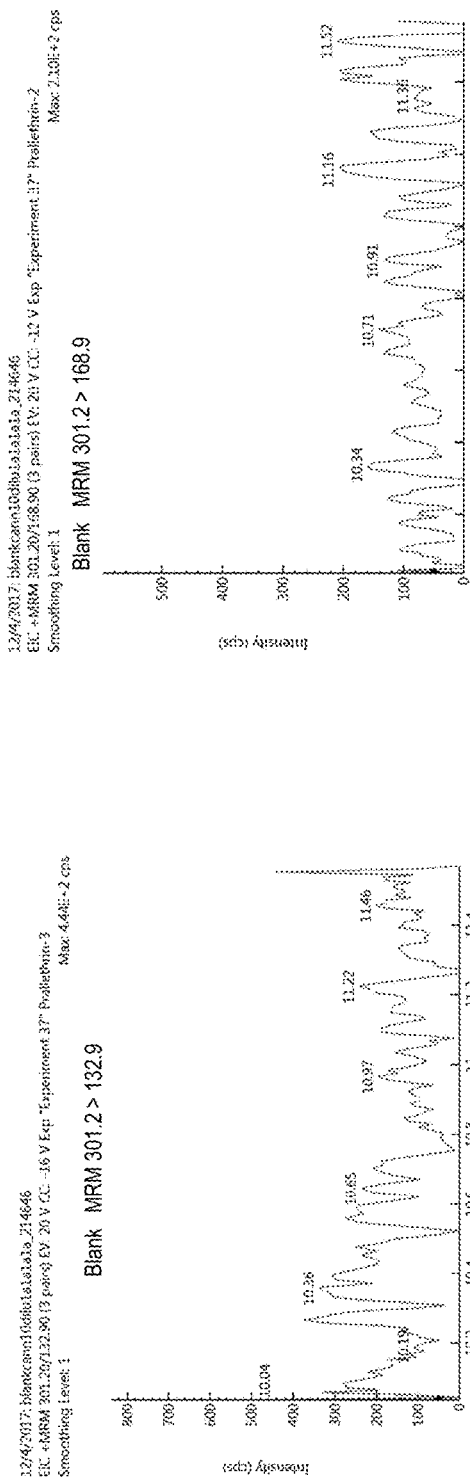
FIG. 88A  FIG. 88B  FIG. 88C  FIG. 88D

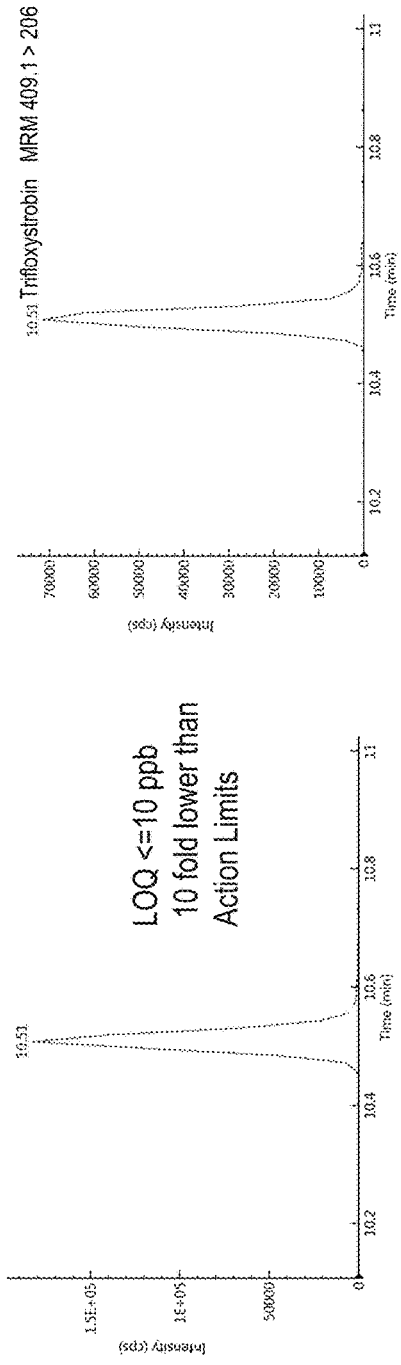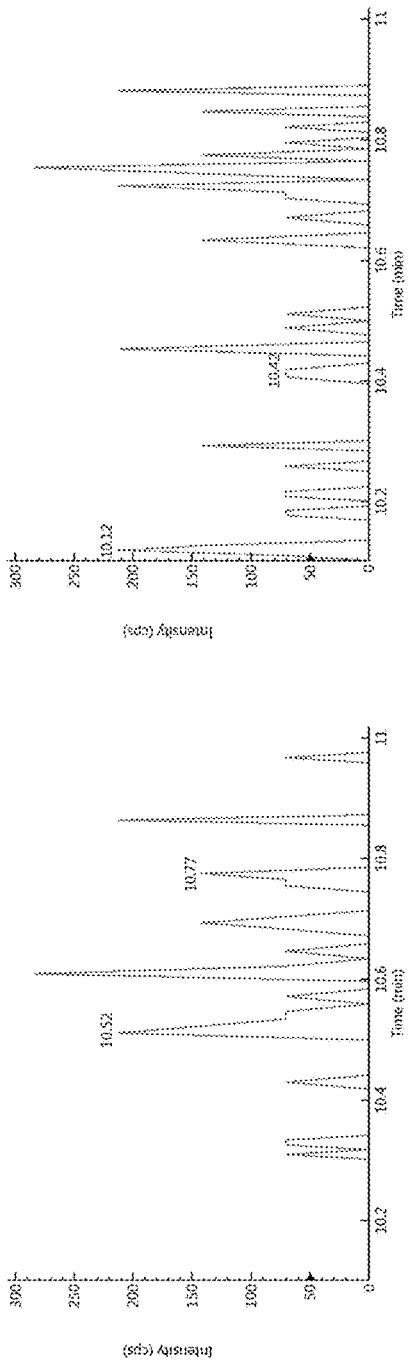

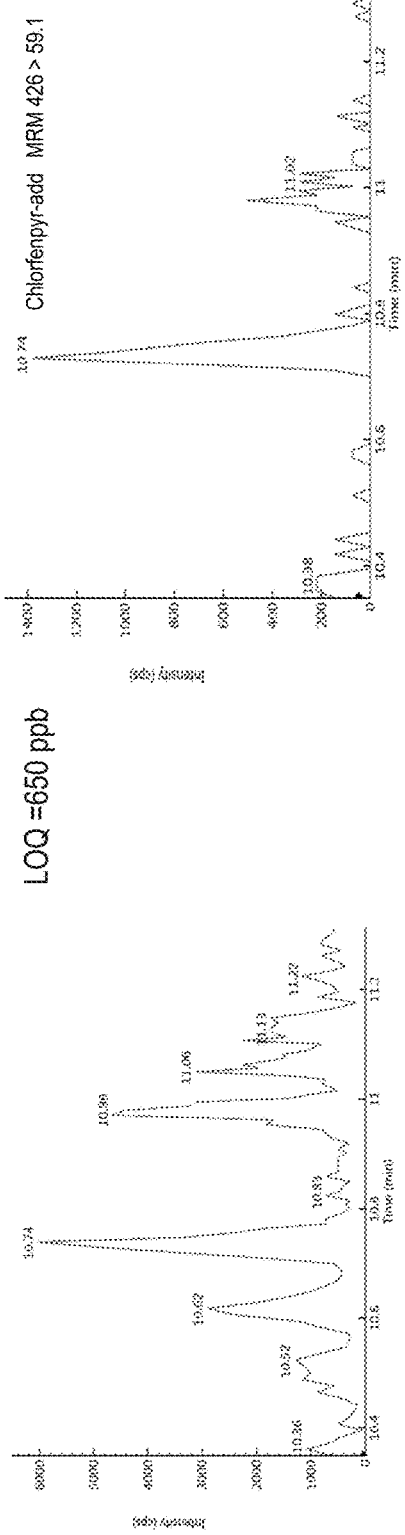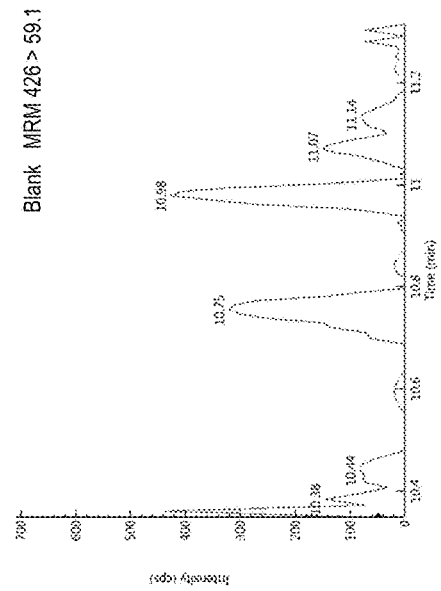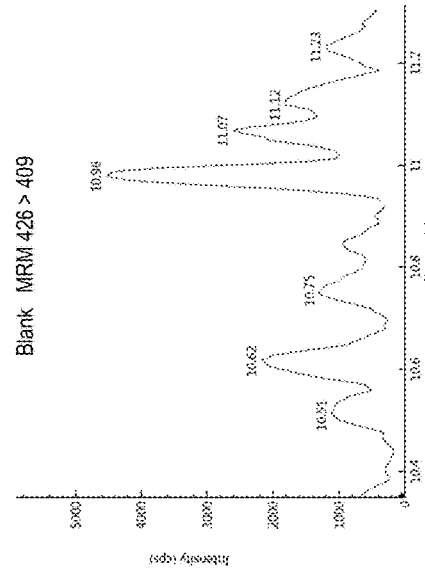
FIG. 93A
FIG. 93B
FIG. 93C
FIG. 93D

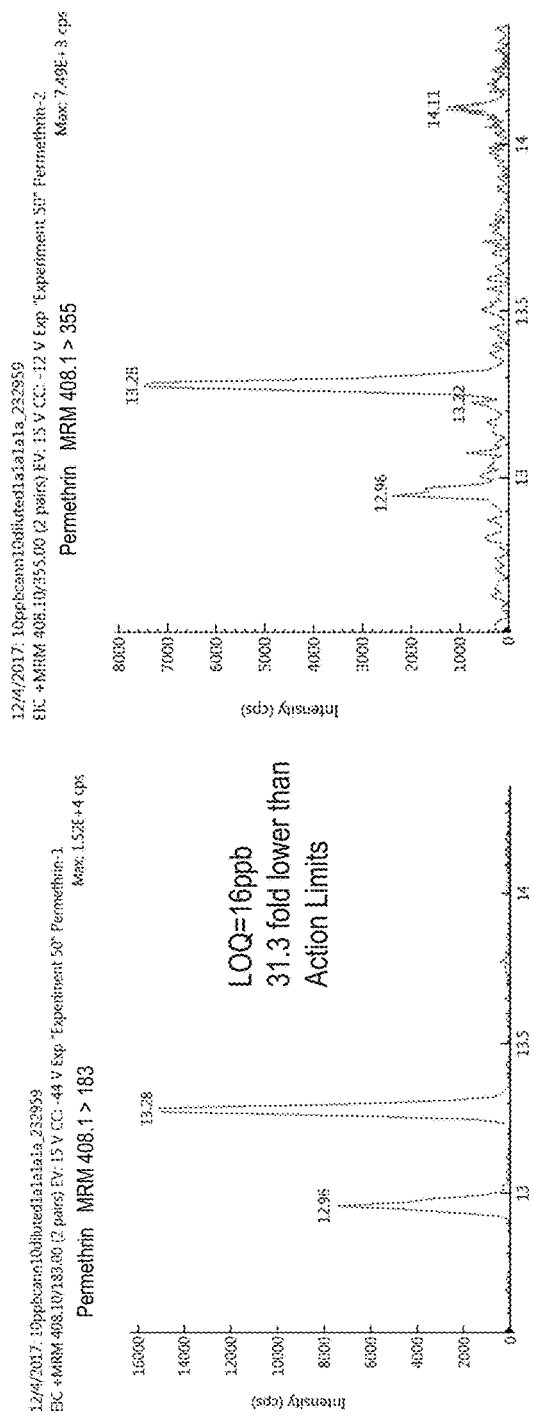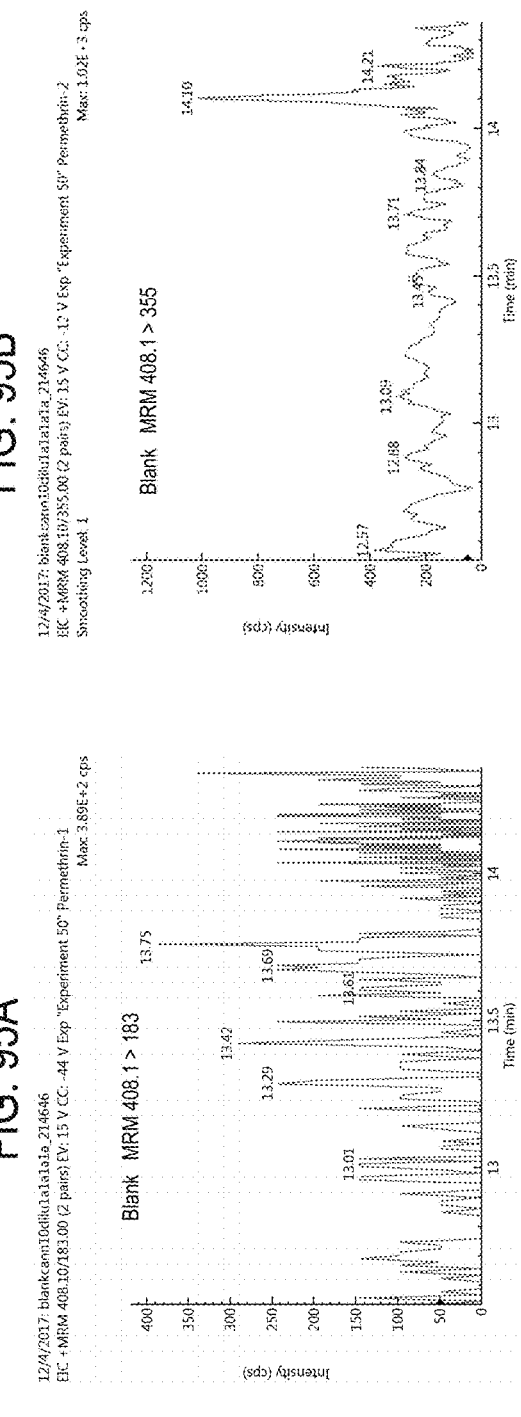

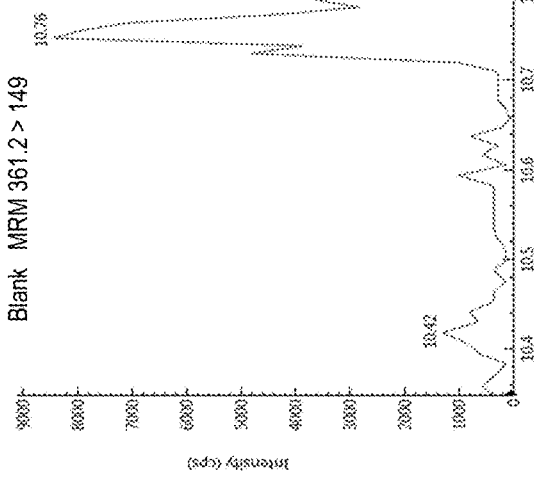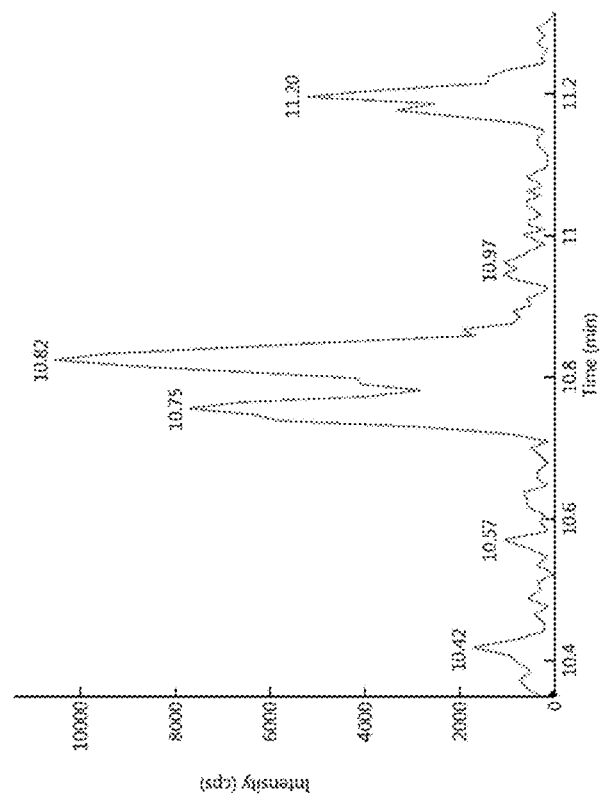
FIG. 96A
FIG. 96B

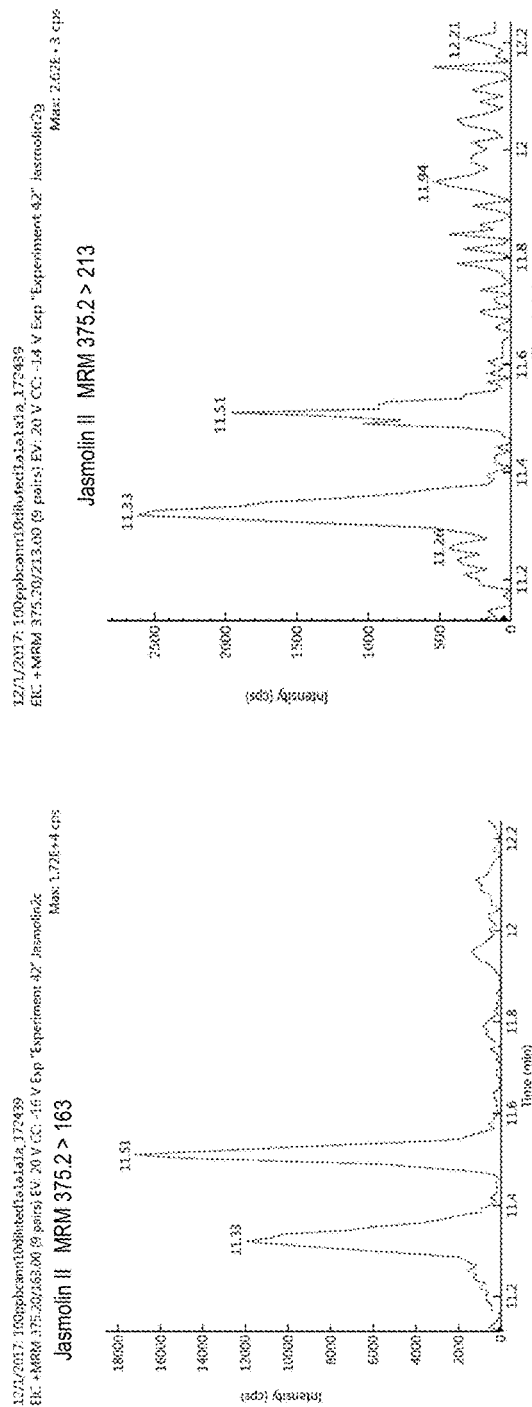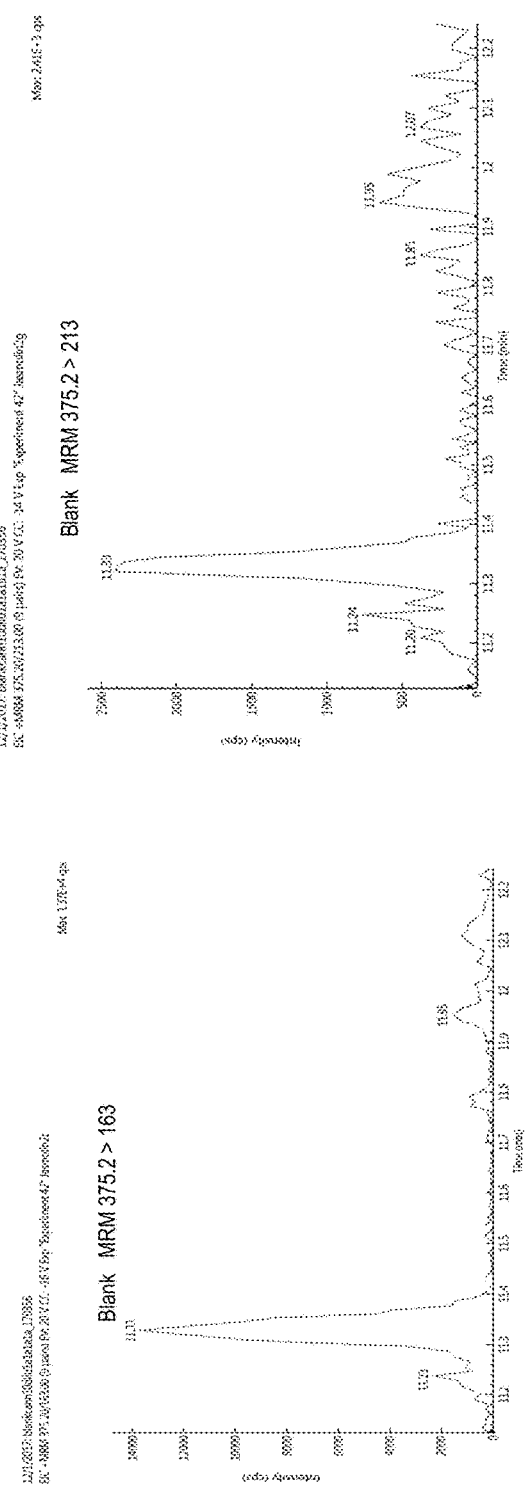

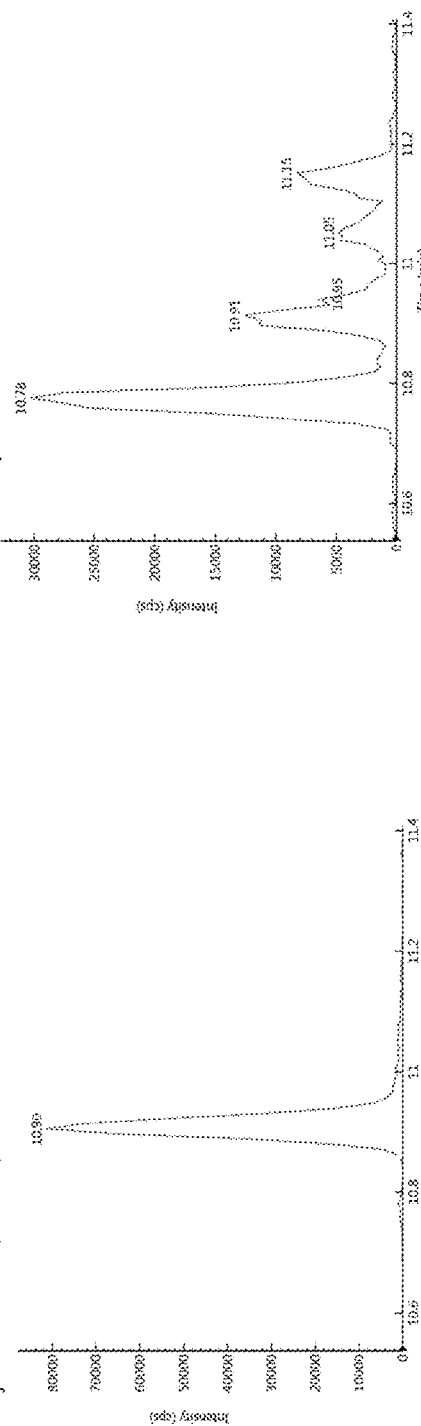
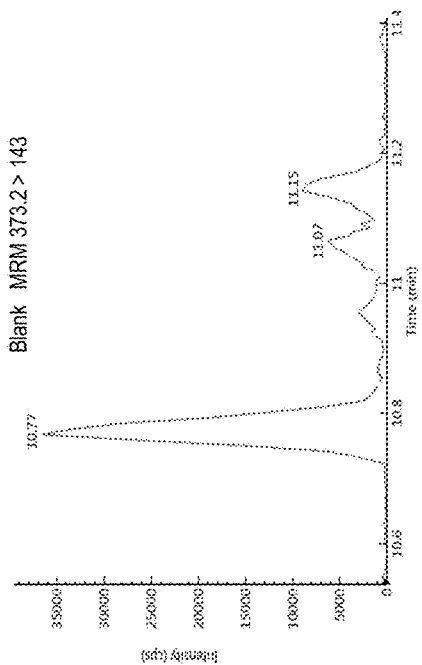
FIG. 98A  FIG. 98B  FIG. 98C  FIG. 98D

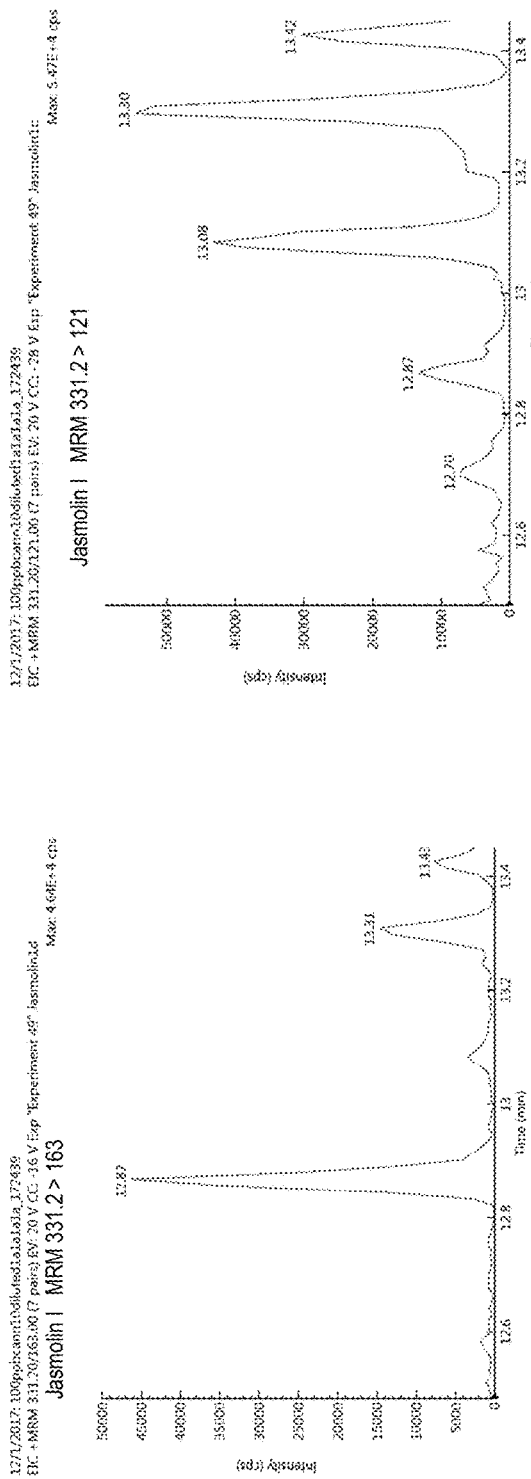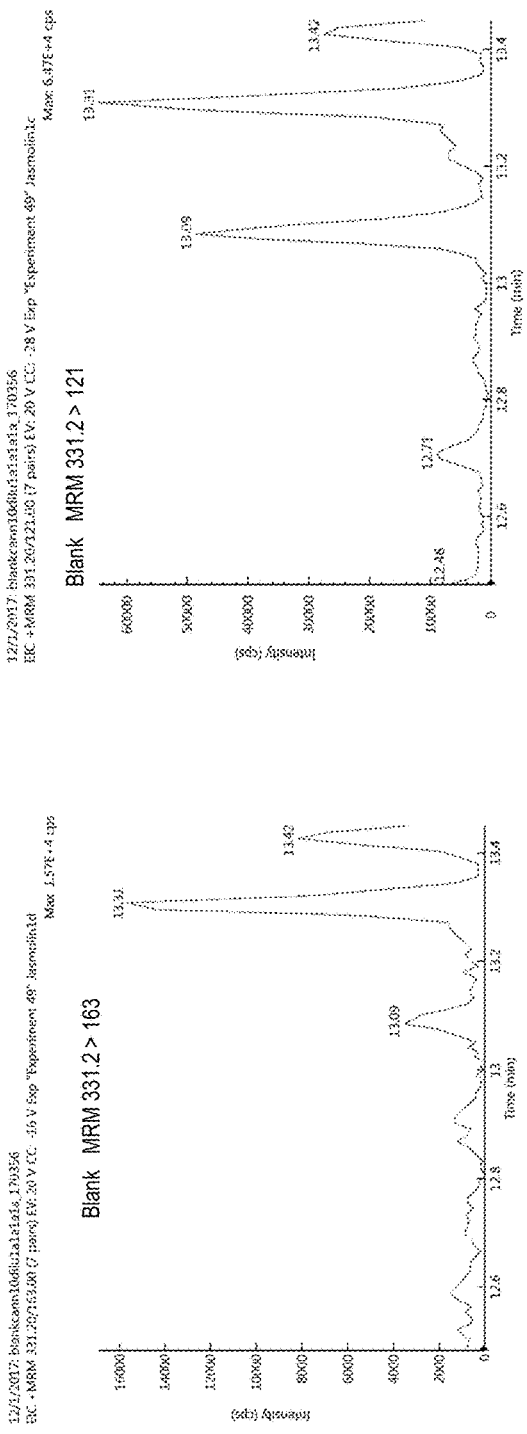
FIG. 99A  FIG. 99B  FIG. 99C  FIG. 99D

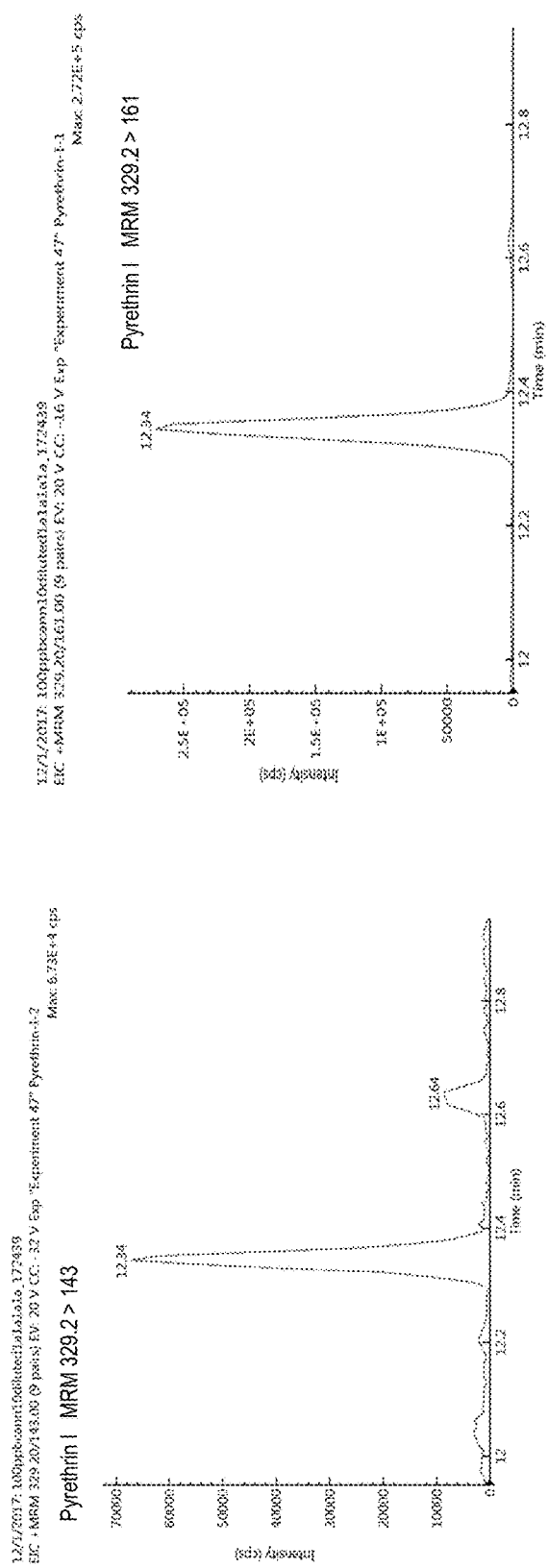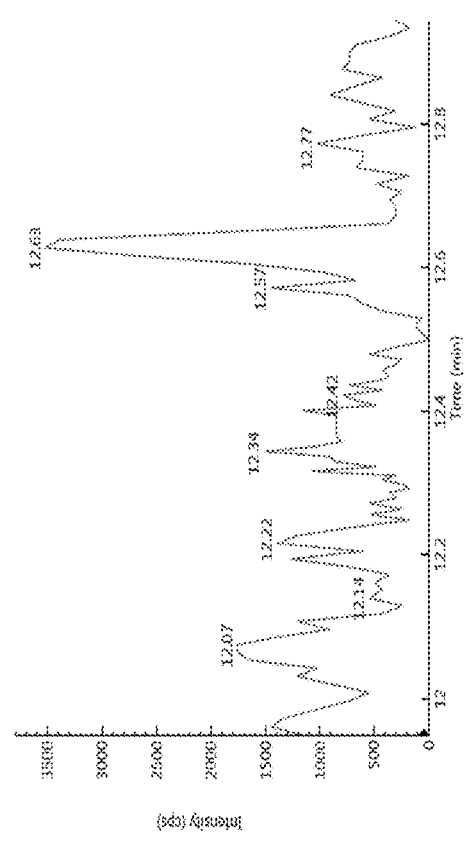
FIG. 101A
FIG. 101B
FIG. 101C

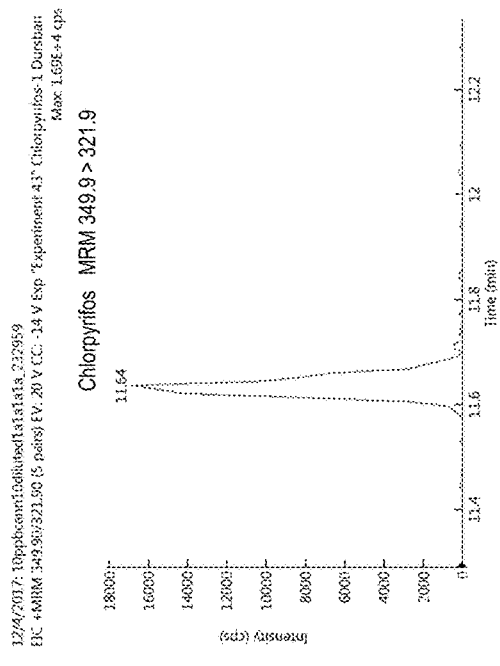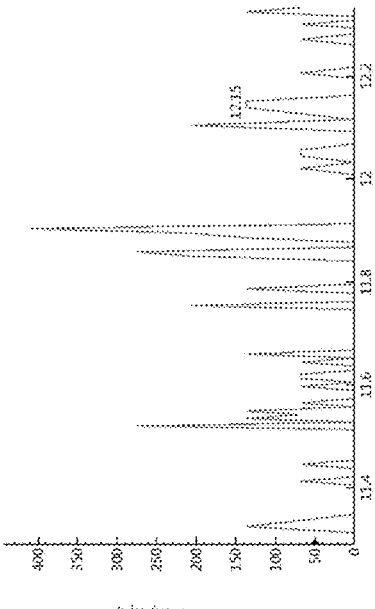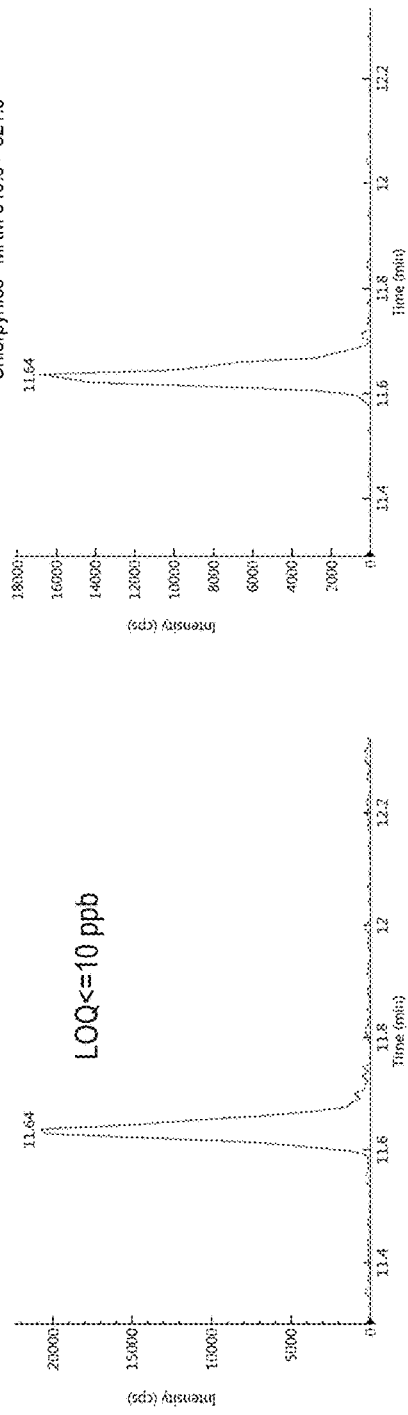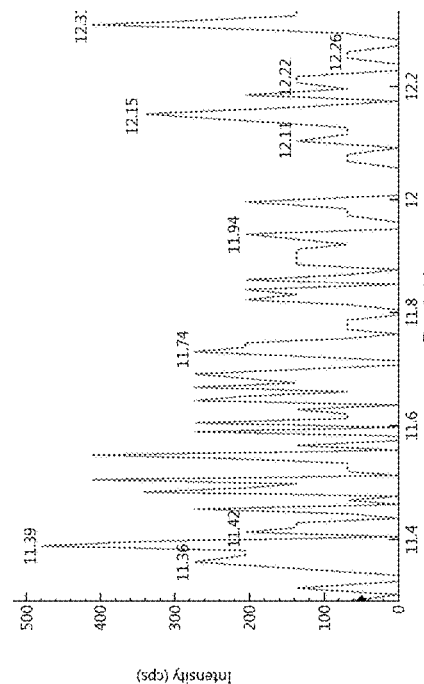
FIG. 102A
FIG. 102B
FIG. 102C
FIG. 102D

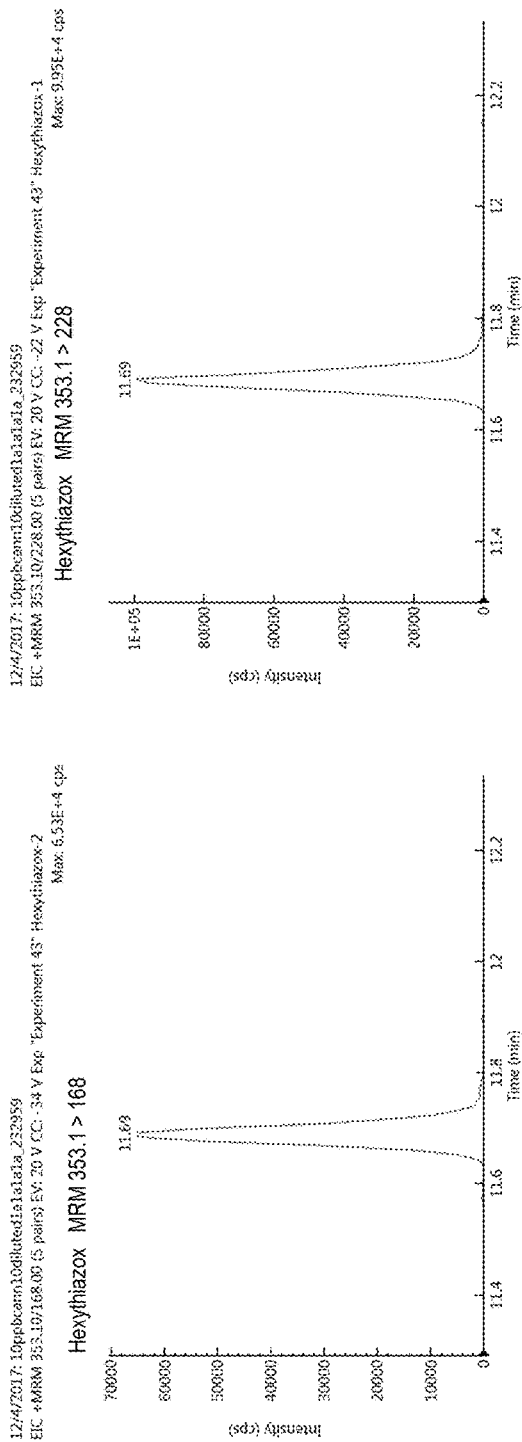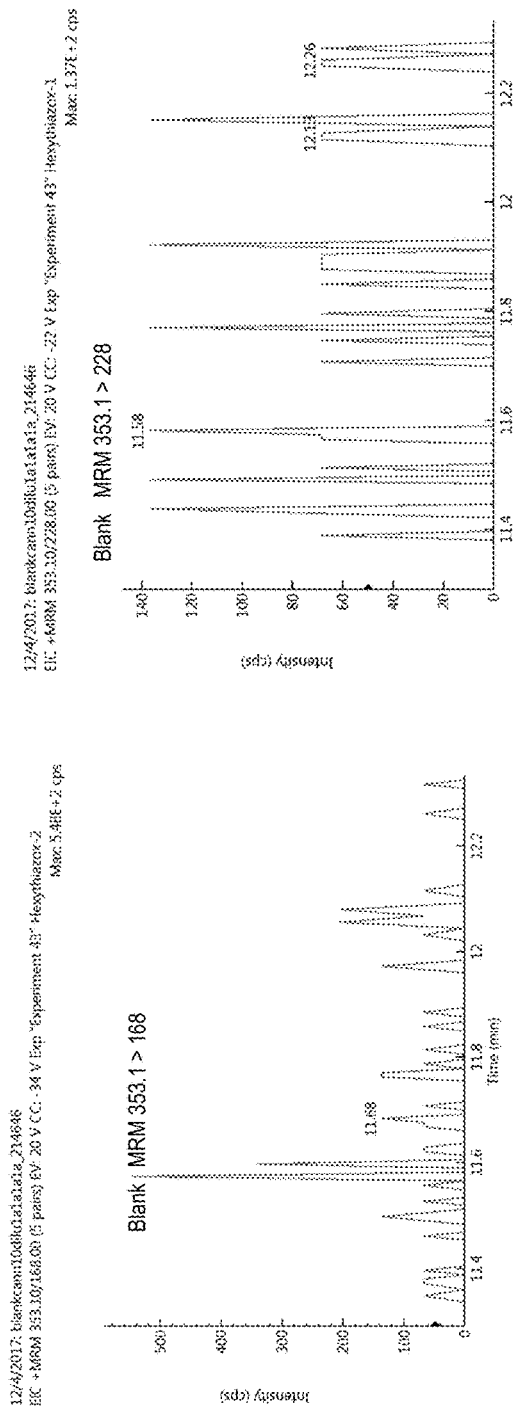
FIG. 104A
FIG. 104B
FIG. 104C
FIG. 104D

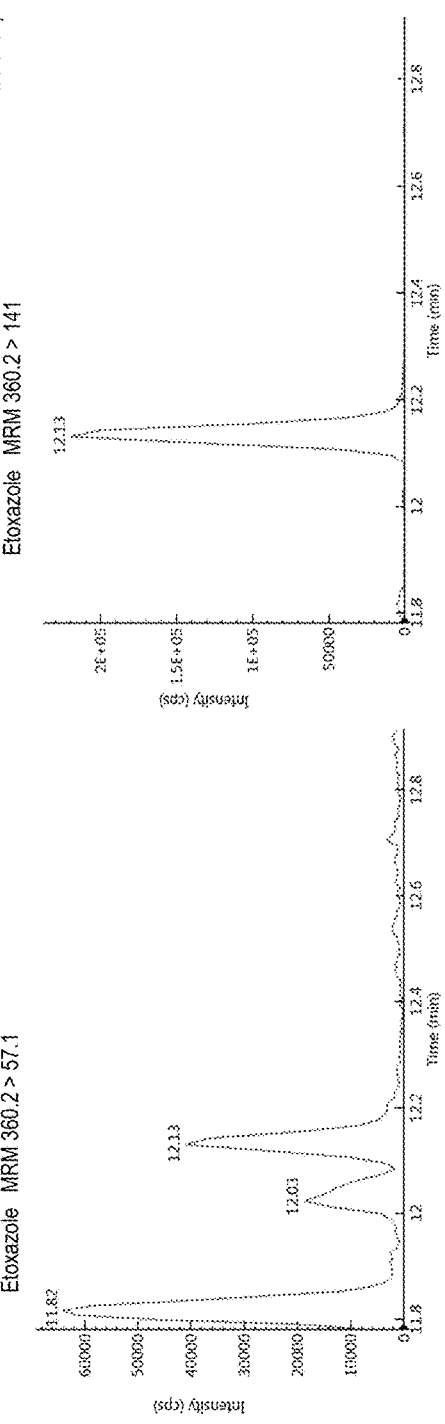
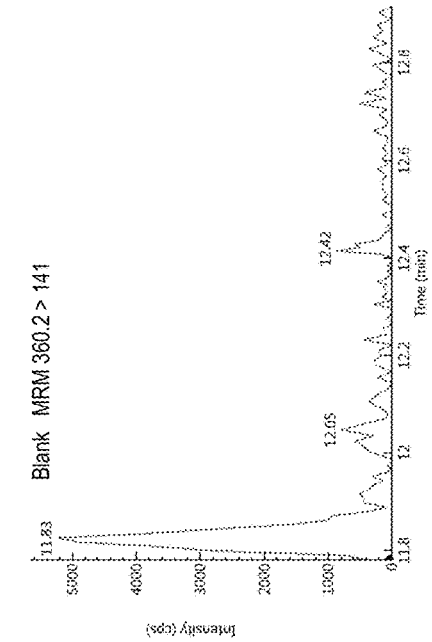
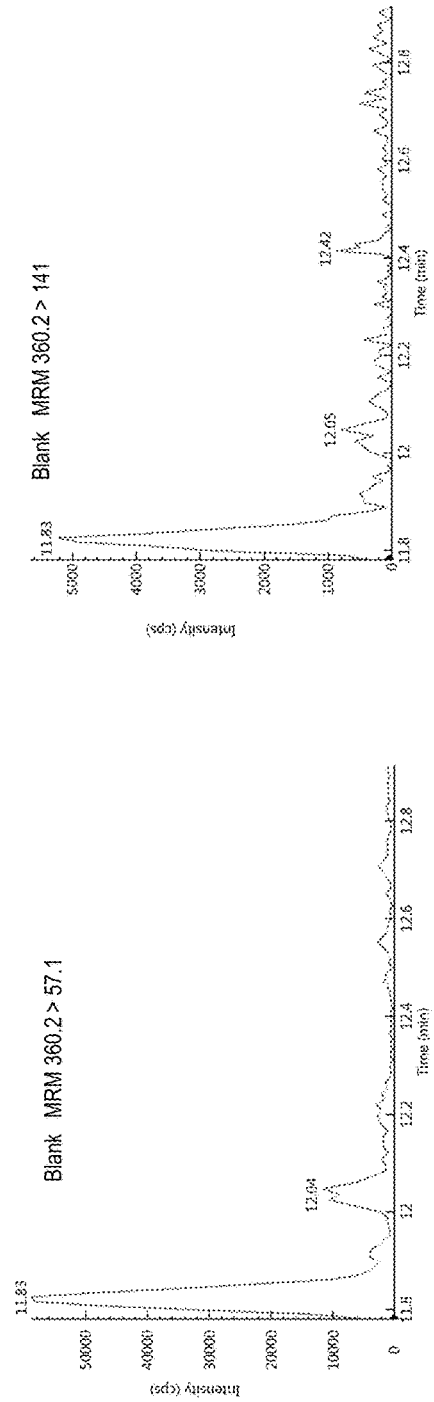
FIG. 105A
FIG. 105B
FIG. 105C
FIG. 105D

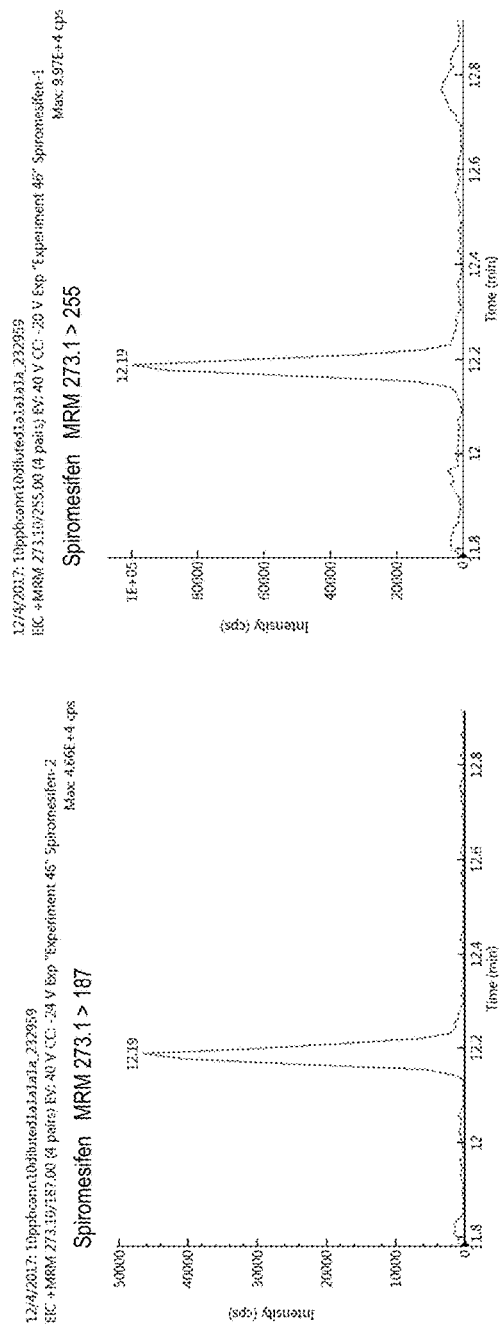
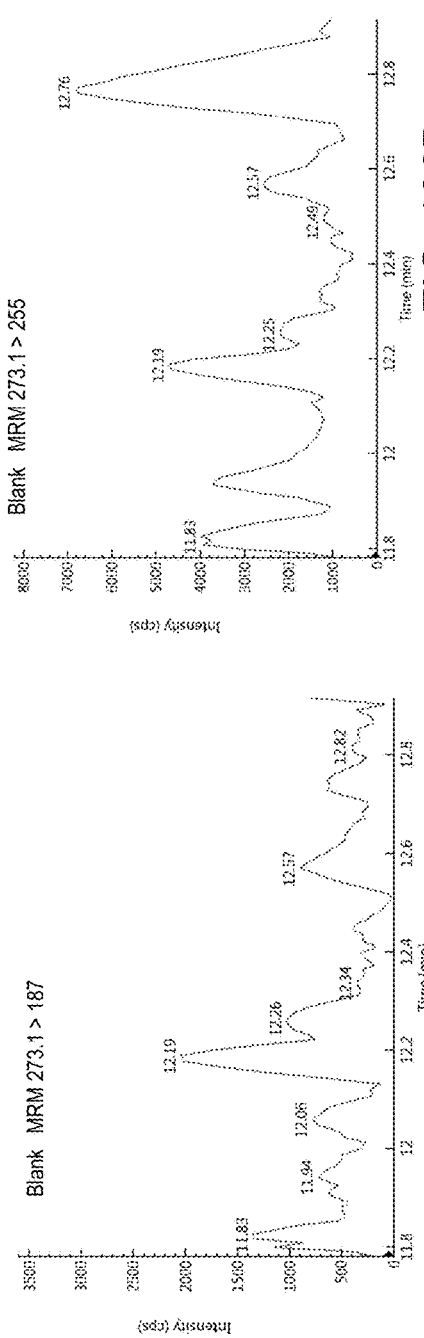
FIG. 106A
FIG. 106B
FIG. 106C
FIG. 106D

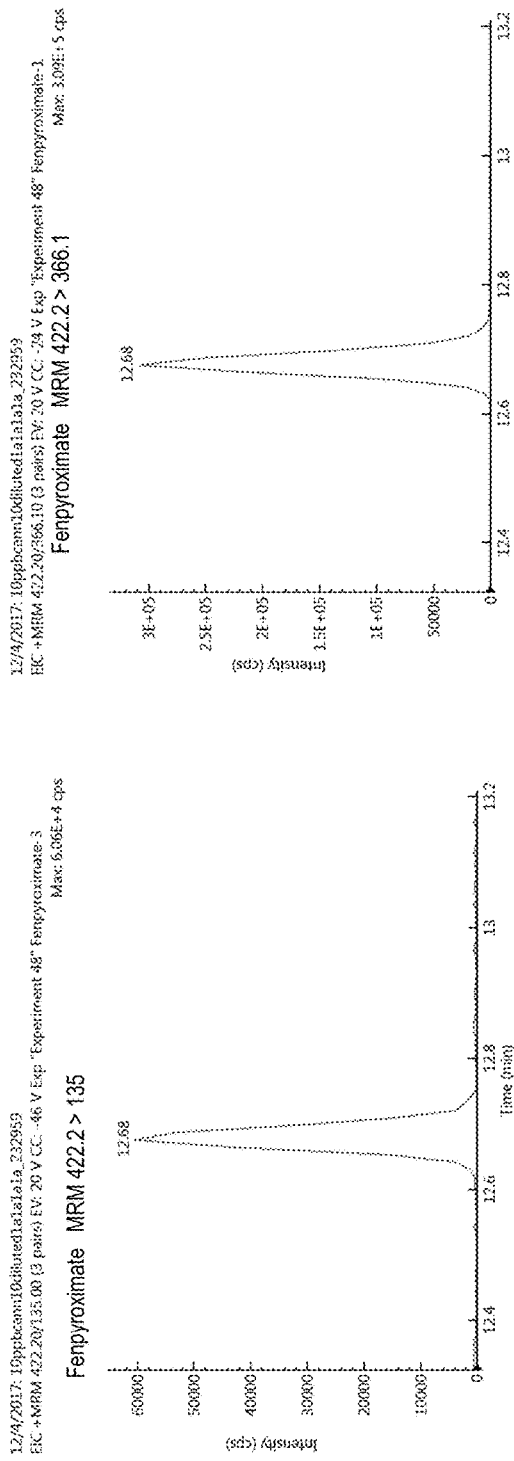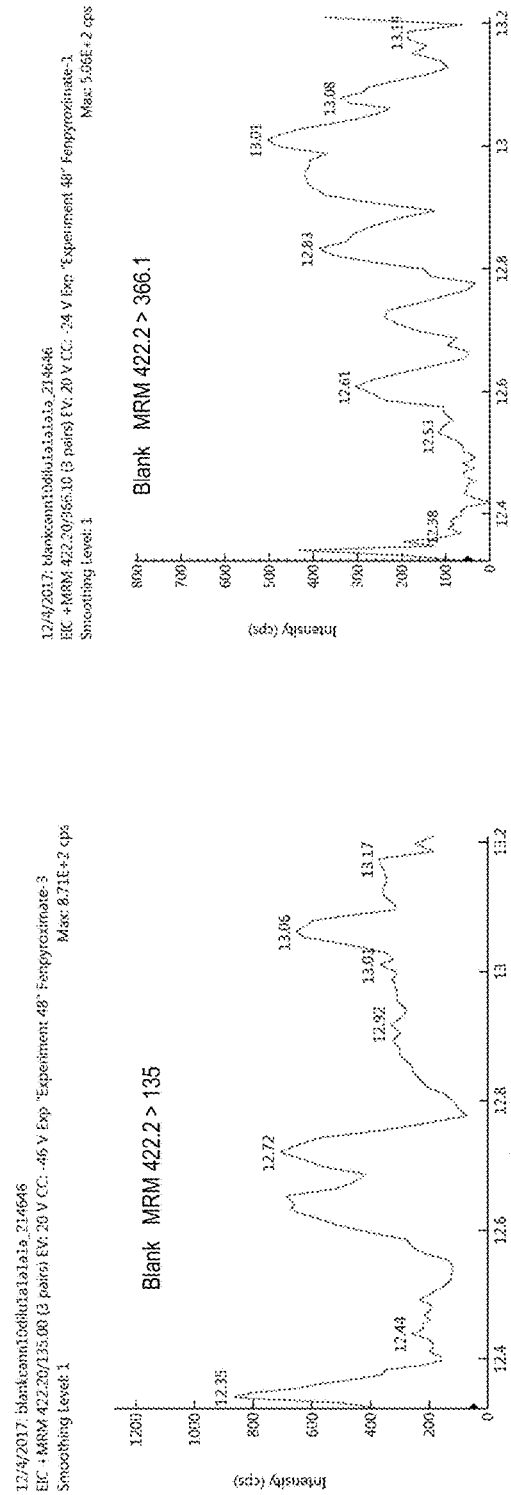
FIG. 107A
FIG. 107B
FIG. 107C
FIG. 107D

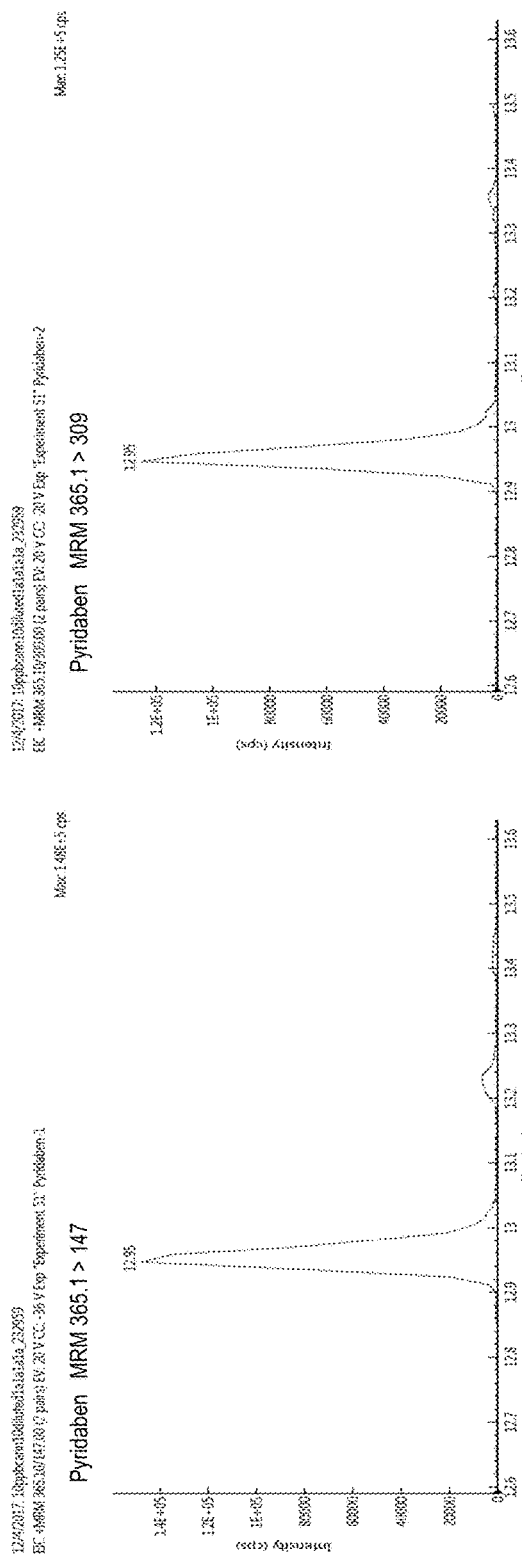
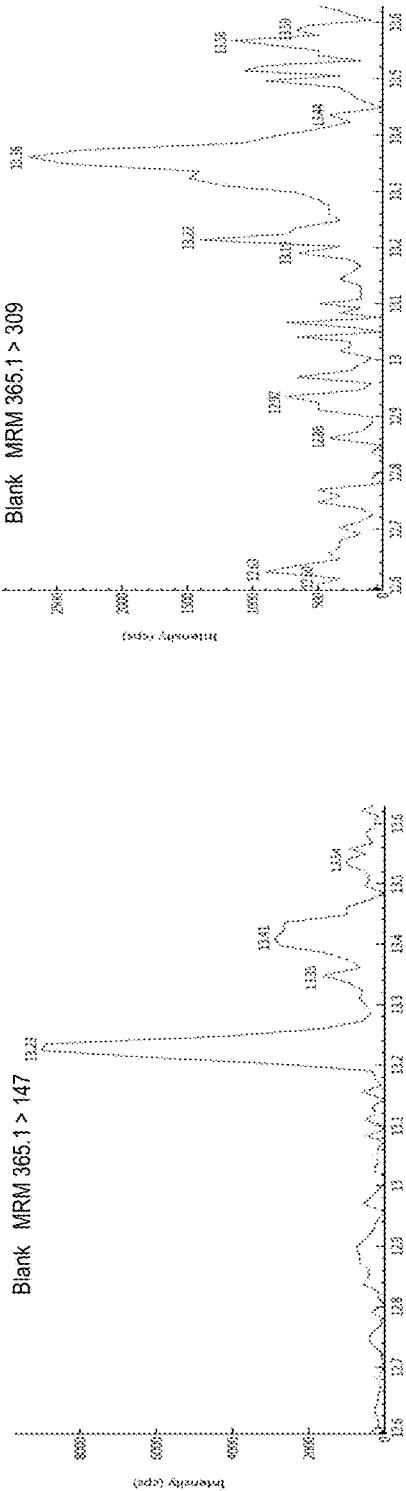
FIG. 108A
FIG. 108B
FIG. 108C
FIG. 108D

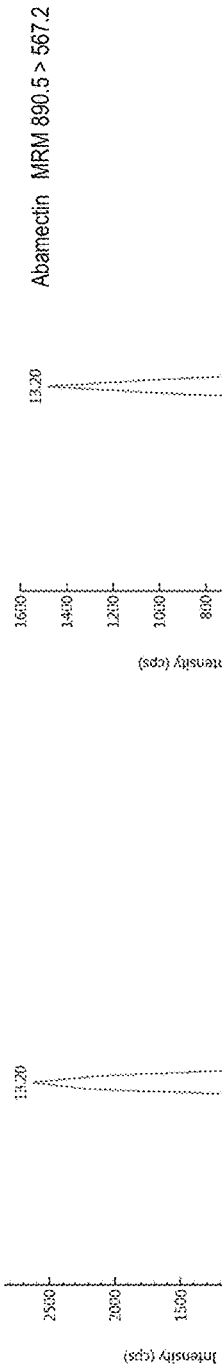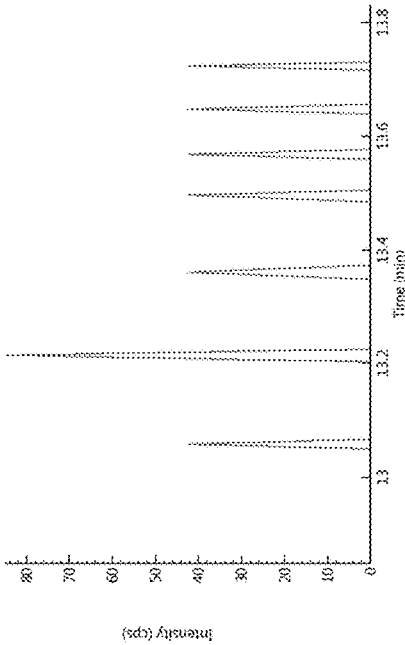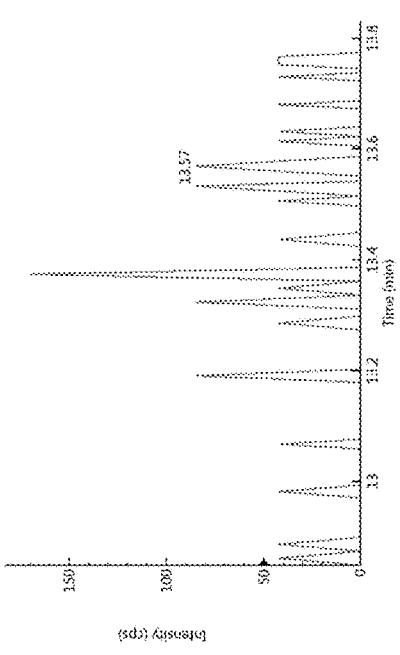
FIG. 109A
FIG. 109B
FIG. 109C
FIG. 109D

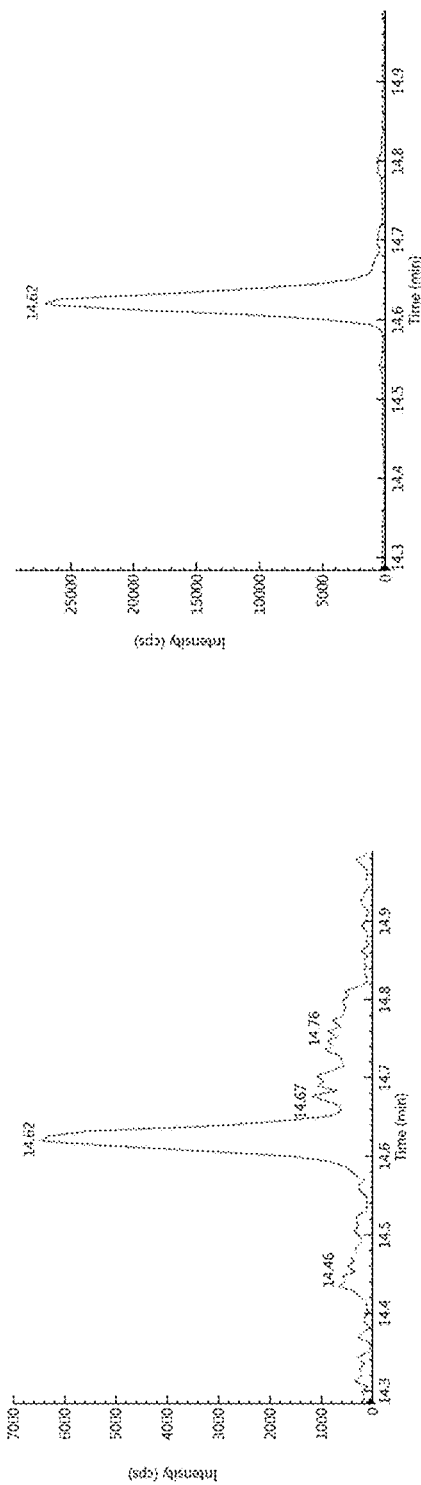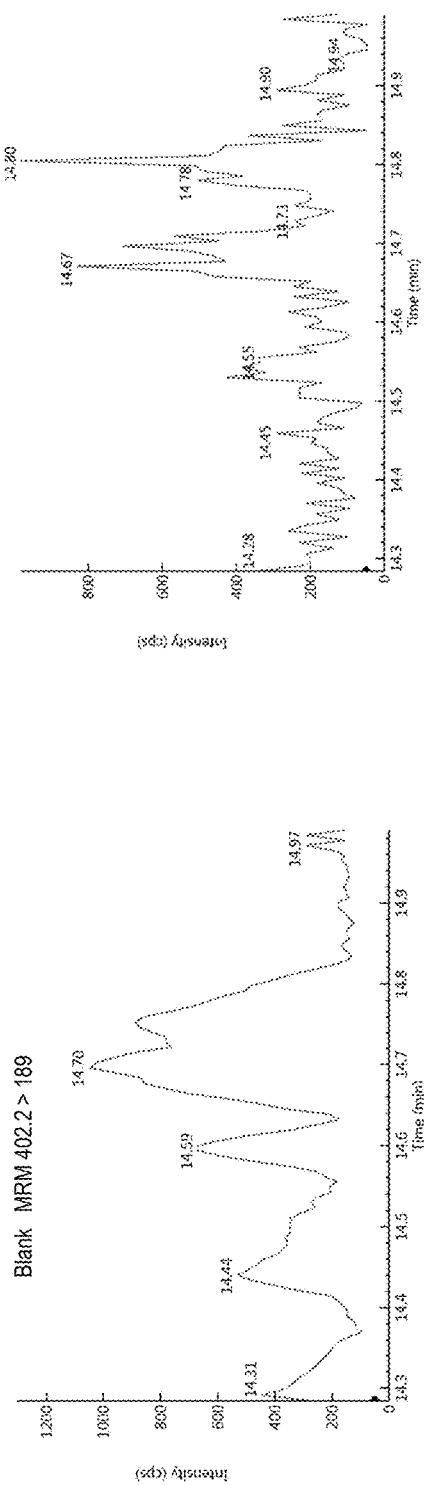
FIG. 111A
FIG. 111B
FIG. 111C
FIG. 111D

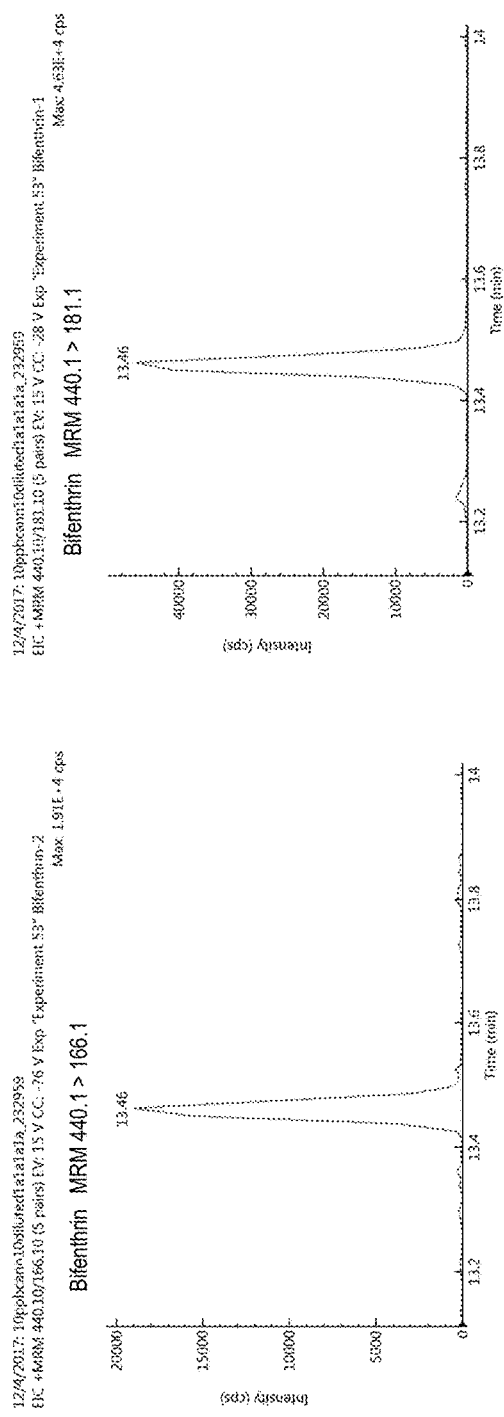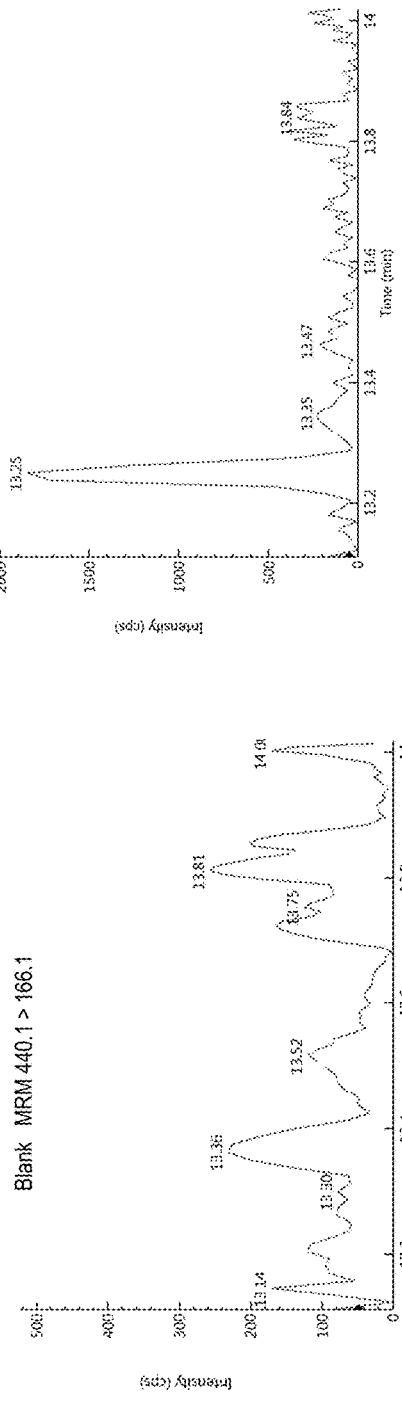

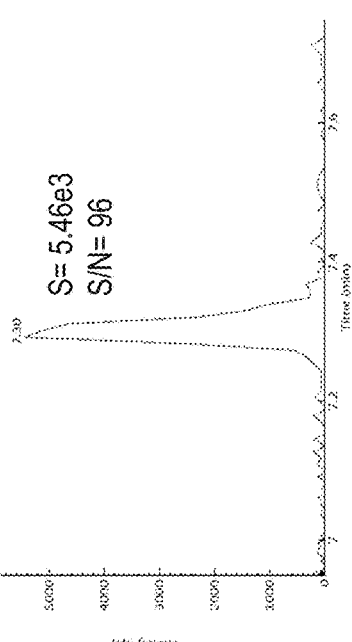
FIG. 113A
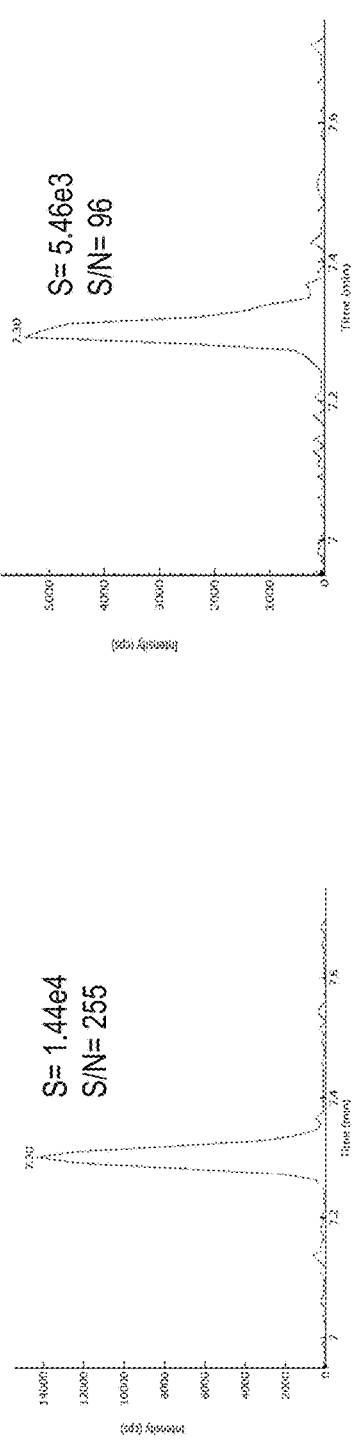
FIG. 113C
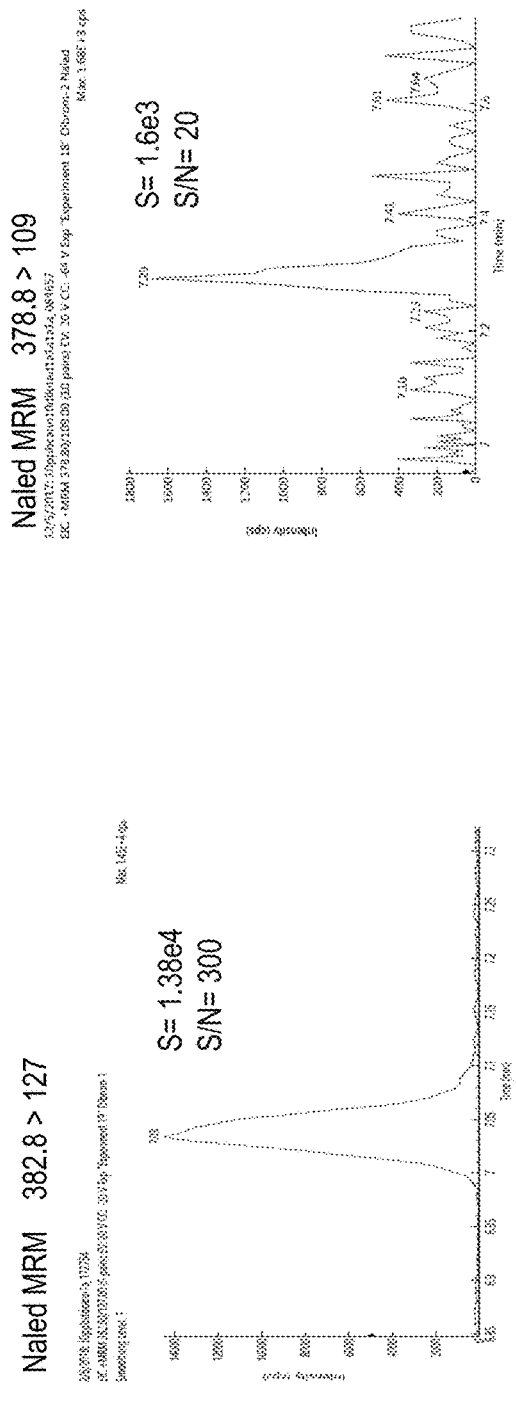
FIG. 113B
FIG. 113D

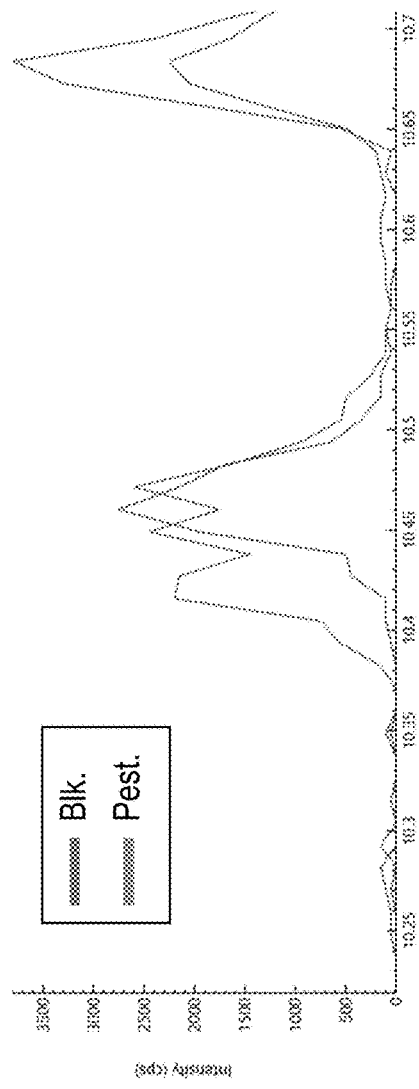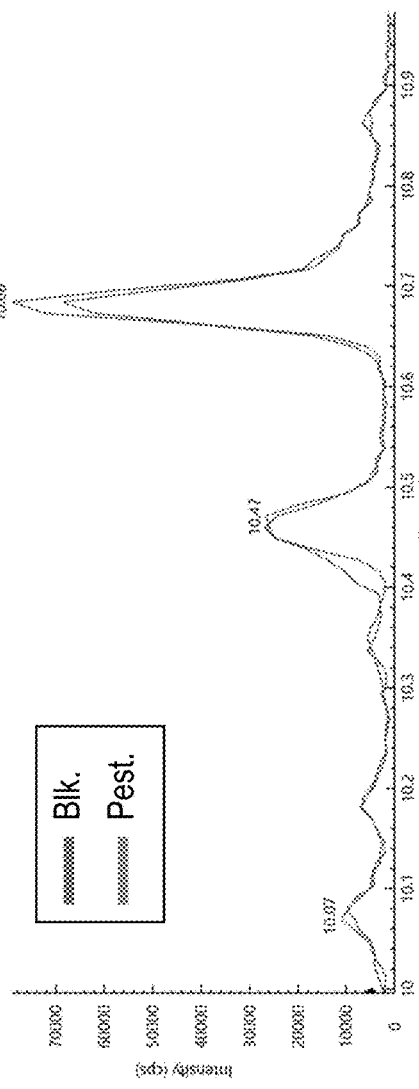
FIG. 115C
FIG. 115D

S/N=50
RSD= 4.37 % (n=8)

S/N=36
RSD= 7.5 % (n=8)

LOD= 3*RSD*Amount Injected/100

LOQ =50 ppb in Cannabis
LOD = 13.5 ppb in Cannabis

SYSTEMS AND METHODS FOR PESTICIDE DETECTION USING MASS SPECTROSCOPY

This application claims priority to and incorporates by reference in their entireties Ser. No. 62/620,961 filed on Jan. 23, 2018 and Ser. No. 62/637,350 filed on Mar. 1, 2018.

Each reference cited in this disclosure is incorporated herein in its entirety.

TECHNICAL FIELD

This disclosure relates generally to systems and methods for detecting and/or quantifying pesticides using mass spectrometry.

BACKGROUND

Mass spectrometry (MS) is an analytical technique for determining the elemental composition of unknown sample substances and has both quantitative and qualitative applications. For example, MS is useful for identifying unknown compounds, determining the isotopic composition of elements in a molecule, and determining the structure of a particular compound by observing its fragmentation, as well as for quantifying the amount of a particular compound in the sample. Mass spectrometers typically operate by ionizing a test sample to form an ion stream of positively charged particles. The ion stream is then subjected to mass differentiation (in time or space) to separate different particle populations in the ion stream according to their mass-to-charge (m/z) ratios. A downstream mass analyzer can detect the intensities of the mass-differentiated ion populations in order to compute analytical data of interest, e.g., the relative concentrations of the different ion populations, mass-to-charge ratios of product or fragment ions, and other potentially useful analytical data.

Ions of interest ("analyte ions") can coexist in the ion stream with other unwanted ion populations ("interferer ions") that have substantially the same nominal m/z ratio as the analyte ions. In some cases, the m/z ratio of an interferer ion will be close enough to the m/z ratio of an analyte ion that it falls within the resolution limits of the mass analyzer, and the analyte and interferer ion cannot be distinguished. Improving the resolution of the mass analyzer is one approach to dealing with this type of interference (commonly referred to as "isobaric" or "spectral interference"). Higher resolution mass analyzers, however, tend to have slower extraction rates and higher loss of ion signals and require more sensitive detectors. Limits on the achievable resolution may also be encountered.

In addition, pesticide analysis in certain samples, such as *cannabis* samples, is hampered by the presence of matrix interference. *Cannabis* contains compounds from different classes such as cannabinoids, terpenes, hydrocarbons, sugars, fatty acids, flavonoids and others, whose presence leads to variable signal ion suppression and matrix interference, particularly because of the large disparity between levels of pesticides and the high concentration levels of naturally occurring cannabinoids and terpenes.

There exists a need for improved systems and methods for detecting and quantifying pesticides.

BRIEF DESCRIPTION OF THE DRAWINGS

FIG. 6A) and source temperature (FIG. 6B).

FIGS. 7A and 7C, *cannabis* samples comprising 100 ppb (parts per billion) acequinocyl. FIGS. 7B and 7D, blank *cannabis* samples. ND, not detected. S/N, signal-to-noise ratio.

FIGS. 9A and 9B, *cannabis* samples comprising 100 ppb acequinocyl. FIGS. 9C and 9D, blank *cannabis* samples.

FIGS. 10B and 10C, *cannabis* samples comprising 100 ppb abamectin. FIGS. 10D and 10E, blank *cannabis* samples.

FIG. 12A, *cannabis* sample comprising 100 ppb methomyl. FIG. 12B, blank *cannabis* sample.

FIG. 13A, *cannabis* sample comprising 1000 ppb captan. FIG. 13B, blank *cannabis* sample.

FIG. 14B, 426>59; FIG. 14C, 426>271; FIG. 14D, 426>376; FIG. 14E, 426>409.

FIG. 14F, 409>41; FIG. 14G, 409>59; FIG. 14H, 409>271; FIG. 14I, 409>379.

FIGS. 16C-F are chromatograms of *cannabis* samples comprising 100 ppb naled and analyzed for the presence of naled using MRM transitions 380.8>127 (FIG. 16C), 378.8>127 (FIG. 16D), 380.8>109 (FIG. 16E), and 378.8>127 (FIG. 16F).

FIG. 17A, High collision energy (CE)=−30 V. FIG. 17B, Low CE=−15 V.

FIG. 18A, *cannabis* sample comprising 100 ppb acephate. FIG. 18B, blank *cannabis* sample.

FIG. 19A is a *cannabis* sample comprising 100 ppb imazalil. FIG. 19B is a blank *cannabis* sample.

FIG. 20A, Low CE=−25 V. FIG. 20B, High CE=−50 V.

FIGS. 21A-D are chromatograms of *cannabis* samples analyzed for the presence of cinerin II using MRM transitions 361.2>213 (FIGS. 21A, 21B) and 361.2>107 (FIGS. 21C, 21D). FIGS. 21A and 21C are *cannabis* samples comprising 1000 ppb cinerin II. FIGS. 21B and 21D are blank *cannabis* samples.

FIG. 22A, *cannabis* samples comprising 1000 ppb cinerin I. FIG. 22B, blank *cannabis* sample.

FIGS. 23A, 23C, and 23E, *cannabis* samples comprising 100 ppb fenoxycarb. FIGS. 23B, 23D, and 23E, blank *cannabis* samples.

FIGS. 24A, 24C, and 24E are *cannabis* samples comprising 100 ppb dimethomorph. FIGS. 24B, 24D, and 24F are blank *cannabis* samples.

FIG. 25A, *cannabis* sample comprising 100 ppb fenhexamid. FIG. 25B, blank *cannabis* sample.

FIG. 26A is a *cannabis* sample comprising 100 ppb spinetoram. FIG. 26B is a blank *cannabis* sample.

FIG. 27A, TIC for a blank *cannabis* sample obtained using a generic liquid chromatography gradient (fixed gradient rate). FIG. 27B, TIC for a *cannabis* sample comprising 100 ppb of pesticides. FIG. 27C, TIC for a blank *cannabis* sample obtained using the conditions described in Example 1. See also Example 2.

FIGS. 28A-C are chromatograms of *cannabis* samples comprising 100 ppb malathion and analyzed for the presence of malathion using MRM transitions 331>99 (FIG. 28A), 331>285 (FIG. 28B), and 331>127 (FIG. 28C).

FIGS. 37A-D are chromatograms of *cannabis* samples analyzed for the presence of quintozene using MRM transitions 275.8>35.1 (FIGS. 37A, 37C) and 273.8>35.1 (FIGS. 37B, 37D). FIGS. 37A and 37B are *cannabis* samples comprising 100 ppb quintozene. FIGS. 37C and 37D are blank *cannabis* samples.

FIGS. 38A and 38B are *cannabis* samples comprising 100 ppb chlordane. FIGS. 38C and 38D are blank *cannabis* samples.

FIGS. 41A-D are chromatograms of *cannabis* samples analyzed for the presence of daminozide using MRM transitions 161.1>143 (FIGS. 41A, 41C) and 161.1>44 (FIGS. 41B, 41D).

FIGS. 41A and 41B are *cannabis* samples comprising 100 ppb daminozide. FIGS. 41C and 41D are blank *cannabis* samples.

FIGS. 42A-D are chromatograms of *cannabis* samples analyzed for the presence of oxamyl using MRM transitions 237.1>72 (FIGS. 42A, 42C) and 237.1>90 (FIGS. 42B, 42D). FIGS. 42A and 42B are *cannabis* samples comprising 100 ppb oxamyl FIGS. 42C and 42D are blank *cannabis* samples.

FIGS. 43A-D are chromatograms of *cannabis* samples analyzed for the presence of flonicamid using MRM transitions 230.1>203 (FIGS. 43A, 43C) and 230.1>174 (FIGS. 43B, 43D).

FIGS. 43A and 43B are *cannabis* samples comprising 100 ppb flonicamid. FIGS. 43C and 43D are blank *cannabis* samples.

FIG. 44A, *cannabis* sample comprising 100 ppb acephate.

FIG. 44B, blank *cannabis* sample.

FIG. 45A, *cannabis* sample comprising 100 ppb methomyl. FIG. 44B, blank *cannabis* sample.

FIGS. 46A-D are chromatograms of *cannabis* samples analyzed for the presence of thiamethoxam using MRM transitions 292>211 (FIGS. 46A, 46C) and 292>181 (FIGS. 46B, 46D).

FIGS. 46A and 46B are *cannabis* samples comprising 100 ppb thiamethoxam. FIGS. 46C and 46D are blank *cannabis* samples.

FIGS. 47A-D are chromatograms of *cannabis* samples analyzed for the presence of imidacloprid using MRM transitions 256.1>209 (FIGS. 47A, 47C) and 256.1>175 (FIGS. 47B, 47D). FIGS. 47A and 47B are *cannabis* samples comprising 100 ppb imidacloprid. FIGS. 47C and 47D are blank *cannabis* samples.

FIGS. 48A-D are chromatograms of *cannabis* samples analyzed for the presence of dimethoate using MRM transitions 230>125 (FIGS. 48A, 48C) and 230>199 (FIGS. 48B, 48D).

FIGS. 48A and 48B are *cannabis* samples comprising 100 ppb dimethoate. FIGS. 48C and 48D are blank *cannabis* samples.

FIGS. 49A-D are chromatograms of *cannabis* samples analyzed for the presence of mevinphos using MRM transitions 225>127 (FIGS. 49A, 49C) and 225>109 (FIGS. 49B, 49D).

FIGS. 49A and 49B are *cannabis* samples comprising 100 ppb mevinphos. FIGS. 49C and 49D are blank *cannabis* samples.

FIGS. 50A and 50B are *cannabis* samples comprising 100 ppb acetamiprid. FIGS. 50C and 50D are blank *cannabis* samples.

FIGS. 51A-D are chromatograms of *cannabis* samples analyzed for the presence of thiacloprid using MRM transitions 253>126 (FIGS. 51A, 51C) and 253>90 (FIGS. 51B, 51D).

FIGS. 51A and 51B are *cannabis* samples comprising 100 ppb thiacloprid. FIGS. 51C and 51D are blank *cannabis* samples.

FIG. 52A is a *cannabis* sample comprising 100 ppb imazalil. FIG. 52B is a blank *cannabis* sample.

FIGS. 53A and 53B are *cannabis* samples comprising 100 ppb thiophanate-methyl. FIGS. 53C and 53D are blank *cannabis* samples.

FIGS. 54A-D are chromatograms of *cannabis* samples analyzed for the presence of aldicarb using MRM transitions 208>89 (FIGS. 54A, 54C) and 208>116 (FIGS. 54B, 54D). FIGS. 54A and 54B are *cannabis* samples comprising 100 ppb aldicarb. FIGS. 54C and 54D are blank *cannabis* samples.

FIGS. 55A and 55B are *cannabis* samples comprising 100 ppb propoxur. FIGS. 55C and 55D are blank *cannabis* samples.

FIGS. 56A-D are chromatograms of *cannabis* samples analyzed for the presence of dichlorvos using MRM transitions 220.9>109 (FIGS. 56A, 56C) and 220.9>127 (FIGS. 56B, 56D).

FIGS. 56A and 56B are *cannabis* samples comprising 100 ppb dichlorvos. FIGS. 56C and 56D are blank *cannabis* samples.

FIGS. 57A-D are chromatograms of *cannabis* samples analyzed for the presence of carbofuran using MRM transitions 222.1>123 (FIGS. 57A, 57C) and 222.1>165 (FIGS. 57B, 57D).

FIGS. 57A and 57B are *cannabis* samples comprising 100 ppb. FIGS. 57C and 57D are blank *cannabis* samples.

FIGS. 58A-D are chromatograms of *cannabis* samples analyzed for the presence of carbaryl using MRM transitions 202.1>127 (FIGS. 58A, 58C) and 202.1>145 (FIGS. 58B, 58D).

FIGS. 58A and 58B are *cannabis* samples comprising 100 ppb carbaryl. FIGS. 58C and 58D are blank *cannabis* samples.

FIGS. 59A-D are chromatograms of *cannabis* samples analyzed for the presence of spiroxamine using MRM transitions 298.3>100.1 (FIGS. 59A, 59C) and 298.3>144.1 (FIGS. 59B, 59D). FIGS. 59A and 59B are *cannabis* samples comprising 100 ppb spiroxamine. FIGS. 59C and 59D are blank *cannabis* samples.

FIGS. 60A-D are chromatograms of *cannabis* samples analyzed for the presence of naled ("dibrom") using MRM transitions 380.8>109 (FIGS. 60A, 60C) and 380.8>127 (FIGS. 60B, 60D). FIGS. 60A and 60B are *cannabis* samples comprising 100 ppb naled. FIGS. 60C and 60D are blank *cannabis* samples.

FIGS. 61A and 61B are *cannabis* samples comprising 100 ppb metalaxyl. FIGS. 61C and 61D are blank *cannabis* samples.

FIGS. 62A-D are chromatograms of *cannabis* samples analyzed for the presence of chlorantraniliprole using MRM transitions 484>285.9 (FIGS. 62A, 62C) and 484>452.9 (FIGS. 62B, 62D). FIGS. 62A and 62B are *cannabis* samples comprising 100 ppb chlorantraniprole. FIGS. 62C and 62D are blank *cannabis* samples.

FIGS. 63A-D are chromatograms of *cannabis* samples analyzed for the presence of phosmet using MRM transitions 318>133 (FIGS. 63A, 63C) and 318>160 (FIGS. 63B, 63D). FIGS. 63A and 63B are *cannabis* samples comprising 100 ppb phosmet. FIGS. 63C and 63D are blank *cannabis* samples.

FIGS. 64A-D are chromatograms of *cannabis* samples analyzed for the presence of methyl parathion using MRM transitions 264>124.9 (FIGS. 64A, 64C) and 264>231.9 (FIGS. 64B, 64D). FIGS. 64A and 64B are *cannabis* samples comprising 100 ppb methyl parathion. FIGS. 64C and 64D are blank *cannabis* samples.

FIGS. 65A and 65B are *cannabis* samples comprising 100 ppb azoxystrobin. FIGS. 65C and 65D are blank *cannabis* samples.

FIGS. 66A-D are chromatograms of *cannabis* samples analyzed for the presence of methiocarb using MRM transitions 226.1>121 (FIGS. 66A, 66C) and 226.1>169 (FIGS. 66B, 66D). FIGS. 66A and 66B are *cannabis* samples comprising 100 ppb methiocarb. FIGS. 66C and 66D are blank *cannabis* samples.

FIG. 67A is a *cannabis* sample comprising 1000 ppb captan. FIG. 67B is a blank *cannabis* sample.

FIGS. 68A-D are chromatograms of *cannabis* samples analyzed for the presence of boscalid using MRM transitions 343>140 (FIGS. 68A, 68C) and 343>272 (FIGS. 68B, 68D). FIGS. 68A and 68B are *cannabis* samples comprising 100 ppb boscalid. FIGS. 68C and 68D are blank *cannabis* samples.

FIGS. 69A-D are chromatograms of *cannabis* samples analyzed for the presence of fludioxonil using MRM transitions 247.1>126 (FIGS. 69A, 69C) and 247.1>180 (FIGS. 69B, 69D).

FIGS. 69A and 69B are *cannabis* samples comprising 100 ppb fludioxonil. FIGS. 69C and 69D are blank *cannabis* samples.

FIGS. 70A-D are chromatograms of *cannabis* samples analyzed for the presence of paclobutrazol using MRM transitions 294.1>125 (FIGS. 70A, 70C) and 294.1>70 (FIGS. 70B, 70D). FIGS. 70A and 70B are *cannabis* samples comprising 100 ppb paclobutrazol. FIGS. 70C and 70D are blank *cannabis* samples.

FIGS. 71A-D are chromatograms of *cannabis* samples analyzed for the presence of malathion using MRM transitions 331>285 (FIGS. 71A, 71C) and 331>127 (FIGS. 71B, 71D).

FIGS. 71A and 71B are *cannabis* samples comprising 100 ppb malathion. FIGS. 71C and 71D are blank *cannabis* samples.

FIGS. 72A-D are chromatograms of *cannabis* samples analyzed for the presence of dimethomorph using MRM transitions 388.1>273 (FIGS. 72A, 72C) and 388.1>301 (FIGS. 72B, 72D). FIGS. 72A and 72B are *cannabis* samples comprising 100 ppb dimethomorph. FIGS. 72C and 72D are blank *cannabis* samples.

FIGS. 73A-D are chromatograms of *cannabis* samples analyzed for the presence of myclobutanil using MRM transitions 289.1>70 (FIGS. 73A, 73C) and 289.1>125 (FIGS. 73B, 73D). FIGS. 73A and 73B are *cannabis* samples comprising 100 ppb myclobutanil. FIGS. 73C and 73D are blank *cannabis* samples.

FIGS. 74A-D are chromatograms of *cannabis* samples analyzed for the presence of bifenazate using MRM transitions 301.1>170 (FIGS. 74A, 74C) and 301.1>198 (FIGS. 74B, 74D).

FIGS. 74A and 74B are *cannabis* samples comprising 100 ppb bifenazate. FIGS. 74C and 74D are blank *cannabis* samples.

FIG. 75A, *cannabis* sample comprising 100 ppb fenhexamid. FIG. 75B, blank *cannabis* sample.

FIGS. 76A-D are chromatograms of *cannabis* samples analyzed for the presence of fipronil using MRM transitions 435>250 (FIGS. 76A, 76C) and 435>330 (FIGS. 76B, 76D). FIGS. 76A and 76B are *cannabis* samples comprising 100 ppb fipronil. FIGS. 76C and 76D are blank *cannabis* samples.

FIGS. 77A-D are chromatograms of *cannabis* samples analyzed for the presence of spirotetromat using MRM transitions 374.2>216 (FIGS. 77A, 77C) and 374.2>302.1 (FIGS. 77B, 77D). FIGS. 77A and 77B are *cannabis* samples comprising 100 ppb spirotetromat. FIGS. 77C and 77D are blank *cannabis* samples.

FIGS. 78A and 78B are *cannabis* samples comprising 100 ppb ethoprophos. FIGS. 78C and 78D are blank *cannabis* samples.

FIGS. 79A-D are chromatograms of *cannabis* samples analyzed for the presence of fenoxycarb using MRM transitions 302.1>256 (FIGS. 79A, 79C) and 302.1>116 (FIGS. 79B, 79D). FIGS. 79A and 79B are *cannabis* samples comprising 100 ppb fenoxycarb. FIGS. 79C and 79D are blank *cannabis* samples.

FIGS. 80A-D are chromatograms of *cannabis* samples analyzed for the presence of kresoxim-methyl using MRM transitions 314.1>222 (FIGS. 80A, 80C) and 314.1>235 (FIGS. 80B, 80D). FIGS. 80A and 80B are *cannabis* samples comprising 100 ppb kresoxim-methyl. FIGS. 80C and 80D are blank *cannabis* samples.

FIGS. 81A-D are chromatograms of *cannabis* samples analyzed for the presence of tebuconazole using MRM transitions 308>70 (FIGS. 81A, 81C) and 308>125 (FIGS. 81B, 81D).

FIGS. 81A and 81B are *cannabis* samples comprising 100 ppb tebuconazole. FIGS. 81C and 81D are blank *cannabis* samples.

FIGS. 82A-D are chromatograms of *cannabis* samples analyzed for the presence of diazinon using MRM transitions 305.1>97 (FIGS. 82A, 82C) and 305.1>169 (FIGS. 82B, 82D).

FIGS. 82A and 82B are *cannabis* samples comprising 100 ppb diazinon FIGS. 82C and 82D are blank *cannabis* samples.

FIGS. 83A-D are chromatograms of *cannabis* samples analyzed for the presence of spinosyn A using MRM transitions 732.5>98 (FIGS. 83A, 83C) and 732.5>142 (FIGS. 83B, 83D).

FIGS. 83A and 83B are *cannabis* samples comprising 100 ppb spinosyn A. FIGS. 83C and 83D are blank *cannabis* samples.

FIGS. 84A-D are chromatograms of *cannabis* samples analyzed for the presence of coumaphos using MRM transitions 363>226.9 (FIGS. 84A, 84C) and 363>306.9 (FIGS. 84B, 84D). FIGS. 84A and 84B are *cannabis* samples comprising 100 ppb coumaphos. FIGS. 84C and 84D are blank *cannabis* samples.

FIGS. 85A-D are chromatograms of *cannabis* samples analyzed for the presence of MGK-264 using MRM transitions 276.2>98 (FIGS. 85A, 85C) and 276.2>210.1 (FIGS. 85B, 85D). FIGS. 85A and 85B are *cannabis* samples comprising 100 ppb MGK-264. FIGS. 85C and 85D are blank *cannabis* samples.

FIGS. 86A-D are chromatograms of *cannabis* samples analyzed for the presence of clofentezine using MRM transitions 303>102 (FIGS. 86A, 86C) and 303>138 (FIGS. 86B, 86D).

FIGS. 86A and 86B are *cannabis* samples comprising 100 ppb clofentezine. FIGS. 86C and 86D are blank *cannabis* samples.

FIGS. 87A-D are chromatograms of *cannabis* samples analyzed for the presence of propiconazole using MRM transitions 342.1>69 (FIGS. 87A, 87C) and 342.1>159 (FIGS. 87B, 87D). FIGS. 87A and 87B are *cannabis* samples comprising 100 ppb propiconazole. FIGS. 87C and 87D are blank *cannabis* samples.

FIGS. 88A-D are chromatograms of *cannabis* samples analyzed for the presence of prallethrin using MRM transitions 301.2>132.9 (FIGS. 88A, 88C) and 301.2>168.9 (FIGS. 88B, 88D). FIGS. 88A and 88B are *cannabis* samples comprising 100 ppb prallethrin. FIGS. 88C and 88D are blank *cannabis* samples.

FIGS. 89A and 89B are *cannabis* samples comprising 100 ppb spinosyn D. FIGS. 89C and 89D are blank *cannabis* samples.

FIGS. 90A-D are chromatograms of *cannabis* samples analyzed for the presence of cyfluthrin using MRM transitions 451.1>191 (FIGS. 90A, 90C) and 451.1>434 (FIGS. 90B, 90D).

FIGS. 90A and 90B are *cannabis* samples comprising 1000 ppb cyfluthrin. FIGS. 90C and 90D are blank *cannabis* samples.

FIGS. 91A-D are chromatograms of *cannabis* samples analyzed for the presence of trifloxystrobin using MRM transitions 409.1>186 (FIGS. 91A, 91C) and 409.1>206 (FIGS. 91B, 91D). FIGS. 91A and 91B are *cannabis* samples comprising 100 ppb trifloxystrobin. FIGS. 91C and 91D are blank *cannabis* samples.

Figures 92A, 92B:
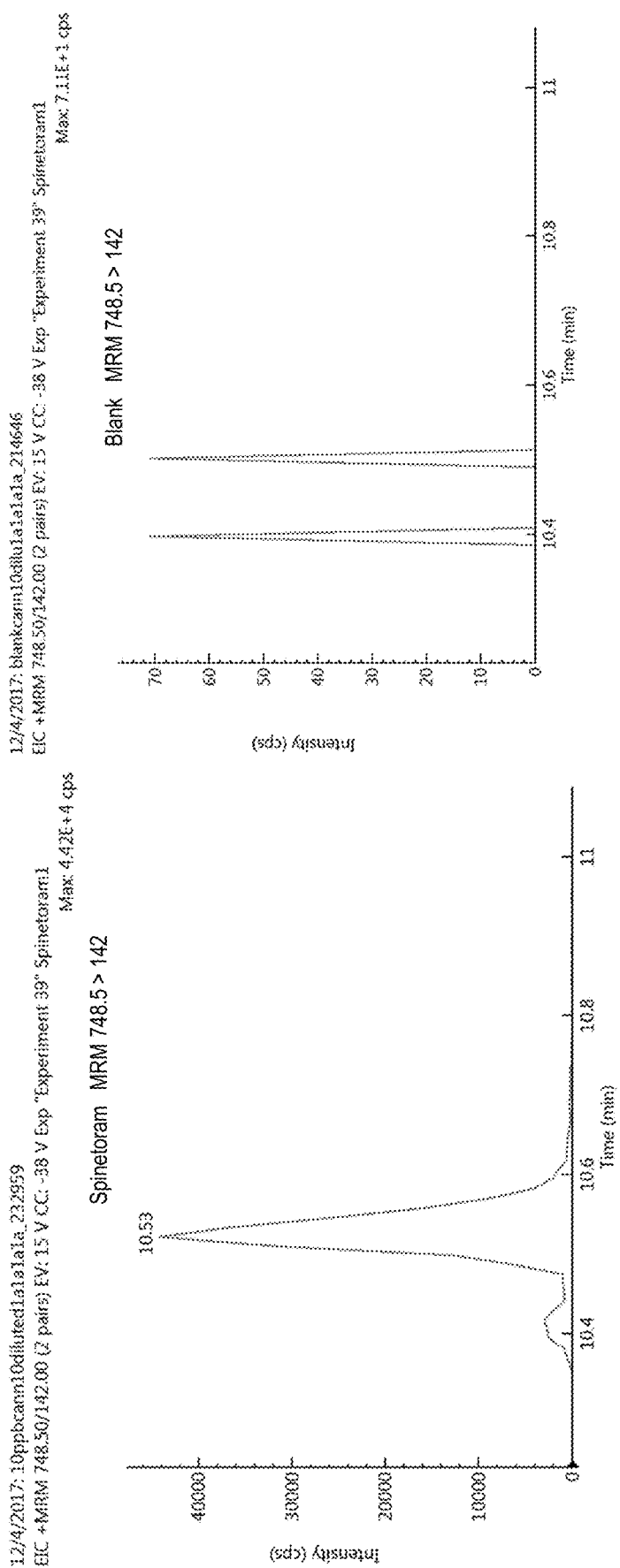

FIGS. 92A-B are chromatograms of *cannabis* samples analyzed for the presence of spinetoram using MRM transition 748.5>142. FIG. 92A is a *cannabis* sample comprising 100 ppb spinetoram. FIG. 92B is a blank *cannabis* sample.

FIGS. 93A-D are chromatograms of *cannabis* samples analyzed for the presence of chlorfenapyr using MRM transitions 426>409 (FIGS. 93A, 93C) and 426>59.1 (FIGS. 93B, 93D).

FIGS. 93A and 93B are *cannabis* samples comprising 1000 ppb chlorfenapyr. FIGS. 93C and 93D are blank *cannabis* samples.

Figure 94A:
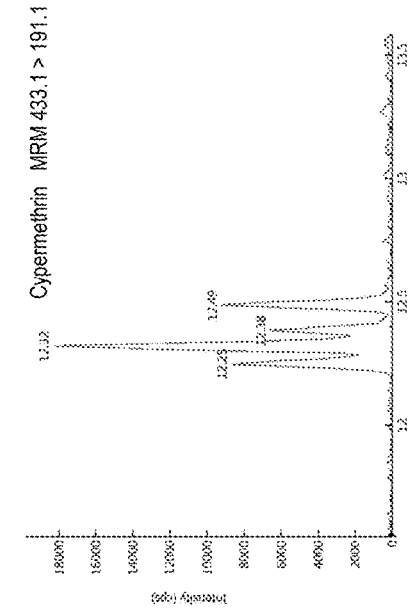
Figure 94C:
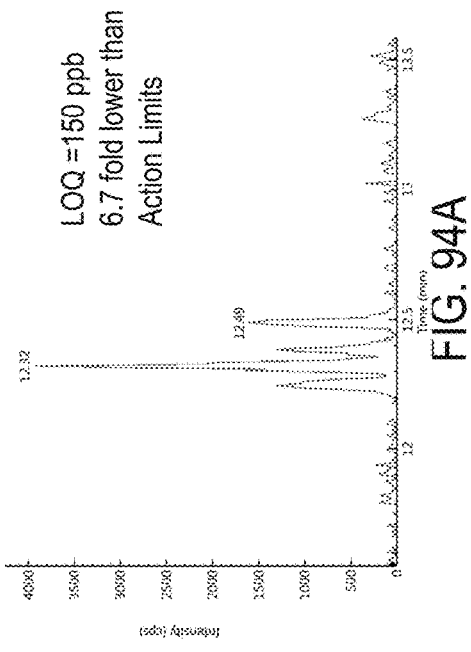
Figure 94B:
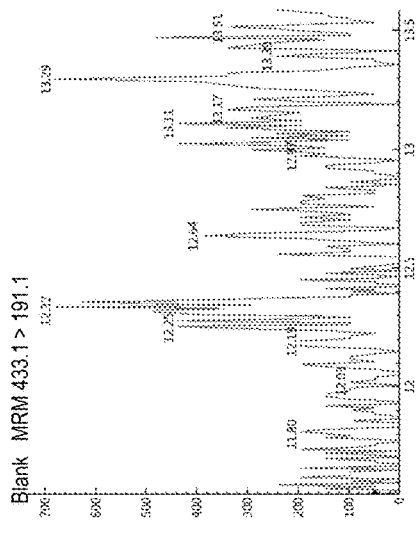
Figure 94D:
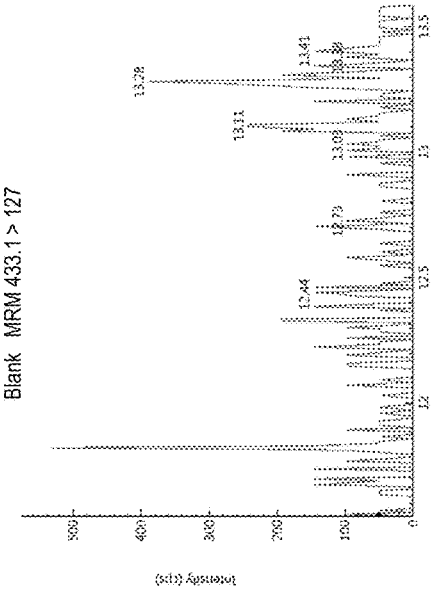

FIGS. 94A-D are chromatograms of *cannabis* samples analyzed for the presence of cypermethrin using MRM transitions 433.1>127 (FIGS. 94A, 94C) and 433.1>191.1 (FIGS. 94B, 94D). FIGS. 94A and 94B are *cannabis* samples comprising 1000 ppb cypermethrin. FIGS. 94C and 94D are blank *cannabis* samples.

FIGS. 95A-D are chromatograms of *cannabis* samples analyzed for the presence of permethrin using MRM transitions 408.1>183 (FIGS. 95A, 95C) and 408.1>355 (FIGS. 95B, 95D).

FIGS. 95A and 95B are *cannabis* samples comprising 100 ppb permethrin. FIGS. 95C and 95D are blank *cannabis* samples.

FIGS. 96A-B are chromatograms of *cannabis* samples analyzed for the presence of cinerin II using MRM transition 361.2>149. FIG. 96A is a *cannabis* sample comprising 1000 ppb cinerin II. FIG. 96B is a blank *cannabis* sample.

FIGS. 97A-D are chromatograms of *cannabis* samples analyzed for the presence of jasmolin II using MRM transitions 375.2>163 (FIGS. 97A, 97C) and 375.2>213 (FIGS. 97B, 97D). FIGS. 97A and 97B are *cannabis* samples comprising 100 ppb jasmolin II. FIGS. 97C and 97D are blank *cannabis* samples.

FIGS. 98A-D are chromatograms of *cannabis* samples analyzed for the presence of pyrethrin II using MRM transitions 373.2>161 (FIGS. 98A, 98C) and 373.2>143 (FIGS. 98B, 98D). FIGS. 98A and 98B are *cannabis* samples comprising 1000 ppb pyrethrin II. FIGS. 98C and 98D are blank *cannabis* samples.

FIGS. 99A-D are chromatograms of *cannabis* samples analyzed for the presence of jasmolin I using MRM transitions 331.2>163 (FIGS. 99A, 99C) and 331.2>121 (FIGS. 99B, 99D). FIGS. 99A and 99B are *cannabis* samples comprising 1000 ppb jasmolin I. FIGS. 99C and 99D are blank *cannabis* samples.

Figures 100A, 100B:
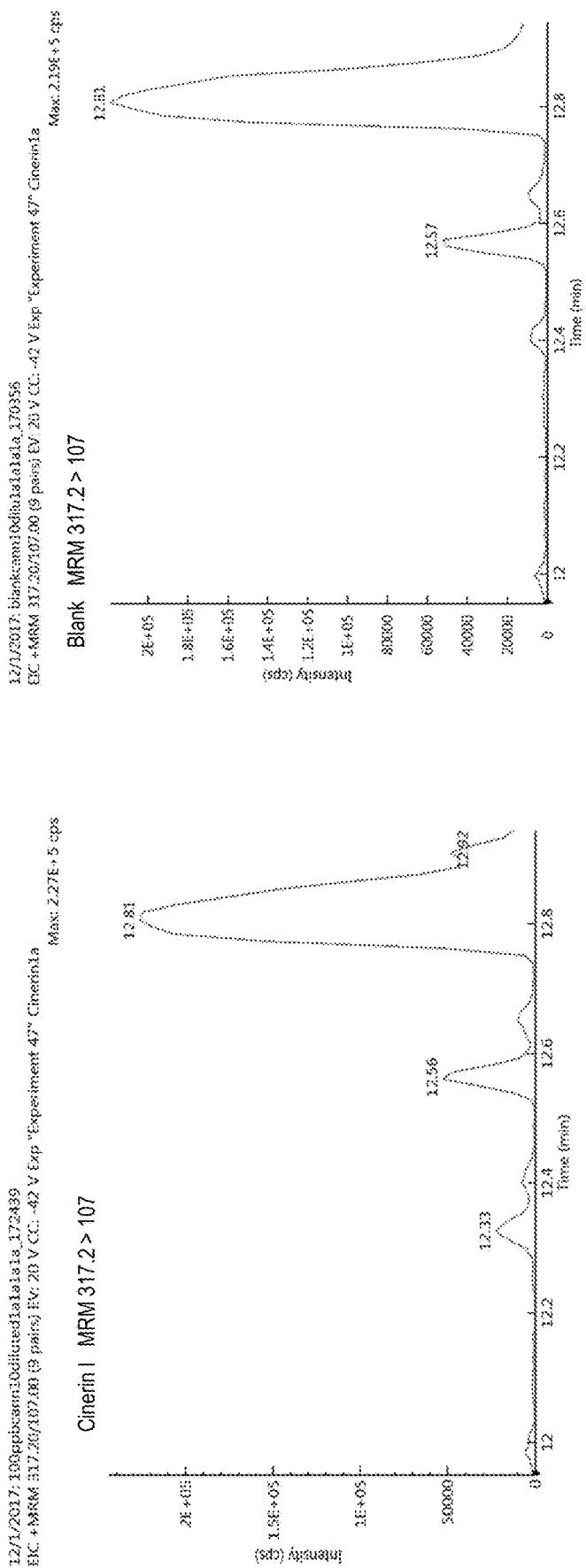

FIGS. 100A-B are chromatograms of *cannabis* samples analyzed for the presence of cinerin 1 using MRM transition 317.2>107. FIG. 100A is a *cannabis* sample comprising 1000 ppb cinerin 1. FIG. 100B is a blank *cannabis* sample.

FIGS. 101A-C are chromatograms of *cannabis* samples analyzed for the presence of pyrethrin I using MRM transitions 329.2>143 (FIG. 101A) and 329.2>161 (FIGS. 101B, 101C). FIGS. 101A and 101B are *cannabis* samples comprising 580 ppb pyrethrin I. FIG. 101C is a blank *cannabis* sample.

FIGS. 102A-D are chromatograms of *cannabis* samples analyzed for the presence of chlorpyrifos using MRM transitions 349.9>97 (FIGS. 102A, 102C) and 349.9>321.9 (FIGS. 102B, 102D). FIGS. 102A and 102B are *cannabis* samples comprising 100 ppb chlorpyrifos. FIGS. 102C and 102D are blank *cannabis* samples.

Figure 103A:
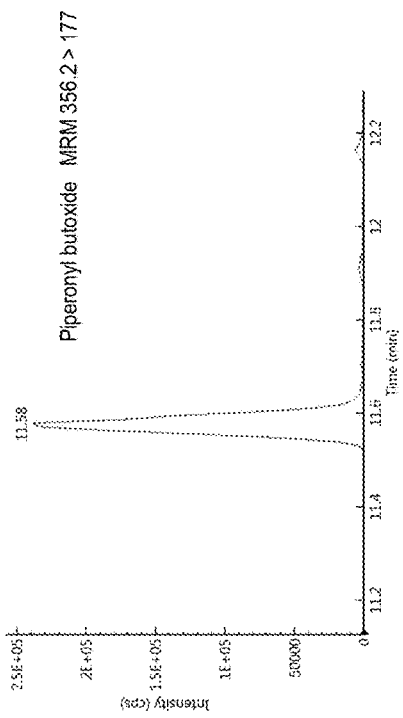
Figure 103B:
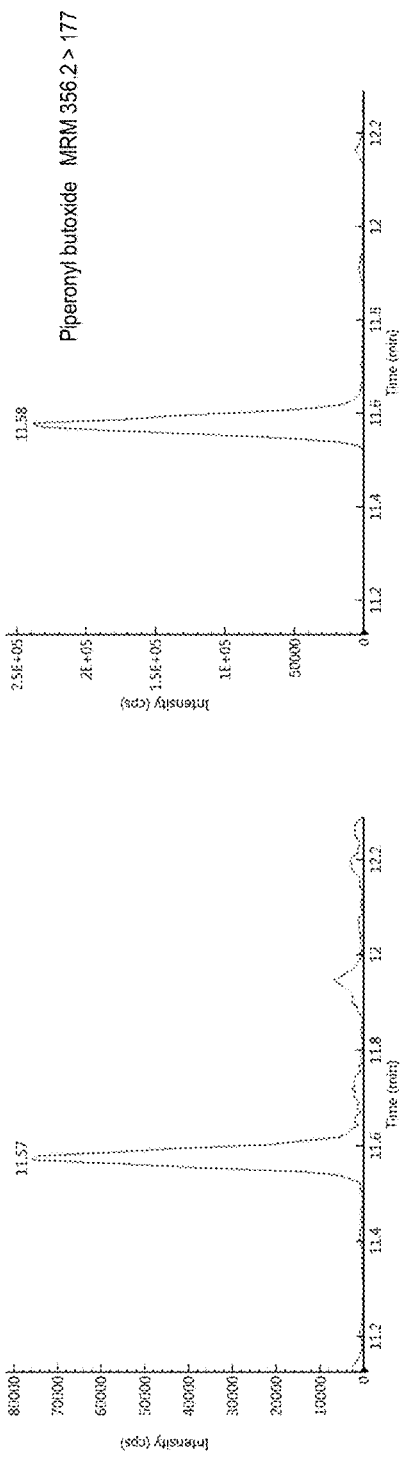
Figure 103C:
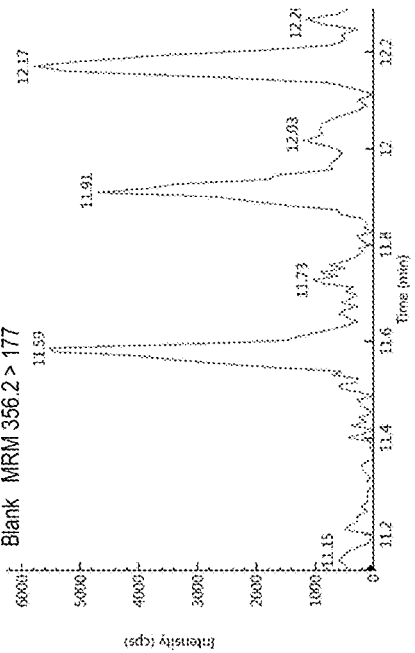
Figure 103D:
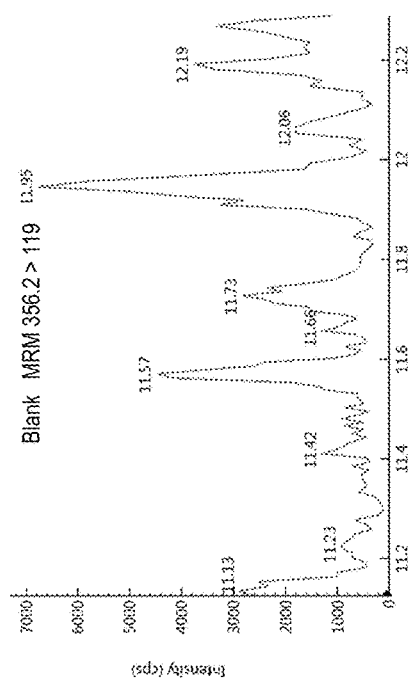

FIGS. 103A-D are chromatograms of *cannabis* samples analyzed for the presence of piperonyl butoxide using MRM transitions 356.2>119 (FIGS. 103A, 103C) and 356.2>177 (FIGS. 103B, 103D). FIGS. 103A and 103B are *cannabis* samples comprising 100 ppb piperonyl butoxide.

FIGS. 103C and 103D are blank *cannabis* samples.

FIGS. 104A-D are chromatograms of *cannabis* samples analyzed for the presence of hexythiazox using MRM transitions 353.1>168 (FIGS. 104A, 104C) and 353.1>228 (FIGS. 104B, 104D). FIGS. 104A and 104B are *cannabis* samples comprising 100 ppb hexythiazox. FIGS. 104C and 104D are blank *cannabis* samples.

FIGS. 105A-D are chromatograms of *cannabis* samples analyzed for the presence of etoxazole using MRM transitions 360.2>57.1 (FIGS. 105A, 105C) and 360.2>141 (FIGS. 105B, 105D). FIGS. 105A and 105B are *cannabis* samples comprising 100 ppb etoxazole. FIGS. 105C and 105D are blank *cannabis* samples.

FIGS. 106A-D are chromatograms of *cannabis* samples analyzed for the presence of spiromesifen using MRM transitions 273.1>187 (FIGS. 106A, 106C) and 273.1>255 (FIGS. 106B, 106D). FIGS. 106A and 106B are *cannabis* samples comprising 100 ppb spiromesifen. FIGS. 106C and 106D are blank *cannabis* samples.

FIGS. 107A-D are chromatograms of *cannabis* samples analyzed for the presence of fenpyroximate using MRM transitions 422.2>135 (FIGS. 107A, 107C) and 422.2>366.1 (FIGS. 107B, 107D). FIGS. 107A and 107B are *cannabis* samples comprising 100 ppb fenpyroximate. FIGS. 107C and 107D are blank *cannabis* samples.

FIGS. 108A-D are chromatograms of *cannabis* samples analyzed for the presence of pyridaben using MRM transitions 365.1>147 (FIGS. 108A, 108C) and 365.1>309 (FIGS. 108B, 108D). FIGS. 108A and 108B are *cannabis* samples comprising 100 ppb pyridaben. FIGS. 108C and 108D are blank *cannabis* samples.

FIGS. 109A-D are chromatograms of *cannabis* samples analyzed for the presence of abamectin using MRM transitions 890.5>305.1 (FIGS. 109A, 109C) and 890.5>567.2 (FIGS. 109B, 109D). FIGS. 109A and 109B are *cannabis* samples comprising 100 ppb abamectin. FIGS. 109C and 109D are blank *cannabis* samples.

Figure 110A:
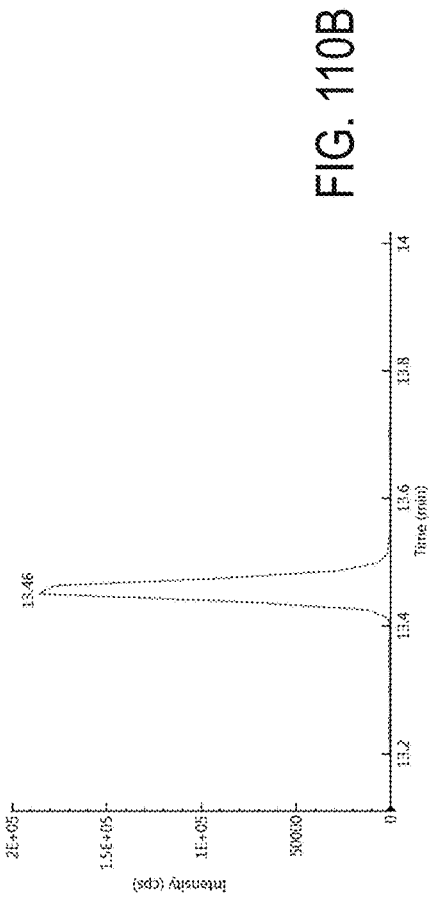
Figure 110B:
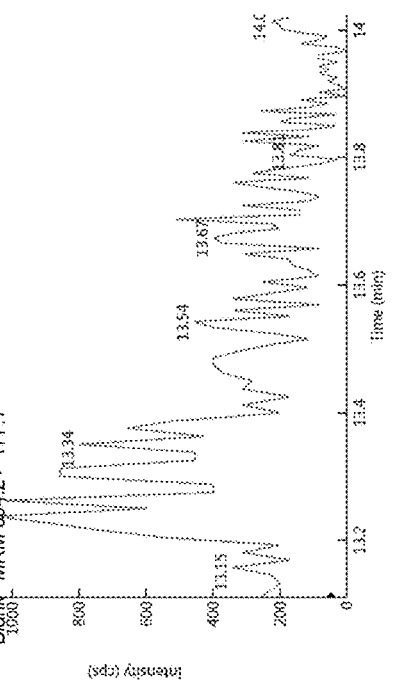
Figure 110C:
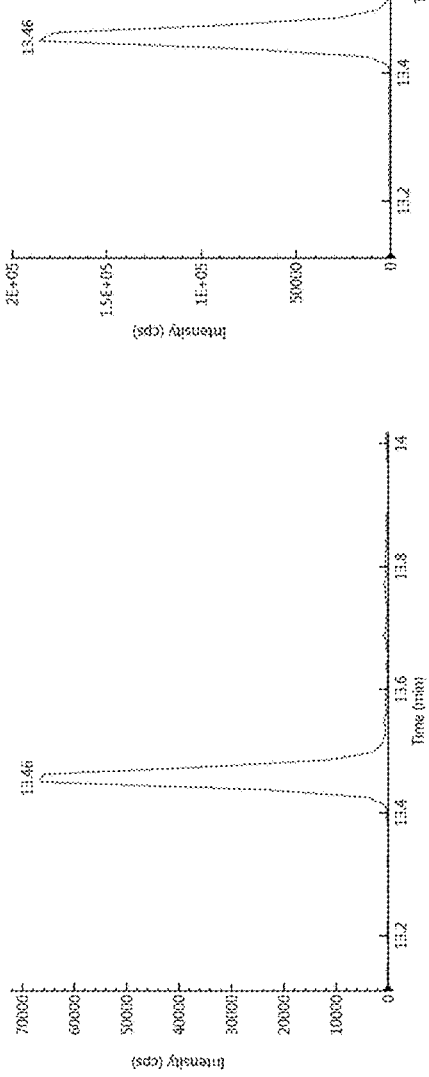
Figure 110D:
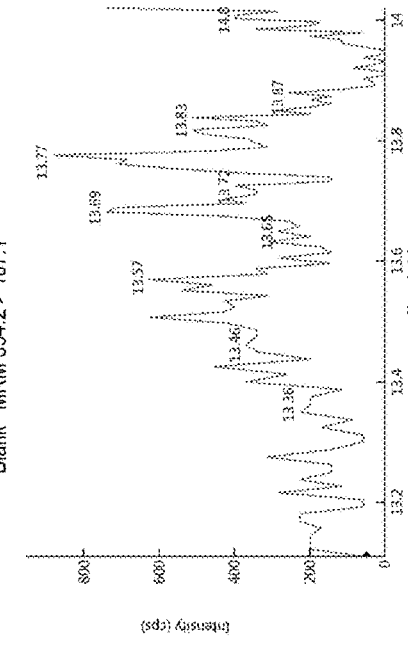

FIGS. 110A-D are chromatograms of *cannabis* samples analyzed for the presence of etofenprox using MRM transitions 394.2>107.1 (FIGS. 110A, 110C) and 394.2>177.1 (FIGS. 110B, 110D). FIGS. 110A and 110B are *cannabis* samples comprising 100 ppb etofenprox. FIGS. 110C and 110D are blank *cannabis* samples.

FIGS. 111A-D are chromatograms of *cannabis* samples analyzed for the presence of acequinocyl using MRM transitions 402.2>189 (FIGS. 111A, 111C) and 402.2>343.1 (FIGS. 111B, 111D). FIGS. 111A and 111B are *cannabis* samples comprising 100 ppb acequinocyl. FIGS. 111C and 111D are blank *cannabis* samples.

FIGS. 112A-D are chromatograms of *cannabis* samples analyzed for the presence of bifenthrin using MRM transitions 440.1>166.1 (FIGS. 112A, 112C) and 440.1>181.1 (FIGS. 112B, 112D). FIGS. 112A and 112B are *cannabis* samples comprising 100 ppb bifenthrin. FIGS. 112C and 112D are blank *cannabis* samples.

FIGS. 113A-D are chromatograms of *cannabis* samples comprising 100 ppb naled (dibrom) analyzed for the presence of naled using MRM transitions 380.8>127 (FIG. 113A), 378.8>127 (FIG. 113B), 382.8>127 (FIG. 113C), and 378.8>109 (FIG. 113D).

Figure 114A:
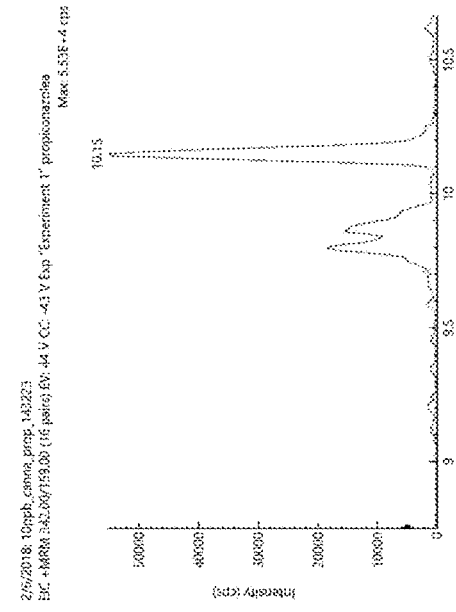
Figure 114B:
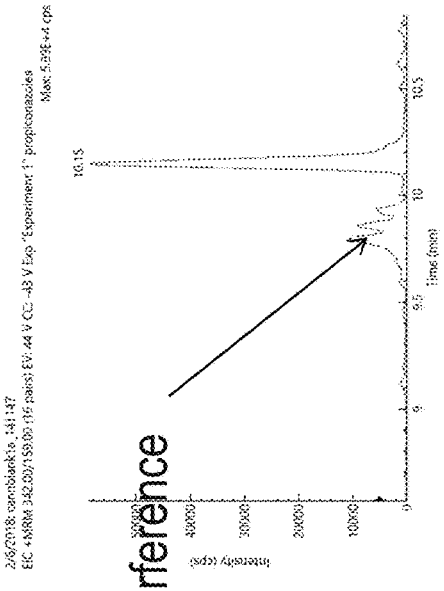
Figure 114C:
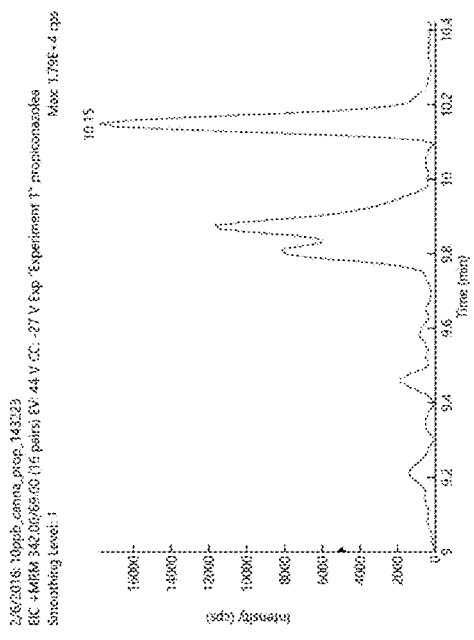
Figure 114D:
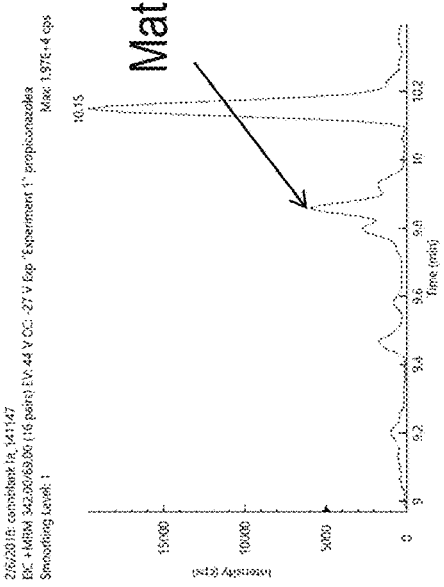
Figure 114E:
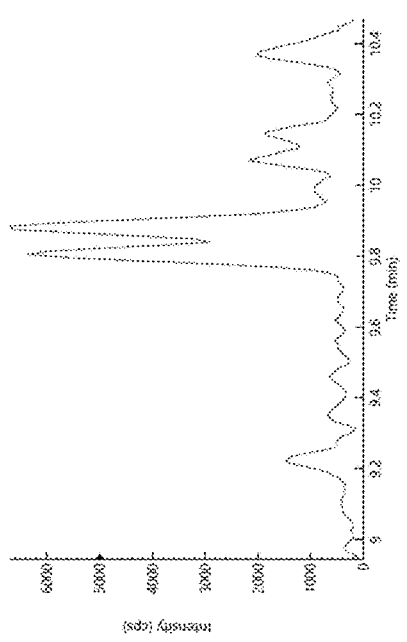
Figure 114F:
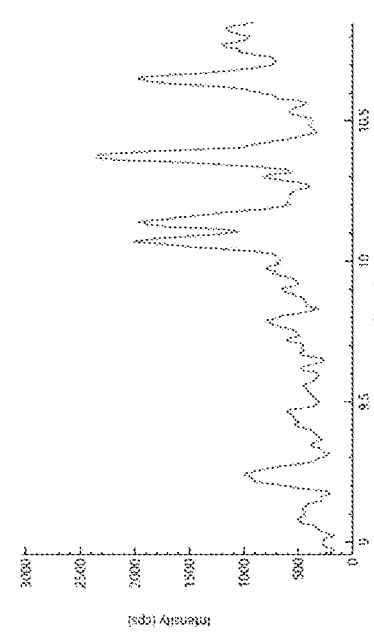
Figure 114G:
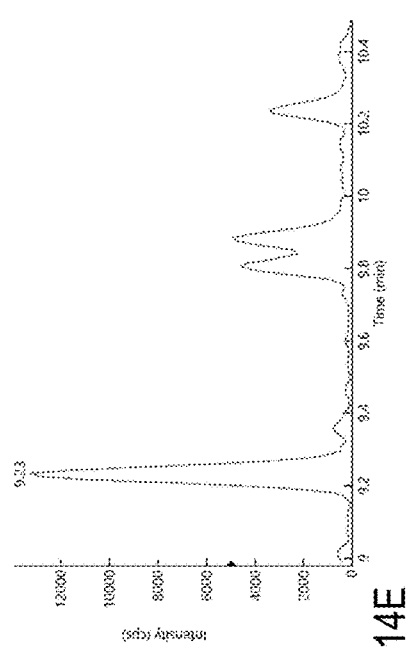
Figure 114H:
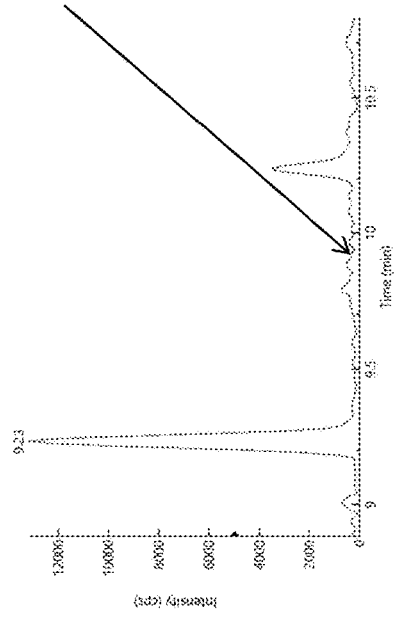

FIGS. 114A-H are chromatograms of *cannabis* samples analyzed for the presence of propiconazole using MRM transitions 342>69 (FIGS. 114A, 114C), 342>159 (FIGS. 114B, 114D), 344>69 (FIGS. 114E, 114G), and 344>161 (FIGS. 114F, 114H). FIGS. 114A, 114B, 114E, and 114F are *cannabis* samples comprising 10 ppb propiconazole. FIGS. 114C, 114D, 114G, and 114H are blank *cannabis* samples.

Figure 114I:
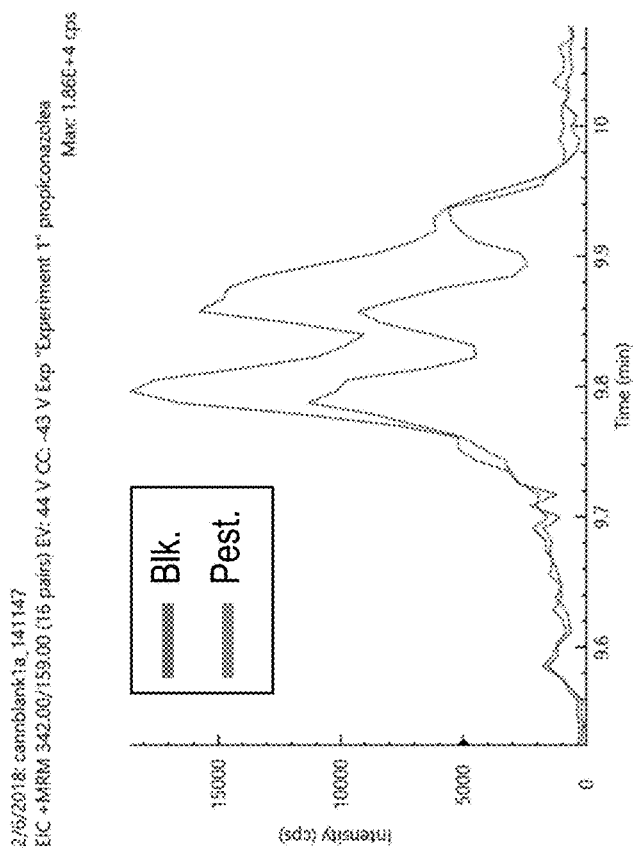
Figure 114J:
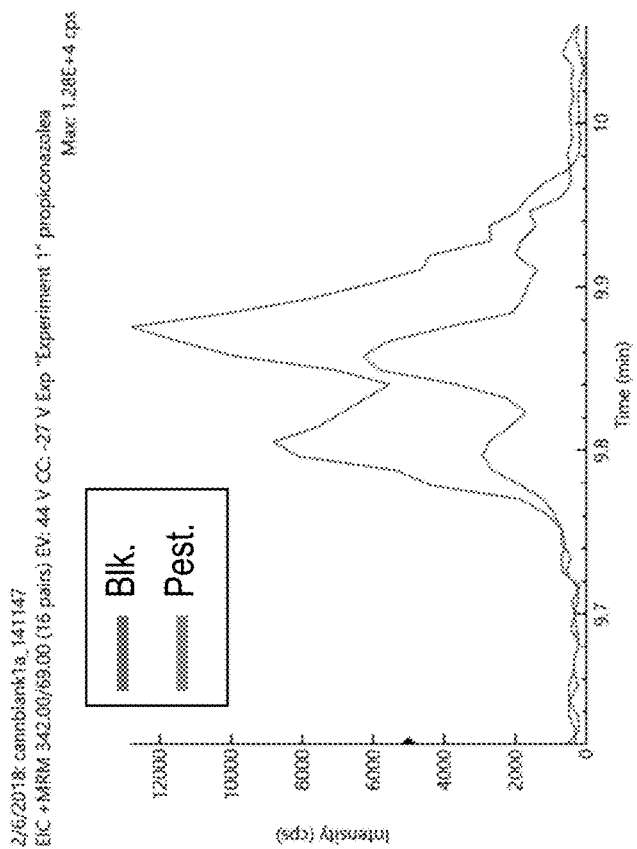

FIGS. 114I-J are chromatograms of *cannabis* samples comprising 100 ppb propiconazole and analyzed for the presence of propiconazole using MRM transitions 342>69 (FIG. 114I) and 342>159 (FIG. 114J).

Figures 114K, 114L:
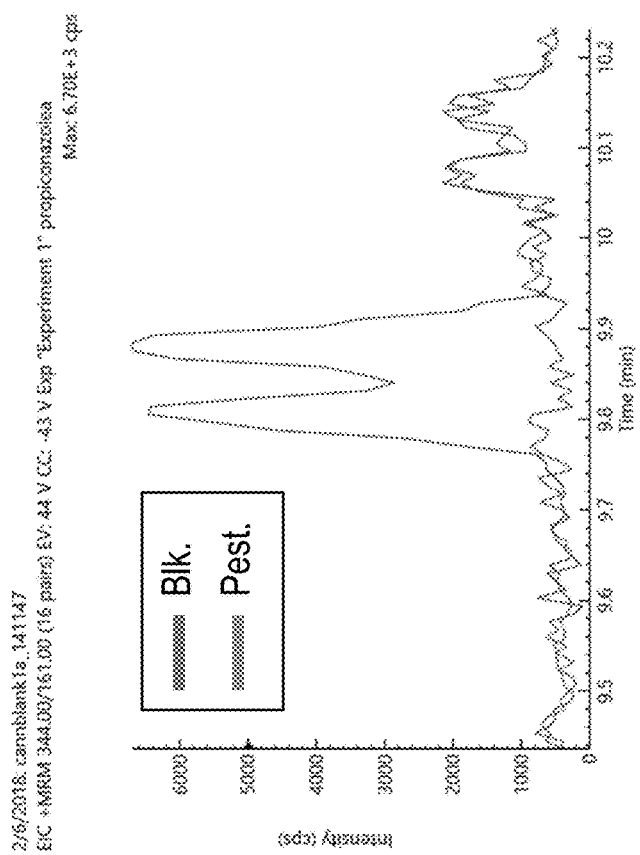

FIGS. 114K-L are chromatograms of *cannabis* samples comprising 100 ppb propiconazole and analyzed for the presence of propiconazole using MRM transitions 344>69 (FIG. 114K) and 344>161 (FIG. 114L).

Figure 115A:
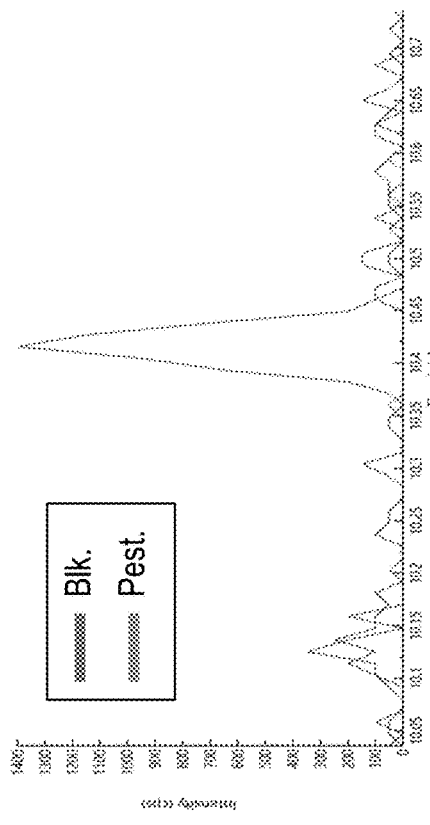
Figure 115B:
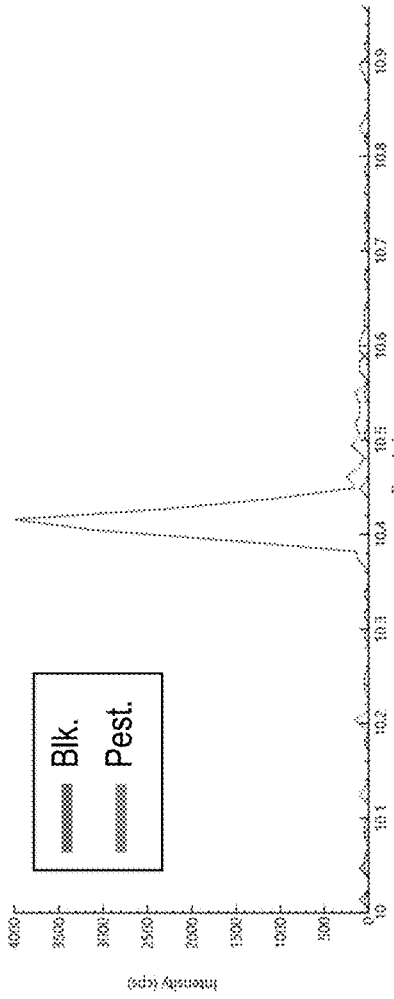
Figures 115E, 115F:
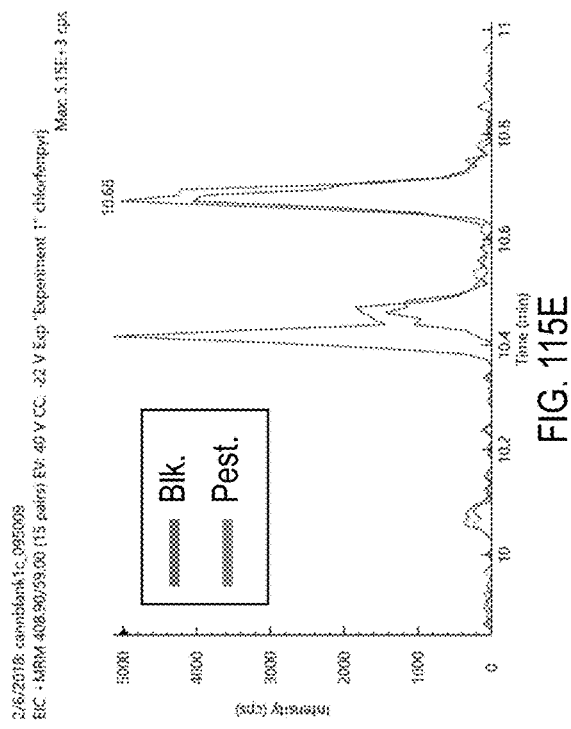
Figure 115G:
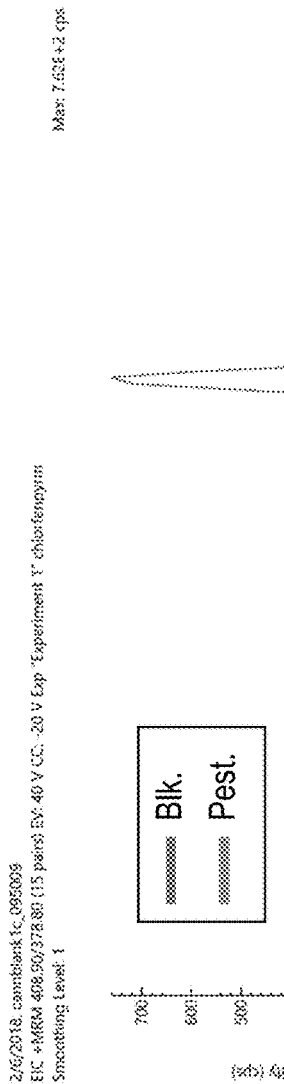
Figure 115H:
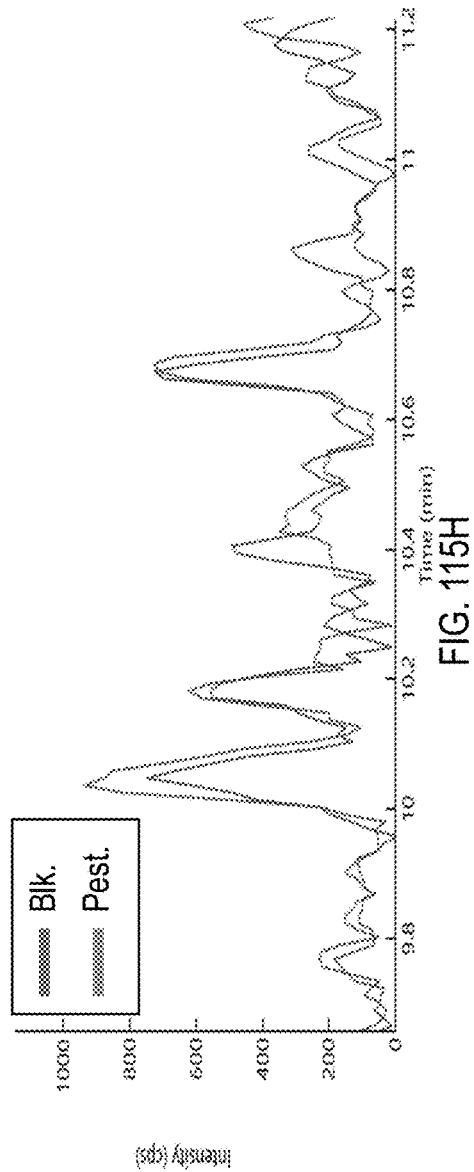

FIGS. 115A-H are chromatograms of *cannabis* samples comprising 1000 ppb chlorfenapyr and analyzed for the presence of chlorfenapyr using MRM transitions 423.9>59 (FIG. 115A), 406.9>59 (FIG. 115B), 425.9>59 (FIG. 115C), 425.9>408.9 (FIG. 115D), 408.9>59 (FIG. 115E), 423.9>406.9 (FIG. 115F), 408.9>378.8 (FIG. 115G), and 408.9>270.9 (FIG. 115H).

Figure 116A:
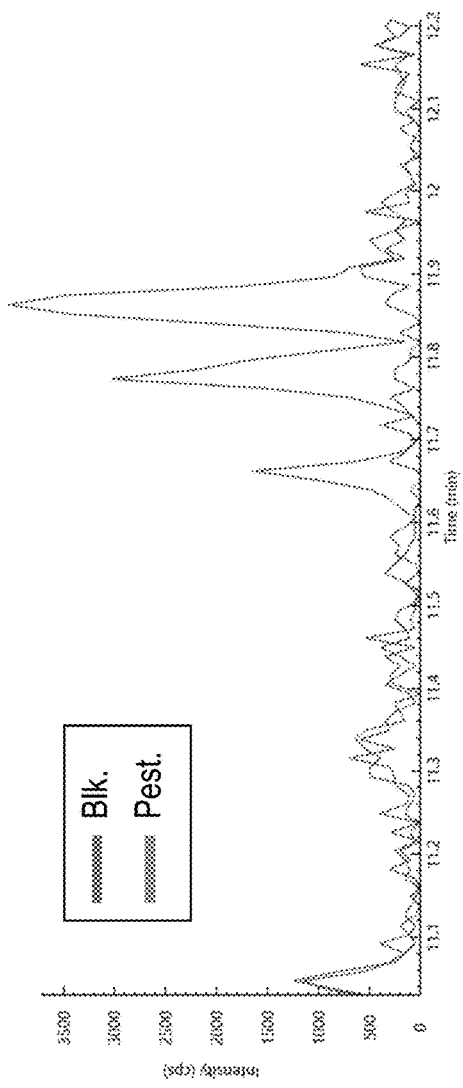
Figure 116B:
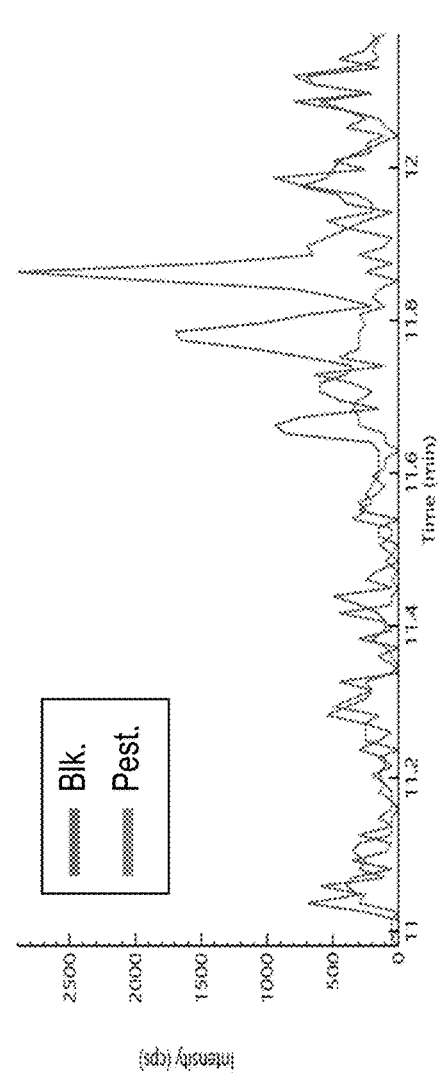
Figure 116C:
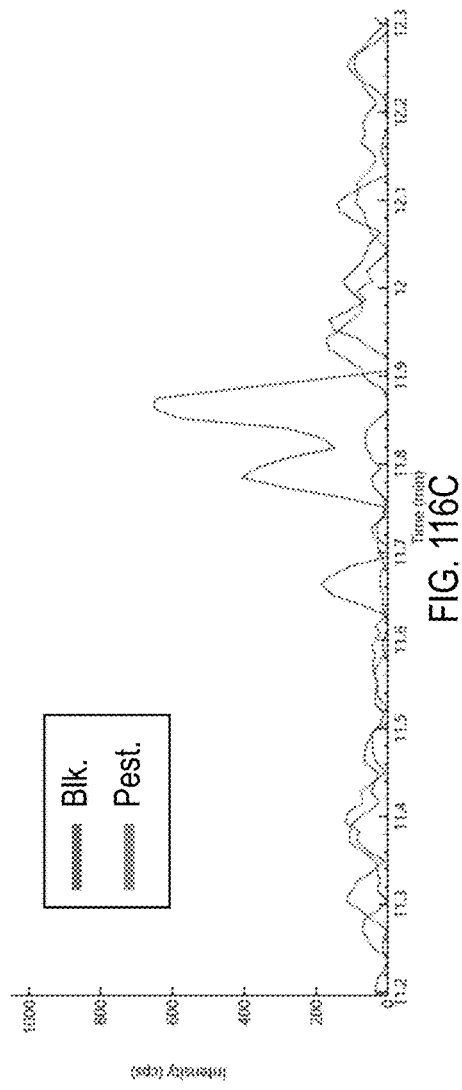
Figure 116D:
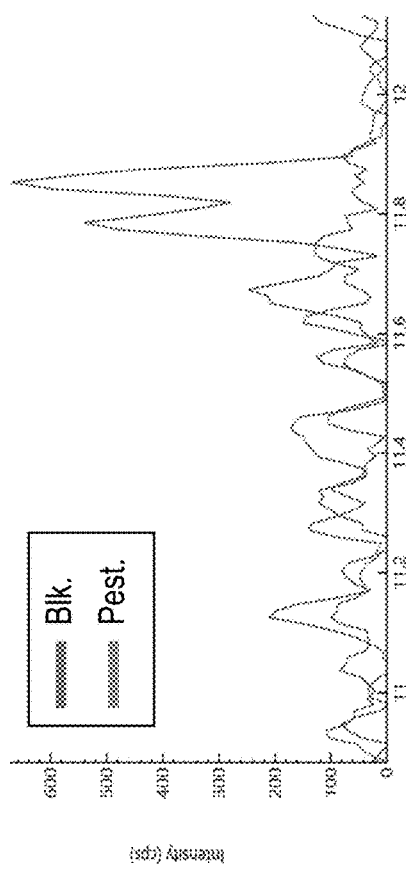
Figure 116E:
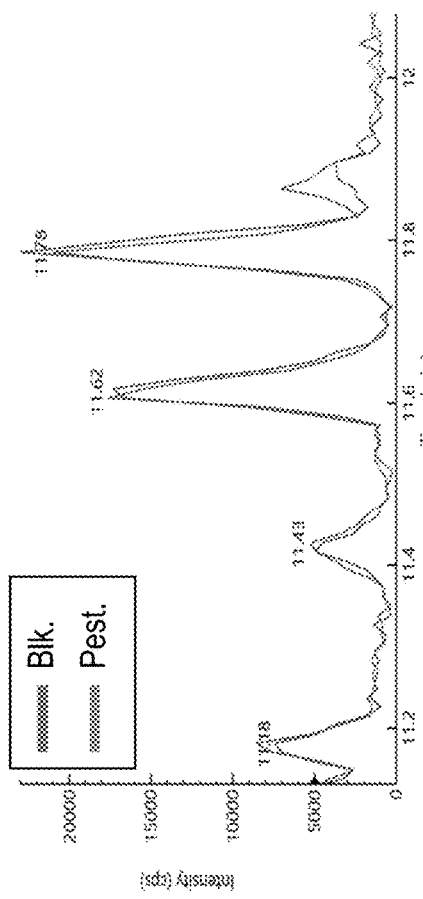
Figure 116F:
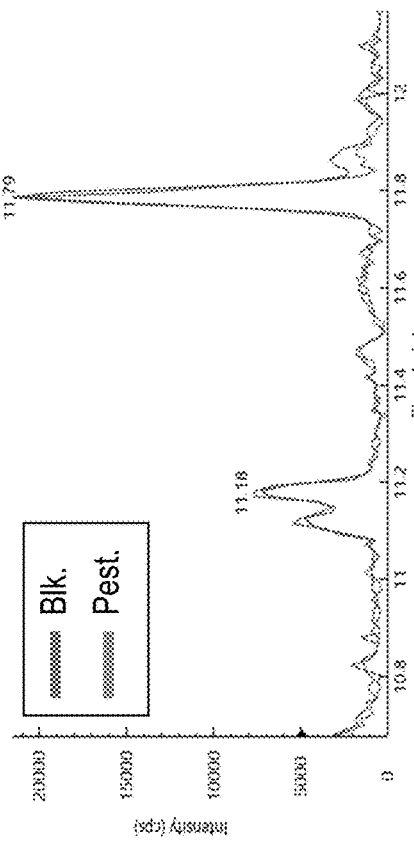

FIGS. 116A-F are chromatograms of *cannabis* samples comprising 1000 ppb cyfluthrin and analyzed for the presence of cyfluthrin using MRM transitions 451>191 (FIG. 116A), 453>193 (FIG. 116B), 451>127 (FIG. 116C), 451>206 (FIG. 116D), 451>434 (FIG. 116E), and 453>436 (FIG. 116F).

Figure 117A:
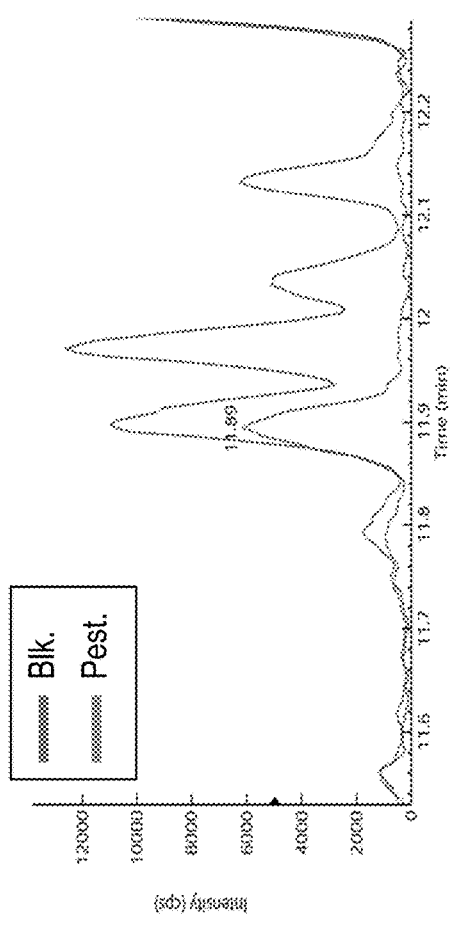
Figure 117B:
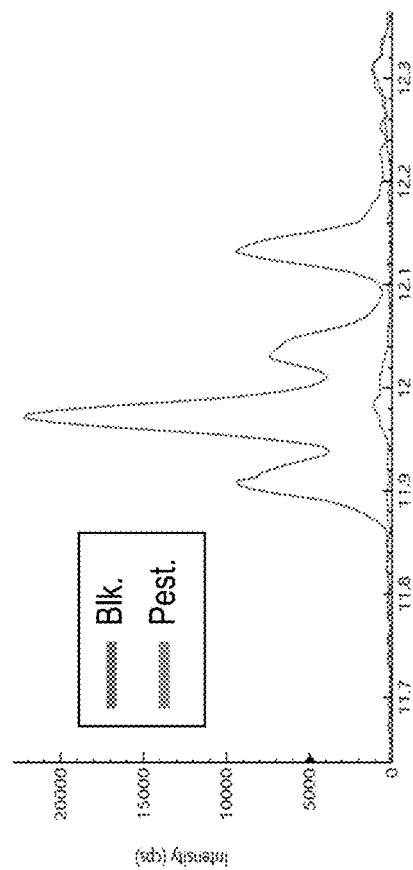
Figure 117C:
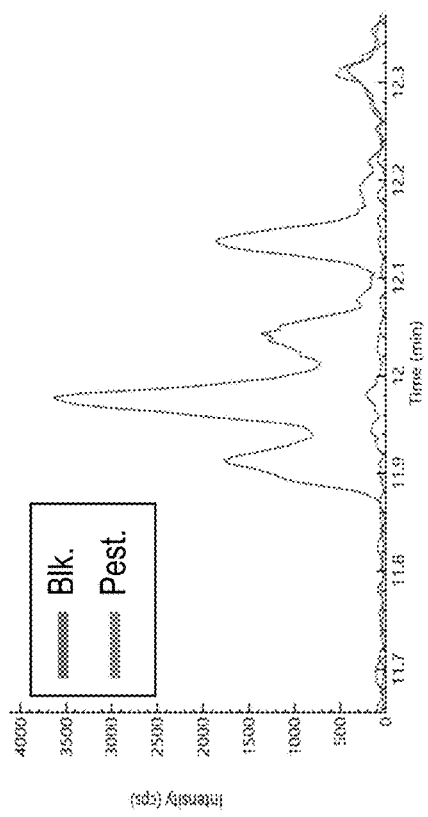
Figure 117D:
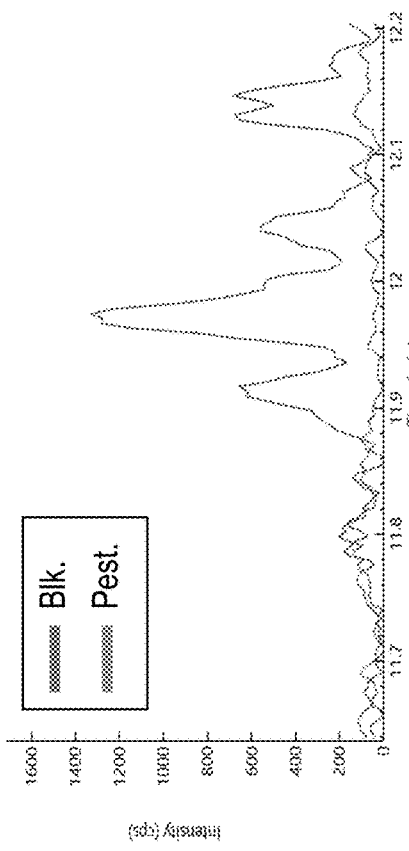
Figure 117E:
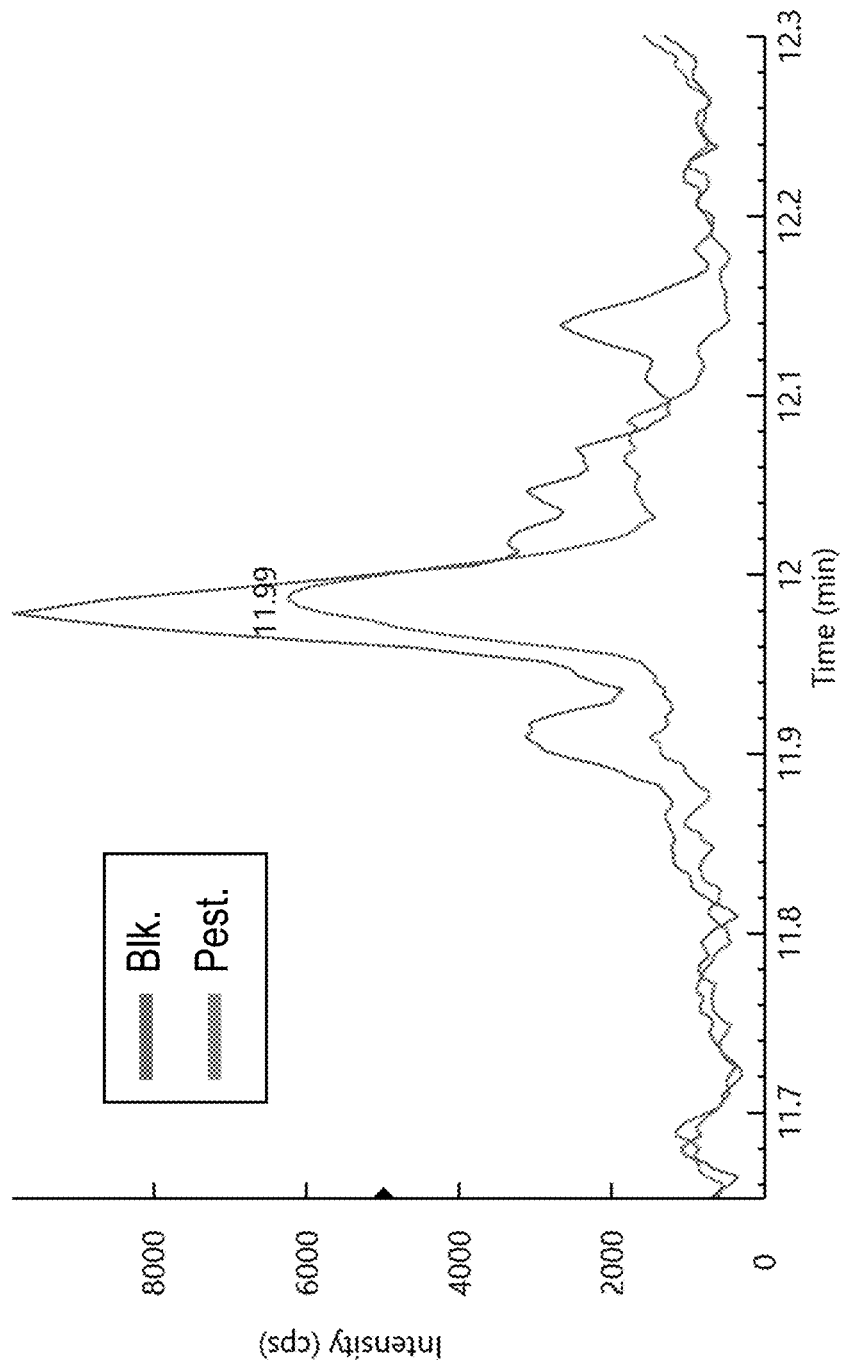

FIGS. 117A-E are chromatograms of *cannabis* samples comprising 1000 ppb cypermethrin and analyzed for the presence of cypermethrin using MRM transitions 435.1>193.1 (FIG. 117A), 433.1>191.1 (FIG. 117B), 433.1>127 (FIG. 117C), 435.1>127 (FIG. 117D), and 433.1>91 (FIG. 117E).

Figure 118A:
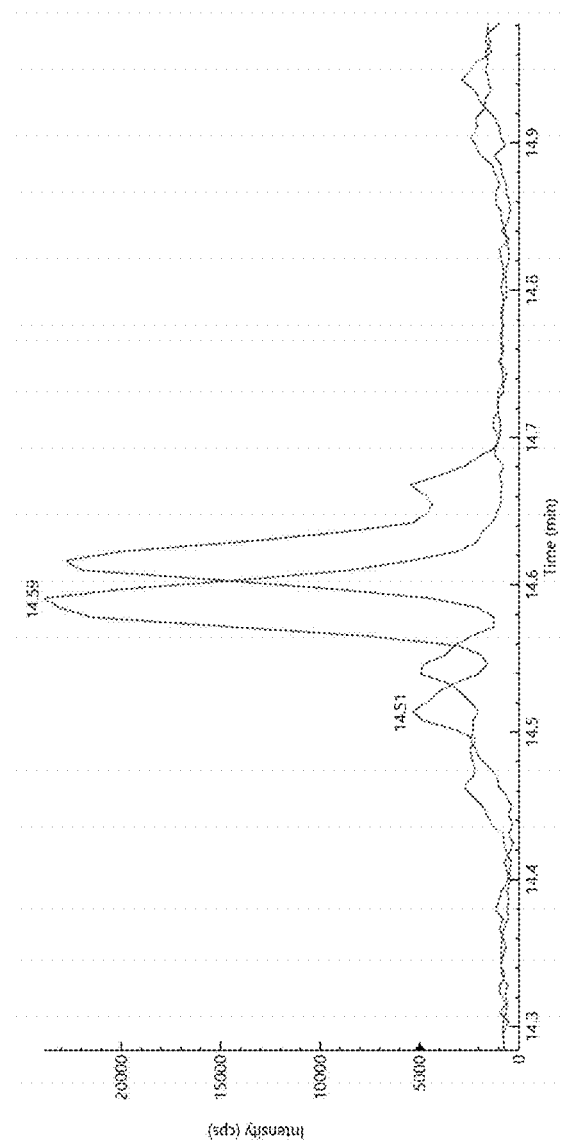

FIG. 118A, overlay of response of *cannabis* matrix (left trace) and acequinocyl (right trace) spiked at level of 0.1 µg/g in *cannabis* matrix with MRM transition based on protonated molecular ion.

Figure 118B:
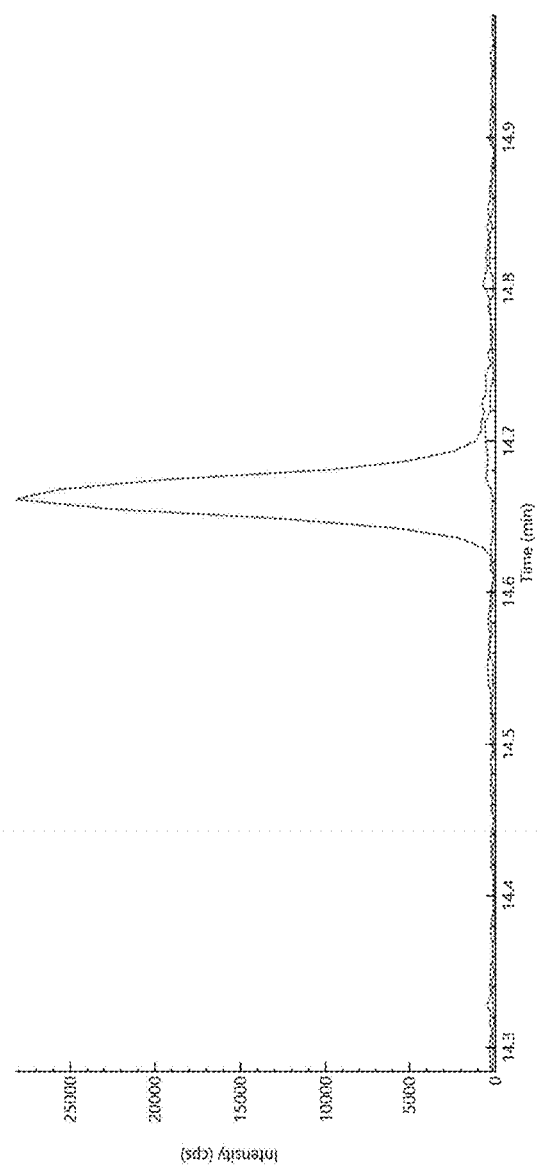

FIG. 118B, overlay of response of *cannabis* matrix (lower trace) and acequinocyl (upper trace) spiked at level of 0.1 µg/g in *cannabis* matrix with MRM transition based on adduct ion.

Figure 119B:
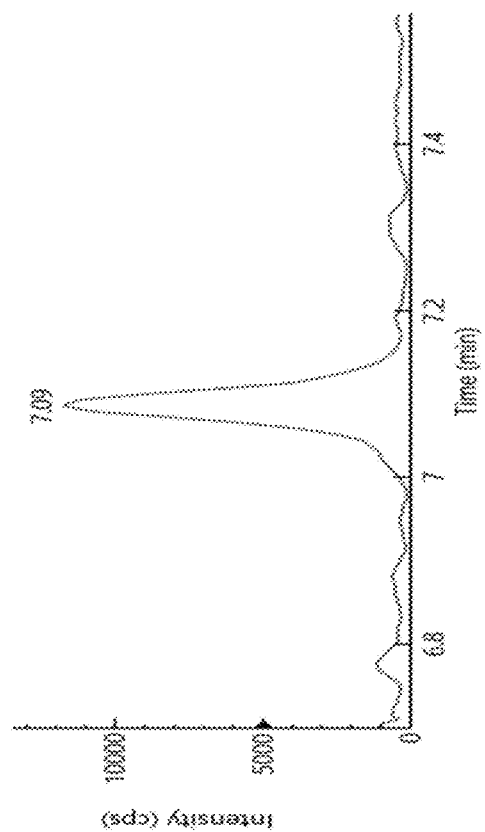
Figure 119A:
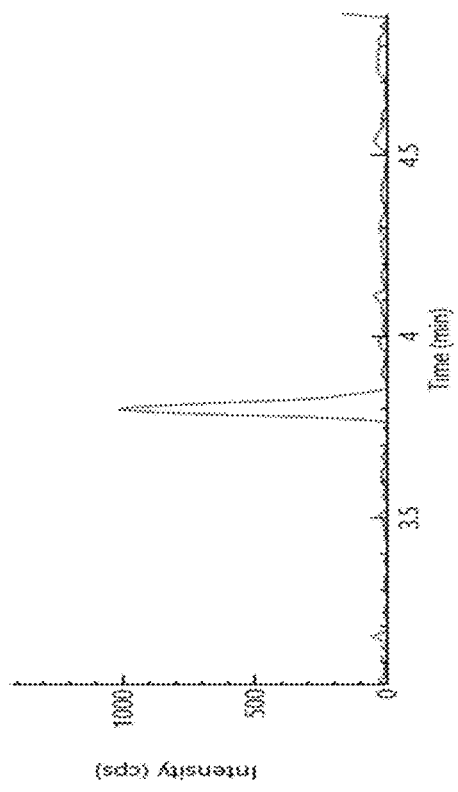
Figure 119D:
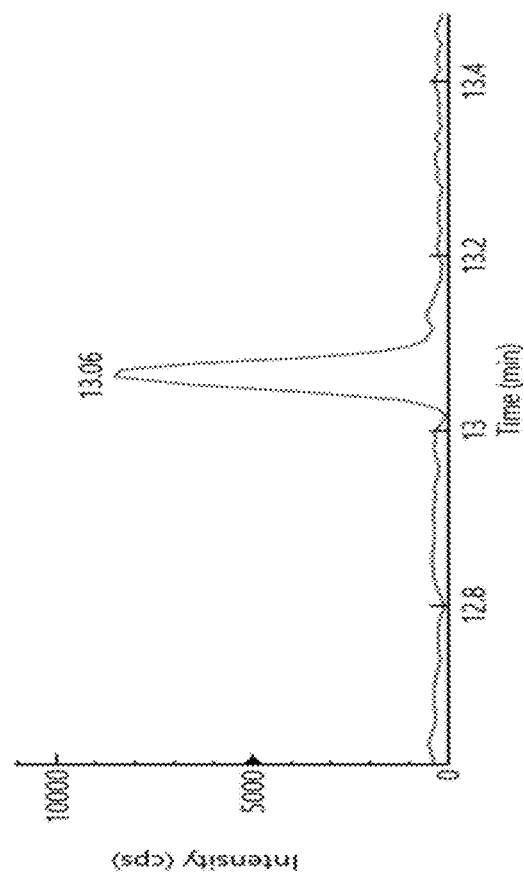
Figure 119C:
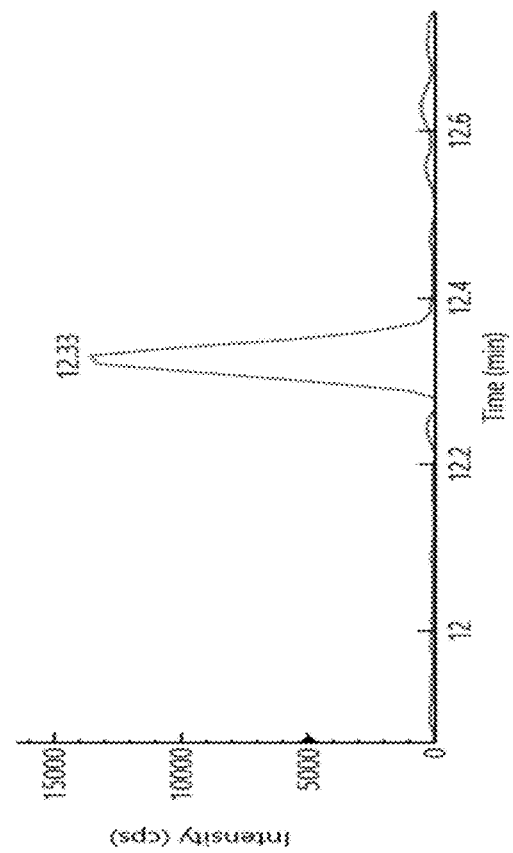
Figure 119F:
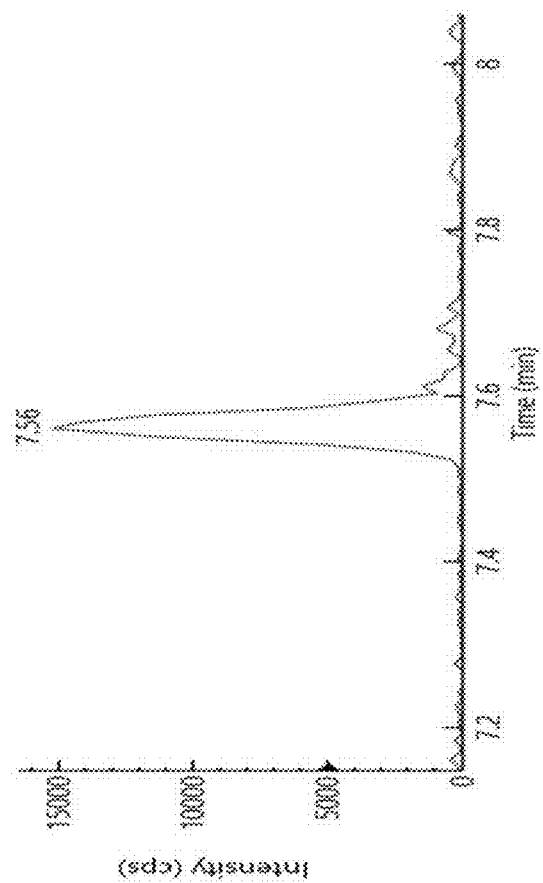
Figure 119E:
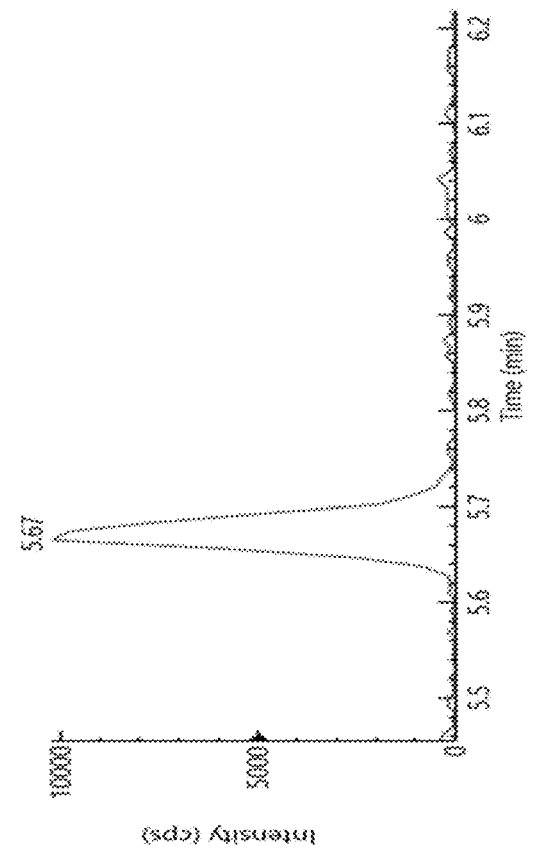

FIGS. 119A-F are chromatograms of a representative set of pesticides spiked at level of 0.01 µg/g in *cannabis* matrix. FIG. 119A, oxamyl; FIG. 119B, metalaxyl; FIG. 119C, fenpyroximate; FIG. 119D, mycyclobutanil; FIG. 119E, etofenprox; and FIG. 119F, azoxystrobin.

Figure 120:
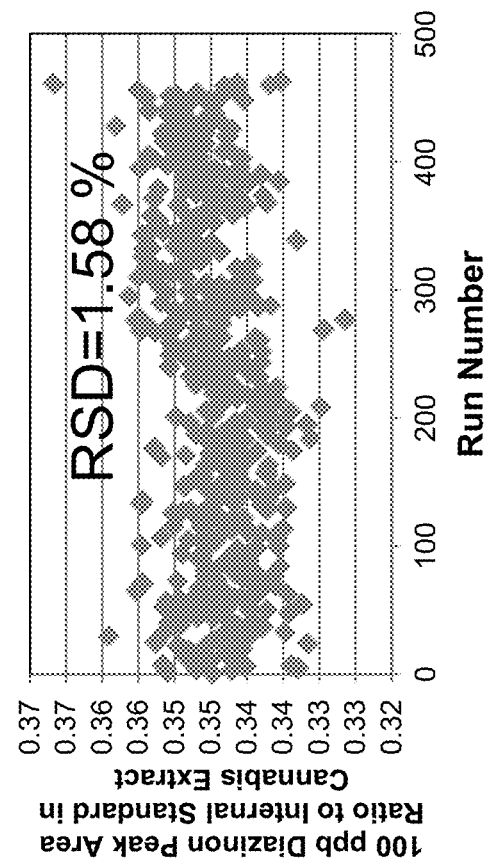

FIG. 120. Long term stability data over 1 week of injections of diazinon at a level of 100 ng/mL spiked in *cannabis* flower matrix extract comprising 100 ng/mL of diazinon.

Figure 121A:
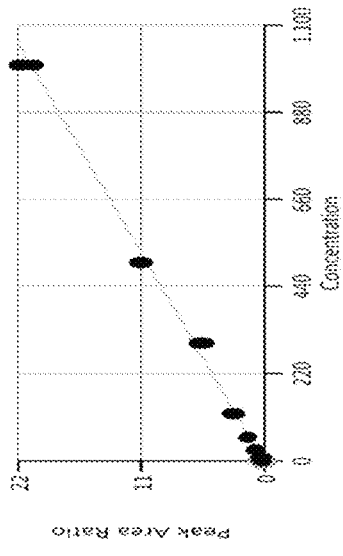
Figure 121B:
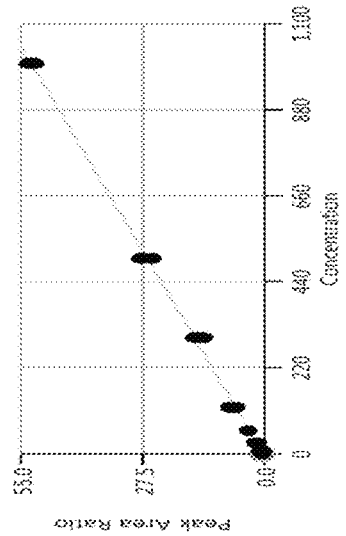
Figure 121C:
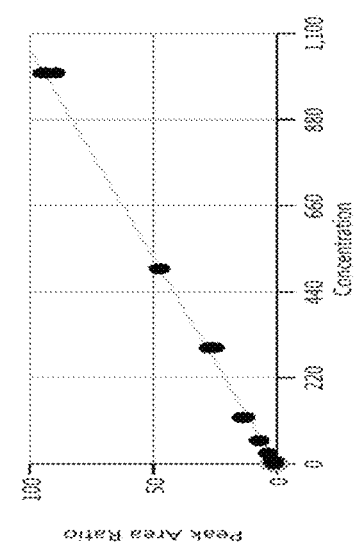
Figure 121D:
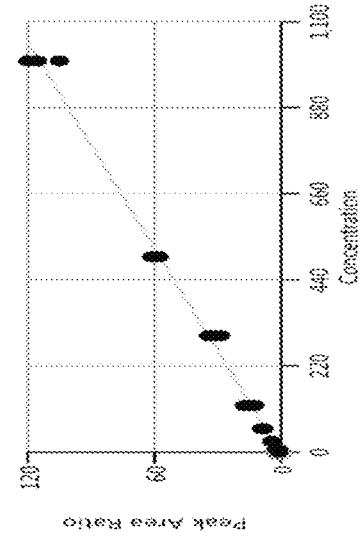

FIGS. 121A-D. Graphs showing examples of matrix matched calibration curves for pesticides in *cannabis*. FIG. 121A, myclobutanil; FIG. 121B, diazinon; FIG. 121C, metalaxyl; and FIG. 121D, phosmet.

Figure 122B:
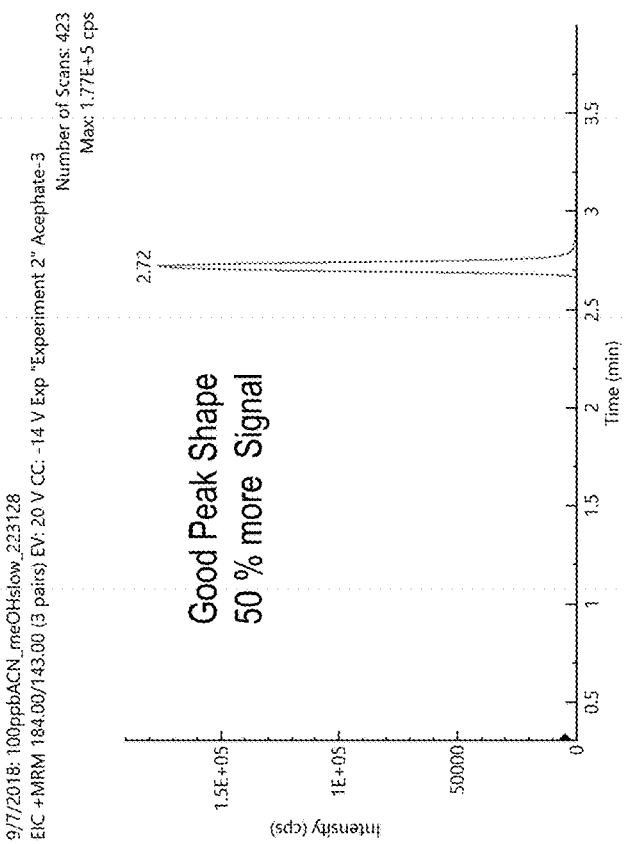
Figure 122A:
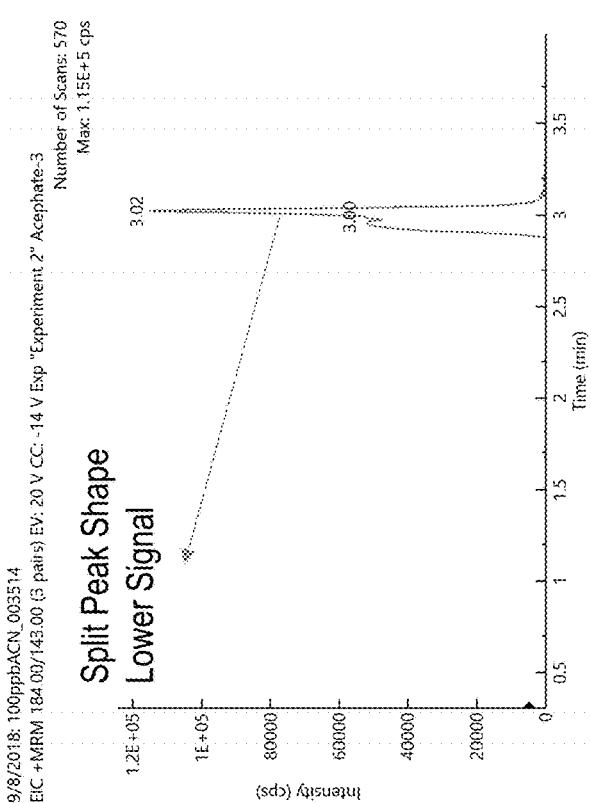

FIGS. 122A-B are chromatograms of *cannabis* samples comprising 100 ppb acephate and prepared using two extraction methods. FIG. 122A, acetonitrile. FIG. 122B, 50:50 acetonitrile and methanol.

Figure 123B:
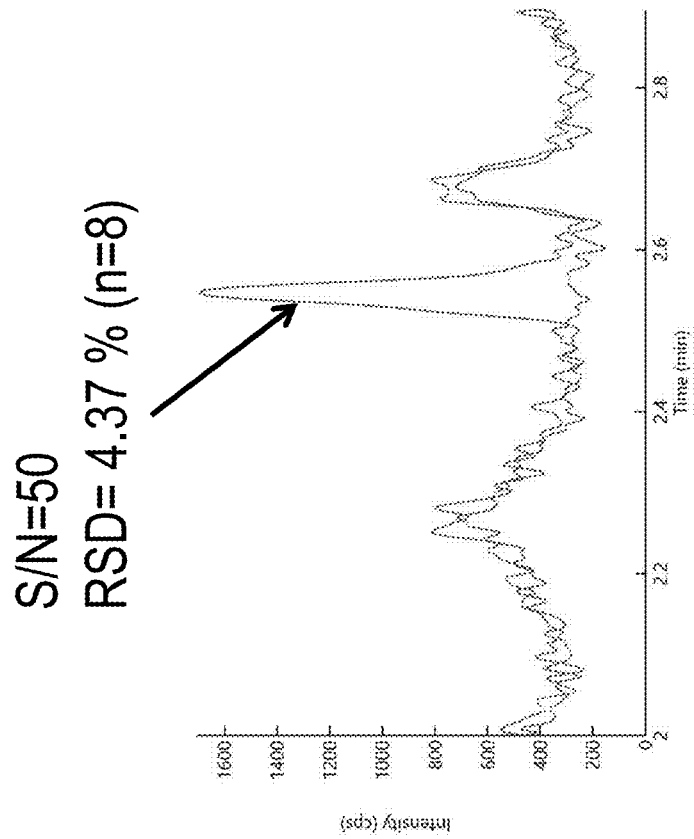
Figure 123A:
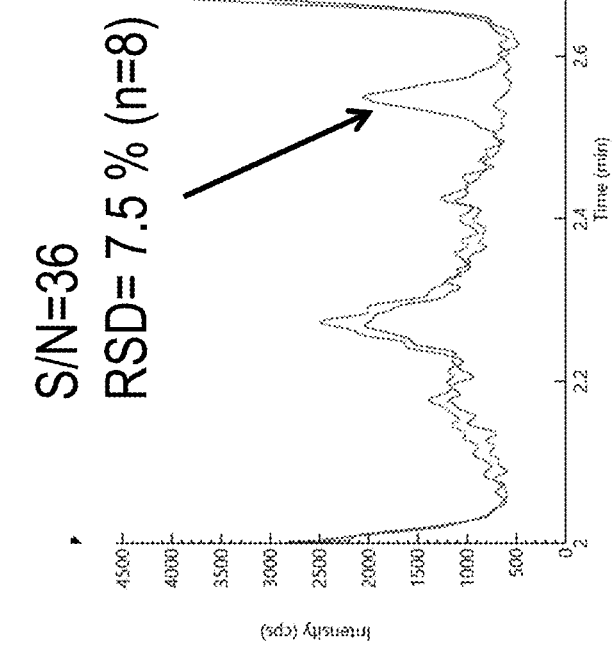

FIGS. 123A-B are chromatograms of *cannabis* samples comprising 100 ppb chlorfenapyr and ionized using an APCI source. FIG. 123A, MRM transition 346.9>79; FIG. 123B, MRM transition 348.09>81.

DETAILED DESCRIPTION

The analysis of pesticides, e.g., in botanical material, typically requires using both gas chromatography mass spectrometry (GC-MS) and liquid chromatography mass spectrometry (LC-MS) methods because some non-polar and chlorinated pesticides are difficult to ionize with the electrospray ion source used in LC-MS systems. This disclosure provides simple, cost-effective, rapid, and robust LC-MS/MS methods that provide limits of quantification (LOQs) for panels of pesticides well below, for example, the action limits set by state regulators for these compounds in, for example, *cannabis* products.

In fact, the disclosed methods and systems are particularly useful for the detection and/or quantification of pesticides in samples comprising *cannabis* plant material. Unless otherwise specified in this disclosure, "*cannabis*" encompasses all varieties of *cannabis* plants including, but not limited to, *cannabis* plants containing relatively high levels of tetrahydrocannabinol (THC), such as marijuana; and *cannabis* plants containing lower levels of THC and higher levels of cannabidiol (CBD), such as hemp. *Cannabis* plant material comprises a complex matrix that includes components such as cannabinoids, terpenes, and other non-cannabinoid compounds. Cannabinoids are typically present in *cannabis* plant material in amounts ranging from 10-20% (corresponding from 100,000 to 200,000 parts per million (ppm)). Terpenes and other non-cannabinoid compounds are also present in high amounts, ranging approximately from 10 to 5,000 ppm. In order to ensure safety for human consumption and/or compliance with regulatory action limits, however, pesticide levels need to be detected in amounts ranging from 0.00001 to 00010% (corresponding to 100 to 1,000 parts per billion (ppb)). Accordingly, interference from matrix components, such as cannabinoids, terpenes, and other compounds, can overwhelm and mask desired signals from trace amounts of pesticides in *cannabis* samples. Moreover, in certain embodiments, samples comprising *cannabis* extracts are diluted by factors of 10 (e.g., to reduce levels of matrix interference). Detection of small quantities of pesticides in diluted samples such as these accordingly requires extremely sensitive techniques. The approaches described herein provide sufficient sensitivity to detect and/or quantify pesticides at levels well below the various action limits specified by Oregon and California regulatory agencies.

In addition, while certain pesticides found in such regulatory panels can be analyzed via ESI, which is implemented in combination with LC separation in LC-based instruments, several cannot. In particular, pesticides that particularly hydrophobic and/or chlorinated (e.g., quintozene (also referred to as pentachloronitrobenzene), chlordane, endosulfan I, endosulfan II, and etridiazole) cannot be analyzed using ESI techniques or other conventional LC-compatible ionization methods. Instead, GC-based techniques are typically used to analyze these pesticides. Accordingly, testing samples for panels of pesticides generally requires multiple runs on multiple mass spectrometry instruments (LC-based instruments and GC-based instruments), making pesticide detection and/or quantification of samples expensive and time-consuming.

The approaches described herein overcome a number of challenges associated with detection of pesticides that limit accuracy and make conventional pesticide detection approaches a costly and time consuming process. First, the methods use one or more MRM transitions for each pesticide that have little or no matrix interference, improving the LOQs for acequinocyl and propiconazole, for example, by 20- and 5-fold, respectively.

Second, the disclosed methods permit detection of pesticides that typically have low signals in *cannabis* samples (e.g., abamectin, naled, daminozide, MGK-264).

Third, the methods use a fast LC method for high sample throughput and can reduce run time from 30 minutes to 18.5 minutes, including equilibration time.

Fourth, the disclosed methods include simple and fast sample preparation procedures with acceptable recoveries.

Fifth, the disclosed methods can detect pesticides which have low proton affinity and, therefore, low ionization efficiency (e.g., cypermethrin, cyfluthrin, captan, naled, permethrin, and pyrethrins).

Sixth, the methods use an APCI source to ionize highly chlorinated and non-polar pesticides (e.g., PCNB, chlordane), which eliminates the need to use GC-MS to detect these pesticides. This permits the analysis of panels of pesticides and mycotoxins to be carried out using only one instrument (e.g., a PerkinElmer QSIGHT® triple quad LC-MS/MS system), eliminating the need to change hardware.

Seventh, even for chlorfenapyr, which typically is analyzed using an ESI source, the disclosed methods provide not only recommended MRM transitions for use with an ESI source, but also MRM transitions that can be used with an APCI source to provide less matrix interference and less ion suppression which provides better sensitivity than ESI source for analysis of this compound in *cannabis* matrix.

Eighth, the testing of pesticides in complex matrices such as can foul conventional GC-MS and LC-MS systems rapidly, increasing maintenance costs and downtime, resulting in loss of productivity. Therefore, in some embodiments, the QSight system's STAYCLEAN™ technology is used. This technology employs hot-surface induced desolvation (HSID™), in which a continuous flow of hot gas acts as a constant cleaning agent to flush away potential deposits. Ions are transferred from the HSID interface to the system's laminar flow ion guide, then moved to the analyzing region by a flow of background gas and no axial electrical fields are necessary. This means that the QSight system is not susceptible to electric field fluctuations and delivers consistently high levels of performance without stopping for periodic maintenance while analyzing pesticides in these complex matrices.

Ninth, conventional LCMSMS approaches that utilize APCI or ESI sources use LC methods that employ mobile phases with additives such as formic acid, ammonium formate, and others. These additives are believed to assist with ionization of analytes in samples. In certain embodiments, however, the APCI technique described herein leverages the surprising discovery that detection and/or quantification limits for certain pesticides improved when LC methods that excluded certain additives (e.g., up to all additives) were used to produce the separation stream that was ionized with the APCI source.

In particular, in order to detect and/or quantify certain particularly hydrophobic and/or chlorinated pesticides (e.g., chlordane, quintozene, endosulfan I, endosulfan II, etridiazole), samples may be processed using LC methods that employ mobile phases without acidic and/or neutral additives (e.g., without any additives) and subsequently ionized with an APCI source. In certain embodiments, LC methods that employ mobile phases that include neutral additives (e.g., ammonium acetate; e g, ammonium formate), but exclude acidic additives are used in combination with APCI.

Without wishing to be bound to a particular theory or observation, it was found that when such pesticides were analyzed using an APCI source, highest signals were observed when LC methods employing mobile phases without any additives were used. Addition of neutral additives, such as ammonium acetate and ammonium formate, was observed to reduce signals by a factor of 2 to 5. Signals for chlorinated pesticides ionized with an APCI source were found to be reduced by factors of 20 to 50 when acidic additives, such as formic acid and acetic acid, were used.

MRM Transitions

This disclosure provides one or more specific MRM transition for each pesticide In this disclosure, MRM transitions are identified by two numbers that correspond to a first and a second m/z value, respectively, separated by ">" or "/" (e.g., 385.2>343.1 or 385.2/343.1). That is, the first value corresponds to the precursor ion, and the second value corresponds to the product ion after fragmentation of the precursor ion in the collision cell. Depending on the sensitivity of the mass spectrometer, some variability is possible for the transitions provided in this disclosure (e.g., ±0.1 or +0.2). Thus, for example, "385.2>343.1" may encompass one or more of 385.1>343.1, 385.0>343.1, 385.3>343.1, 385.4>343.1, 385.1>343.2, 385.0>343.2, 385.3>343.2, 385.4>343.2, 385.1>343.3, 385.0>343.3, 385.3>343.3, 385.4>343.3, 385.1>343.0, 385.0>343.0, 385.3>343.0, 385.4>343.0, 385.1>342.9, 385.0>342.9, 385.3>342.9, and 385.4>342.9.

Pesticides that can be detected using the disclosed methods are listed in Table 1 and include pesticides (in bold) that typically are analyzed using GC-MS. The unique MRM transitions used to detect these pesticides are provided in Table 2A and in Table 3. Recommended MRM transitions for detecting mycotoxins are provided in Table 4.

The following abbreviations are used in Tables 2A, 2B, 3, and 4: Q1 (first quadrupole), Q2 (second quadrulpole), CE (collision energy), EV (electronvolt), and CCL2 (collision cell lens 2). In Table 2B, Table 3, and Table 4, the columns labeled "Expected R.T." (expected retention time), "ΔTime" (Total+-change in retention time from expected retention time), "Res" (resolution settings on quadrupole 1 and 2, and "Res_Diff" (Resolution different when default unit/unit resolution setting is not used) refer to those parameters when a PerkinElmer QSight LC-MS/MS system is used.

TABLE 1

Pesticides and CAS Numbers

| Pesticide | CAS Number |
| --- | --- |
| Abamectin | 71751-41-2 |
| Acephate | 30560-19-1 |
| Acequinocyl | 57960-19-17 |
| Acetamiprid | 135410-20-7 |
| Aldicarb | 116-06-3 |
| Azoxystrobin | 131860-33-8 |
| Bifenazate | 149877-41-8 |
| Bifenthrin | 82657-04-3 |
| Boscalid | 188425-85-6 |
| Captan | 133-06-2 |
| Carbaryl | 63-25-2 |
| Carbofuran | 1563-66-2 |
| Chlorantraniliprole | 500008-45-7 |
| Chlordane | 57-74-9 |
| Chlorfenapyr | 122453-73-0 |
| Chlorpyrifos | 2921-88-2 |
| Clofentezine | 74115-24-5 |
| Coumaphos | 56-72-4 |
| Cyfluthrin | 68359-37-5 |
| Cypermethrin | 52315-07-8 |
| daminozide | 1596-84-5 |
| DDVP (Dichlorvos) | 62-73-7 |
| Diazinon | 333-41-5 |
| Dimethoate | 60-51-5 |
| Dimethomorph | 110488-70-5 |
| Ethoprop(hos) | 131947-48-4 |
| Etofenprox | 80844-07-1 |
| Etoxazole | 153233-91-1 |
| Etridiazole | 2593-15-9 |
| Fenhexamid | 126833-17-8 |
| Fenoxycarb | 72490-01-8 |
| Fenpyroximate | 111812-58-9 |
| Fipronil | 120068-37-3 |
| Flonicamid | 158062-67-0 |
| Fludioxonil | 131341-86-1 |
| Hexythiazox | 78587-05-0 |
| Imazalil | 35554-44-0 |
| Imidacloprid | 138261-41-3 |
| Kresoxim-methyl | 143390-89-0 |
| Malathion | 121-75-5 |
| Metalaxyl | 57837-19-1 |
| Methiocarb | 2032-65-7 |
| Methomyl | 16752-77-5 |

TABLE 1-continued

Pesticides and CAS Numbers

| Pesticide | CAS Number |
| --- | --- |
| Methyl parathion (also referred to as parathion methyl or methylparathion) | 298-00-0 |
| Mevinphos | 7786-34-7 |
| Myclobutanil | 88671-89-0 |
| Naled | 300-76-5 |
| N-Octyl bicycloheptene dicarboximide (MGK-264) | 113-48-4 |
| Oxamyl | 23125-22-0 |
| Paclobutrazol | 76738-62-0 |
| Pentachloronitrobenzene (PCNB; quintozene) | 82-68-8 |
| Permethrin | 52645-53-1 |
| Phosmet | 731-11-6 |
| Piperonylbutoxide | 51-03-6 |
| Prallethrin | 23031-36-9 |
| Propiconazole | 60207-90-1 |
| Propoxur | 114-26-1 |
| Pyrethrins | 8003-34-7 |
| Pyridaben | 96489-71-3 |
| Spinetoram | 187166-15-0, 187166-40-1 |
| Spinosad | 131929-60-7, 131929-63-0 |
| Spiromesifen | 283594-90-1 |
| Spirotetramat | 203313-25-1 |
| Spiroxamine | 118134-30-8 |
| Tebuconazole | 107534-96-3 |
| Thiacloprid | 111988-49-9 |
| Thiamethoxam | 153719-23-4 |
| Trifloxystrobin | 141517-21-7 |

TABLE 2A

Recommended MRM transitions for ESI-MS.

| Mode | Target | Q1 | Q2 | CE | EV | CCL2 |
| --- | --- | --- | --- | --- | --- | --- |
| + | Abamectin-1 | 890.5 | 145.0 | −48 | 10 | −110 |
| + | Abamectin-2 | 890.5 | 305.1 | −36 | 10 | −100 |
| + | Abamectin-3 | 890.5 | 567.2 | −18 | 20 | −90 |
| + | Acephate-1 | 184.0 | 49.0 | −28 | 20 | −40 |
| + | Acephate-2 | 184.0 | 95.0 | −32 | 20 | −40 |
| + | Acephate-3 | 184.0 | 143.0 | −14 | 20 | −50 |
| + | Acequinocyl-1 | 402.2 | 343.1 | −20 | 10 | −70 |
| + | Acequinocyl-2 | 402.2 | 189.0 | −40 | 10 | −70 |
| + | Acetamiprid-1 | 223.1 | 99.0 | −58 | 20 | −80 |
| + | Acetamiprid-2 | 223.1 | 126.0 | −30 | 20 | −70 |
| + | Aldicarb-1 | 208.0 | 116.0 | −8 | 15 | −30 |
| + | Aldicarb-2 | 208.0 | 89.0 | −22 | 15 | −30 |
| + | Atrazine-D$_5$ | 221.1 | 179.0 | −24 | 10 | −70 |
| + | Azoxystrobin-1 | 404.1 | 344.0 | −32 | 20 | −90 |
| + | Azoxystrobin-2 | 404.1 | 372.0 | −20 | 20 | −70 |
| + | Bifenazate-1 | 301.1 | 170.0 | −30 | 20 | −70 |
| + | Bifenazate-2 | 301.1 | 198.0 | −18 | 20 | −45 |
| + | Bifenthrin-1 | 440.1 | 166.1 | −76 | 15 | −90 |
| + | Bifenthrin-2 | 440.1 | 181.1 | −28 | 15 | −70 |
| + | Boscalid-1 | 343.0 | 140.0 | −28 | 20 | −70 |
| + | Boscalid-2 | 343.0 | 272.0 | −44 | 20 | −100 |
| + | Boscalid-3 | 343.0 | 307.0 | −26 | 20 | −65 |
| + | Captan-1 | 316.9 | 263.9 | −16 | 12 | −55 |
| + | Captan-2 | 316.9 | 235.9 | −24 | 12 | −65 |
| + | Captan-3 | 318.9 | 265.9 | −16 | 12 | −55 |
| + | Captan-4 | 318.9 | 237.9 | −24 | 12 | −65 |
| + | Carbaryl-1 | 202.1 | 127.0 | −42 | 20 | −40 |
| + | Carbaryl-2 | 202.1 | 145.0 | −20 | 20 | −40 |
| + | Carbaryl-D$_7$ | 209.2 | 152.1 | −25 | 20 | −70 |
| + | Carbofuran-1 | 222.1 | 123.0 | −30 | 20 | −60 |
| + | Carbofuran-2 | 222.1 | 165.0 | −18 | 20 | −50 |
| + | Chlorantraniliprole-1 | 484.0 | 285.9 | −18 | 20 | −60 |
| + | Chlorantraniliprole-2 | 484.0 | 452.9 | −22 | 20 | −80 |
| + | Chlorfenapyr-1 | 409.0 | 59.1 | −22 | 35 | −60 |
| + | Chlorfenapyr-2 | 407.0 | 59.1 | −22 | 35 | −50 |
| + | Chlorfenapyr-3 | 424.0 | 59.1 | −26 | 10 | −60 |
| + | Chlorfenapyr-4 | 426.0 | 59.1 | −26 | 10 | −60 |

TABLE 2A-continued

Recommended MRM transitions for ESI-MS.

| Mode | Target | Q1 | Q2 | CE | EV | CCL2 |
|---|---|---|---|---|---|---|
| + | Chlorpyrifos-1 | 349.9 | 97.0 | −66 | 20 | −90 |
| + | Chlorpyrifos-2 | 349.9 | 198.0 | −28 | 20 | −70 |
| + | Chlorpyrifos-3 | 349.9 | 321.9 | −14 | 20 | −60 |
| + | Cinerin-I-1 | 317.2 | 107.0 | −42 | 20 | −70 |
| + | Cinerin-I-2 | 317.2 | 121.0 | −25 | 20 | −70 |
| + | Cinerin-I-3 | 317.2 | 149.0 | −16 | 20 | −70 |
| + | Cinerin-II-1 | 361.2 | 149.0 | −18 | 20 | −75 |
| + | Cinerin-II-2 | 361.2 | 213.0 | −16 | 20 | −75 |
| + | Clofentezine-1 | 303.0 | 102.0 | −54 | 20 | −70 |
| + | Clofentezine-2 | 303.0 | 138.0 | −22 | 20 | −60 |
| + | Coumaphos-1 | 363.0 | 306.9 | −22 | 30 | −80 |
| + | Coumaphos-2 | 363.0 | 334.9 | −20 | 30 | −75 |
| + | Coumaphos-3 | 363.0 | 226.9 | −32 | 30 | −100 |
| + | Cyfluthrin-1 | 453.1 | 193.0 | −21 | 15 | −60 |
| + | Cyfluthrin-2 | 451.1 | 127.0 | −46 | 15 | −75 |
| + | Cyfluthrin-3 | 451.1 | 191.0 | −24 | 15 | −60 |
| + | Cyfluthrin-4 | 451.1 | 206.0 | −66 | 15 | −60 |
| + | Cypermethrin-1 | 435.1 | 193.1 | −23 | 15 | −60 |
| + | Cypermethrin-2 | 435.1 | 127.0 | −50 | 15 | −70 |
| + | Cypermethrin-3 | 433.1 | 127.0 | −52 | 15 | −70 |
| + | Cypermethrin-4 | 433.1 | 191.1 | −24 | 15 | −60 |
| + | Daminozide-1 | 161.1 | 44.0 | −50 | 20 | −30 |
| + | Daminozide-2 | 161.1 | 45.0 | −30 | 20 | −30 |
| + | Daminozide-3 | 161.1 | 143.0 | −14 | 20 | −30 |
| + | Daminozide-$D_4$ | 165.1 | 147.0 | −14 | 15 | −40 |
| + | Diazinon-1 | 305.1 | 97.0 | −66 | 20 | −60 |
| + | Diazinon-2 | 305.1 | 169.0 | −34 | 20 | −60 |
| + | Diazinon-$D_{10}$ | 315.2 | 170.0 | −33 | 10 | −68 |
| + | Dichlorvos-1 | 220.9 | 109.0 | −22 | 20 | −50 |
| + | Dichlorvos-2 | 220.9 | 127.0 | −32 | 20 | −60 |
| + | Dichlorvos-$D_6$ | 227.0 | 115.0 | −13 | 10 | −60 |
| + | Dimethoate-1 | 230.0 | 125.0 | −32 | 20 | −60 |
| + | Dimethoate-2 | 230.0 | 199.0 | −12 | 20 | −40 |
| + | Dimethoate-$D_6$ | 236.1 | 205.0 | −12 | 10 | −60 |
| + | Dimethomorph-1 | 388.1 | 301.0 | −26 | 15 | −80 |
| + | Dimethomorph-2 | 388.1 | 273.0 | −42 | 15 | −85 |
| + | Ethoprophos-1 | 243.1 | 131.0 | −28 | 20 | −50 |
| + | Ethoprophos-2 | 243.1 | 173.0 | −20 | 20 | −50 |
| + | Etofenprox-1 | 394.2 | 107.1 | −78 | 15 | −90 |
| + | Etofenprox-2 | 394.2 | 177.1 | −28 | 15 | −60 |
| + | Etofenprox-3 | 394.2 | 359.1 | −14 | 15 | −60 |
| + | Etoxazole-1 | 360.2 | 57.1 | −60 | 20 | −80 |
| + | Etoxazole-2 | 360.2 | 141.0 | −50 | 20 | −70 |
| + | Fenhexamid-1 | 302.1 | 55.0 | −68 | 30 | −80 |
| + | Fenhexamid-2 | 302.1 | 97.0 | −32 | 30 | −55 |
| + | Fenoxycarb-1 | 302.1 | 88.0 | −32 | 20 | −60 |
| + | Fenoxycarb-2 | 302.1 | 116.0 | −14 | 20 | −50 |
| + | Fenoxycarb-3 | 302.1 | 256.0 | −14 | 20 | −50 |
| + | Fenpyroximate-1 | 422.2 | 135.0 | −46 | 20 | −75 |
| + | Fenpyroximate-2 | 422.2 | 138.0 | −74 | 20 | −110 |
| + | Fenpyroximate-3 | 422.2 | 366.1 | −24 | 20 | −60 |
| − | Fipronil-1 | 435.0 | 250.0 | 36 | −20 | 80 |
| − | Fipronil-2 | 435.0 | 330.0 | 20 | −20 | 70 |
| + | Flonicamid-1 | 230.1 | 174.0 | −22 | 20 | −60 |
| + | Flonicamid-2 | 230.1 | 203.0 | −22 | 20 | −50 |
| − | Fludioxonil-1 | 247.1 | 126.0 | 42 | −20 | 80 |
| − | Fludioxonil-2 | 247.1 | 180.0 | 39 | −20 | 70 |
| + | Hexythiazox-1 | 353.1 | 168.0 | −34 | 20 | −70 |
| + | Hexythiazox-2 | 353.1 | 228.0 | −22 | 20 | −60 |
| + | Imazalil-1 | 297.0 | 41.0 | −76 | 20 | −80 |
| + | Imazalil-2 | 297.0 | 159.0 | −28 | 20 | −60 |
| + | Imazalil-3 | 297.0 | 201.0 | −24 | 20 | −60 |
| + | Imidacloprid-1 | 256.1 | 175.0 | −24 | 20 | −60 |
| + | Imidacloprid-2 | 256.1 | 209.0 | −22 | 20 | −60 |
| + | Imidacloprid-$D_4$ | 260.2 | 213.0 | −18 | 20 | −60 |
| + | Jasmolin-I-2 | 331.2 | 121.0 | −28 | 20 | −50 |
| + | Jasmolin-I-3 | 331.2 | 163.0 | −16 | 20 | −50 |
| + | Jasmolin-II-2 | 375.2 | 163.0 | −16 | 20 | −60 |
| + | Jasmolin-II-3 | 375.2 | 213.0 | −14 | 20 | −65 |
| + | Kresoxim-methyl-1 | 314.1 | 222.0 | −22 | 20 | −60 |
| + | Kresoxim-methyl-2 | 314.1 | 235.0 | −20 | 20 | −50 |
| + | Malathion-1 | 331.0 | 127.0 | −16 | 20 | −60 |
| + | Malathion-2 | 331.0 | 285.0 | −10 | 20 | −60 |
| + | Metalaxyl-1 | 280.2 | 192.1 | −22 | 20 | −60 |
| + | Metalaxyl-2 | 280.2 | 220.1 | −18 | 20 | −50 |
| + | Metalaxyl-3 | 280.2 | 248.1 | −14 | 20 | −50 |
| + | Methiocarb-1 | 226.1 | 121.0 | −26 | 20 | −45 |
| + | Methiocarb-2 | 226.1 | 169.0 | −14 | 20 | −35 |
| + | Methomyl-1 | 163.1 | 88.0 | −14 | 20 | −30 |
| + | Methomyl-2 | 163.1 | 106.0 | −14 | 20 | −30 |
| + | Mevinphos-1 | 242.2 | 127.0 | −20 | 12 | −50 |
| + | Mevinphos-2 | 242.0 | 109.0 | −48 | 12 | −80 |
| + | Mevinphos-3 | 225.0 | 127.0 | −20 | 25 | −50 |
| + | Mevinphos-4 | 225.0 | 109.0 | −48 | 25 | −80 |
| + | Myclobutanil-1 | 289.1 | 70.0 | −24 | 20 | −60 |
| + | Myclobutanil-2 | 289.1 | 125.0 | −48 | 20 | −90 |
| + | Myclobutanil-$D_9$ | 298.0 | 70.0 | −22 | 20 | −40 |
| + | Naled-1 | 380.8 | 127.0 | −20 | 20 | −80 |
| + | Naled-2 | 382.8 | 127.0 | −20 | 20 | −80 |
| + | Naled-3 | 380.8 | 109.0 | −64 | 20 | −80 |
| + | N-Octyl bicycloheptene dicarboximide (MGK-264)-1 | 276.2 | 210.0 | −20 | 20 | −60 |
| + | N-Octyl bicycloheptene dicarboximide (MGK-264)-2 | 276.2 | 98.0 | −32 | 20 | −60 |
| + | Oxamyl-1 | 237.1 | 72.0 | −36 | 15 | −80 |
| + | Oxamyl-2 | 237.1 | 90.0 | −12 | 15 | −35 |
| + | Paclobutrazol-1 | 294.1 | 70.0 | −25 | 20 | −60 |
| + | Paclobutrazol-2 | 294.1 | 125.0 | −48 | 20 | −70 |
| + | Parathion methyl-1 | 264.0 | 124.9 | −24 | 20 | −70 |
| + | Parathion methyl -2 | 264.0 | 231.9 | −20 | 20 | −50 |
| + | Permethrin-1 | 408.1 | 183.0 | −44 | 15 | −70 |
| + | Permethrin-2 | 408.1 | 355.0 | −12 | 15 | −60 |
| + | Phosmet-1 | 318.0 | 133.0 | −62 | 20 | −75 |
| + | Phosmet-2 | 318.0 | 160.0 | −34 | 20 | −60 |
| + | Piperonyl butoxide-1 | 356.2 | 119.0 | −52 | 10 | −60 |
| + | Piperonyl butoxide-2 | 356.2 | 177.0 | −28 | 10 | −50 |
| + | Prallethrin-1 | 301.2 | 123.0 | −22 | 20 | −50 |
| + | Prallethrin-2 | 301.2 | 132.9 | −16 | 20 | −50 |
| + | Prallethrin-3 | 301.2 | 168.9 | −12 | 20 | −50 |
| + | Propiconazole-1 | 342.1 | 69.0 | −28 | 20 | −60 |
| + | Propiconazole-2 | 342.1 | 159.0 | −52 | 20 | −80 |
| + | Propiconazole-3 | 344.1 | 69.0 | −28 | 20 | −60 |
| + | Propiconazole-4 | 344.1 | 161.0 | −52 | 20 | −80 |
| + | Propoxur-1 | 210.1 | 111.0 | −22 | 20 | −40 |
| + | Propoxur-2 | 210.1 | 168.0 | −12 | 20 | −40 |
| + | Pyrethrin-I-2 | 329.2 | 143.0 | −32 | 20 | −60 |
| + | Pyrethrin-I-3 | 329.2 | 161.0 | −16 | 20 | −50 |
| + | Pyrethrin-II-2 | 373.2 | 143.0 | −38 | 20 | −50 |
| + | Pyrethrin-II-3 | 373.2 | 161.0 | −14 | 20 | −50 |
| + | Pyridaben-1 | 365.1 | 147.0 | −36 | 20 | −70 |
| + | Pyridaben-2 | 365.1 | 309.0 | −20 | 20 | −60 |
| + | Pyridaben-$D_{13}$ | 378.0 | 160.0 | −36 | 20 | −65 |
| + | Spinetoram-1 | 748.5 | 98.0 | −96 | 15 | −140 |
| + | Spinetoram-2 | 748.5 | 142.0 | −38 | 15 | −120 |
| + | Spinosyn A-1 | 732.5 | 98.0 | −80 | 20 | −100 |
| + | Spinosyn A-2 | 732.5 | 142.0 | −38 | 20 | −90 |
| + | Spinosyn D-1 | 746.5 | 98.0 | −76 | 20 | −100 |
| + | Spinosyn D-2 | 746.5 | 142.0 | −40 | 20 | −90 |
| + | Spiromesifen-1 | 273.1 | 187.0 | −24 | 40 | −50 |
| + | Spiromesifen-2 | 273.1 | 255.0 | −22 | 40 | −50 |
| + | Spirotetramat-1 | 374.2 | 216.0 | −46 | 20 | −90 |
| + | Spirotetramat-2 | 374.2 | 302.1 | −22 | 20 | −60 |
| + | Spiroxamine-1 | 298.3 | 100.1 | −50 | 20 | −70 |
| + | Spiroxamine-2 | 298.3 | 144.1 | −28 | 20 | −60 |
| + | Tebuconazole-1 | 308.0 | 70.0 | −28 | 20 | −55 |
| + | Tebuconazole-2 | 308.0 | 125.0 | −52 | 20 | −90 |
| + | Thiachloprid-1 | 253.0 | 99.0 | −66 | 20 | −100 |
| + | Thiachloprid-2 | 253.0 | 126.0 | −30 | 20 | −80 |
| + | Thiamethoxam-1 | 292.0 | 181.0 | −34 | 20 | −70 |
| + | Thiamethoxam-2 | 292.0 | 211.0 | −18 | 20 | −60 |
| + | Thiamethoxam-$D_4$ | 296.0 | 215.0 | −18 | 20 | −60 |
| + | Thiophanate methyl-1 | 343.1 | 151.0 | −30 | 20 | −60 |
| + | Thiophanate methyl-2 | 343.1 | 268.0 | −14 | 20 | −60 |
| + | Trifloxystrobin-1 | 409.1 | 186.0 | −28 | 20 | −60 |
| + | Trifloxystrobin-2 | 409.1 | 206.0 | −20 | 20 | −60 |

TABLE 2B

| | Parameters for PerkinElmer QSight | | | |
|---|---|---|---|---|
| Target | Expected R.T. | ΔTime | Res | Res_Diff |
| Abamectin-1 | 12.71 | 0.7 | Low_Low | Low_Low |
| Abamectin-2 | 12.71 | 0.7 | Low_Low | Low_Low |
| Abamectin-3 | 12.71 | 0.7 | Low_Low | Low_Low |
| Acephate-1 | 2.10 | 3.6 | Low_Unit | Low_Unit |
| Acephate-2 | 2.10 | 3.6 | Low_Unit | Low_Unit |
| Acephate-3 | 2.10 | 3.6 | Low_Unit | Low_Unit |
| Acequinocyl-1 | 14.09 | 0.7 | Unit_Unit | |
| Acequinocyl-2 | 14.09 | 0.7 | Unit_Unit | |
| Acetamiprid-1 | 5.05 | 0.7 | Unit_Unit | |
| Acetamiprid-2 | 5.05 | 0.7 | Unit_Unit | |
| Aldicarb-1 | 5.55 | 0.7 | Unit_Unit | |
| Aldicarb-2 | 5.55 | 0.7 | Unit_Unit | |
| Atrazine-D5 | 6.82 | 0.7 | Unit_Unit | |
| Azoxystrobin-1 | 7.58 | 0.7 | Unit_Unit | |
| Azoxystrobin-2 | 7.58 | 0.7 | Unit_Unit | |
| Bifenazate-1 | 8.22 | 0.7 | Unit_Unit | |
| Bifenazate-2 | 8.22 | 0.7 | Unit_Unit | |
| Bifenthrin-1 | 12.96 | 0.7 | Unit_Unit | |
| Bifenthrin-2 | 12.96 | 0.7 | Unit_Unit | |
| Boscalid-1 | 7.77 | 0.7 | Unit_Unit | |
| Boscalid-2 | 7.77 | 0.7 | Unit_Unit | |
| Boscalid-3 | 7.77 | 0.7 | Unit_Unit | |
| Captan-1 | 7.19 | 0.7 | Unit_Unit | |
| Captan-2 | 7.19 | 0.7 | Unit_Unit | |
| Captan-3 | 7.19 | 0.7 | Unit_Unit | |
| Captan-4 | 7.19 | 0.7 | Unit_Unit | |
| Carbaryl-1 | 6.23 | 0.7 | Unit_Unit | |
| Carbaryl-2 | 6.23 | 0.7 | Unit_Unit | |
| Carbaryl-D7 | 6.18 | 0.7 | Unit_Unit | |
| Carbofuran-1 | 6.02 | 0.7 | Unit_Unit | |
| Carbofuran-2 | 6.02 | 0.7 | Unit_Unit | |
| Chlorantraniliprole-1 | 7.11 | 0.7 | Low_Unit | Low_Unit |
| Chlorantraniliprole-2 | 7.11 | 0.7 | Low_Unit | Low_Unit |
| Chlorfenapyr-1 | 10.31 | 0.7 | Unit_Unit | |
| Chlorfenapyr-2 | 10.31 | 0.7 | Unit_Unit | |
| Chlorfenapyr-3 | 10.31 | 0.7 | Unit_Unit | |
| Chlorfenapyr-4 | 10.31 | 0.7 | Unit_Unit | |
| Chlorpyrifos-1 | 11.21 | 0.7 | Unit_Unit | |
| Chlorpyrifos-2 | 11.21 | 0.7 | Unit_Unit | |
| Chlorpyrifos-3 | 11.21 | 0.7 | Unit_Unit | |
| Cinerin-I-1 | 11.85 | 0.7 | Unit_Unit | |
| Cinerin-I-2 | 11.85 | 0.7 | Unit_Unit | |
| Cinerin-I-3 | 11.85 | 0.7 | Unit_Unit | |
| Cinerin-II-1 | 10.40 | 0.7 | Unit_Unit | |
| Cinerin-II-2 | 10.40 | 0.7 | Unit_Unit | |
| Clofentezine-1 | 9.70 | 0.7 | Unit_Unit | |
| Clofentezine-2 | 9.70 | 0.7 | Unit_Unit | |
| Coumaphos-1 | 9.61 | 0.7 | Unit_Unit | |
| Coumaphos-2 | 9.61 | 0.7 | Unit_Unit | |
| Coumaphos-3 | 9.61 | 0.7 | Unit_Unit | |
| Cyfluthrin-1 | 11.60 | 1.5 | Unit_Unit | |
| Cyfluthrin-2 | 11.60 | 1.5 | Unit_Unit | |
| Cyfluthrin-3 | 11.60 | 1.5 | Unit_Unit | |
| Cyfluthrin-4 | 11.60 | 1.5 | Unit_Unit | |
| Cypermethrin-1 | 11.85 | 1.5 | Unit_Unit | |
| Cypermethrin-2 | 11.85 | 1.5 | Unit_Unit | |
| Cypermethrin-3 | 11.85 | 1.5 | Unit_Unit | |
| Cypermethrin-4 | 11.85 | 1.5 | Unit_Unit | |
| Daminozide-1 | 1.50 | 3 | Unit_Unit | |
| Daminozide-2 | 1.50 | 3 | Unit_Unit | |
| Daminozide-3 | 1.50 | 3 | Unit_Unit | |
| Daminozide-$D_4$ | 1.50 | 3 | Unit_Unit | |
| Diazinon-1 | 9.55 | 0.7 | Unit_Unit | |
| Diazinon-2 | 9.55 | 0.7 | Unit_Unit | |
| Diazinon-$D_{10}$ | 9.46 | 0.7 | Unit_Unit | |
| Dichlorvos-1 | 5.96 | 0.7 | Unit_Unit | |
| Dichlorvos-2 | 5.96 | 0.7 | Unit_Unit | |
| Dichlorvos-$D_6$ | 5.93 | 0.7 | Unit_Unit | |
| Dimethoate-1 | 4.94 | 0.8 | Unit_Unit | |
| Dimethoate-2 | 4.94 | 0.8 | Unit_Unit | |
| Dimethoate-$D_6$ | 4.90 | 0.8 | Unit_Unit | |
| Dimethomorph-1 | 8.17 | 1.2 | Unit_Unit | |
| Dimethomorph-2 | 8.17 | 1.2 | Unit_Unit | |
| Ethoprophos-1 | 8.87 | 0.7 | Unit_Unit | |
| Ethoprophos-2 | 8.87 | 0.7 | Unit_Unit | |

TABLE 2B-continued

| | Parameters for PerkinElmer QSight | | | |
|---|---|---|---|---|
| Target | Expected R.T. | ΔTime | Res | Res_Diff |
| Etofenprox-1 | 12.96 | 0.7 | Unit_Unit | |
| Etofenprox-2 | 12.96 | 0.7 | Unit_Unit | |
| Etofenprox-3 | 12.96 | 0.7 | Unit_Unit | |
| Etoxazole-1 | 11.68 | 0.7 | Unit_Unit | |
| Etoxazole-2 | 11.68 | 0.7 | Unit_Unit | |
| Fenhexamid-1 | 8.39 | 0.7 | Unit_Unit | |
| Fenhexamid-2 | 8.39 | 0.7 | Unit_Unit | |
| Fenoxycarb-1 | 8.96 | 0.7 | Unit_Unit | |
| Fenoxycarb-2 | 8.96 | 0.7 | Unit_Unit | |
| Fenoxycarb-3 | 8.96 | 0.7 | Unit_Unit | |
| Fenpyroximate-1 | 12.21 | 0.7 | Unit_Unit | |
| Fenpyroximate-2 | 12.21 | 0.7 | Unit_Unit | |
| Fenpyroximate-3 | 12.21 | 0.7 | Unit_Unit | |
| Fipronil-1 | 8.62 | 0.7 | Low_Low | Low_Low |
| Fipronil-2 | 8.62 | 0.7 | Low_Low | Low_Low |
| Flonicamid-1 | 4.10 | 1 | Unit_Unit | |
| Flonicamid-2 | 4.10 | 1 | Unit_Unit | |
| Fludioxonil-1 | 7.70 | 0.7 | Low_Low | Low_Low |
| Fludioxonil-2 | 7.70 | 0.7 | Low_Low | Low_Low |
| Hexythiazox-1 | 11.25 | 0.7 | Unit_Unit | |
| Hexythiazox-2 | 11.25 | 0.7 | Unit_Unit | |
| Imazalil-1 | 6.14 | 1.4 | Unit_Unit | |
| Imazalil-2 | 6.14 | 1.4 | Unit_Unit | |
| Imazalil-3 | 6.14 | 1.4 | Unit_Unit | |
| Imidacloprid-1 | 4.60 | 0.8 | Unit_Unit | |
| Imidacloprid-2 | 4.60 | 0.8 | Unit_Unit | |
| Imidacloprid-D4 | 4.60 | 0.8 | Unit_Unit | |
| Jasmolin-I-2 | 12.36 | 0.7 | Unit_Unit | |
| Jasmolin-I-3 | 12.36 | 0.7 | Unit_Unit | |
| Jasmolin-II-2 | 11.05 | 0.7 | Unit_Unit | |
| Jasmolin-II-3 | 11.05 | 0.7 | Unit_Unit | |
| Kresoxim-methyl-1 | 9.16 | 0.7 | Unit_Unit | |
| Kresoxim-methyl-2 | 9.16 | 0.7 | Unit_Unit | |
| Malathion-1 | 7.98 | 0.7 | Unit_Unit | |
| Malathion-2 | 7.98 | 0.7 | Unit_Unit | |
| Metalaxyl-1 | 7.11 | 0.7 | Unit_Unit | |
| Metalaxyl-2 | 7.11 | 0.7 | Unit_Unit | |
| Metalaxyl-3 | 7.11 | 0.7 | Unit_Unit | |
| Methiocarb-1 | 7.72 | 0.7 | Unit_Unit | |
| Methiocarb-2 | 7.72 | 0.7 | Unit_Unit | |
| Methomyl-1 | 4.10 | 1 | Unit_Unit | |
| Methomyl-2 | 4.10 | 1 | Unit_Unit | |
| Mevinphos-1 | 5.33 | 2 | Unit_Unit | |
| Mevinphos-2 | 5.33 | 2 | Unit_Unit | |
| Mevinphos-3 | 5.33 | 2 | Unit_Unit | |
| Mevinphos-4 | 5.33 | 2 | Unit_Unit | |
| Myclobutanil-1 | 8.17 | 0.7 | Unit_Unit | |
| Myclobutanil-2 | 8.17 | 0.7 | Unit_Unit | |
| Myclcobutanil-D$_9$ | 8.17 | 0.7 | Unit_Unit | |
| Naled-1 | 7.05 | 0.7 | Low_Unit | Low_Unit |
| Naled-2 | 7.05 | 0.7 | Low_Unit | Low_Unit |
| Naled-3 | 7.05 | 0.7 | Low_Unit | Low_Unit |
| N-Octyl bicycloheptene dicarboximide (MGK-264)-1 | 10.4 | 1.2 | Unit_Unit | |
| N-Octyl bicycloheptene dicarboximide (MGK-264)-2 | 10.4 | 1.2 | Unit_Unit | |
| Oxamyl-1 | 3.80 | 0.8 | Unit_Unit | |
| Oxamyl-2 | 3.80 | 0.8 | Unit_Unit | |
| Paclobutrazol-1 | 7.90 | 0.7 | Unit_Unit | |
| Paclobutrazol-2 | 7.90 | 0.7 | Unit_Unit | |
| Parathion methyl-1 | 7.49 | 0.7 | Low_Unit | Low_Unit |
| Parathion methyl-2 | 7.49 | 0.7 | Low_Unit | Low_Unit |
| Permethrin-1 | 12.79 | 1.5 | Unit_Unit | |
| Permethrin-2 | 12.79 | 1.5 | Unit_Unit | |
| Phosmet-1 | 7.29 | 0.7 | Unit_Unit | |
| Phosmet-2 | 7.29 | 0.7 | Unit_Unit | |
| Piperonyl butoxide-1 | 11.14 | 0.7 | Unit_Unit | |
| Piperonyl butoxide-2 | 11.14 | 0.7 | Unit_Unit | |
| Prallethrin-1 | 10.25 | 1.2 | Unit_Unit | |
| Prallethrin-2 | 10.25 | 1.2 | Unit_Unit | |
| Prallethrin-3 | 10.25 | 1.2 | Unit_Unit | |
| Propiconazole-1 | 9.76 | 1 | Unit_Unit | |
| Propiconazole-2 | 9.76 | 1 | Unit_Unit | |
| Propiconazole-3 | 9.76 | 1 | Unit_Unit | |
| Propiconazole-4 | 9.76 | 1 | Unit_Unit | |

TABLE 2B-continued

Parameters for PerkinElmer QSight

| Target | Expected R.T. | ΔTime | Res | Res_Diff |
|---|---|---|---|---|
| Propoxur-1 | 5.94 | 0.7 | Unit_Unit | |
| Propoxur-2 | 5.94 | 0.7 | Unit_Unit | |
| Pyrethrin-I-2 | 11.88 | 0.7 | Unit_Unit | |
| Pyrethrin-I-3 | 11.88 | 0.7 | Unit_Unit | |
| Pyrethrin-II-2 | 10.49 | 0.7 | Unit_Unit | |
| Pyrethrin-II-3 | 10.49 | 0.7 | Unit_Unit | |
| Pyridaben-1 | 12.46 | 0.7 | Unit_Unit | |
| Pyridaben-2 | 12.46 | 0.7 | Unit_Unit | |
| Pyridaben-$D_{13}$ | 12.46 | 0.7 | Unit_Unit | |
| Spinetoram-1 | 10.19 | 0.7 | Low_Low | Low_Low |
| Spinetoram-2 | 10.19 | 0.7 | Low_Low | Low_Low |
| Spinosyn A-1 | 9.56 | 0.7 | Low_Low | Low_Low |
| Spinosyn A-2 | 9.56 | 0.7 | Low_Low | Low_Low |
| Spinosyn D-1 | 10.09 | 0.7 | Low_Low | Low_Low |
| Spinosyn D-2 | 10.09 | 0.7 | Low_Low | Low_Low |
| Spiromesifen-1 | 11.73 | 0.7 | Unit_Unit | |
| Spiromesifen-2 | 11.73 | 0.7 | Unit_Unit | |
| Spirotetramat-1 | 8.70 | 0.7 | Unit_Unit | |
| Spirotetramat-2 | 8.70 | 0.7 | Unit_Unit | |
| Spiroxamine-1 | 7.20 | 1.4 | Unit_Unit | |
| Spiroxamine-2 | 7.20 | 1.4 | Unit_Unit | |
| Tebuconazole-1 | 9.27 | 0.7 | Unit_Unit | |
| Tebuconazole-2 | 9.27 | 0.7 | Unit_Unit | |
| Thiachloprid-2 | 5.29 | 0.8 | Unit_Unit | |
| Thiachloprid-3 | 5.29 | 0.8 | Unit_Unit | |
| Thiamethoxam-1 | 4.20 | 0.8 | Unit_Unit | |
| Thiamethoxam-2 | 4.20 | 0.8 | Unit_Unit | |
| Thiamethoxam-$D_4$ | 4.20 | 0.8 | Unit_Unit | |
| Thiophanate methyl-1 | 5.74 | 0.6 | Unit_Unit | |
| Thiophanate methyl-2 | 5.74 | 0.6 | Unit_Unit | |
| Trifloxystrobin-1 | 10.12 | 0.7 | Unit_Unit | |
| Trifloxystrobin-2 | 10.12 | 0.7 | Unit_Unit | |

TABLE 2C

Challenging pesticides and associated MRM transitions. MRM transitions emphasized in bold either provide high signal and > or reduced (e.g., less or no) matrix interference from *cannabis* matrix.

| Pesticide | MRM transition 1 | 2 | 3 | 4 |
|---|---|---|---|---|
| Acephate | 184.0 > 145.0 | 184.0 > 49.0 | 184.0 > 95.0 | |
| Acequinocyl | 402.2 > 343.1 | 402.2 > 189.0 | 343.1 > 189.0 | 343.1 > 115.0 |
| Captan | 316.9 > 263.9 | 318.9 > 265.9 | | |
| Chlordane | 439.8 > 35.0 | 441.8 > 35.0 | | |
| Chlorfenapyr | 406.9 > 59.0 | 408.9 > 59.0 | 426.0 > 59.0 | 424.0 > 59.0 |
| | | | | 426.0 > 409.0 |
| Cinerin I | 317.2 > 149.0 | 317.2 > 107.0 | | |
| Cinerin II | 361.2 > 149.0 | 361.2 > 213.0 | | |
| Cyfluthrin | 451.1 > 191.0 | 453.1 > 193.0 | 451.1 > 127.0 | |
| Cypermethrin | 433.1 > 191.0 | 435.1 > 193.0 | 433.1 > 127.0 | |
| Daminozide | 161.1 > 143.0 | 161.1 > 44.0 | 161.1 > 45.0 | |
| Dimethomorph | 388.1 > 301.0 | 388.1 > 273.0 | 388.1 > 165.0 | |
| Etridiazole | 216.8 > 35.0 | 218.8 > 35.0 | | |
| Fenoxycarb | 302.1 > 116.0 | 302.1 > 256.0 | 302.1 > 88.0 | |
| Imazalil | 297.0 > 41.0 | 297.0 > 159.0 | 297.0 > 201.0 | |
| Jasmolin II | 375.2 > 163.0 | 375.2 > 213.0 | | |
| Malathion | 331.0 > 127.0 | 331.0 > 285.0 | 331.0 > 99.0 | |
| Mevinphos | 242.0 > 127.0 | 225.0 > 127.0 | 242.0 > 109.0 | 225.0 > 109.0 |
| MGK-264 | 276.2 > 210.0 | 276.2 > 98.0 | | |
| Naled | 380.8 > 127.0 | 382.8 > 127.0 | 378.8 > 127.0 | 380.8 > 109.0 |
| PCNB | 275.8 > 35.0 | 273.8 > 35.0 | 275.8 > 201.8 | 273.8 > 199.8 |
| Propiconazole | 344.1 > 161.0 | 344.1 > 69.0 | 342.1 > 159.0 | 342.1 > 69.0 |
| Pyrethrin I | 329.2 > 163.0 | 329.2 > 143.0 | 329.2 > 133.0 | |
| Pyrethrin II | 373.2 > 163.0 | 373.2 > 143.0 | 373.2 > 133.0 | |

TABLE 2D

Challenging pesticides and associated MRM transitions that provide high signal and > or reduced (e.g., less or no) interference from *cannabis* matrix.

| Pesticide | MRM transition 1 | 2 | 3 | 4 |
|---|---|---|---|---|
| Acephate | | 184.0 > 49.0 | | |
| Acequinocyl | 402.2 > 343.1 | 402.2 > 189.0 | 343.1 > 189.0 | 343.1 > 115.0 |
| Captan | 316.9 > 263.9 | 318.9 > 265.9 | | |
| Chlordane | 439.8 > 35.0 | 441.8 > 35.0 | | |
| Chlorfenpyr | 406.9 > 59.0 | 408.9 > 59.0 | | 424 > 59.0 |
| | | | | 426 > 409.0 |
| Cinerin I | | 317.2 > 107.0 | | |
| Cinerin II | | 361.2 > 213.0 | | |
| Cyfluthrin | | 453.1 > 193.0 | | |
| Cypermethrin | | 435.1 > 193.0 | | |
| Daminozide | | 161.1 > 44.0 | 161.1 > 45.0 | |
| Dimethomorph | | 388.1 > 273.0 | | |
| Etridiazole | 216.8 > 35.0 | 218.8 > 35.0 | | |
| Fenoxycarb | | 302.1 > 256.0 | | |
| Imazalil | 297 > 41.0 | | | |
| Jasmolin II | | 375.2 > 213.0 | | |
| Malathion | | 331.0 > 285.0 | | |
| Mevinphos | 242 > 127.0 | 225.0 > 127.0 | | |
| MGK-264 | | 276.2 > 98.0 | | |
| Naled | | 382.8 > 127.0 | | |
| PCNB | 275.8 > 35.0 | 273.8 > 35.0 | 275.8 > 201.8 | 273.8 > 199.8 |
| Propiconazole | 344.1 > 161.0 | 344.1 > 69.0 | | |
| Pyrethrin I | 329.2 > 163.0 | | | |
| Pyrethrin II | 373.2 > 163.0 | | | |

TABLE 3

Recommended MRM transitions for APCI-MS

| Mode | Target | Q1 | Q2 | Expected R.T. | ΔTime | CE | EV | CCL2 | Res |
|---|---|---|---|---|---|---|---|---|---|
| − | Chlordane-1 | 439.8 | 35.1 | 3.1 | 0.6 | 95 | −15 | 100 | Low_Low |
| − | Chlordane-2 | 441.8 | 35.1 | 3.1 | 0.6 | 99 | −15 | 100 | Low_Low |
| − | PCNB-1 | 275.8 | 35.1 | 3.1 | 0.6 | 85 | −10 | 70 | Low_Low |
| − | PCNB-2 | 273.8 | 35.1 | 3.1 | 0.6 | 82 | −10 | 60 | Low_Low |
| − | PCNB-3 | 275.8 | 201.8 | 3.1 | 0.6 | 36 | −30 | 120 | Low_Low |
| − | Chlorfenapyr-5 | 346.9 | 79.0 | 2.5 | 0.6 | 44 | −33 | 70 | Low_Low |
| − | Chlorfenapyr-6 | 348.9 | 81.0 | 2.5 | 0.6 | 44 | −33 | 70 | Low_Low |
| − | Etridiazole | 216.8 | 35.0 | 2.3 | 0.7 | 88 | −20 | 100 | Low_Low |
| − | Etridiazole | 218.8 | 35.0 | 2.3 | 0.7 | 88 | −20- | 100 | Low_Low |

TABLE 4

Recommended MRM transitions for Mycotoxins

| Mode | Target | Q1 | Q2 | R.T. | ΔT | CE | EV | CCL2 | Res |
|---|---|---|---|---|---|---|---|---|---|
| + | Mycotoxin B1-1 | 313.1 | 285.0 | 5.900 | 1 | −30 | 30 | −90 | Unit_Unit |
| + | Mycotoxin B1-2 | 313.1 | 269.0 | 5.900 | 1 | −40 | 30 | −116 | Unit_Unit |
| + | Mycotoxin B1-3 | 313.1 | 241.0 | 5.900 | 1 | −46 | 30 | −132 | Unit_Unit |
| + | Mycotoxin B2-1 | 315.1 | 287.0 | 5.800 | 1 | −34 | 30 | −116 | Unit_Unit |
| + | Mycotoxin B2-2 | 315.1 | 243.0 | 5.800 | 1 | −50 | 30 | −129 | Unit_Unit |
| + | Mycotoxin G1-1 | 329.1 | 243.0 | 5.500 | 1 | −34 | 30 | −108 | Unit_Unit |
| + | Mycotoxin G1-2 | 329.1 | 214.0 | 5.500 | 1 | −44 | 30 | −128 | Unit_Unit |
| + | Mycotoxin G1-3 | 329.1 | 200.0 | 5.500 | 1 | −54 | 30 | −150 | Unit_Unit |
| + | Mycotoxin G2-1 | 331.1 | 245.0 | 5.400 | 1 | −38 | 25 | −125 | Unit_Unit |
| + | Mycotoxin G2-2 | 331.1 | 189.0 | 5.400 | 1 | −56 | 30 | −150 | Unit_Unit |
| + | Ochratoxin A-1 | 404.1 | 358.0 | 8.400 | 1 | −18 | 30 | −80 | Unit_Unit |
| + | Ochratoxin A-2 | 404.1 | 239.0 | 8.400 | 1 | −30 | 30 | −88 | Unit_Unit |
| + | Ochratoxin A-3 | 404.1 | 221.0 | 8.400 | 1 | −50 | 30 | −96 | Unit_Unit |

Use of the disclosed systems and methods to analyze pesticides in *cannabis* samples (typically plants containing relatively high levels of THC) is described in the Examples below. These examples demonstrate advantages of the systems and methods with respect to matrix effects and isobaric interference (e.g., see Example 6, acequinocyl) in *cannabis* extracts. However, the disclosed systems and methods can be applied to detect pesticides and mycotoxins in a variety of samples, including marijuana and hemp products such as flowers; concentrates (e.g., oils, tinctures, distillates);

edibles such as candy (e.g., gummies, chocolates), cooking oil, baked goods, beverages, ice cream; topicals (e.g., gels, ointments, lotions), botanical samples such as other edible plants and plant products (e.g., herbs, vegetables, fruit, edible flowers, spices, olive oil); other medicinal plants and plant products; other plants and plant products which can be smoked (e.g., tobacco, mint, sage); environmental samples (e.g., water); and clinical samples (e.g., blood serum, urine). Any combination of pesticides disclosed above can be analyzed.

Pesticide Analysis in *Cannabis*

In embodiments of the disclosed methods, using a simple organic solvent extraction method with dilution, the recommended MRM transitions, and an LC gradient with a high efficiency ultra-high-performance liquid chromatography (UHPLC) column, the disclosed methods can be used to avoid matrix effects, permitting the detection of pesticides—including very hydrophobic and chlorinated pesticides typically detected using GCMS—in *cannabis* samples at low levels (e.g., 0.005 to 0.3 µg/g) well below the lowest action levels established by U.S. states such as California and Oregon and other countries such as Canada for *cannabis* products, including inhalable products. Mycotoxins can also be detected. For example, in *cannabis* samples comprising regulated pesticides and mycotoxins and extracted using a simple acetonitrile extraction method, the recovery of all pesticides and mycotoxins is in the acceptable range of 70-120% with a relative standard deviation (RSD) of less than 20%.

FIGS. 119A-F show sample MRM chromatograms with excellent signal-to-noise ratios for a representative set of pesticides spiked at the low level of 0.01 µg/g in *cannabis* flower extracts.

As demonstrated by the data provided in this disclosure, the LOQs are well below current California action limit by a factor of 2 to 600 for all category II pesticides and mycotoxins listed in California's current regulatory document. The response RSD for each pesticide and mycotoxin at its LOQ level in *cannabis* matrix was less than 20%. The retention time for each analyte was reproducible within ±0.1 minute over 24 hour period. This demonstrates that the method is more than adequately sensitive and reproducible for pesticides and mycotoxins analysis in *cannabis* at the regulatory limits specified by California.

Pesticides Typically Analyzed Using GC-MS with an EI Source

A number of pesticides (e.g., chlorfenapyr, cypermethrin, cyfluthrin, captan, naled, permethrin, and pyrethrins) have low proton affinity which results in low ionization efficiency with ESI source. These pesticides typically are analyzed using GC-MS with an electron-ionization (EI) source. Use of a heated electrospray source with coaxial heating gas, as in the QSight LC-MS/MS system, ionizes these pesticides with much higher ionization efficiency than a conventional ESI source with no heating gas. Using the recommended MRM transitions with a heated electrospray source, the LOQ for these pesticides were in range of 10-25 ppb, which, for example, is well below the action limits for *cannabis* in California and in other states.

For example, pyrethrins are a class of organic compounds derived from *Chrysanthemum cinerariifolium* that have potent insecticidal activity by targeting the nervous systems of insects. The naturally-occurring pyrethrins, extracted from *chrysanthemum* flowers, are esters of chrysanthemic acid (pyrethrin I, cinerin I, and jasmolin I) and esters of pyrethric acid (pyrethrin II, cinerin II, and jasmolin II); their structures are shown below.

Pyrethrin I C21H28O3

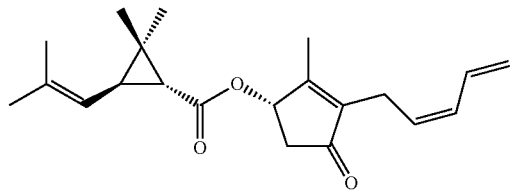

Pyrethrin II C22H28O5

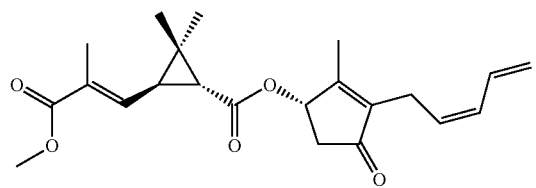

Jasmolin I C21H30O3

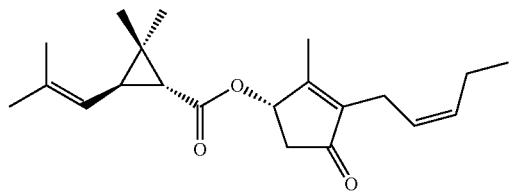

Jasmolin II C22H30O5

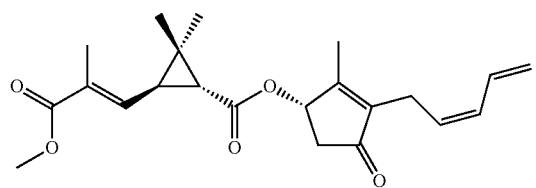

Cinerin I C20H28O3

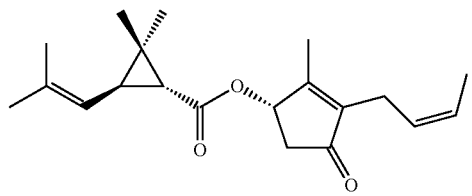

Cinerin II C21H28O5

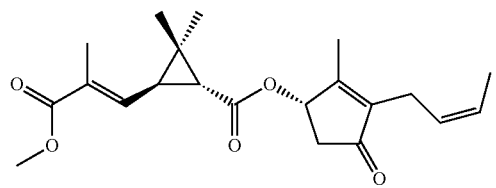

In the United States, pyrethrum extract is standardized as 45-55% w/w total pyrethrins and in a commercially available pyrethrin standard, the percentage of pyrethrin I, pyrethrin II, cinerin I, cinerin II, jasmolin I and jasmolin II is about 56.1, 27.8, 5.7, 3.8, 4 and 2.6%, respectively. A number of compounds in *cannabis* mimic the structure of pyrethrins and therefore the analysis of pyrethrins in *cannabis* is very difficult due to matrix interference. The LOQs, with LC-MS/MS method which utilizes recommended MRM transitions and LC gradient, for pyrethrin I, pyrethrin II, cinerin I, cinerin II, jasmolin I and jasmolin II were 0.1, 0.1, 0.01, 0.03, 0.025 and 0.01 µg/g, respectively in *cannabis* flower.

Calibration

In conventional approaches, matrix matched calibration is performed for more accurate quantitation of pesticides and other analytes in different matrices, such as food matrices. In certain embodiments, use of solvent based analytical standards at different concentrations is more practical and convenient. In particular, quantitation of pesticides in different food matrices is challenging since it can be difficult and/or expensive to obtain a standard food matrix which is free of pesticides and other analytes.

In certain embodiments, since some of pesticides may experience ion suppression due to matrix effects, a mixture of isotopically labelled internal standards can be added to both solvent based calibration standards and samples (see Example 1). This approach can reduce the error in quantitation of pesticides and other analytes in matrices due to ion suppression.

Another approach for reducing ion suppression from matrix effects is to dilute the sample extracts further with methanol or acetonitrile (e.g., by a factor of 1.5 to 50). This approach can reduce ion suppression but may also reduce the sensitivity by increasing the limits of quantitation of pesticides in different food matrices. In certain embodiments, an acetonitrile extract is diluted further with methanol by 50% to get better peak shapes for earlier eluting compounds when LC uses methanol as strong solvent mobile phase. See FIG. 125.

Liquid Chromatography

Conventional LC-MS/MS approaches with APCI and/or ESI sources use LC mobile phases with additives such as formic acid, ammonium formate, and other additives to assist in ionization of analytes in samples. However, to assist ionization of analytes such as chlordane, quintozene, chlorfenapyr, etridiazole, endosulfan I, endosulfan II, etridiazole, chlorfenapyr, etridiazole, and other pesticides that are either very hydrophobic or chlorinated with an APCI source, LC mobile phases without additives provide better performance ESI ionization, however, typically requires either acidic additives, such as formic acid and acetic acid, and/or neutral additives, such as ammonium formate and ammonium acetate.

In certain embodiments, two sequential LC-MS/MS methods may be used, wherein a first LC separation method is used to produce a first separation stream that is ionized with an ESI source, and a second LC separation method is used to produce a second separation stream that ionized with an APCI source. In this manner, the first LC separation method may employ mobile phases that use acidic and/or neutral additives to assist with ESI ionization, while the second LC method may employ mobile phases without any such additives (e.g., without any acidic and/or neutral additives; without any additives).

In certain embodiments, a single LC-MS/MS method is used that allows for simultaneous ionization and measurement of sample from single injection using ESI and APCI ionization (e.g., in both positive and negative ion mode). In this approach, a single LC method is used and LC column eluent from sample can be split into a first separation stream that is ionized by the ESI source and a second separation stream that is ionized using the APCI source. For example, LC column eluent may be diverted, using a T fitting, to both ESI and APCI ion sources present in a LC-MS/MS system (e.g., such as PerkinElmer's QSight system) for analysis. The LC-MS/MS system can be operated in both ESI and APCI mode with negligible cross talk or interference between ionization modes and polarities.

As described above, use of LC methods that employ mobile phases without acidic and/or neutral additives (e.g., without any additives) allows for analysis of analytes using an APCI source. In particular, for analysis of various chlorinated pesticides using an APCI source, it has been observed that signal is highest when no additives are used and that signal decreases by factor of 2 to 5 with addition of neutral additives such as ammonium acetate and ammonium formate. The signal for chlorinated pesticides ionized with an APCI source goes down by a factor of 20-50 with addition of acidic additives such as formic and acetic acid. Accordingly, since ESI requires presence of some ionic additives to aid in ionization and analysis of analytes, in certain embodiments, a single LC method that employs mobile phases with neutral additives, such as ammonium acetate or ammonium formate may be used. The approach provides a compromise that allows both ESI and APCI sources to be used with a single LC method. By allowing analysis to proceed with only a single LC injection, this approach provides for increased throughput.

EXAMPLES OF EMBODIMENTS

Figure 1A:
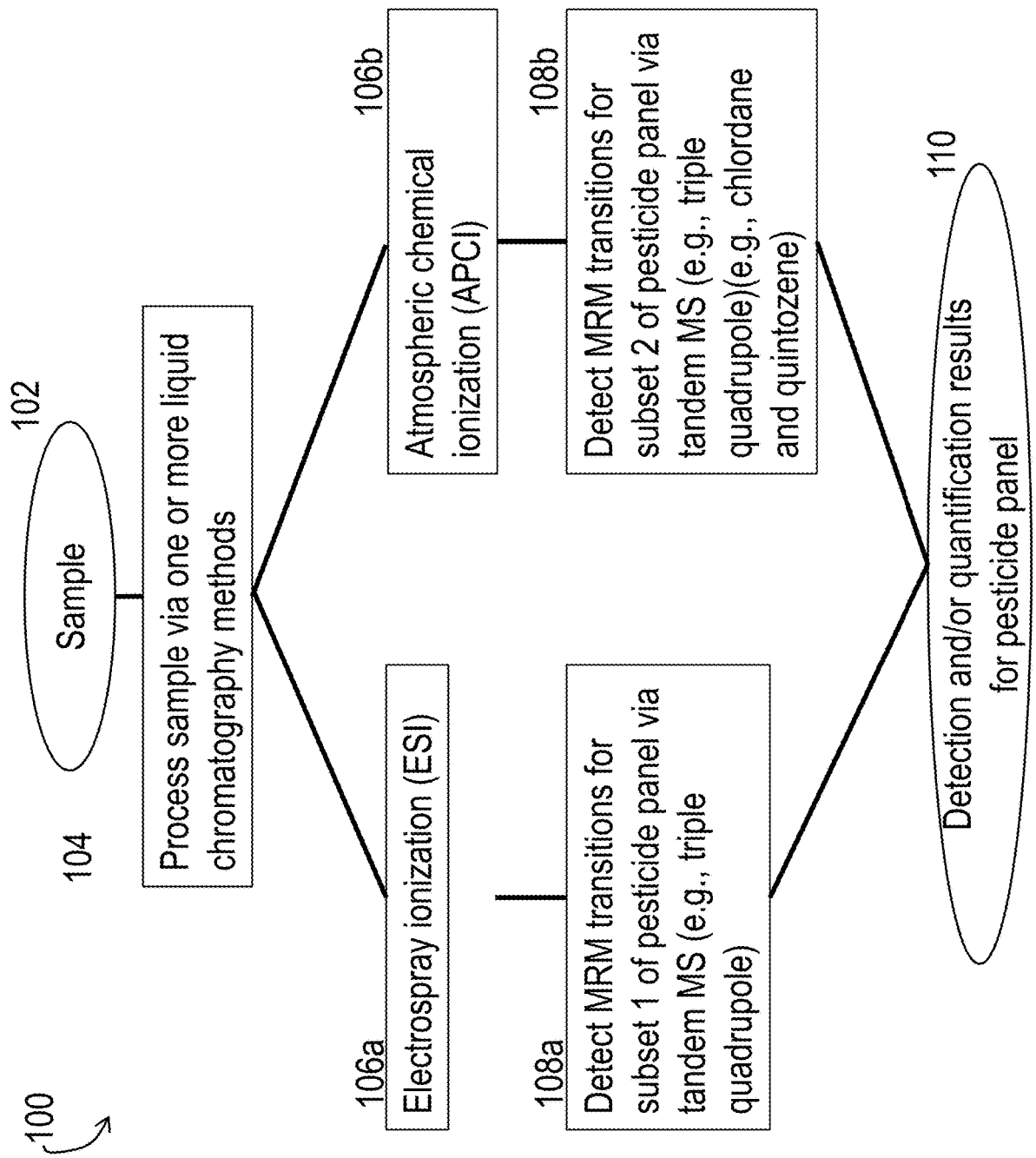
FIG. 1A and FIG. 1B are block diagrams of processes for detecting and/or quantifying a panel of pesticides.
Figure 1B:
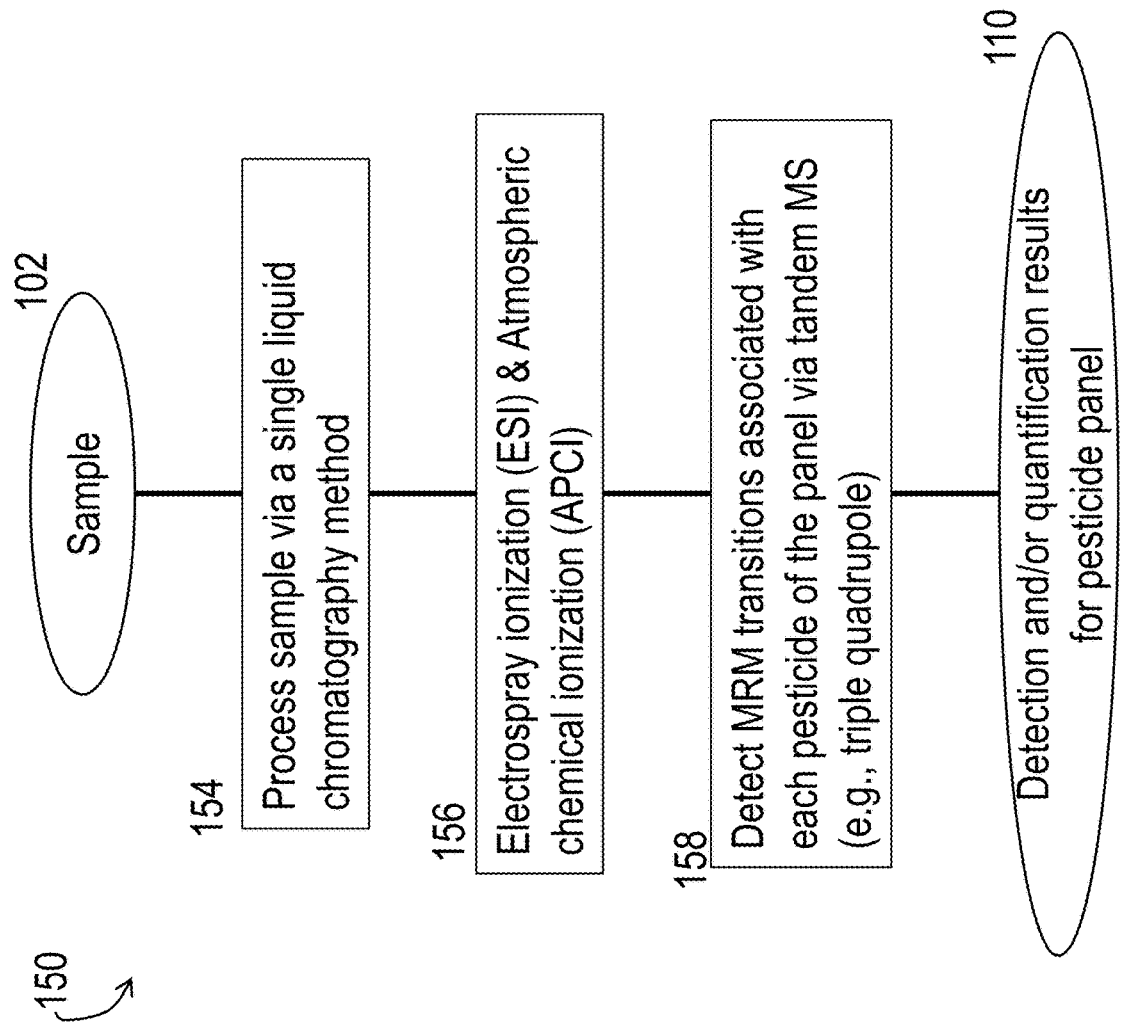

FIG. 1 shows an example process 100 for detecting and/or quantifying a panel of pesticides (e.g., 72 pesticides) in a sample (e.g., comprising *cannabis* plant material) according to the approaches described herein. In process 100, the sample 102 is processed by one or more LC methods 104 to produce a first and a second separation stream. The first separation stream is ionized using an ESI source 106a to produce a first ionized sample stream. Tandem mass spectrometry (e.g., triple quadrupole mass spectrometry) is used to detect and/or quantify a first subset of pesticides of the panel in the first ionized sample stream by detecting intensities of MRM transitions associated with each pesticide of the first subset 108a. The second separation stream is ionized using an APCI source 106b to produce a second ionized sample stream. Tandem mass spectrometry is used to detect and/or quantify a second subset of pesticides of the panel in the second ionized sample stream by detecting intensities of MRM transitions associated with each pesticide of the second subset 108b. Each pesticide can be detected (e.g., identified as present in the sample) and/or quantified based on the detected intensities of one or more MRM transitions associated with the pesticide. By applying two parallel LC-MS/MS techniques in this manner, detection and/or quantification results for the full panel 110 are obtained.

Figure 2:
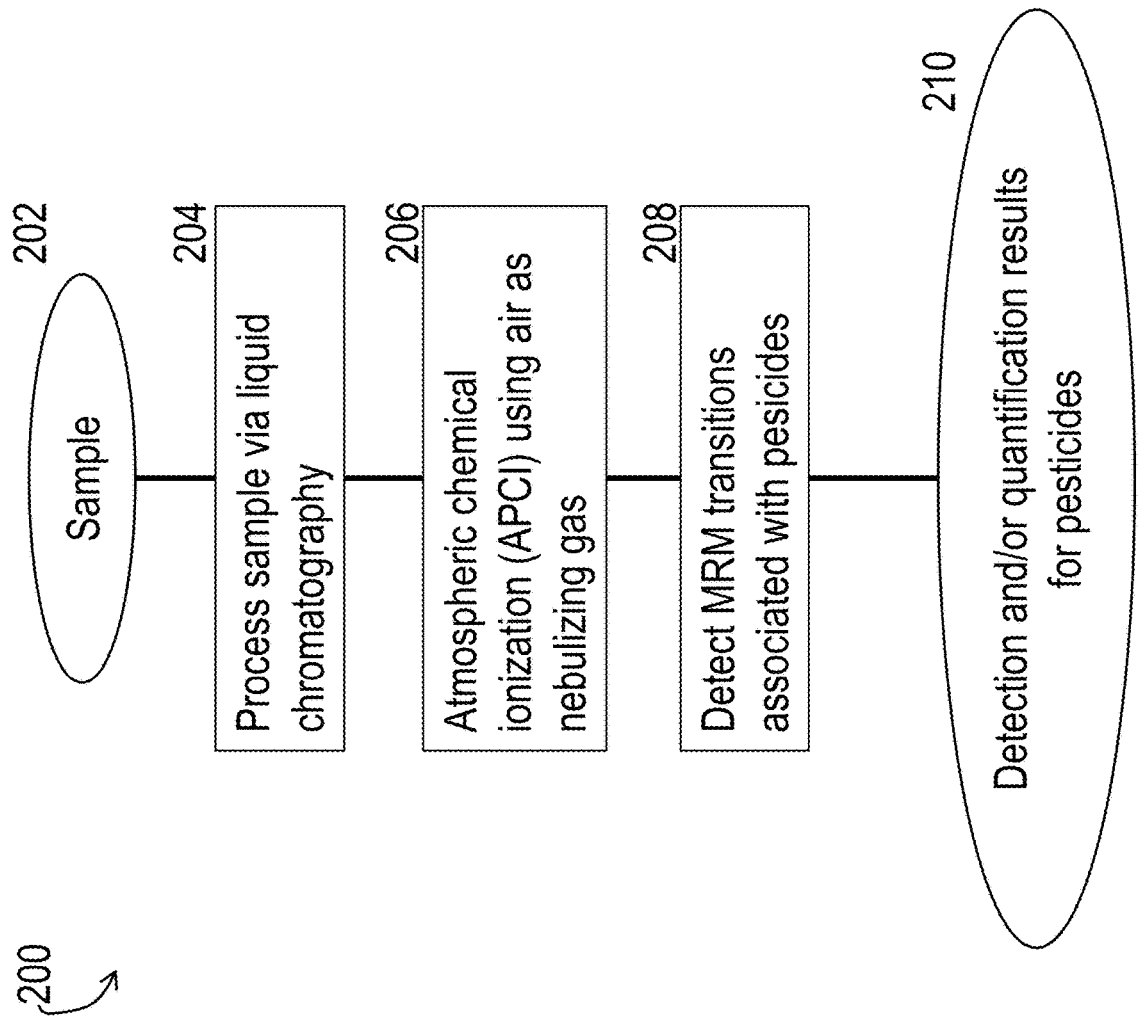
FIG. 2 is a block diagram of a process for detecting and/or quantifying pesticides via tandem mass spectrometry, using atmospheric chemical ionization (APCI) with air as a nebulizing gas.

FIG. 2 shows an example process 200 for detecting and/or quantifying one or more pesticides in a sample using LC-MS/MS with an APCI source. In process 200, the sample 202 is processed via an LC method 204 to produce a separation stream. The separation stream is ionized using and APCI source and air as a nebulizing gas 206. Tandem mass spectrometry (e.g., triple quadrupole mass spectrometry) is used to detect intensities of one or more MRM transitions associated with the pesticides 208. Intensities of the one or more MRM transitions associated can be used to detect (e.g., identify as present in the sample) and/or quantify the pesticides 210.

Figure 3:
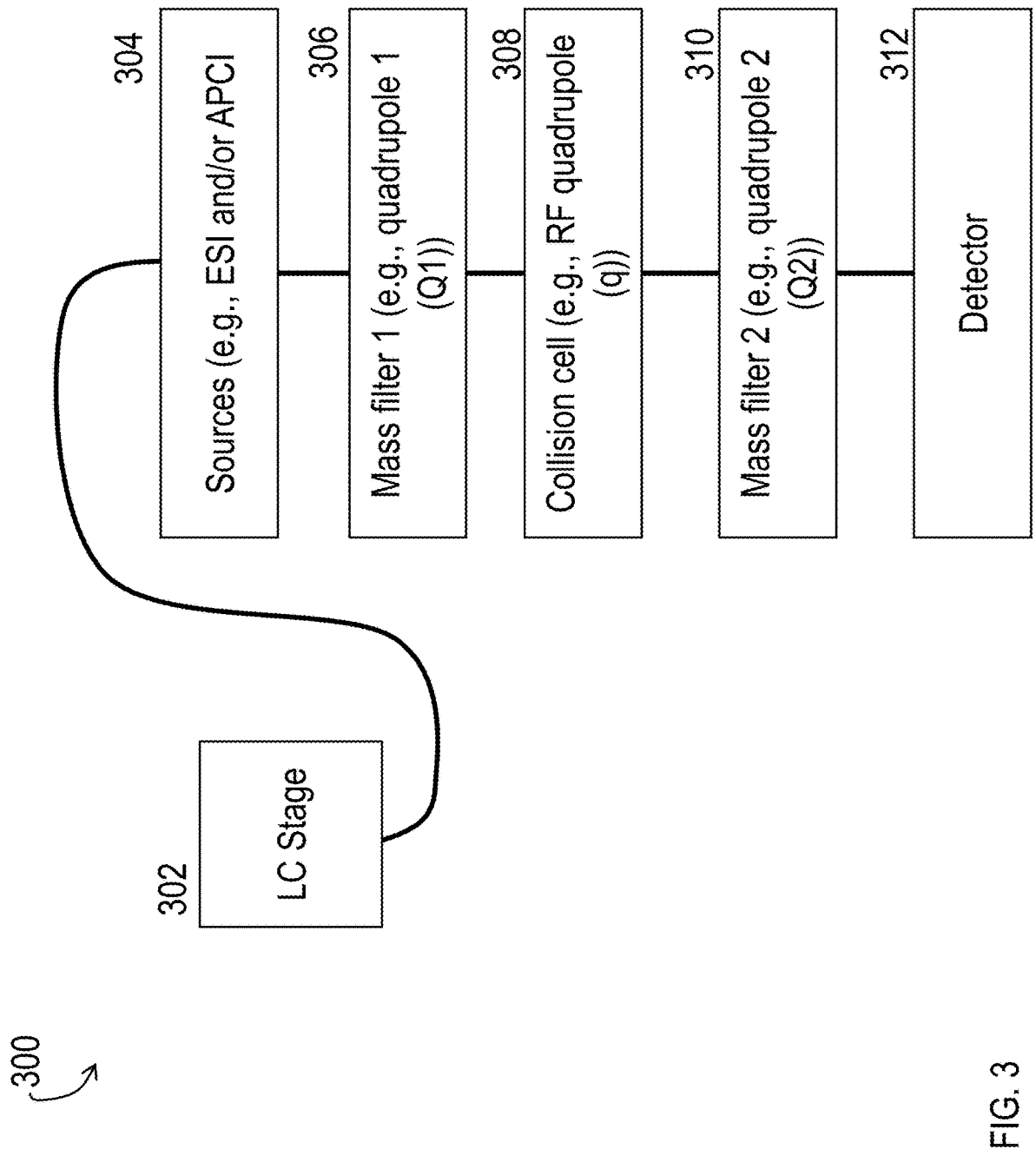
FIG. 3 is schematic of a liquid chromatography and tandem mass spectrometry system.

FIG. 3 shows an example LC-MS/MS system 300 used in certain embodiments to perform the LC-MS/MS techniques described herein. The LC-MS/MS 300 comprises a LC stage 302, ionization sources (e.g., an ESI source and/or an APCI source) 304, and two mass filters 306 and 310 in series with a collision cell 308 in between. In certain embodiments, the two mass filters (Q1 and Q2) are quadrupoles. In certain embodiments, the collision cell is a quadrupole (q)(e.g., an RF quadrupole). In certain embodiments, the LC-MS/MS 300 is a triple quadrupole system. The LC-MS/MS 300 includes a detector 312 for detecting ions.

In one aspect, a method for detecting and/or quantifying a plurality of pesticides of a pesticide panel in a sample via liquid-chromatography tandem mass spectrometry (LC-MS/MS) comprises (a) processing the sample using one or more liquid chromatography (LC) method(s) to produce a first separation stream and a second separation stream; (b) ionizing the first separation stream using an electrospray ionization (ESI) source to produce a first ionized sample stream; (c) ionizing the second separation stream using an atmospheric chemical ionization (APCI) source to produce a second ionized sample stream; and (d) detecting, via tandem mass spectrometry (e.g., using a triple quadrupole system): (i) for each pesticide of a first subset of the panel, an intensity of one or more multiple reaction monitoring (MRM) transitions associated with the pesticide using the first ionized sample stream; and (ii) for each pesticide of a second subset of the panel, an intensity of one or more multiple reaction monitoring (MRM) transitions associated with the pesticide using the second ionized sample stream, thereby detecting and/or quantifying the plurality of pesticides of the pesticide panel.

In certain embodiments, the sample comprises *cannabis* plant material (e.g., wherein the *cannabis* plant material is diluted, for example, by a factor of 10 or more). In certain embodiments, the sample comprises edible material (e.g., food). In certain embodiments, the sample comprises plant material.

In certain embodiments, the sample comprises an extract and the method comprises producing the sample extract using an extraction procedure comprising combining a base sample with one or more solvents and, following dilution of the base sample, filtering the diluted base sample.

In certain embodiments, the one or more solvents comprise methanol. In certain embodiments, the one or more solvents comprise acetonitrile (e.g., acetonitrile and/or acetonitrile with formic acid). In certain embodiments, the extraction procedure further comprises a dispersive solid phase extraction procedure applied following dilution of the base sample with the one or more solvents (e.g., using PSA (primary and secondary amine) sorbents, C18, alumina graphitized carbon, and the like; e.g., to reduce ion suppression and matrix interference).

In certain embodiments, the method comprises, for each pesticide of at least a portion of the plurality of pesticides, quantifying a level (e.g., micrograms per gram) of the pesticide in the sample based the detected intensities of the one or more MRM transitions associated with the pesticide (for example, wherein the sample comprises *cannabis* plant material and/or wherein an LOQ for the level of the pesticide is below a California and/or Oregon action level by, for example, a factor of 2, 10, 20, or 50).

In certain embodiments, for at least one of the plurality of pesticides, quantifying the level of the pesticide in the sample comprises using a solvent based analytical calibration standard (e.g., an isotopically labeled internal standard). In certain embodiments, the method comprises spiking the calibration standard and/or the sample with an internal standard mixture (see Table 10).

In certain embodiments, the panel comprises 72 pesticides. In some embodiments, for example when the sample is a *cannabis* sample, a first subset comprises 70 pesticides and a second subset comprises 3 pesticides such as chlordane, chlorfenapyr, and quintozene (PCNB).

In certain embodiments, a first subset of the panel comprises one or more high molecular weight and/or thermally unstable pesticides (e.g., abamectin).

In certain embodiments, a first subset of the panel comprises one or more category 2 pesticides selected from the group consisting of: abamectin, acephate, acequinocyl, acetamiprid, azoxystrobin, bifenazate, bifenthrin, boscalid, captan, carbaryl, chlorantraniliprole, cinerin I, cinerin II, clofentezine, cyfluthrin, cypermethrin, diazinon, dimethomorph, etoxazole, fenhexamid, fenpyroximate, flonicamid, fludioxonil, hexythiazox, imidacloprid, jasmolin I, jasmolin II, kresoxim-methyl, malathion, metalaxyl, methomyl, myclobutanil, naled, oxamyl, permethrin, phosmet, piperonyl butoxide, prallethrin, propiconazole, pyrethrin I, pyrethrin II, pyridaben, spinetoram, spinosad, spiromesifen, spirotetramat, tebuconazole, thiamethoxam, and trifloxystrobin.

In certain embodiments, a first subset of the panel comprises one or more category 1 pesticides selected from the group consisting of: aldicarb, carbofuran, chlorfenapyr, chlorpyrifos, coumaphos, daminozide, DDVP (dichlorvos), dimethoate, Ethoprop(hos), etofenprox, fenoxycarb, fipronil, imazalil, methiocarb, methyl parathion, mevinphos, paclobutrazol, propoxur, spiroxamine, thiacloprid, MGK-264.

In certain embodiments, a second subset of the panel comprises one or more hydrophobic and/or chlorinated pesticides.

In certain embodiments, a second subset of the panel comprises one or more pesticides selected from the group consisting of pentachloronitrobenzene, chlordane, chlorfenapyr endosulfan I, endosulfan II, and etridiazole.

In certain embodiments, a second subset of the panel comprises chlordane, chlorfenapyr and/or quintozene (PCNB).

In certain embodiments, step (c) comprises using air and/or other gases, such as nitrogen, argon, and carbon dioxide, as a nebulizing gas (e.g., to generate negatively charged oxygen ions that act as reagent ions and assist in ionization of chlordane and/or quintozene).

In certain embodiments, step (a) comprises processing the sample using a single LC method (e.g., and splitting the eluent of the single LC method into the first separation stream and the second separation stream). In certain embodiments, the single LC method employs mobile phases with neutral additives such as ammonium acetate, ammonium formate, ammonium hydroxide, and ammonium carbonate. In certain embodiments, the single LC method employs mobile phases without acidic additives (e.g., without formic acid and/or without acetic acid). In certain embodiments, the single LC comprises a fast LC method with a fast gradient (e.g., 10-20%/minute or greater organic change) and a slow gradient [e.g., 1-10%/minute (e.g., 5-6%) organic change] to minimize overlap between pesticide signal peaks and matrix interference peaks.

In certain embodiments, step (a) comprises processing the sample using a first LC method to produce the first separation stream and using a second LC method to produce the second separation stream. In some embodiments, the second LC method employs mobile phases with neutral additives such as ammonium acetate, ammonium formate, ammonium hydroxide, and ammonium carbonate. In some embodiments, the second LC method employs mobile phases without acidic additives (e.g., without formic acid and/or without acetic acid). In some embodiments, the second LC method uses mobile phases without any neutral and/or acidic additives. In certain embodiments, the first LC method and/or the second LC method comprises a fast LC method with a fast gradient (e.g., 10-20%/minute or greater organic change) and a slow gradient [e.g., 1-10%/minute (e.g., 5-6%) organic change] to minimize overlap between pesticide signal peaks and matrix interference peaks.

In certain embodiments, for each pesticide of the first subset and/or for each pesticide of the second subset, at least a portion of the one or more MRM transitions associated with the pesticide are substantially distinct from matrix interferences. In some embodiments, the sample comprises *cannabis* plant material and the matrix interferences are *cannabis* matrix interferences, such as interferences associated with cannabinoids, terpenes, and/or other non-cannabinoid compounds.

In certain embodiments, for each of at least a portion of the plurality of pesticides of the panel, the one or more associated MRM transitions comprises one or more of the MRM transitions of Table 2A.

In certain embodiments, for each of at least a portion of the plurality of pesticides of the panel, the one or more associated MRM transitions comprises one or more of the MRM transitions of Table 2C.

In certain embodiments, for each of at least a portion of the plurality of pesticides of the panel, the one or more associated MRM transitions comprises one or more of the MRM transitions of Table 2D.

In certain embodiments, for each of at least a portion of the plurality of pesticides of the panel, the one or more associated MRM transitions comprises one or more of the MRM transitions of Table 3.

In some embodiments, a method for detecting and/or quantifying one or more pesticides (e.g., very hydrophobic and/or chlorinated pesticides) levels in a sample using LC-MS/MS comprises: (a) processing the sample using a liquid chromatography (LC) method to produce a separation stream; (b) ionizing the separation stream using APCI source using air and/or other gases, such as nitrogen, argon, and carbon dioxide, as a nebulizing gas as a nebulizing gas to produce an ionized sample stream; and (d) detecting, via tandem mass spectrometry (e.g., using a triple quadrupole system), for each pesticide of the one or more pesticides, an intensity of one or more multiple reaction monitoring (MRM) transitions using the ionized sample stream, each MRM transition associated with the pesticide, thereby detecting and/or quantifying the one or more pesticides.

In certain embodiments, the sample comprises *cannabis* plant material (e.g., wherein the *cannabis* plant material is diluted, e.g., by a factor of 10 or more). In certain embodiments, the sample comprises edible material (e.g., food). In certain embodiments, the sample comprises plant material.

In certain embodiments, the sample is an extract and the method comprises producing the sample extract using an extraction procedure comprising combining (e.g., diluting) a base sample with one or more solvents [e.g., and, following dilution of the base sample, filtering the diluted base sample]. In certain embodiments, the one or more solvents comprise methanol. In certain embodiments, the one or more solvents comprise acetonitrile (e.g., acetonitrile and/or acetonitrile with formic acid). In certain embodiments, when LC uses methanol as strong solvent mobile phase, the acetonitrile extract is further diluted with methanol by 50% or more to obtain better peak shapes for earlier eluting compounds. In certain embodiments, the extraction procedure further comprises a dispersive solid phase extraction procedure applied following dilution of the base sample with the one or more solvents (e.g., using PSA (primary and secondary amine) sorbents, C18, alumina graphitized carbon, and the like; e.g., to reduce ion suppression and matrix interference).

In certain embodiments, the method comprises, for each pesticide of the one or more pesticides, quantifying a level (e.g., micrograms per gram) of the pesticide in the sample based the detected intensities of the one or more MRM transitions associated with the pesticide [e.g., wherein the sample comprises *cannabis* plant material and/or wherein a limit of quantitation (LOQ) for the level of the pesticide is below (e.g., a factor of 2, 10, 20, or 50 smaller than) a California action level and/or an Oregon action level for the pesticide].

In certain embodiments, for at least one of the pesticides, quantifying the level of the pesticides in the sample comprises using a solvent based analytical calibration standard (e.g., an isotopically labeled internal standard). In certain embodiments, the method comprises spiking the calibration standard and/or the sample with the internal standard mixture of Table 6.

In certain embodiments, the one or more pesticides comprise one or more hydrophobic and/or chlorinated pesticides. In certain embodiments, the one or more pesticides comprise one or more pesticides selected from the group consisting of pentachloronitrobenzene, chlordane, chlorfenapyr, endosulfan I, endosulfan II, and etridiazole. In certain embodiments, the one or more pesticides comprises chlordane and/or quintozene (also referred to as pentachloronitrobenzene).

In certain embodiments, the LC method employs mobile phases with neutral additives such as ammonium acetate, ammonium formate, ammonium hydroxide, and ammonium carbonate. In certain embodiments, the LC method employs mobile phases without acidic additives (for example, without formic acid and/or without acetic acid). In certain embodiments, the LC method employs mobile phases without any neutral and/or acidic additives (e.g., without any additives).

In certain embodiments, for each pesticide of at least a portion of the one or more pesticides, the one or more MRM transitions associated with the pesticide are substantially distinct from matrix interferences, such as wherein the sample comprises *cannabis* plant material and the matrix interferences are *cannabis* matrix interferences associated with cannabinoids, terpenes, and/or other non-cannabinoid compounds.

In certain embodiments, the one or more pesticides comprises chlordane, and step (d) comprises detecting an intensity of one or more MRM transitions associated with chlordane, wherein the one or more MRM transitions associated with chlordane comprise one or more members selected from the group consisting of a 439.8>35 transition, and a 441.8>35 transition.

In certain embodiments, the one or more pesticides comprises quintozene, and step (d) comprises detecting an intensity of one or more MRM transitions associated with quintozene, wherein the one or more MRM transitions associated with quintozene comprise one or more members selected from the group consisting of a 275.8>35 transition, a 273.8>35 transition, a 275.8>201.8 transition, and a 273.8>199.8 transition.

In certain embodiments, the one or more pesticides comprises chlorfenapyr, and step (d) comprises detecting an intensity of one or more MRM transitions associated with chlorfenapyr, wherein the one or more MRM transitions associated with chlorfenapyr comprises one or more members selected from the group consisting of a 346.9>79 transition and a 348.9>81 transition.

In certain embodiments, the one or more pesticides comprises etridiazole, and step (d) comprises detecting an intensity of one or more MRM transitions associated with etridiazole, wherein the one or more MRM transitions associated with etridiazole comprises one or more members selected from the group consisting of a 216.8>35 transition and a 218.8>35 transition.

In certain embodiments, the LC method is a fast LC method with fast gradient (e.g., 10-20%/minute or greater organic change) and slow gradient [e.g., 1-10%/minute (e.g., 5-6%) organic change] to minimize overlap between pesticides peak and matrix interference peaks.

vortex mixture, and vortexed for 10 minutes, then centrifuged for 10 minutes at 3000 rpm. The solvent was filtered into a 5 mL glass amber vial using a 0.22 micron nylon syringe-filter, and the vial was capped and labeled.

LC-MS/MS Analysis.

0.5 mL of the extracted sample was placed into a 2 mL HPLC vial, diluted with 0.5 mL of LC-MS grade acetonitrile, and mixed. Three μL of this sample was injected for LC-MS/MS analysis, using the LC method and MS source conditions shown in Table 5.

Table 5. LC Method and MS Source Conditions

TABLE 5

| LC Method and MS Source Conditions | |
|---|---|
| LC Conditions | |
| LC column | PerkinElmer Quasar Pesticide column (100 mm × 4.6 mm, 2.7 μM) |
| Mobile-phase A (ESI method) | 2 mM ammonium formate + 0.1% formic acid (in water) |
| Mobile-phase B (ESI method) | 2 mM ammonium formate + 0.1% formic acid (in methanol) |
| Mobile-phase gradient | A 18.5 and 6 minute LC method with gradient for LC-MS/MS method with ESI and APCI source, respectively |
| Column oven temperature | 30 C. |
| Auto sampler temperature | 10 C. |
| Injection volume | 3.0 μL for LC-MS/MS method with ESI source. 10 μL for LC-MS/MS method with APCI source. |
| MS Source Conditions for ESI Source and APCI Source | |
| ESI voltage (positive) | +5500 V |
| ESI voltage (negative) | −4200 V |
| APCI Corona Discharge | −5 μA |
| Drying gas | 120 arbitrary units |
| Nebulizer gas | 350 arbitrary units |
| Source temperature | 315° C. |
| HSID temperature | 200° C. |
| Detection mode | Time-managed MRM |

In another aspect, this disclosure provides a system comprising a liquid chromatography tandem mass spectrometer (e.g., a triple quadrupole mass LC mass spectrometer) for performing any one of the methods described herein.

Those skilled in the art will appreciate that there are numerous variations and permutations of the above described embodiments that fall within the scope of the appended claims.

Example 1

Hardware and Software.

In examples below, chromatographic separation was conducted on a PERKINELMER® LC-MS/MS® LX50 UHPLC system, and detection was achieved using a PerkinElmer QSIGHT® 220 MS/MS detector with a dual ionization ESI and APCI source, which operate independently with two separate inlets. All instrument control, data acquisition and data processing was performed using the Simplicity 3Q™ software platform.

Preparation of Cannabis Samples.

Approximately 5 grams of cannabis flower were finely ground, and 1 g of the ground mixture was placed into a 50 mL centrifuge tube and comprising 10 μL of the internal standard solution shown in Table 6. Three 10 mm steel balls were added to the tube together with 5 mL of LC-MS grade acetonitrile. The tube was capped, placed on a multi-tube Sample Matrix-Matched Calibration Standards.

Matrix matched calibration is the gold standard for quantitation because it compensates for matrix effects. Matrix effects are common for LCMS based analysis in complex matrices such as cannabis. The decrease or increase in response is attributed to ion suppression of the analytes during ionization by the presence of co-eluted matrix compounds. Due to sample matrix effects, a matrix matched calibration curve was used for quantitation and generated by injecting blank cannabis flower extracts and blank cannabis flower extract samples comprising varying concentrations of pesticides and mycotoxins over range of 0.1-1000 ng/mL at least seven or more different concentration levels.

Table 6. Composition of an Example Internal Standard Mixture

TABLE 6

| Composition of an example internal standard mixture | | |
|---|---|---|
| Internal Standard | Concentration/ppb | Retention Time |
| $D_4$ daminozide | 2000 | 1.63 |
| $D_4$ Imidacloprid | 800 | 4.59 |
| Naled-$D_6$ | 2000 | 7.02 |
| phosmet-$D_6$ | 400 | 7.26 |
| methylparathion $D_6$ | 4000 | 7.48 |
| $D_4$ boscalid | 600 | 7.8 |

TABLE 6-continued

Composition of an example internal standard mixture

| Internal Standard | Concentration/ppb | Retention Time |
|---|---|---|
| malathion $D_6$ | 600 | 7.97 |
| $D_9$ Myclobutanil | 400 | 8.13 |
| spirotetramat-$D_5$ | 400 | 8.7 |
| Diazinon-$^{13}C_4$ | 400 | 9.55 |
| Propiconazole-$D_7$ | 1000 | 9.78 |
| trifloxystrobin-$D_6$ | 200 | 10.2 |
| piperonylbutoxide-$D_9$ | 400 | 11.236 |
| Chlorpyrifos (diethyl-$D_{10}$) | 800 | 11.3 |
| cyfluthrin-phenoxy $D_5$ | 4000 | 11.7 |
| cypermethrin-phenoxy-$D_5$ | 4000 | 11.9 |
| permethrin-$D_5$ | 2000 | 12.886 |
| Aceequinocyl-$D_{25}$ | 2000 | 14.1 |

FIGS. 121A-D show representative examples of calibration curve for pesticides in *cannabis* extract over four orders of magnitude. The calibration curves for all pesticides and mycotoxins were linear with calibration fit of $R^2$ greater than 0.99 for all analytes tested.

Example 2. Liquid Chromatography Methods

Figure 27A:
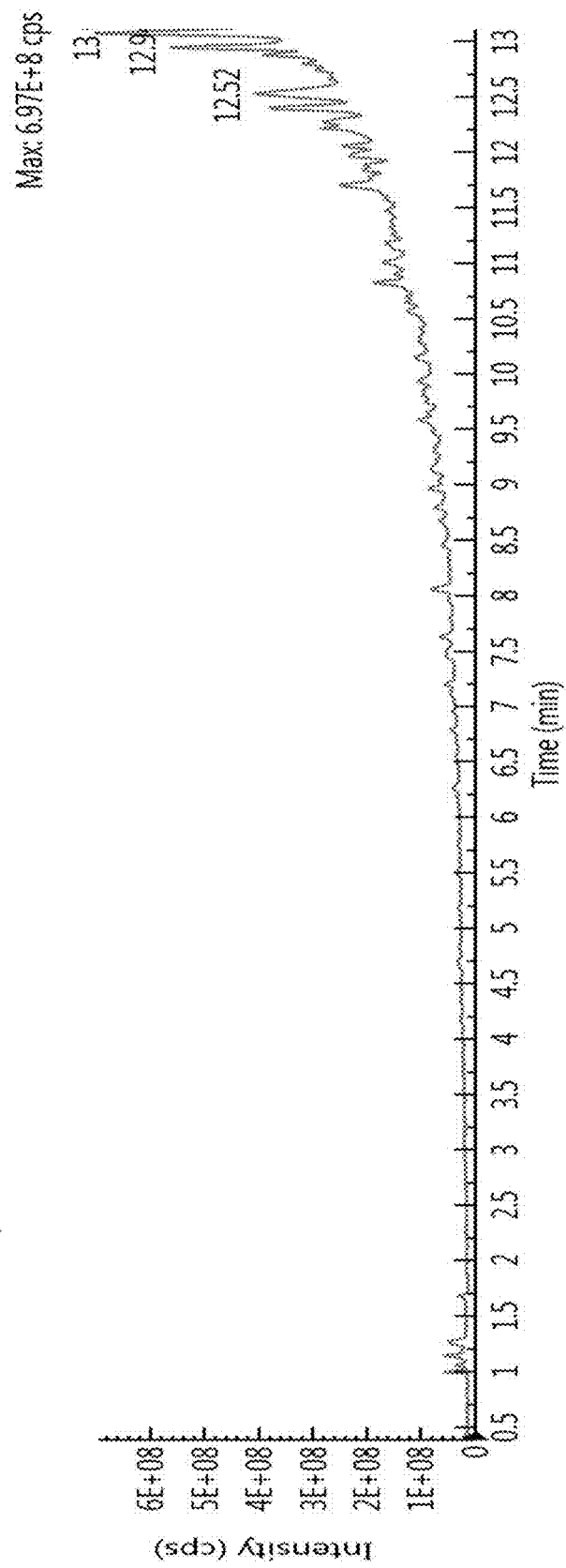
FIGS. 27A-C are total ion chromatograms (TICs).
Figure 27B:
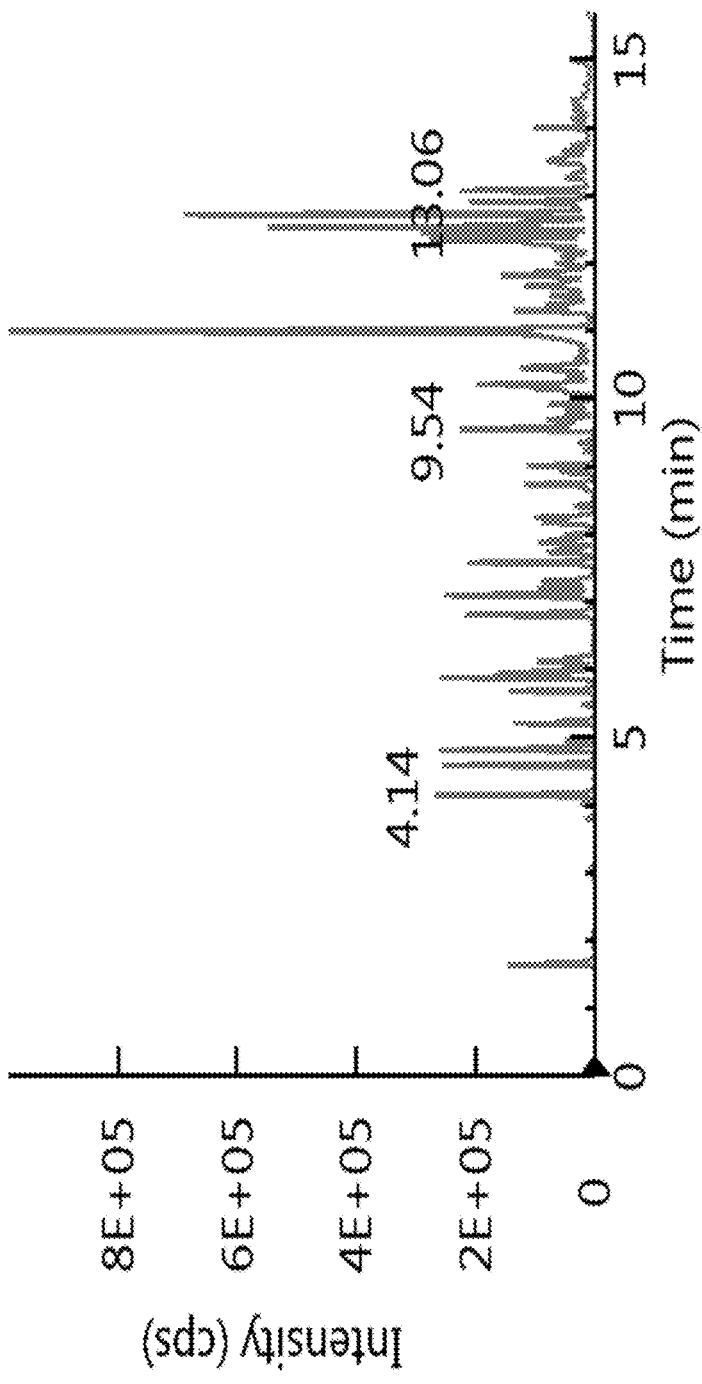
Figure 27C:
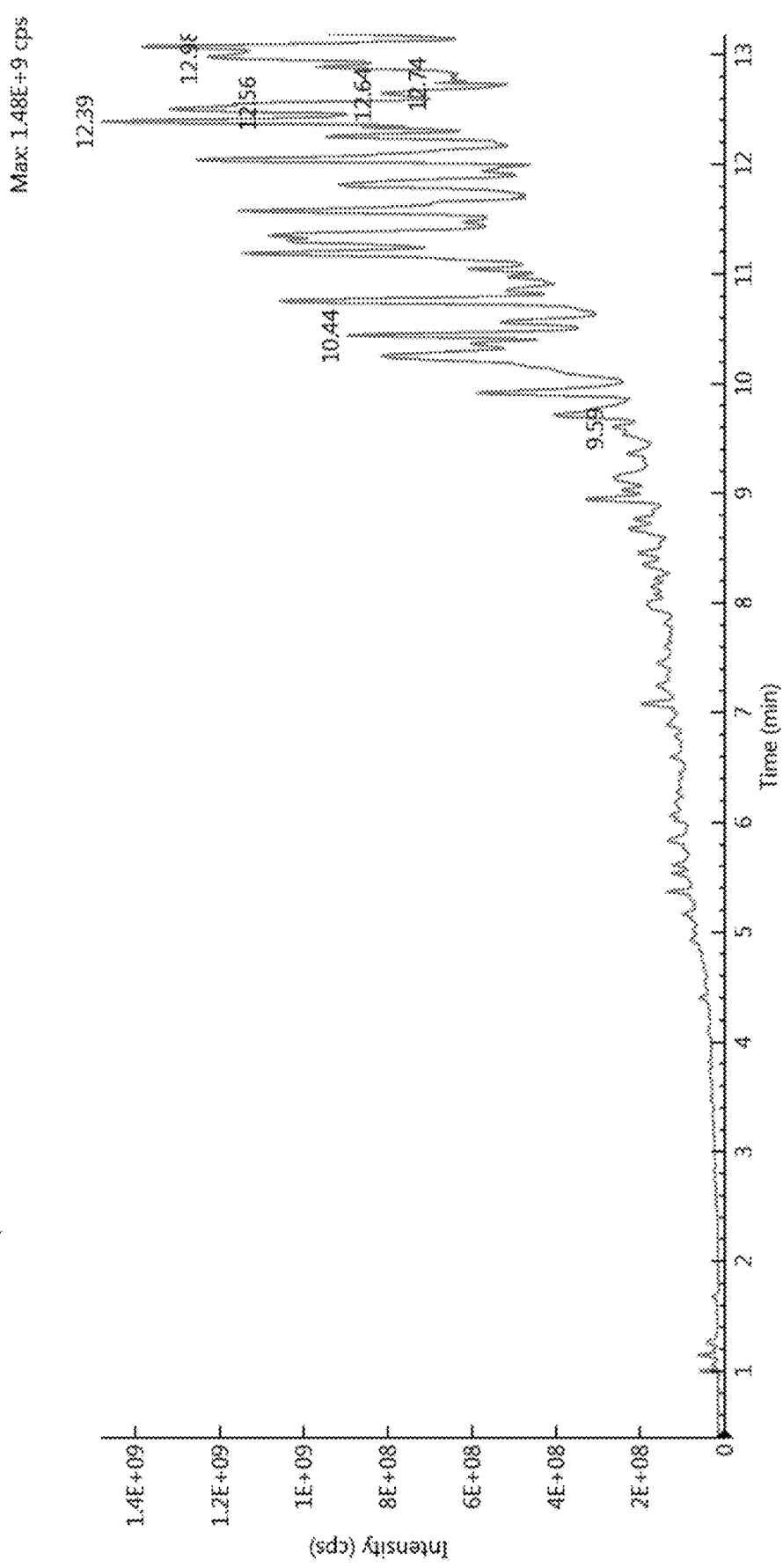
Figure 27D:
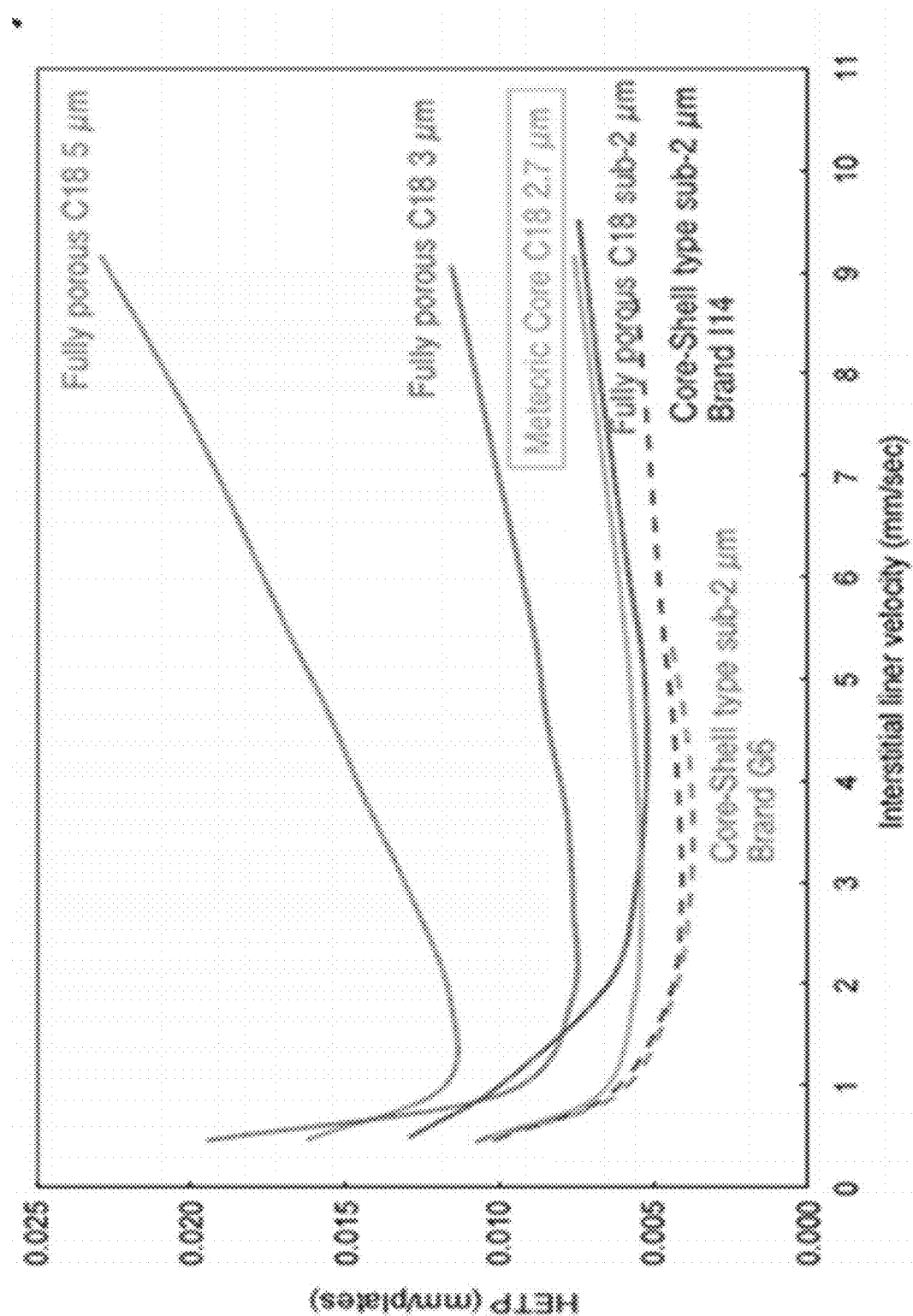
FIG. 27D is a graph showing Van Deemter curves for various types of liquid chromatography (LC) columns.

FIG. 27A is a graph showing a total ion chromatogram (TIC) obtained over 14 minutes for a (blank) sample comprising *cannabis* plant material using a generic (fixed gradient rate) liquid chromatography gradient. FIG. 27B is a graph showing a TIC of a sample comprising *cannabis* plant material comprising 100 ppb of pesticides. FIG. 27C is a graph showing a TIC obtained using the example LC method described in Example 1, above. FIG. 27D are Van Deemter curves for various LC columns.

Figure 29A:
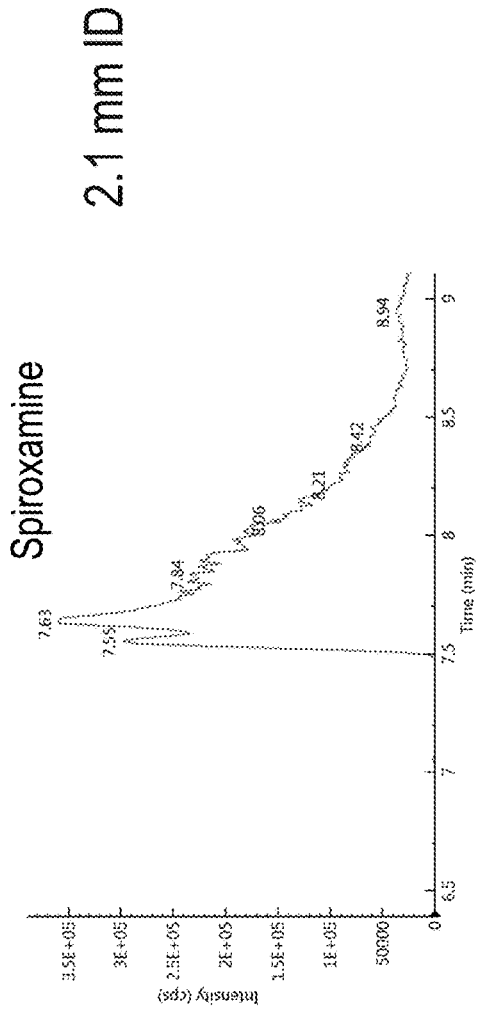
FIG. 29A is a chromatogram of a *cannabis* sample analyzed for the presence of spiroxamine using a 2.1 mm inner diameter (ID) LC column.
Figure 29B:
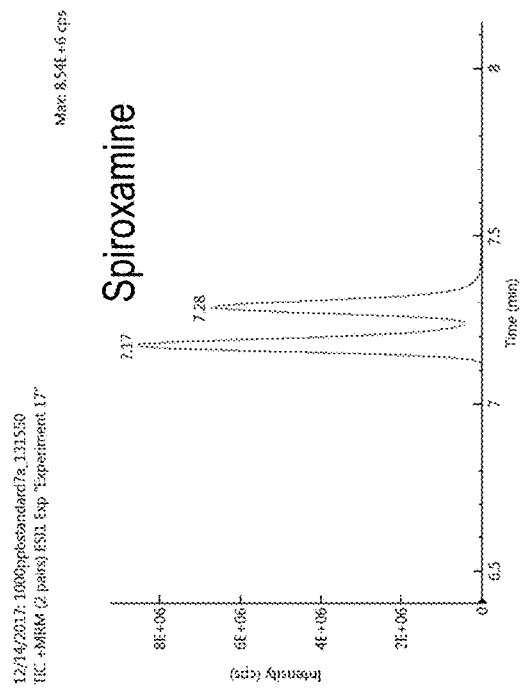
FIG. 29B is a chromatogram of a *cannabis* sample analyzed for the presence of spiroxamine using a 4.6 mm ID column.

Column inner diameter. The inner diameter (ID) of a column can be adjusted to improve response and ability to accurately detect and/or quantify various pesticides in botanical samples. FIG. 29A and FIG. 29B plot intensities of a MRM transition for pesticide sample comprising spiroxamine (and *cannabis* plant material) measured for a 2.1 mm ID column and a 4.6 mm ID column, respectively. The data show that a smaller ID column can distort peak shape, believed to be due to overloading of the smaller ID column with *cannabis* matrix components.

Flow Rate.

Figure 27E:
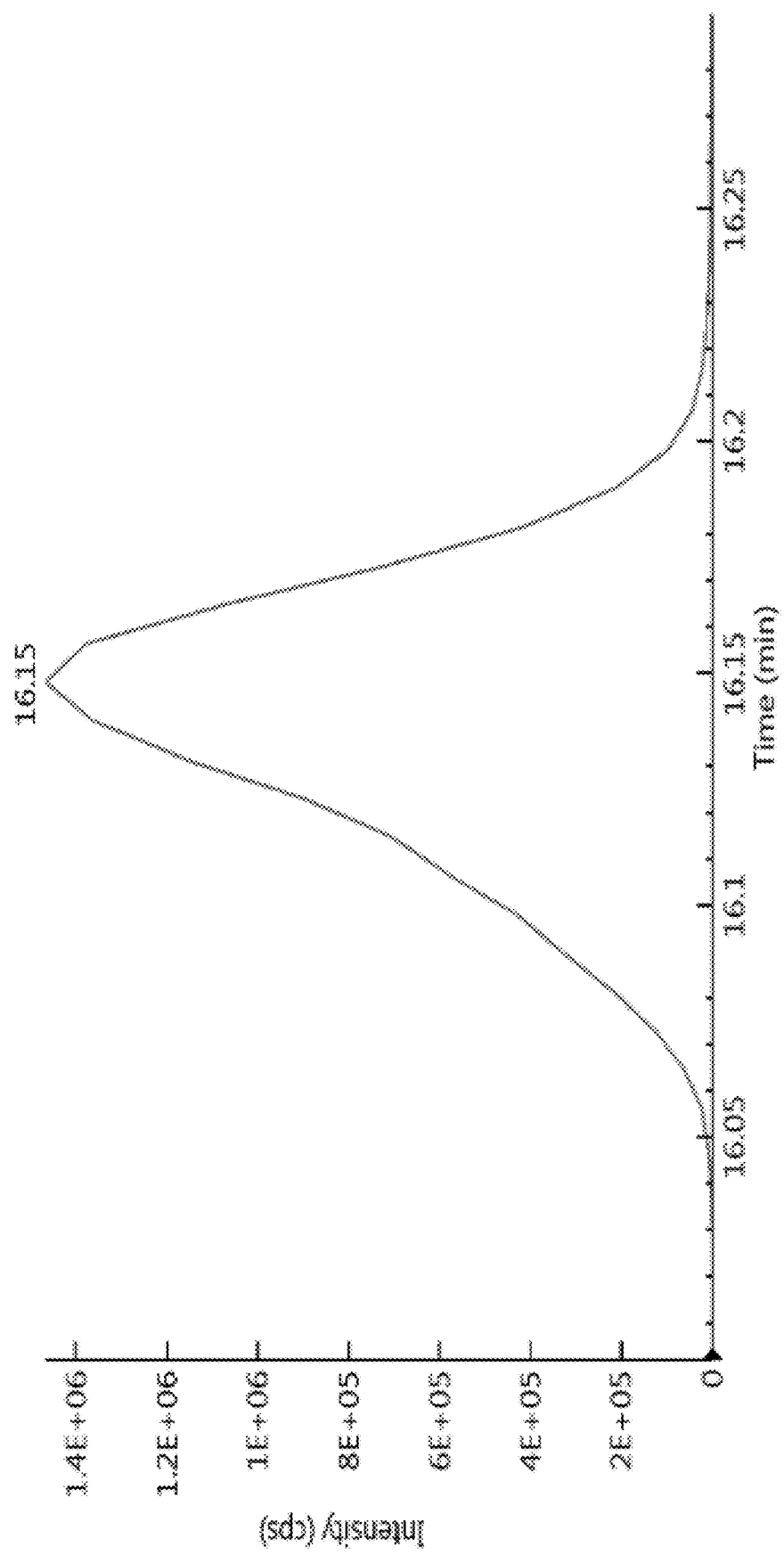
FIGS. 27E and 27F are graphs showing the effect of flow rate on an azoxystrobin signal.
Figure 27F:
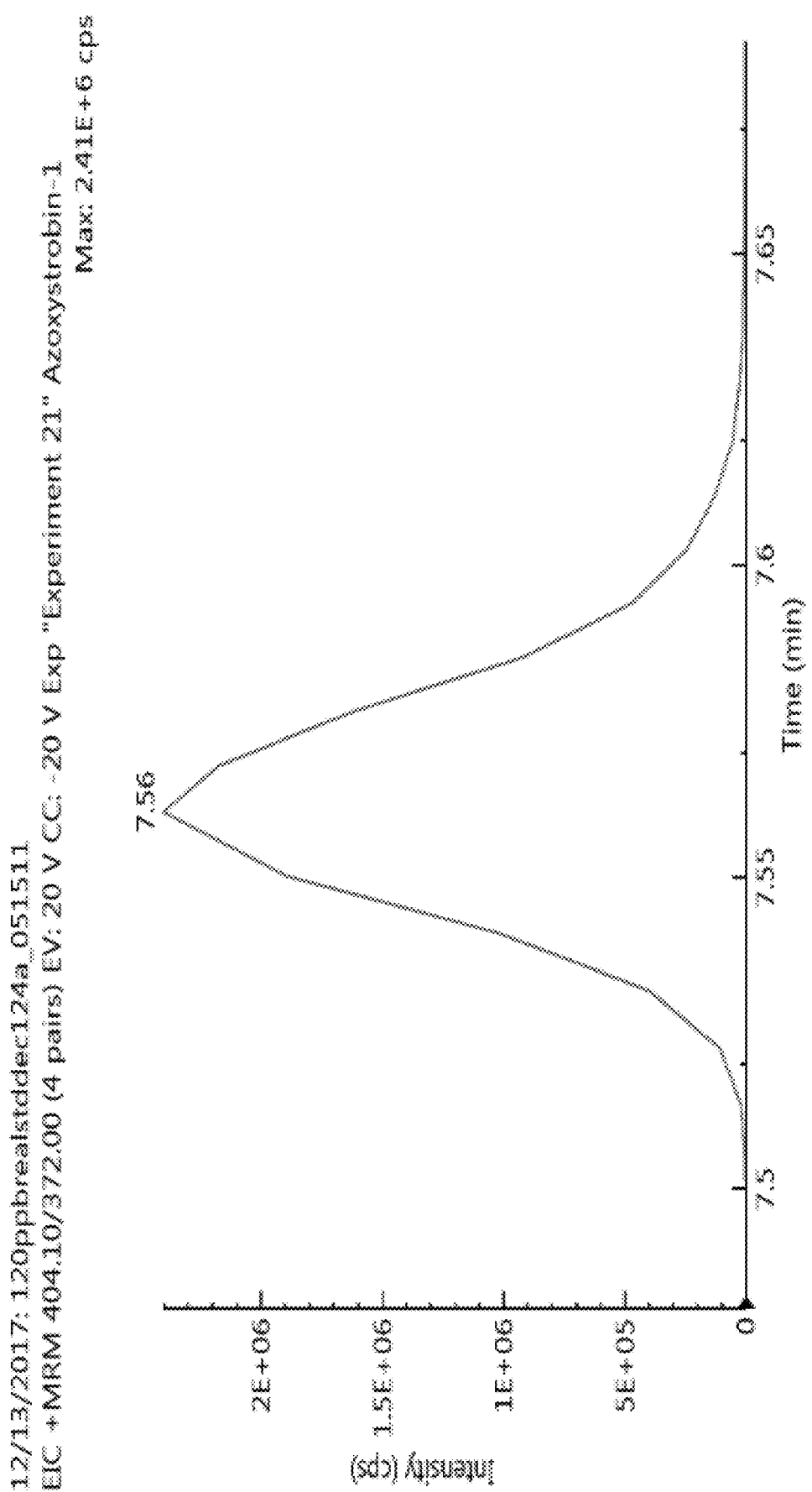

Flow rate is an LC parameter that can influence performance of an LC method and the signal obtained in a mass spectrometry measurement used to detect and/or quantify a particular pesticide. FIG. 27E and FIG. 27F are graphs that plot intensities of a 404.1>372.1 MRM transition measured for a sample comprising azoxystrobin. FIG. 27E shows intensity of the MRM transition when a 0.5 mL>min flow rate was used. The peak width and signal amplitudes obtained were 0.19 min and $1.47\times10^6$, respectively. FIG. 27F shows intensity of the MRM transition when a flow rate of 0.8 mL>min was used. The peak width and signal amplitude obtained were 0.12 min and $2.41\times10^6$, respectively. The peak width for the 0.5 mL>min flow rate LC method was 1.58 times larger than the peak width obtained with the 0.8 mL>min flow rate LC method, while the signal amplitude obtained with the 0.8 mL>min method was a factor of 1.64 larger than that of the 0.5 mL>min method. Accordingly with an improved flow rate of 0.8 mL>min a narrower and larger amplitude peak was obtained. Effects of flow rate on signals for various other pesticides were examined, and it was determined that for the 4.6 mm ID column used in this example, detection limits could be improved by about 50% for all analytes.

Eluting Solvent.

Figures 30A, 30B:
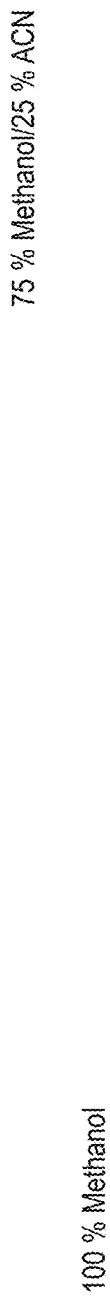
FIG. 30A is a graph showing intensity of a MRM transition associated with acequinocyl as a function of time for a sample processed via a LC method employing a 100% methanol eluting solvent.
FIG. 30B is a graph showing intensity of a MRM transition associated with acequinocyl as a function of time for a sample processed via a LC method employing a 75% methanol: 25% acetonitrile eluting solvent.
Figure 30C:
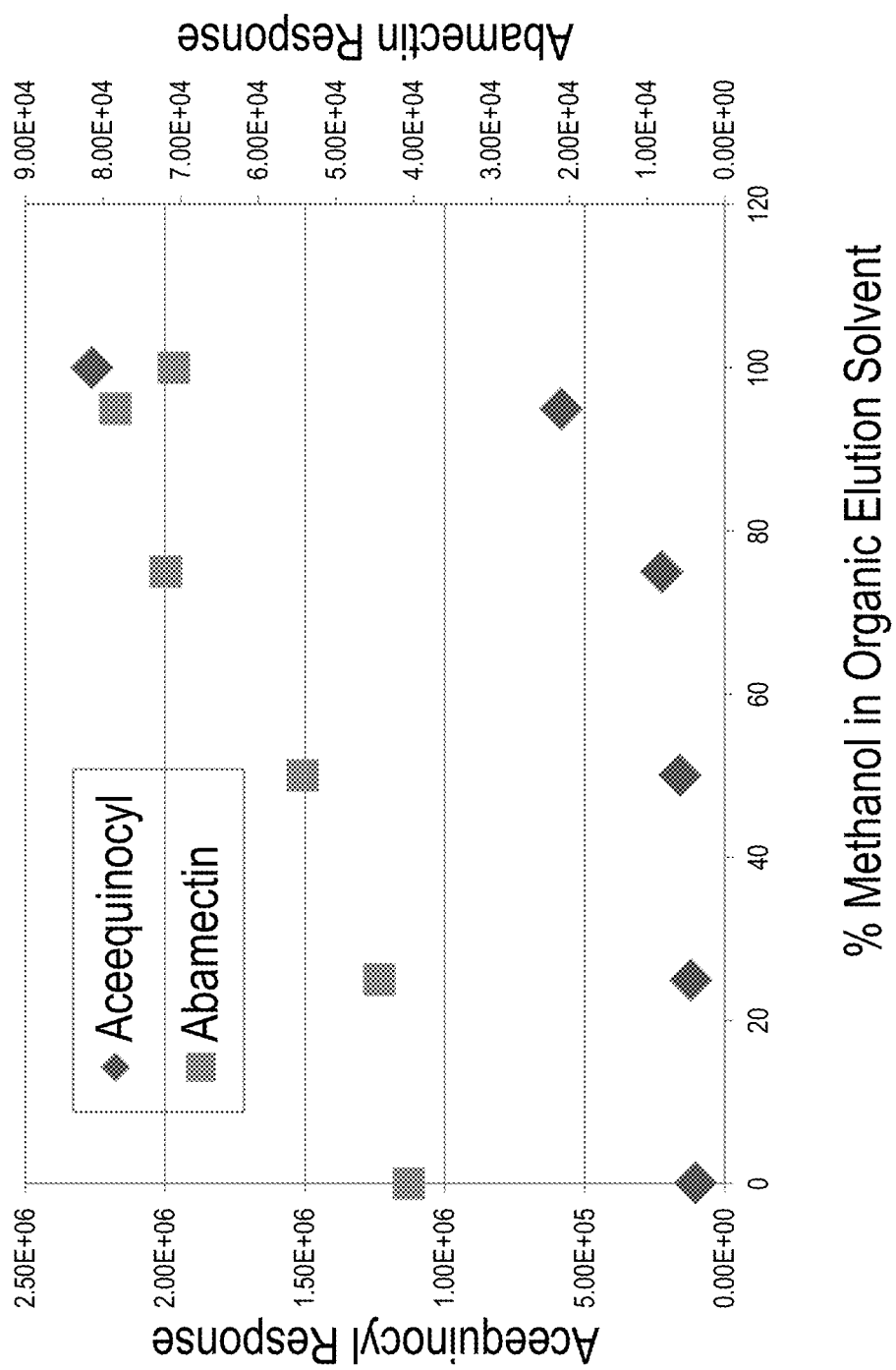
FIG. 30C is a graph showing MRM transition signal intensities for acequinocyl and abamectin as a function of percentage methanol concentration of an organic elution solvent used in a LC method.

FIGS. 30A-C show data directed to effect of organic eluting solvent used in a LC method on response for various pesticides. FIG. 30A and FIG. 30B plot intensities of a MRM transition measured for a *cannabis* extract comprising acequinocyl, following separation by LC methods in which two different organic solvent compositions were used. FIG. 30A shows the intensity of the MRM transition obtained when the organic eluting solvent was 100% methanol solvent, and FIG. 30B shows an intensity of the MRM transition obtained when the organic eluting solvent was 75% methanol and 25% acetonitrile. FIG. 30C shows the effect of various percentages of methanol in the organic elution solvent on the responses observed for acequinocyl and abamectin.

Example 3

Detection and quantification of pesticides in *cannabis* samples was demonstrated using embodiments of the disclosed methods. The results are shown in the figures identified in Table 7. Detection and quantification of additional pesticides is described in Examples 4-17.

TABLE 7

Figures Showing Detection and Quantification of Pesticides in *Cannabis* Samples

| Pesticide | FIG. |
|---|---|
| Acetamiprid | 50A-D |
| Aldicarb | 11A-D, 54A-D |
| Azoxystrobin | 65A-D |
| Bifenazate | 74A-D |
| Bifenthrin | 112A-D |
| Boscalid | 68A-D |
| Captan | 13A-B, 67A-B |
| Carbaryl | 58A-D |
| Carbofuran | 57A-D |
| Chlorantraniliprole | 62A-D |
| Chlorpyrifos | 102A-D |
| Clofentezine | 86A-D |
| Coumaphos | 84A-D |
| Diazinon | 82A-D |
| Dichlorvos | 56A-D |
| Dimethoate | 48A-D |
| Ethoprophos | 78A-D |
| Etofenprox | 110A-D |
| Etoxazole | 105A-D |
| Fenhexamid | 25A-B, 75A-B |
| Fenoxycarb | 23A-F, 79A-B |
| Fenpyroximate | 107A-D |
| Fipronil | 76A-D |
| Flonicamid | 43A-D |
| Fludioxonil | 69A-D |
| Hexythiazox | 104A-D |
| Imazalil | 19A-B, 52A-B |
| Imidacloprid | 47A-D |
| Jasmolin I | 99A-D |
| Jasmolin II | 97A-D |
| Kresoxim-methyl | 80A-D |
| Malathion | 28A-B, 71A-B |
| Metalaxyl | 61A-D |
| Methiocarb | 66A-D |
| Methomyl | 12A-B, 45A-B |
| Mevinphos | 49A-D |
| Myclobutanil | 73A-D |
| Oxamyl | 42A-D |
| Palcobutrazol | 70A-D |
| Parathion methyl (also referred to as methyl parathion or methylparathion) | 64A-D |
| Permethrin | 95A-D |
| Phosmet | 63A-D |
| Piperonylbutoxide | 103A-D |
| Prallethrin | 88A-D |

TABLE 7-continued

Figures Showing Detection and Quantification
of Pesticides in Cannabis Samples

| Pesticide | FIG. |
| --- | --- |
| Propoxur | 55A-D |
| Pyrethrin I | 101A-D |
| Pyrethrin II | 98A-D |
| Pyridaben | 108A-D |
| Spinetoram | 26A-B, 92A-B |
| Spinosyn A | 83A-D |
| Spinosyn D | 89A-D |
| Spiromesifen | 106A-D |
| Spirotetramat | 77A-D |
| Spiroxamine | 59A-D |
| Tebuconazole | 81A-D |
| Thiachloprid | 51A-D |
| Thiamethoxam | 46A-D |
| Thiophanate methyl | 53A-D |
| Trifloxystrobin | 91A-D |

Because the pesticides detected include both polar and non-polar compounds, 100% acetonitrile was used to extract all the analytes from sample extracts. Cannabis matrix is quite hydrophobic, and further dilution of cannabis extract with aqueous mobile phase to make it compatible with reverse phase LC resulted in lower recoveries of some of pesticides due to precipitation. Therefore, cannabis extracts are diluted with acetonitrile by overall factor of 10 to achieve high recovery of pesticides and reduce matrix effects. However, the reverse phase LC method uses aqueous mobile phase at the beginning of LC run to help better retain the polar compounds on the column. Injecting an organic solvent such as an acetonitrile sample extract on the LC leads to poor chromatographic peaks for early eluting polar compounds. To overcome this problem, a small sample injection volume of 3 microliter was used in the experiments reported in this example.

The experiments described in this example evaluated the performance of various MRM transitions for use in detection and/or quantification of different pesticides in samples comprising cannabis plant material. For a specific MRM transition associated with a particular pesticide, performance was evaluated by measuring intensity variations of the specific MRM transition (as a function of elution time) for two different samples: (i) a pesticide sample that comprises cannabis plant material and the particular pesticide (spiked at a particular concentration) and (ii) a blank cannabis sample that comprises cannabis plant material, but not the particular pesticide. By comparing amplitudes of one or more peaks observed in measurements for the pesticide sample with amplitude fluctuations in the blank cannabis sample, a signal-to-noise ratio (S/N) was calculated for each of the one or more peaks.

For various MRM transitions, limits of quantification (LOQ) were also calculated and compared with state regulatory agency-specified action limits for the particular pesticide with which they are associated. The LOQs are well below the California action limit by a factor of 2 to 600 for all category II pesticides and mycotoxins listed. The response relative standard deviation (RSD) for each pesticide and mycotoxin at its LOQ level in the cannabis matrix was less than 20%. The retention time for each analyte was reproducible within ±0.1 min over a 24-h period. This demonstrates that the method is more than adequately sensitive and reproducible for pesticides and mycotoxins analysis in cannabis at the regulatory limit specified by the state of California.

As explained above, cannabis is a challenging matrix to test, and this is compounded by the low concentration level of the pesticides. To ensure the highest analytical confidence, multiple MRM transitions for a number of pesticides with minimal matrix interference in the cannabis matrix were determined for low-level detection. For example, acequinocyl can be ionized easily as a protonated molecular ion in a standard, but the MRM transitions based on the protonated molecular ion in the cannabis matrix showed a poor LOQ of 0.5-1 µg/g, about 5-10 times higher than its California action limit. Therefore, MRM transitions based on alternative modes of ionization, such as adduct formation, were determined to reduce matrix interference and achieve, for example, an LOQ of 0.025 µg/g (four times below action limits) for acequinocyl in cannabis matrix.

Example 4. Abamectin

Figure 6A:
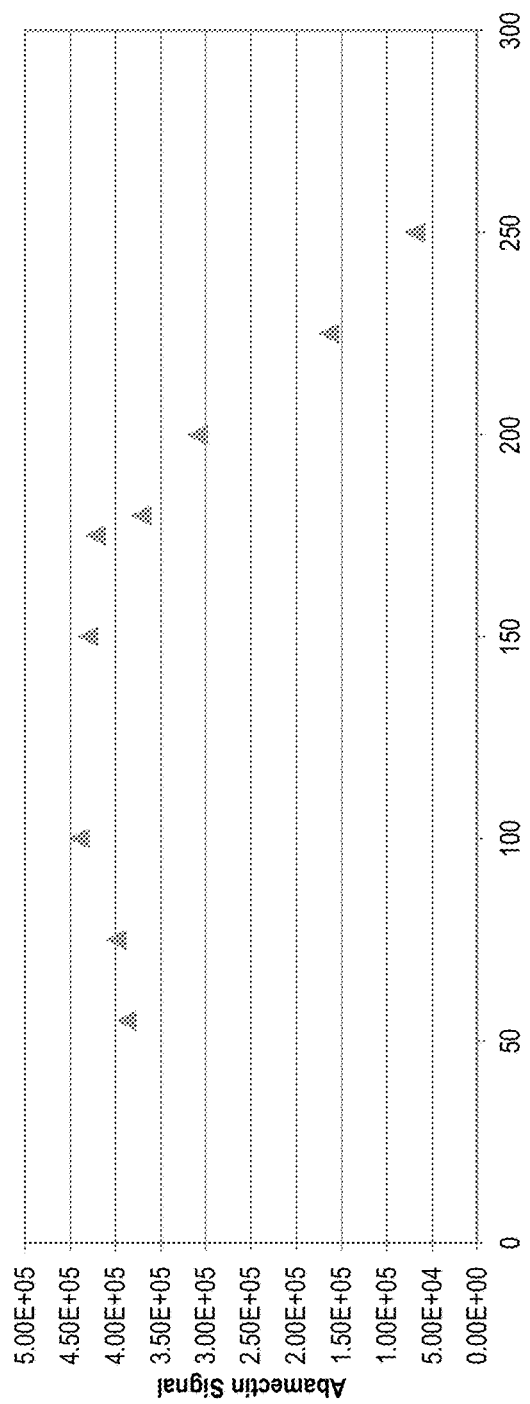
FIGS. 6A-B are graphs showing abamectin signal as a function of HSID (hot-surface induced desolvation.
Figure 6B:
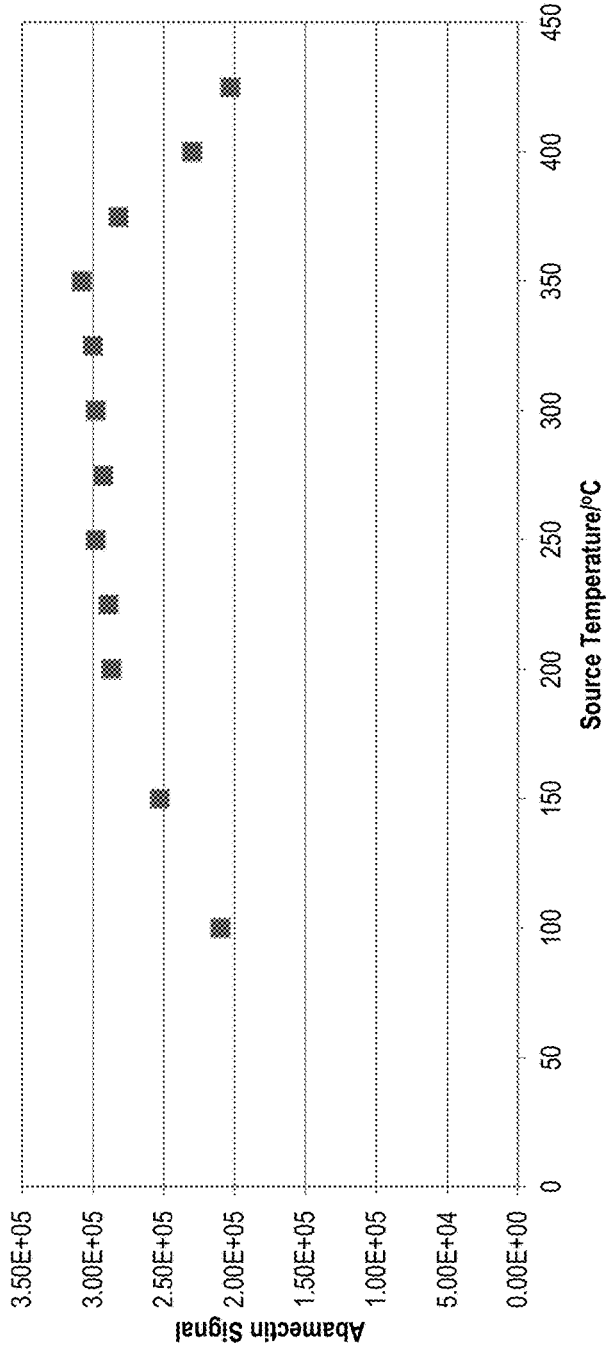

High molecular weight compounds such as abamectin and some early eluting polar compounds such as daminozide and others are difficult to measure at low levels using GCMS because they decompose at high temperature in the GC injector or in the GC oven. Although these compounds can be ionized with ESI source, they also are prone to decomposition at high temperature in ESI source (see, for example, FIGS. 6A, 6B). Suitable temperatures for the ESI source and HSID temperature were therefore determined to maximize signal for high molecular weight and polar pesticides.

Abamectin is also prone to sodium and potassium adduct formation from sodium and potassium ions leached into the mobile phase from glassware. Because the amount of leached ions is difficult to control, use of a sodium adduct for abamectin as the Q1 mass for analysis would lead to unacceptable response variation. Therefore, to reduce sodium or potassium adduct formation, a controlled amount of ammonium salt (acetate or formate) was added in the mobile phase to form an ammonium adduct of abamectin. Use of ammonium salt in the mobile phase and the correct temperature conditions results in a good and reproducible signal for abamectin.

Figure 10A:
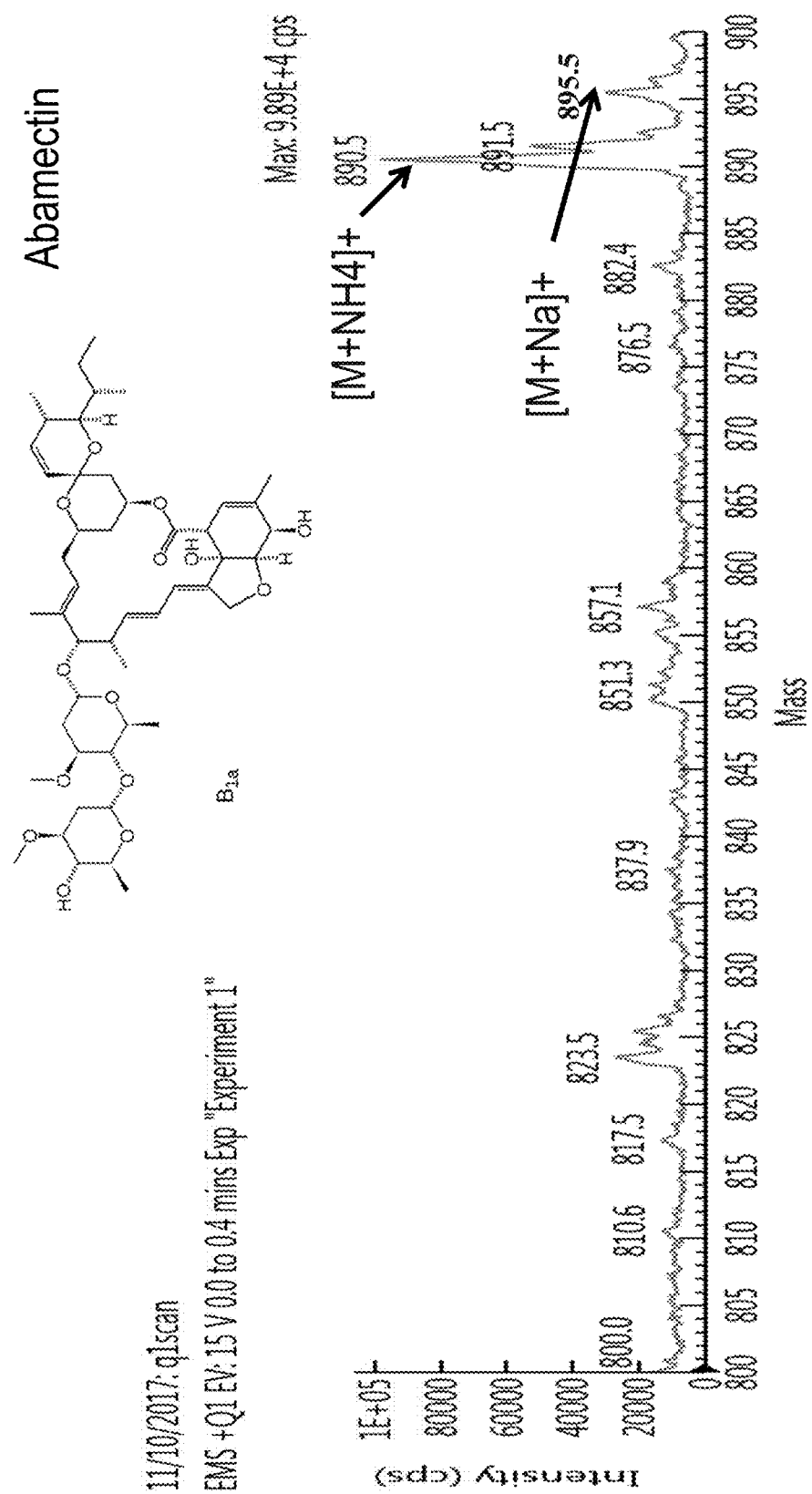
FIG. 10A is a precursor (parent) ion mass scan for abamectin.
Figure 10C:
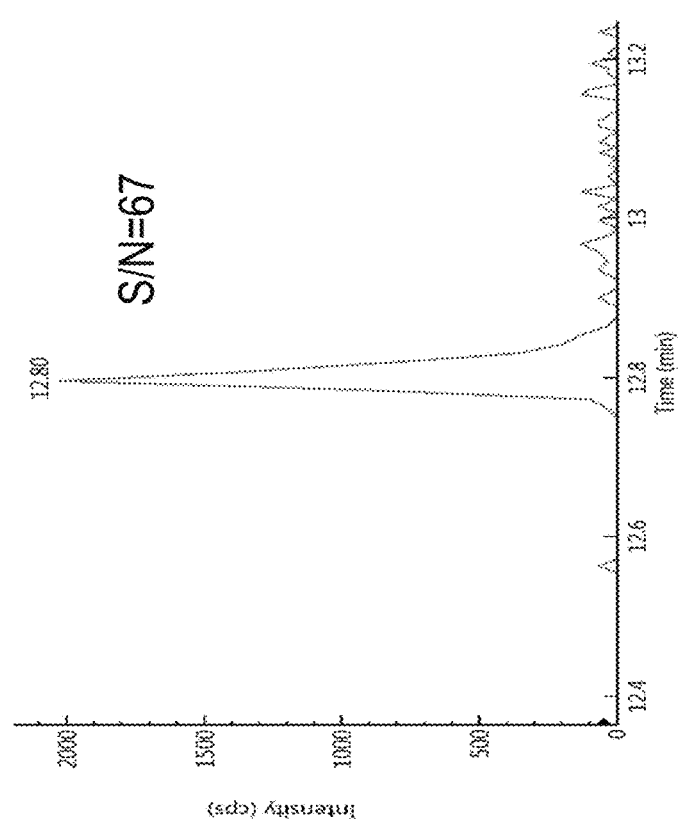
FIGS. 10B-E are chromatograms of *cannabis* samples analyzed for the presence of abamectin using an MRM transition of 890.5>567.2 (FIGS. 10B, 10D) or 890.5>305.1 (FIGS. 10C, 10E).

FIG. 10A is a precursor (parent) ion mass scan for abamectin in Q1 scan mode. FIGS. 10B-E and FIGS. 109A-D are chromatograms that compare intensities of two different MRM transitions associated with abamectin for cannabis samples comprising 100 ppb abamectin (FIGS. 10B, 10D; FIGS. 109A, 109B) and blank cannabis samples (FIGS. 10C, 10E; FIGS. 109C, 109D). Both MRM transitions use a precursor (parent) mass corresponding to an ammonium adduct instead of a sodium adduct.

Figure 10B:
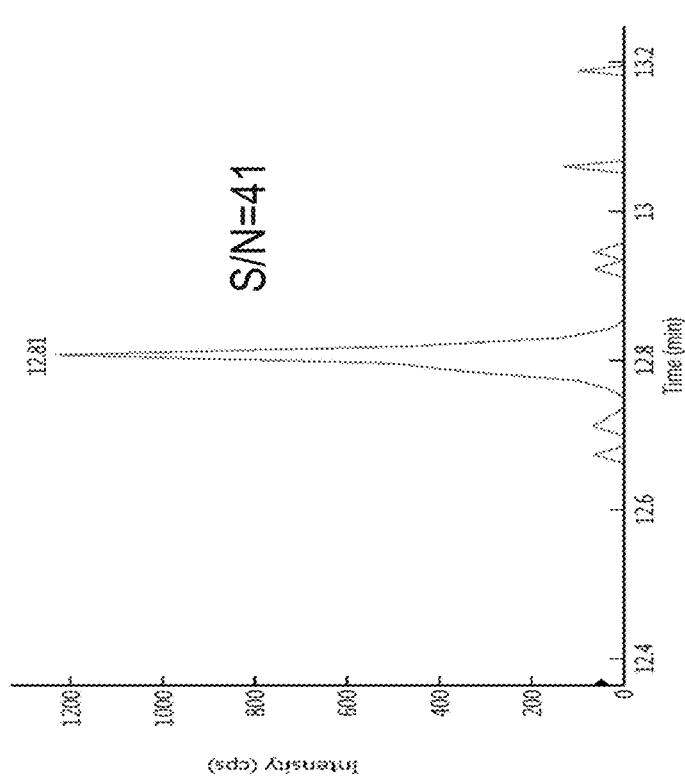
Figure 10E:
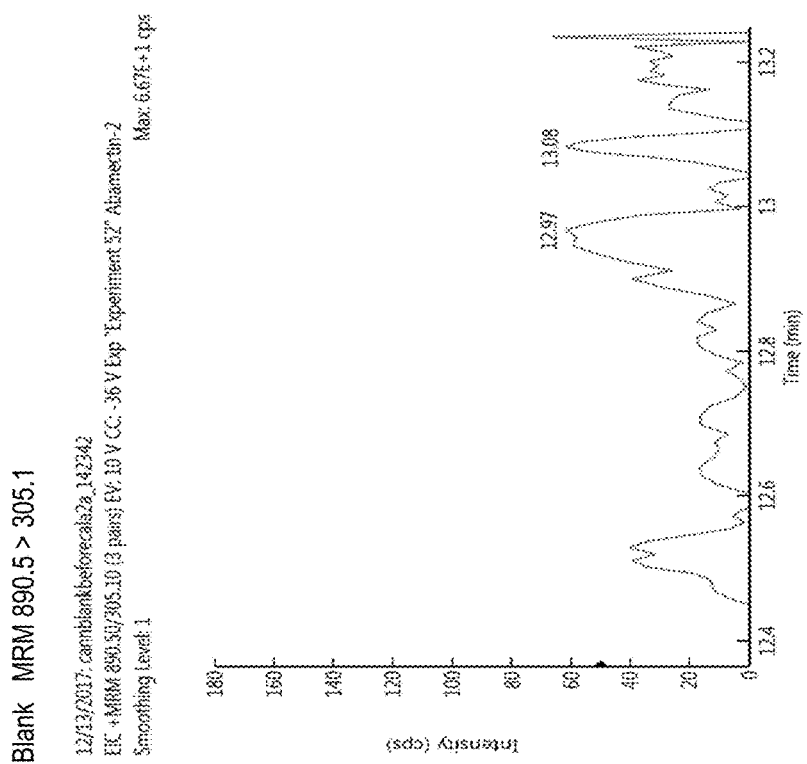
Figure 10D:

Using an MRM transition of 890.5>567.2 (FIGS. 10B, 10D; FIGS. 109B, 109D) results in a signal-to-noise (S/N) ratio of 41. Using an MRM transition of 890.5>305.1 (FIGS. 10C, 10E; FIGS. 109A, 109C) results in an S/N ratio of 67. The LOQ for abamectin using these MRM transitions was improved approximately ten-fold, to approximately 30 ppb.

Example 5. Acephate

FIGS. 18A-B and FIGS. 44A-B are chromatograms that compare intensities of two different MRM transitions associated with acephate for cannabis samples comprising 100 ppb acephate and for blank cannabis samples. Use of an MRM transition of 184>143 MRM (FIGS. 18A, 18B) provides an S/N ratio of 500. Use of an MRM transition of 184>49 (FIGS. 44A, 44B) provides an S/N ratio of 90. These MRM transitions can improve the LOQ for acetate to 10 ppb.

Example 6. Acequinocyl

Acequinocyl can be ionized easily as a protonated molecular ion in solvent standard, but because of matrix interference the MRM transitions based on the protonated molecular ion in *cannabis* matrix result in a poor LOQ of 0.5 to 1 µg/g, which is about 5 to 10 times higher than California's action limit for acequinocyl. As described below, MRM transitions based on alternative modes of ionization such as adduct formation reduce matrix interference and achieve The LOQ was approximately 25 ppb.

Figure 7A:
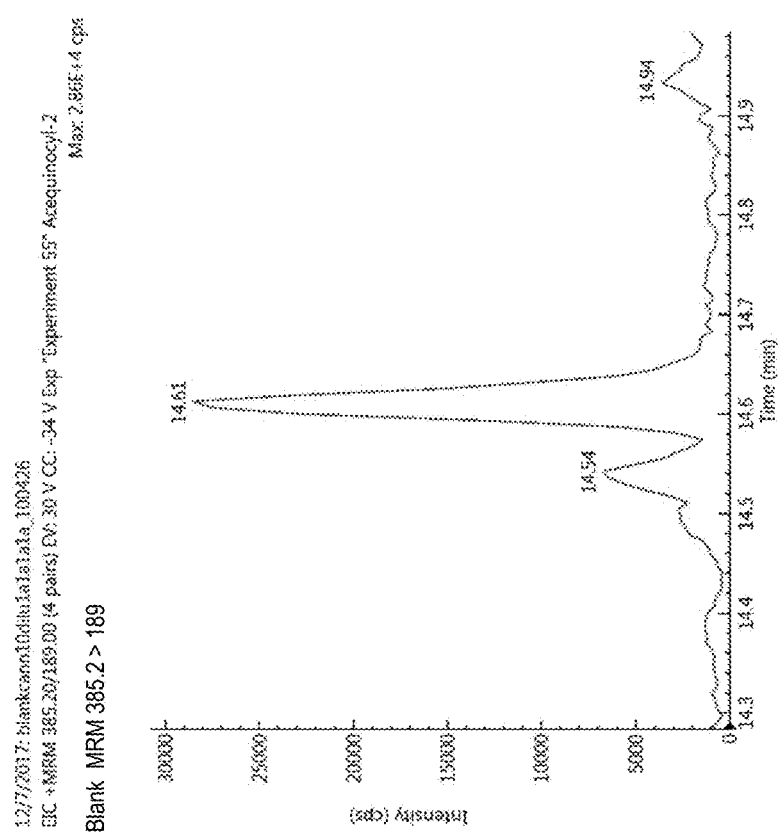
FIGS. 7A-D are chromatograms of *cannabis* samples analyzed for the presence of acequinocyl using a Multiple Reaction Monitoring (MRM) transition of 385.2>189 (FIGS. 7A, 7B) or at 385.2>343.1 (FIGS. 7C, 7D).
Figure 7B:
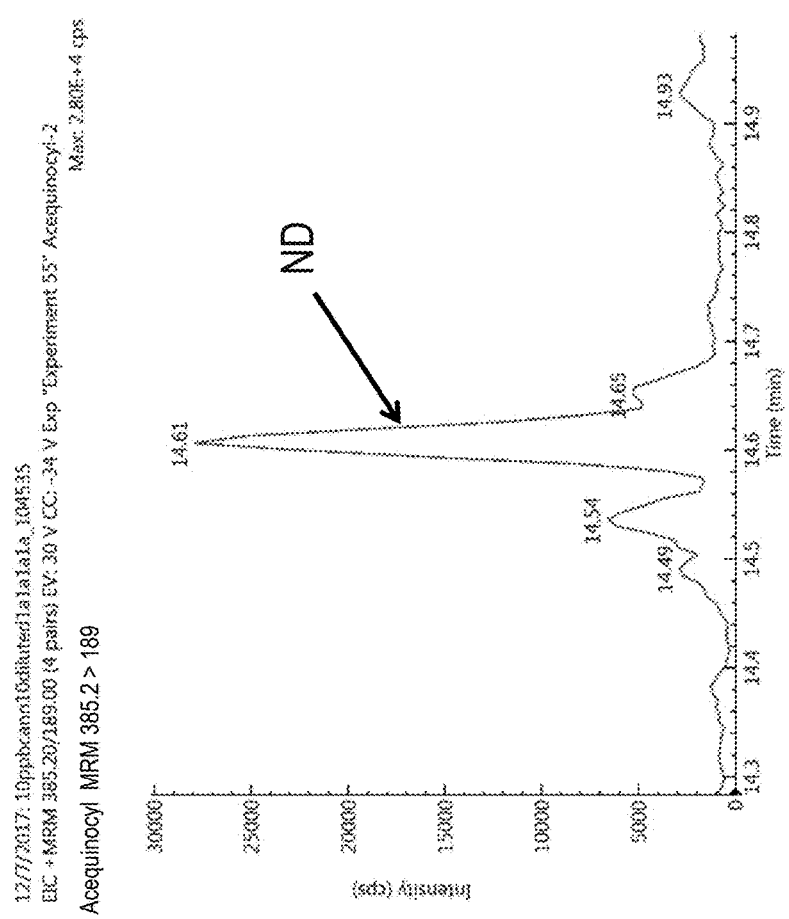
Figure 7D:
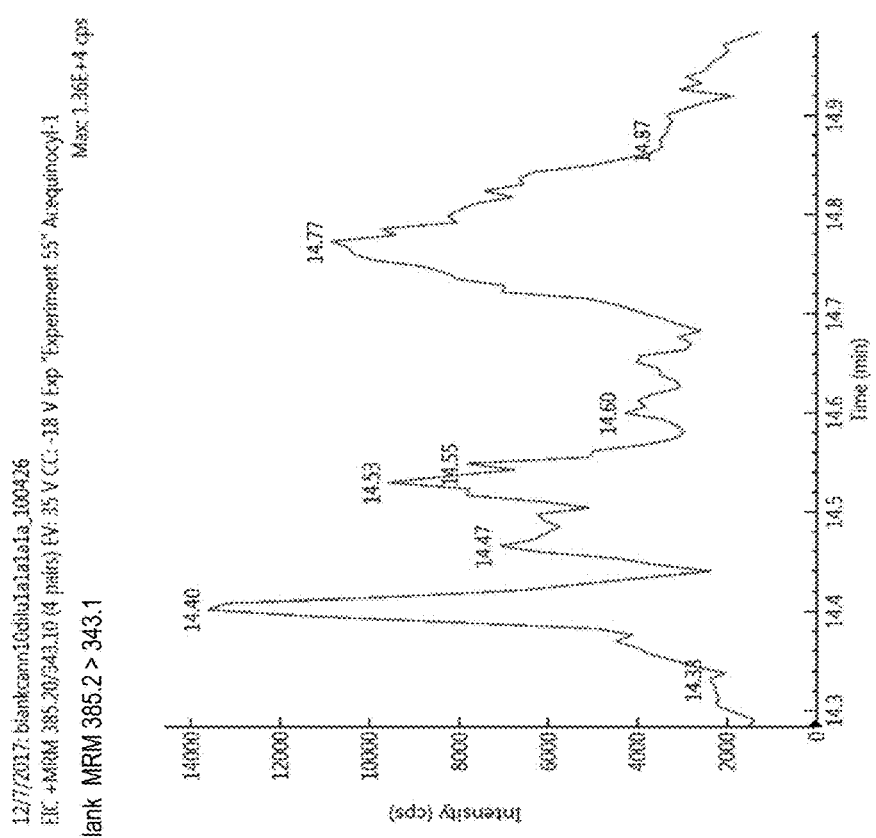
Figure 7C:
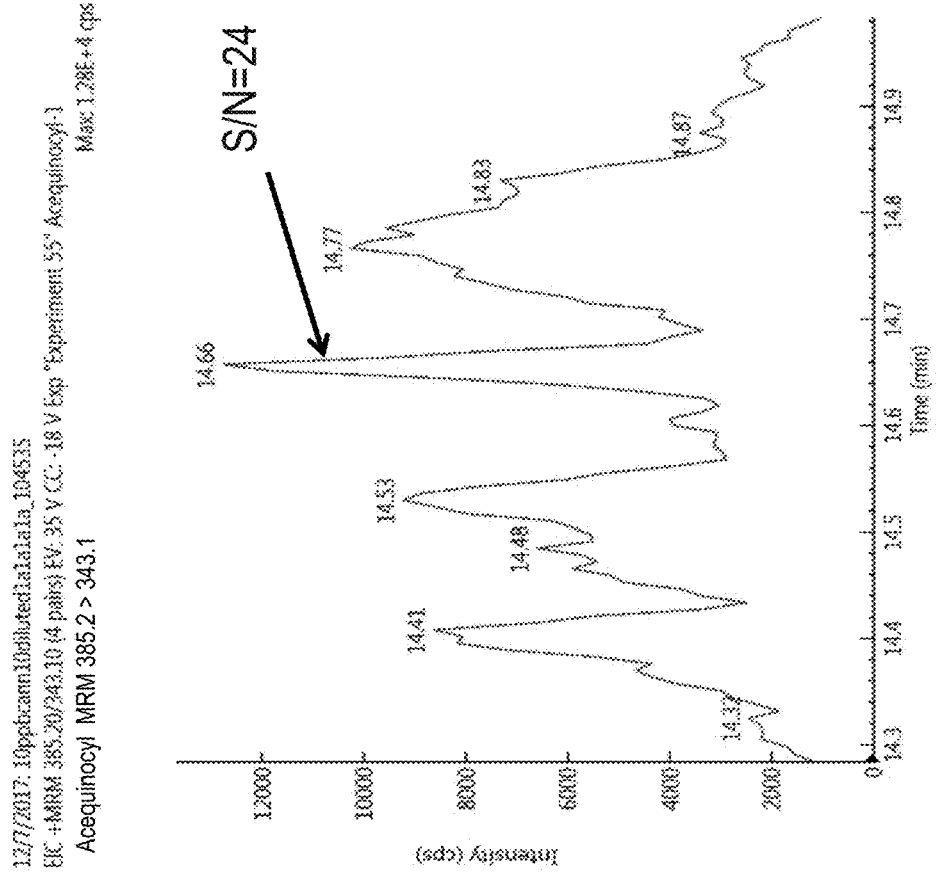

FIGS. 7A-D are four graphs that compare intensities of two different MRM transitions associated with acequinocyl for *cannabis* samples comprising 100 ppb acequinocyl and blank *cannabis* samples. FIGS. 7B and 7D plot intensities of a 385.2>343.1 MRM transition for an acequninocyl and a blank *cannabis* sample, respectively. While a large amplitude intensity peak is observed in the graph of FIG. 7B, a similar peak also appears, at the same time, in the blank *cannabis* sample data shown in FIG. 7D. The data show that this MRM transition is dominated by *cannabis* matrix interference, and is undesirable for use in detection and/or quantification of acequinocyl in the presence of *cannabis* matrix components.

FIG. 7A and FIG. 7B compare intensities of another MRM transition, 385.2>189.1, for an acequninocyl and a blank *cannabis* sample. Based on the data shown in FIGS. 7A and 7B, an S/N ratio of 24 was determined for the 385.2>189.1 MRM transition. These two transitions were determined to provide a LOQ ranging from 0.5 to 1 ppm.

Figure 8:
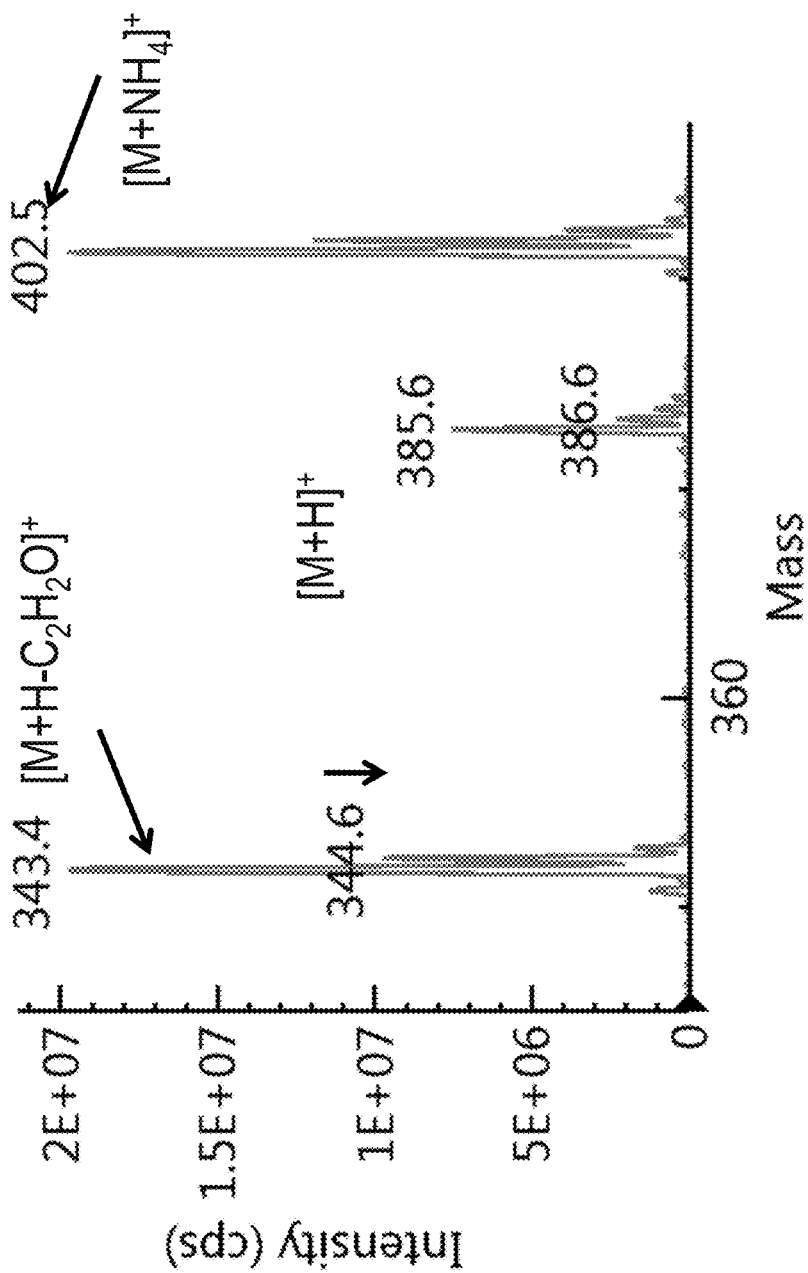
FIG. 8 is a precursor (parent) ion mass scan for acequinocyl.
Figures 9A, 9B:
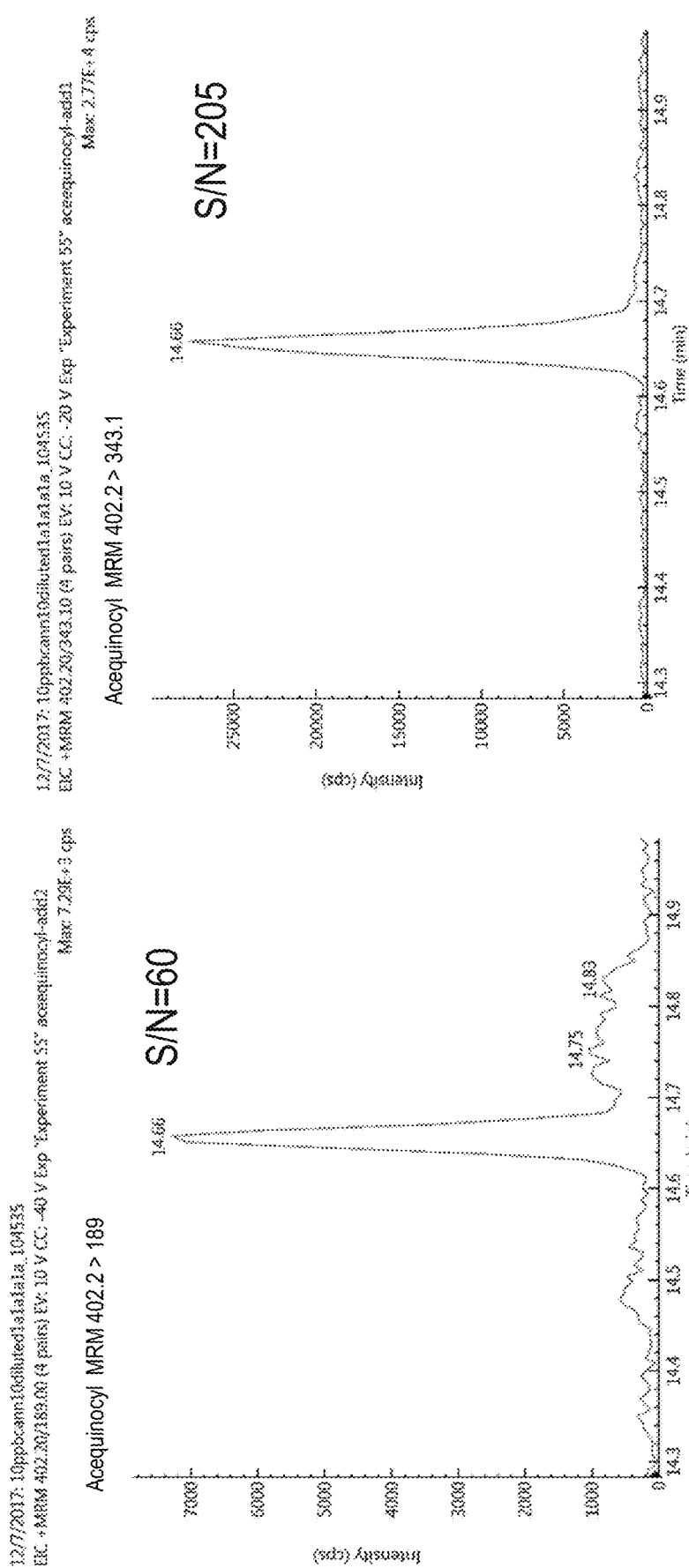
FIGS. 9A-D are chromatograms of *cannabis* samples analyzed for the presence of acequinocyl using an MRM transition of 402.2>189 (FIGS. 9A, 9C) or 402.2>343.1 (FIGS. 9B, 9D).
Figures 9C, 9D:
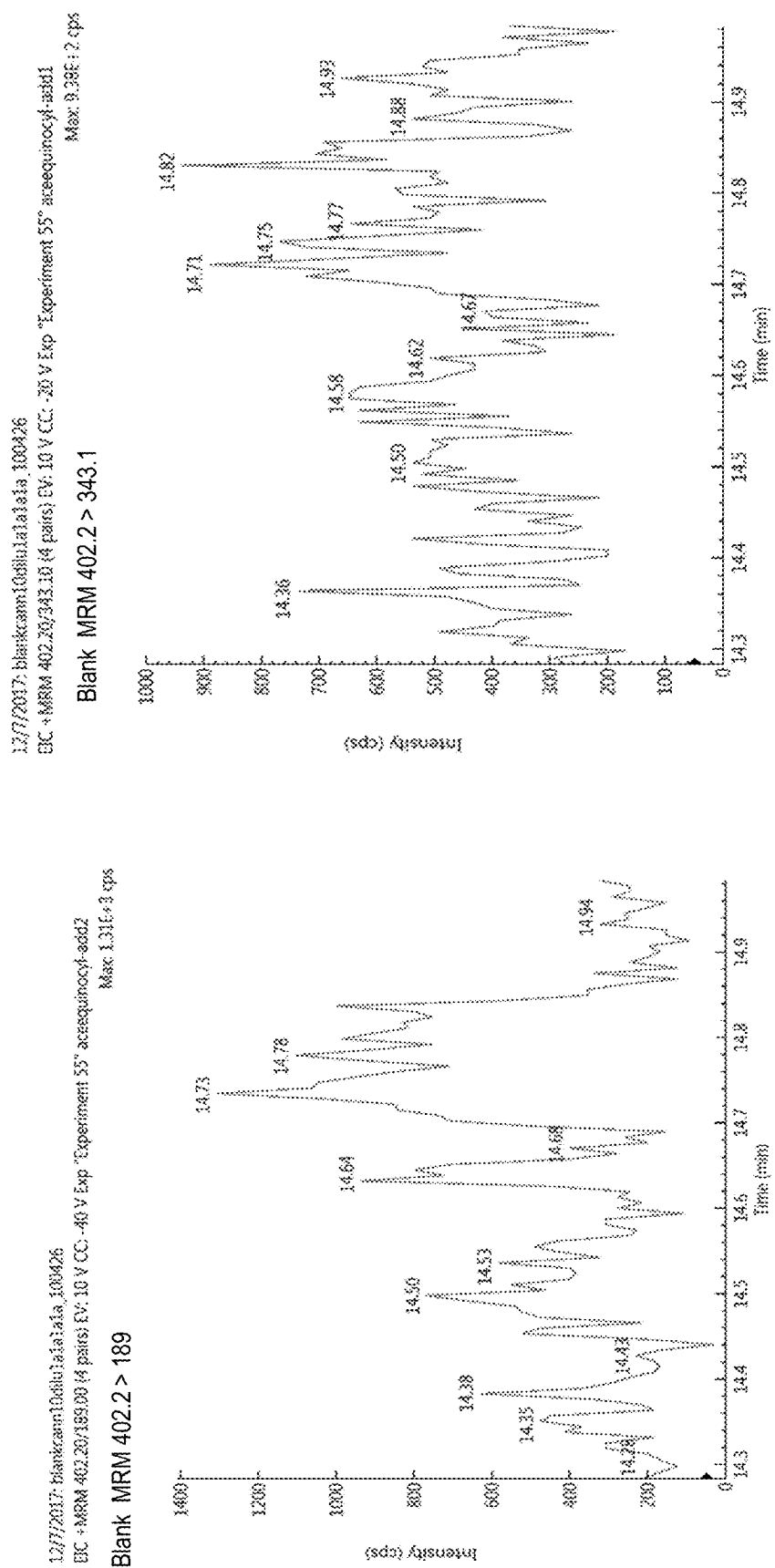

FIG. 8 is a graph showing a mass scan of acequinocyl showing different precursor (parent) ion masses. As shown in the data presented in FIGS. 9 and 111, MRM transitions corresponding to a 402.2 precursor (parent) ion provide higher S/N ratios for detection and/or quantification of acequinocyl. An MRM transition of 402.2>189 (FIGS. 9A, 9C; FIGS. 111A, 111C) provides an S/N ratio of 60. An MRM transition of 402.2>343.1 (FIGS. 9B, 9D; FIGS. 111B, 111D) provides an S/N of 205 and an improvement in LOQ to e.g., 25 or 42 ppb.

Example 7. Chlorfenapyr

The structure of chlorfenapyr is shown below:

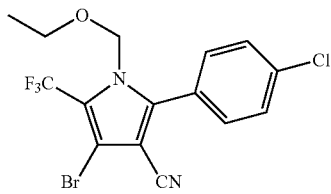 [SMILES: CCOCn1c(-c2ccc(Cl)cc2)c(C#N)c(Br)c1C(F)(F)F]

ESI Ionization Source

Figure 14A:
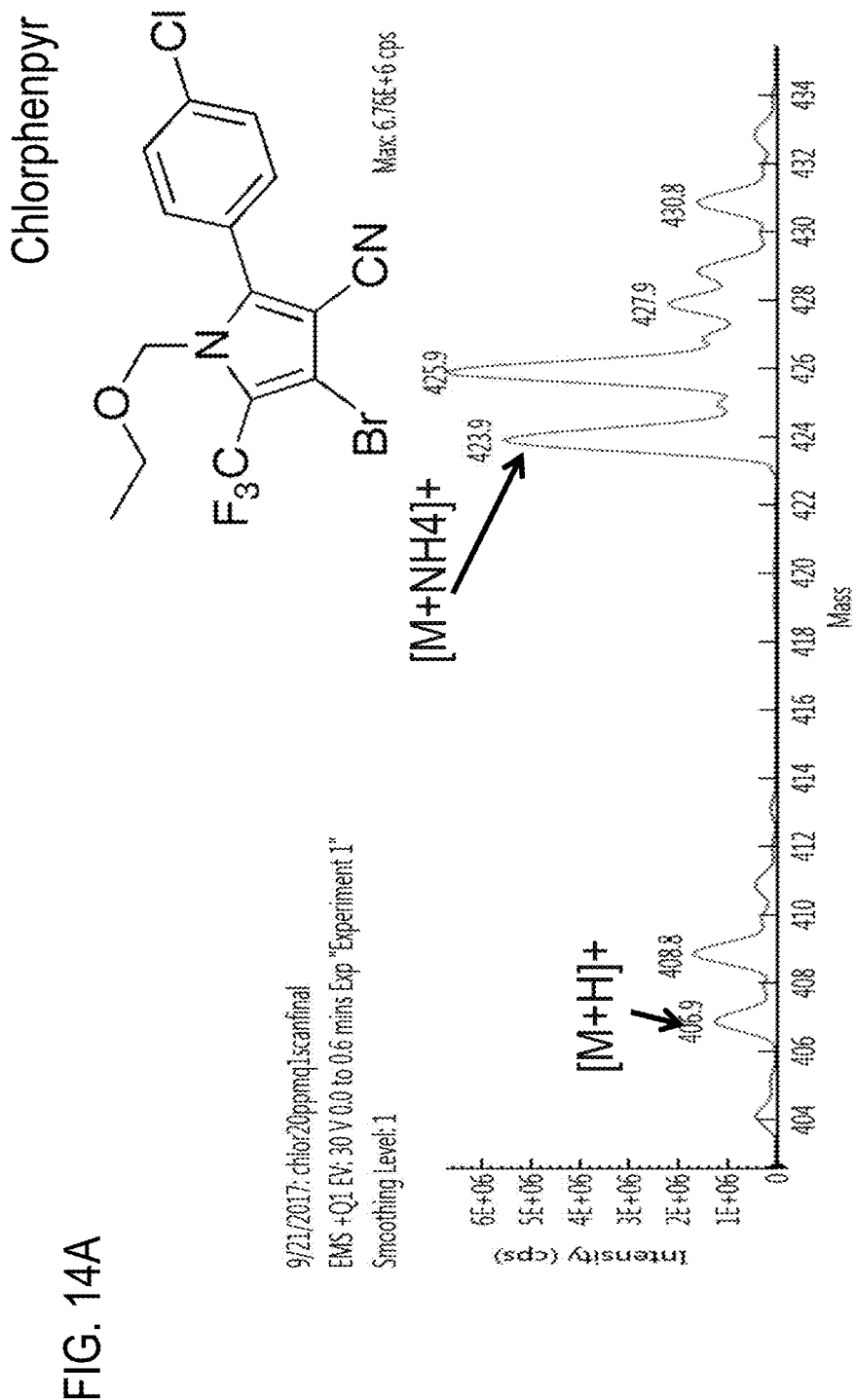
FIG. 14A is a precursor (parent) ion mass scan for chlorfenapyr.

FIG. 14A is a graph showing a mass scan of chlorfenapyr showing different precursor (parent) ion masses. Peaks at mass values of 406.9 and 423.9 correspond to a protonated molecule ([M+H]$^+$) and an ammonium adduct ([M+NH$_4$]$^+$), respectively.

Figures 14B, 14C:
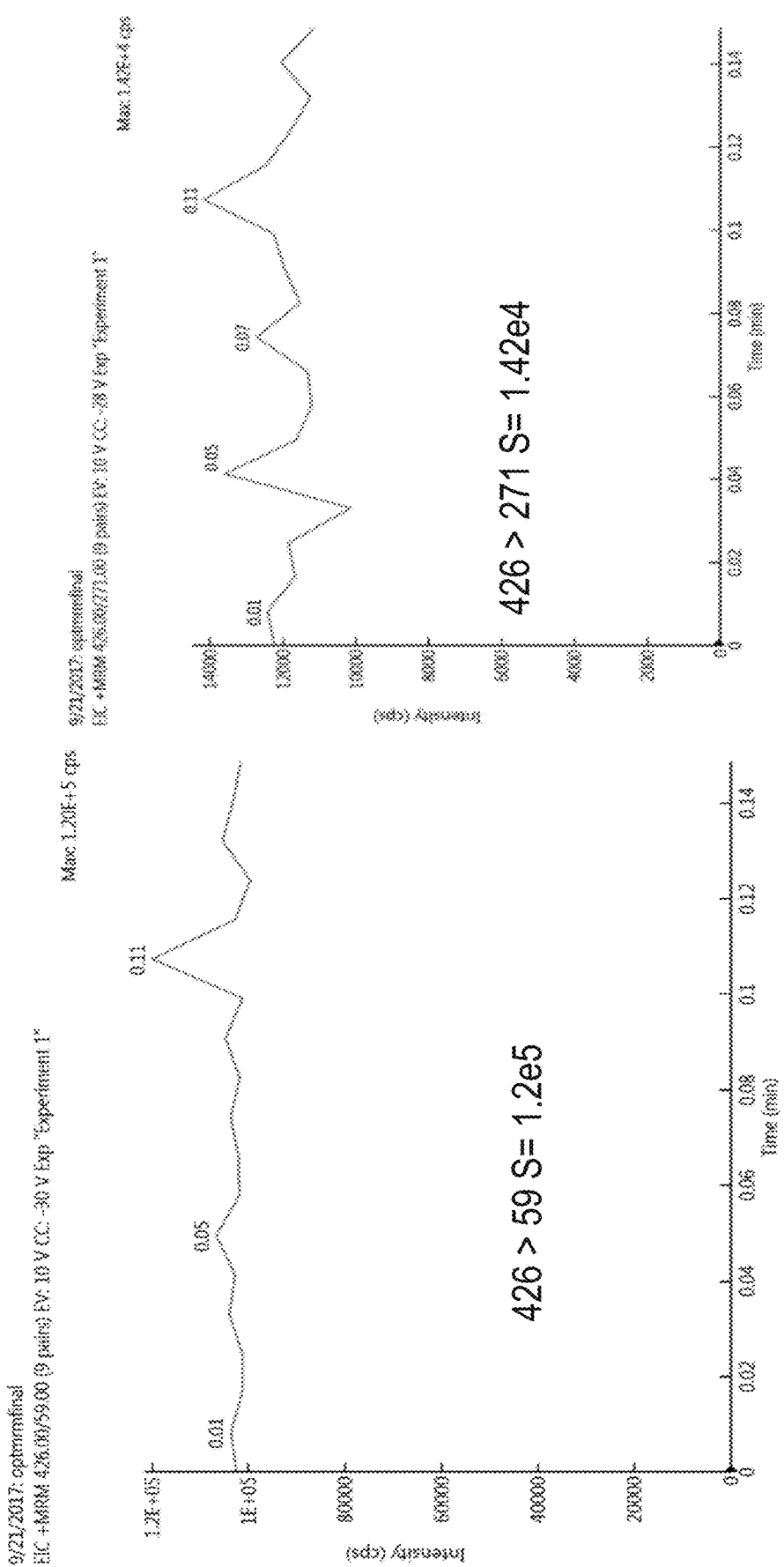
FIGS. 14B-E are chromatograms showing signal amplitudes obtained for an ammonium ([M+NH4]+) adduct of chlorfenapyr using for different MRM transitions.
Figures 14D, 14E:
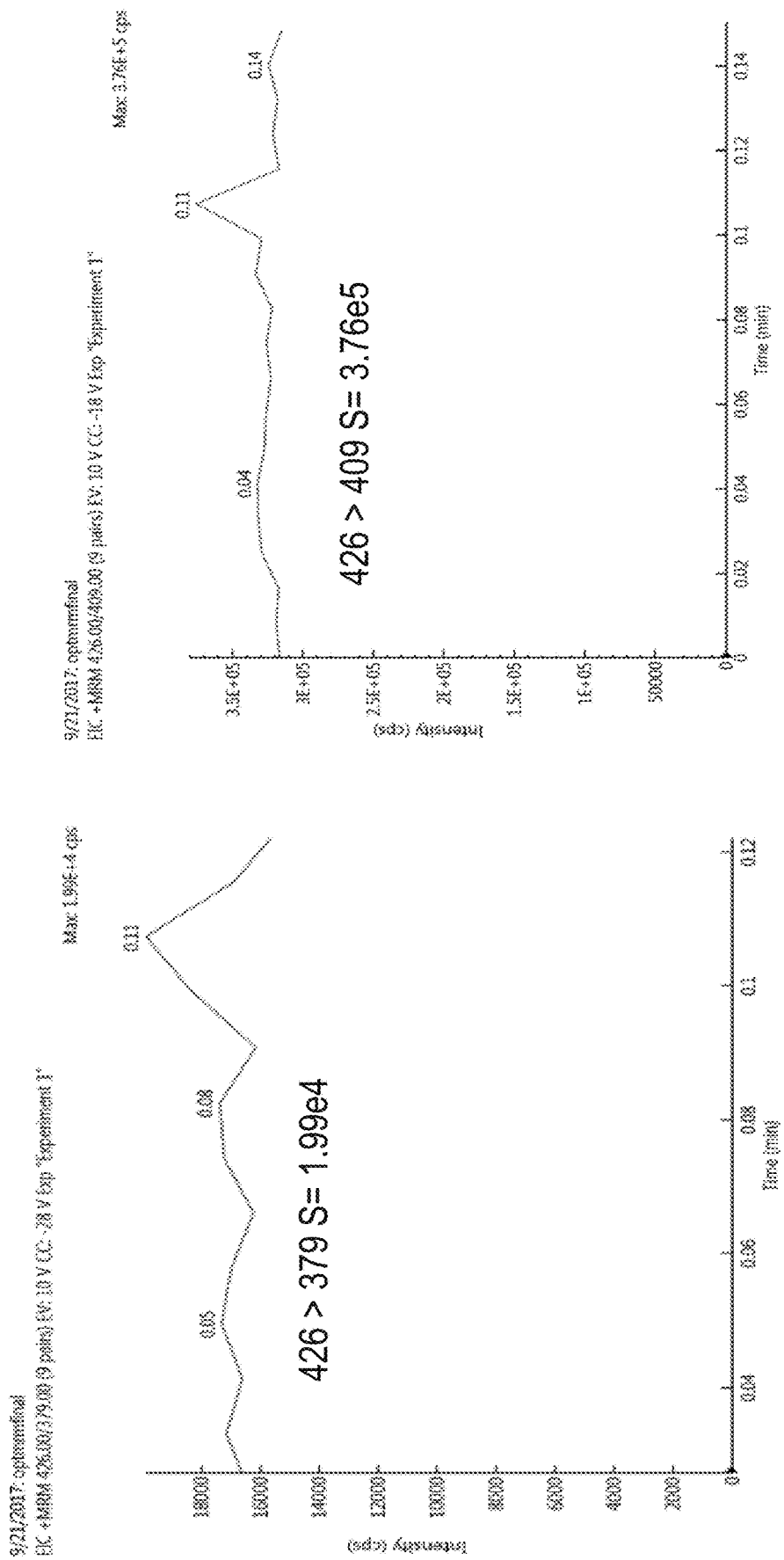

FIGS. 14B-E plot intensities of MRM transitions for which the precursor (parent) mass corresponds to the ammonium ([M+NH$_4$]$^+$) adduct of chlorfenapyr. An MRM transition of 426>59 provides a signal amplitude of 1.2×10$^5$ (FIG. 14B). An MRM transition of 426>271 provides a signal amplitude of 1.42×10$^4$ (FIG. 14C). An MRM transition of 426>379 provides a signal amplitude of 1.99×10$^4$ (FIG. 14D). An MRM transition of 426>409 provides a signal amplitude of 3.76×10$^5$ (FIG. 14E).

Figure 14G:
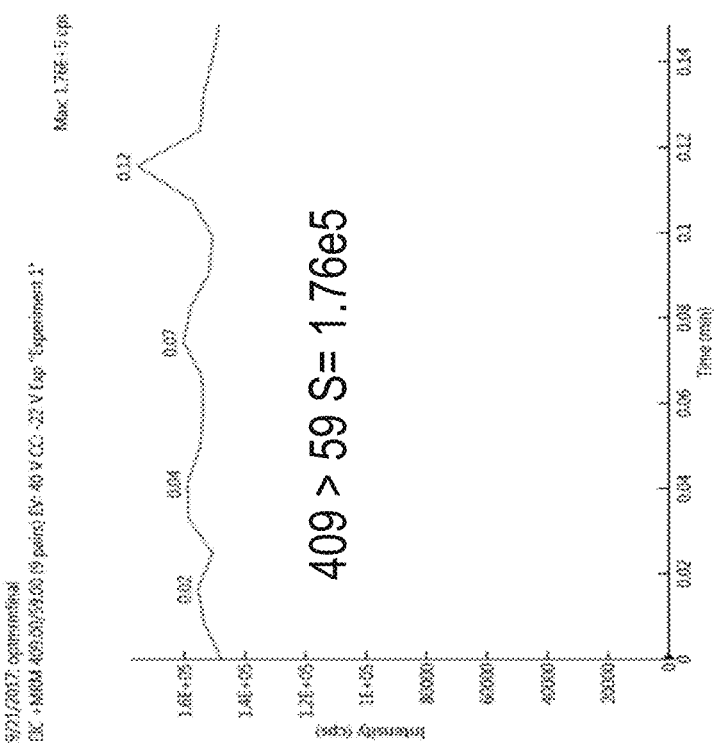
FIGS. 14F-I are chromatograms showing signal amplitudes obtained for protonated chlorfenapyr ([M+H]+) using for different MRM transitions.
Figure 14F:
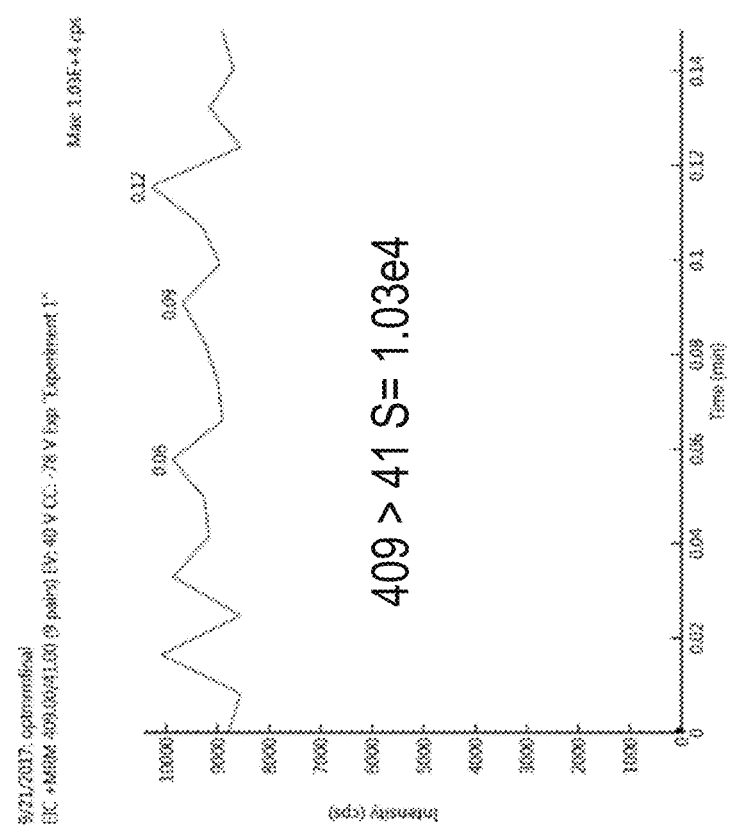
Figures 14H, 14I:
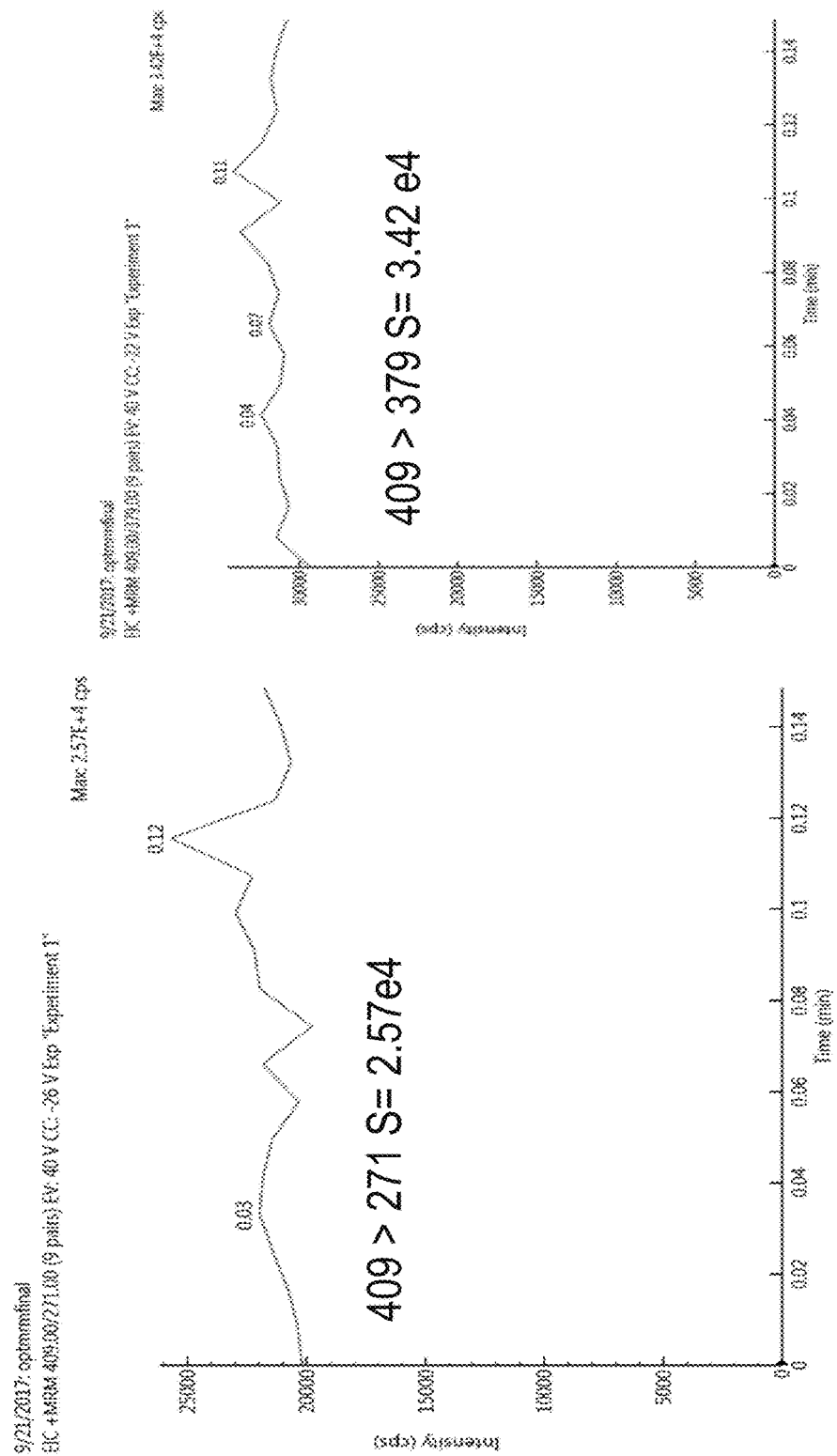
Figures 14J, 14K:
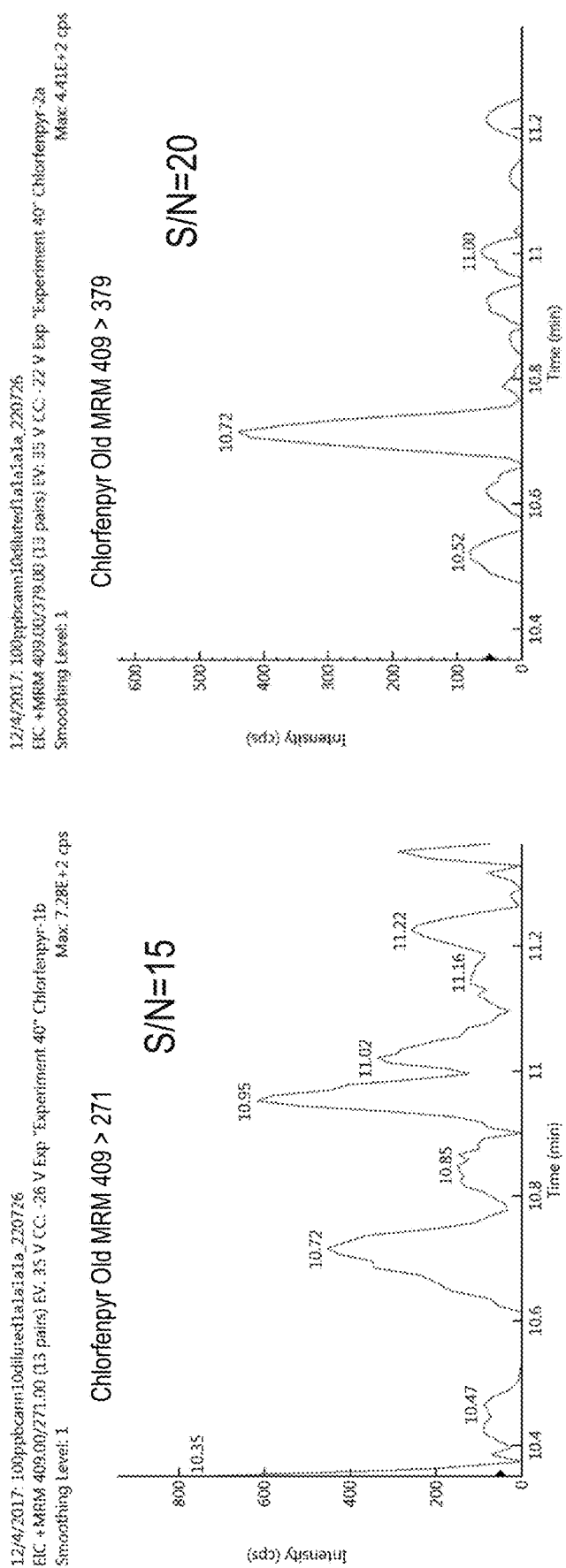
FIGS. 14J-K are chromatograms of *cannabis* samples comprising 100 ppb chlorfenapyr and obtained using MRM transitions 409>271 (FIG. 14J) and 409>379 (FIG. 14K).

FIGS. 14F-I plot intensities of MRM transitions for which the precursor (parent) mass corresponds to protonated chlorfenapyr ([M+H]$^+$). FIG. 14F plots an intensity of 409>41 MRM transition, which provides a signal amplitude of 1.03×10$^4$. FIG. 14G plots an intensity of a 409>59 MRM transition, which provides a signal amplitude of 1.76×10$^5$. FIG. 14H plots an intensity of a 409>271 MRM transition, which provides a signal amplitude of 2.57×10$^4$. FIG. 14I plots an intensity of a 409>379 MRM transition, which provides a signal amplitude of 3.42×10$^4$.

Figure 14L:
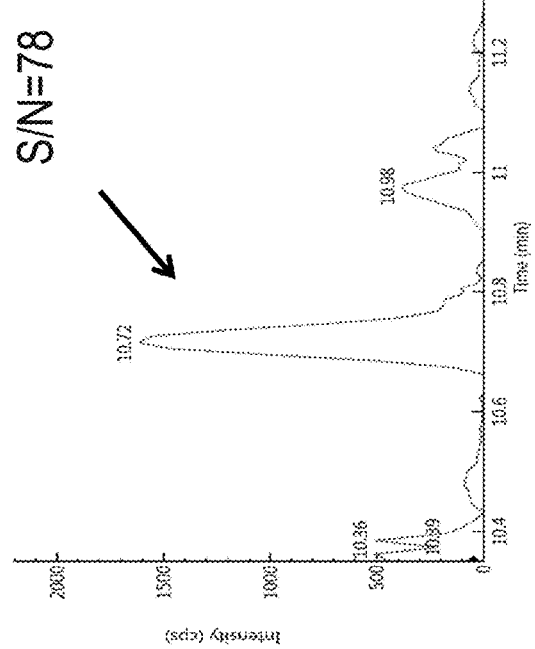
FIGS. 14L-N are chromatograms of *cannabis* samples comprising 100 ppb chlorfenapyr and obtained using MRM transitions 409>59 (FIG. 14L), 426>59 (FIG. 14M), and 426>409 (FIG. 14N).
Figure 14M:
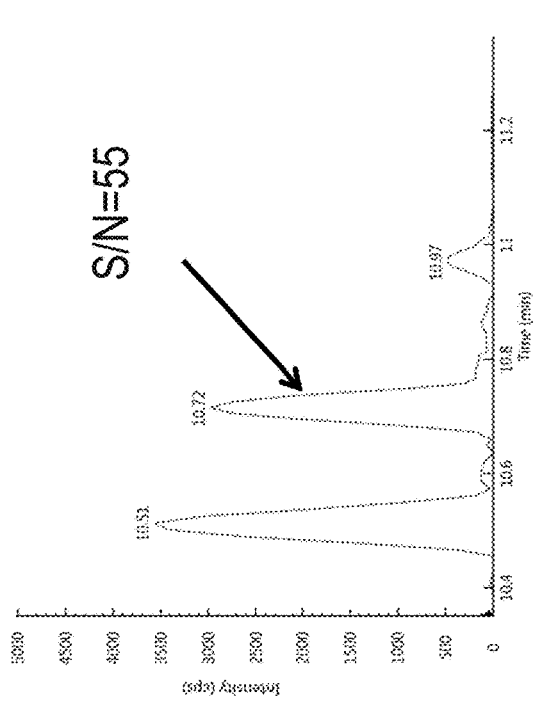
Figure 14N:
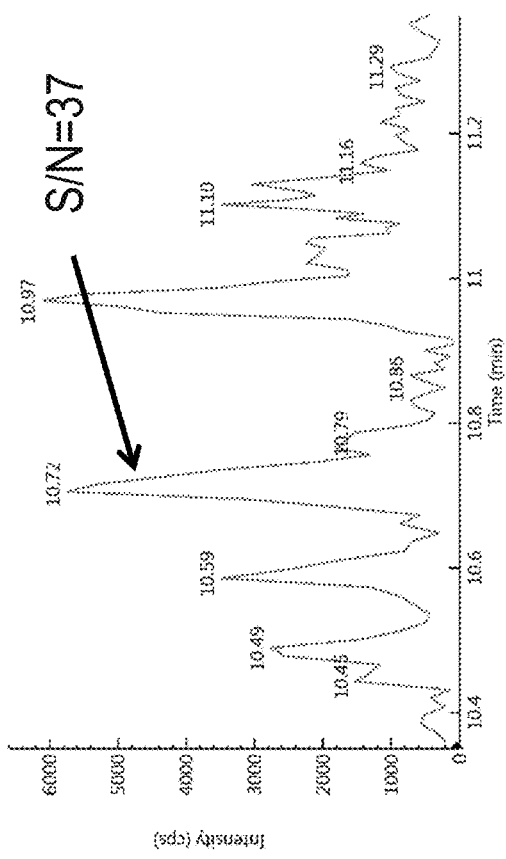

FIGS. 14J-N are chromatograms for *cannabis* samples comprising 1000 ppb chlorfenapyr. The chromatograms in FIGS. 14J and 14K were obtained using previously used MRM transitions of 409>271, which provides an S/N ratio of 15 (FIG. 14J), and 409>379 (FIG. 14K), which provides an S/N ratio of 20. In contrast, FIGS. 14L-N are chromatograms obtained using the appropriate MRM transitions disclosed here, which can improve sensitivities by a factor of 3. The MRM transition of 409>59 (FIG. 14L) provides an S/N ratio of 55. The MRM transition of 426>59 (FIG. 14M) provides an S/N ratio of 78. The MRM transition of 426>409 (FIG. 14N) provides an S/N ratio of 37.

Figures 15A, 15B:
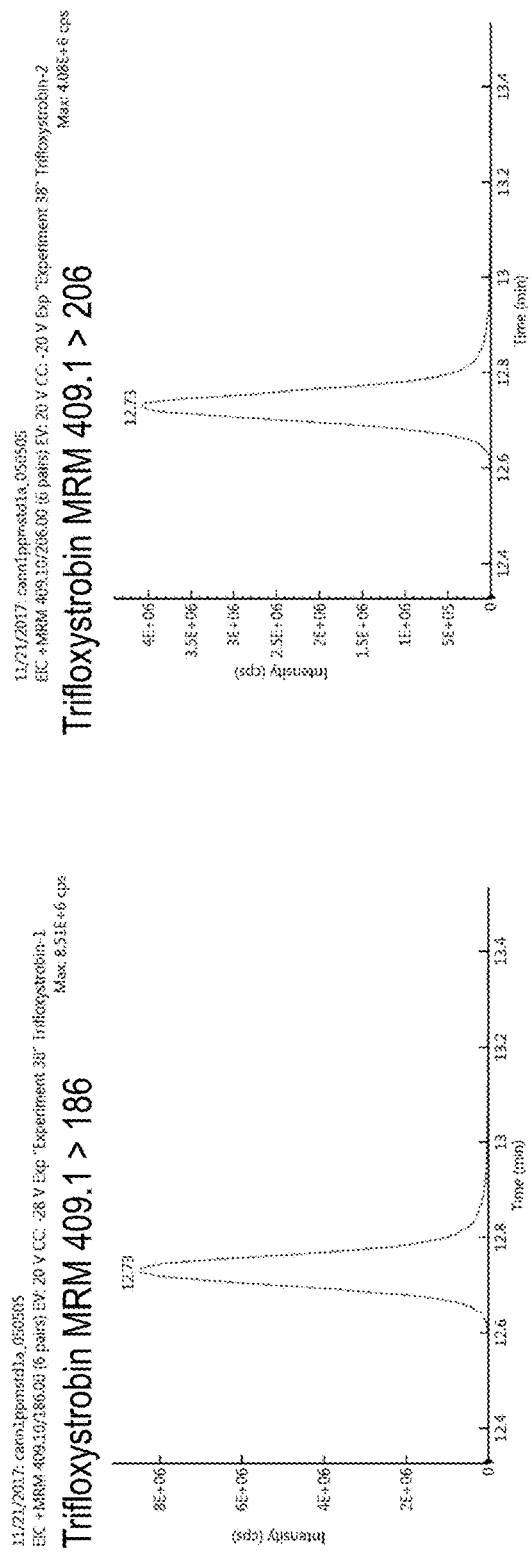
FIGS. 15A-B are chromatograms of *cannabis* samples analyzed for the presence of trifloxystrobin using MRM transitions 409.1>186 (FIG. 15A) and 409.1>206 (FIG. 15B).
Figure 15C:
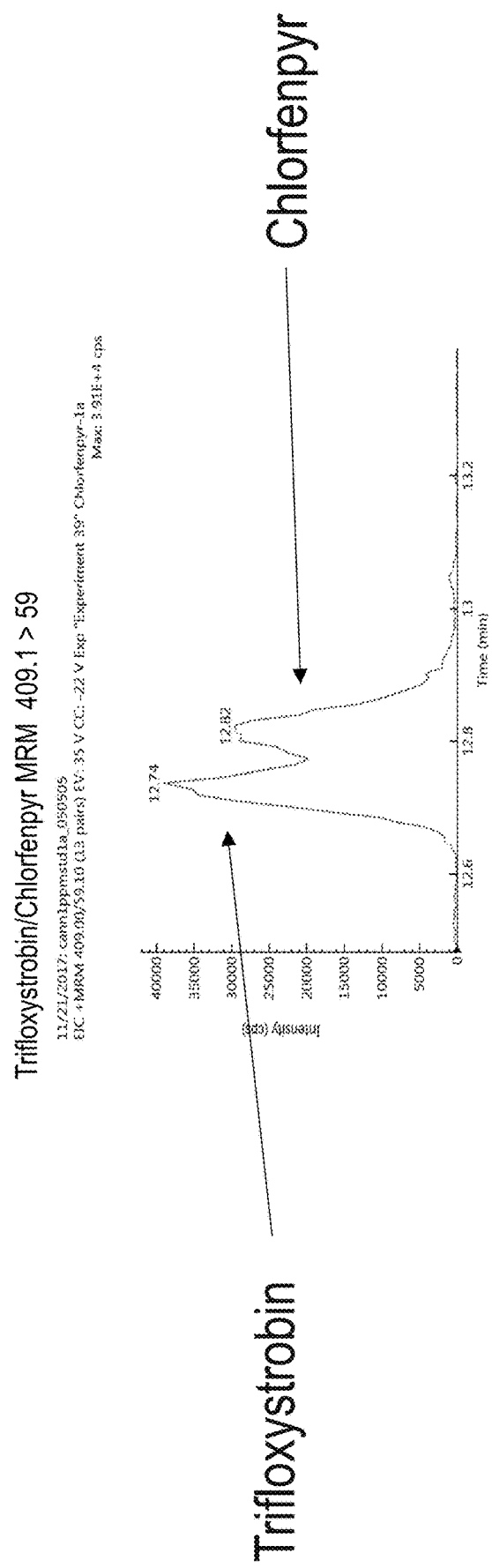
FIG. 15C is a chromatogram analyzed for the presence of trifloxystrobin and chlorfenapyr using MRM transition 409.1>59.

The type of LC column can impact identification of chlorfenapyr. For example, use of a biphenyl column may cause mis-identification of trifloxytrobin as chlorfenapyr as the two compounds may co-elute. Use of a C18 column instead of a biphenyl column for baseline resolution can address this issue. FIG. 15A and FIG. 15B are chromatograms obtained using the MRM transitions of 409.1>186 and 409.1>206, respectively. A single peak is obtained using each of these MRM transitions. In contrast, two peaks occur using the MRM transition 409.1>59 (FIG. 15C); a first (earlier occurring) corresponding to trifloxystrobin and a second (later occurring) corresponding to chlorfenapyr.

FIGS. 93A-D compare MRM transition intensities for *cannabis* samples comprising 100 ppb chlorfenapyr with blank *cannabis* sample measurements. FIGS. 93A and 93C compare intensities of a 426>409 MRM transition for a pesticide sample comprising 1000 ppb chlorfenapyr and a blank *cannabis* sample, respectively. FIGS. 93B and 93D compare intensities of a 426>59.1 MRM transition for a pesticide sample comprising 1000 ppb chlorfenapyr and a blank *cannabis* sample, respectively. The LOQ was approximately 650 ppb.

FIG. 115A and FIG. 115B show intensity measurements for other MRM transitions that are associated with chlorfenapyr and avoid matrix interference. FIG. 115A plots intensity of a 423.9>59 MRM transition for a pesticide sample comprising 100 ppb chlorfenapyr and a blank *cannabis* sample. FIG. 115B plots intensity of a 406.9>59 MRM transition for a pesticide sample comprising 1000 ppb chlorfenapyr and a blank *cannabis* sample. For both of these MRM transitions, peaks are observed in the pesticide sample measurements, while the intensities for the blank *cannabis* sample measurements are relatively flat. The 423.9>59 MRM transition provided an S/N ratio of 51, and the 406.9>59 MRM transition provided an S/N ratio of 145. The LOQ using these transitions was 100 ppb.

FIGS. 115C-F show intensity measurements for various MRM transitions that are associated with chlorfenapyr but suffer from matrix interference, in particular, a 425.9>59 MRM transition (FIG. 115C), a 425.9>408.9 MRM transition (FIG. 115D), a 408.9>59 MRM transition (FIG. 115E), and a 423.9>406.9 MRM transition (FIG. 115F). FIG. 115G and FIG. 115H compare intensities of two different MRM transitions measured for *cannabis* samples comprising 100 ppb with blank *cannabis* sample measurements. These MRM transitions were determined to provide lower sensitivity than those shown in FIG. 115A and FIG. 115B. The 408.9>378.8 MRM transition shown in FIG. 115G provided an S/N ratio of 30. FIG. 115H plots intensity of a 408.9>270 MRM transition, which provides a minimal S/N ratio. The LOQ obtained using these transitions was 1000 ppb.

APCI Ionization Source

Chlorfenapyr is typically analyzed using an ESI source, but using an APCI source and MRM transitions 346.9>79 and 348.9>81, better ionization was achieved, and there was less matrix interference, improving detection limits to ~25 ppb. See FIGS. 123A-B.

Example 8. Cinerin I

Figures 11A, 11B:
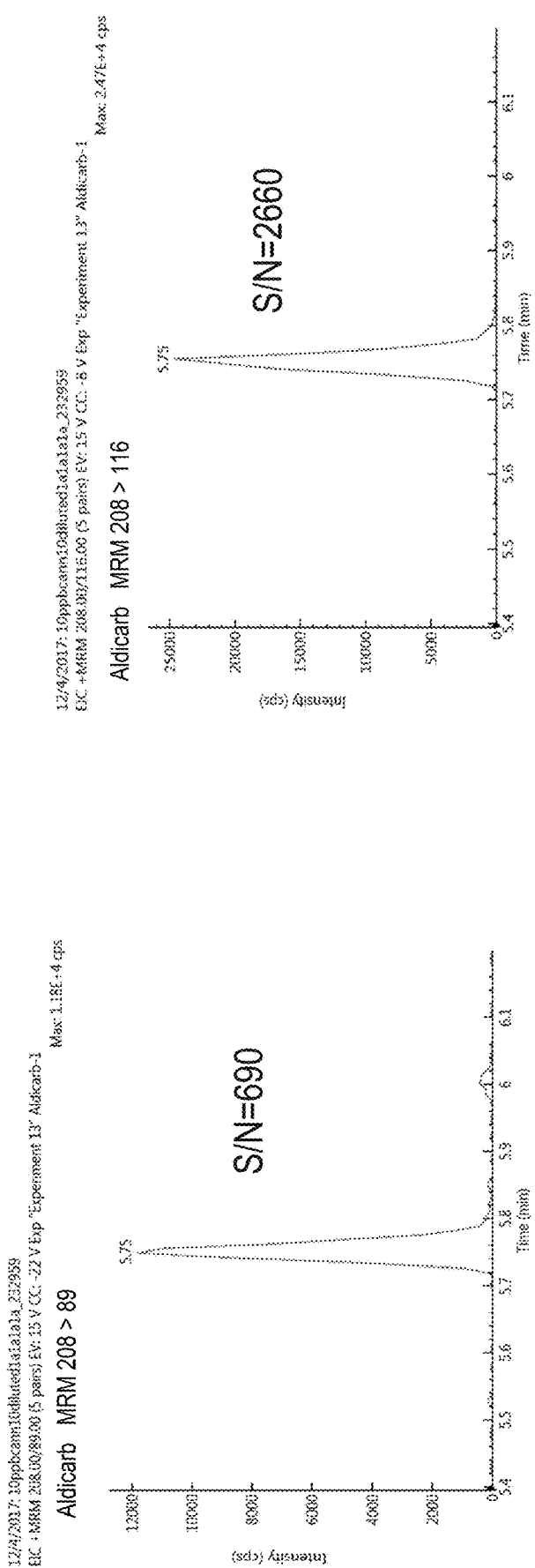
FIGS. 11A-D are chromatograms of *cannabis* samples comprising 100 ppb aldicarb and analyzed for the presence of aldicarb using MRM transitions of 208>89 (FIG. 11A), 208>116 (FIG. 11B), 116>70 (FIG. 11C), and 116>89 (FIG. 11D).
Figures 11C, 11D:
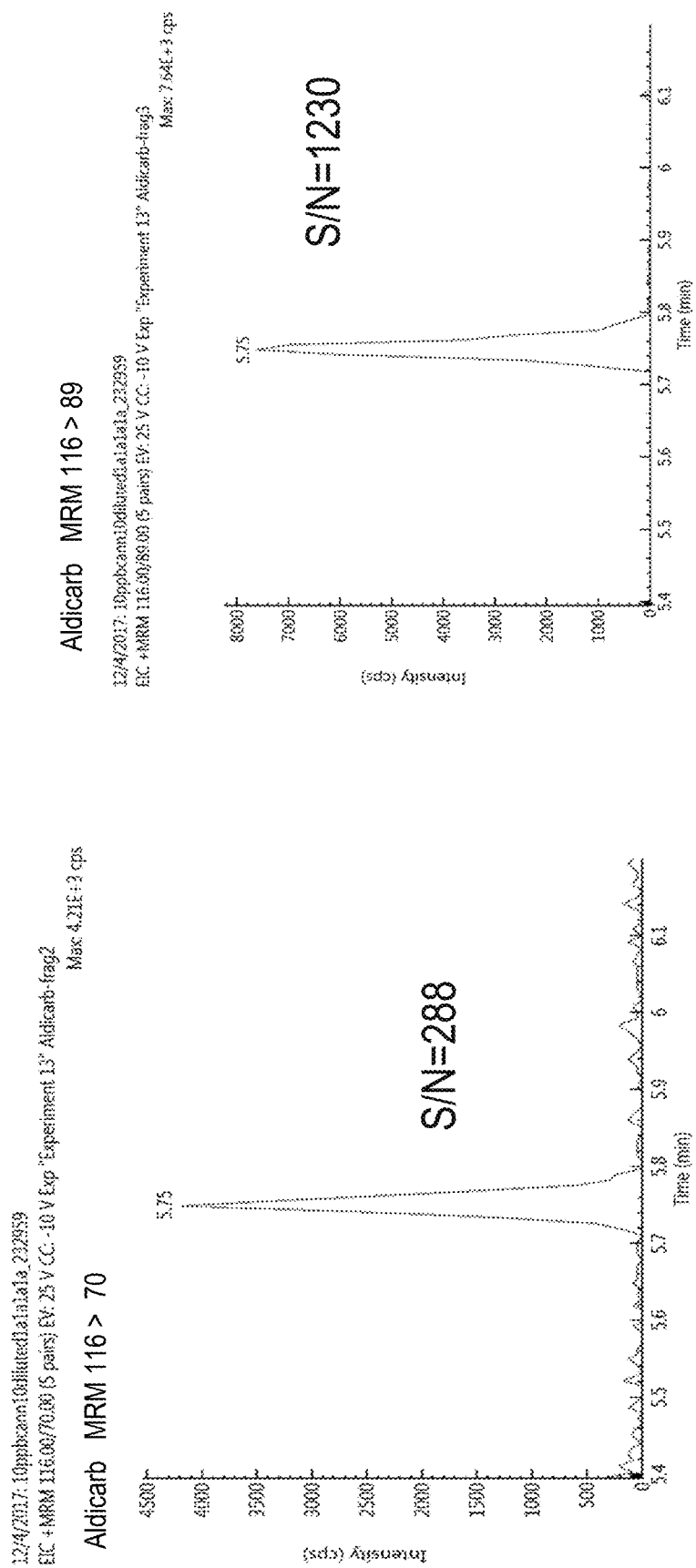
Figures 12A, 12B:
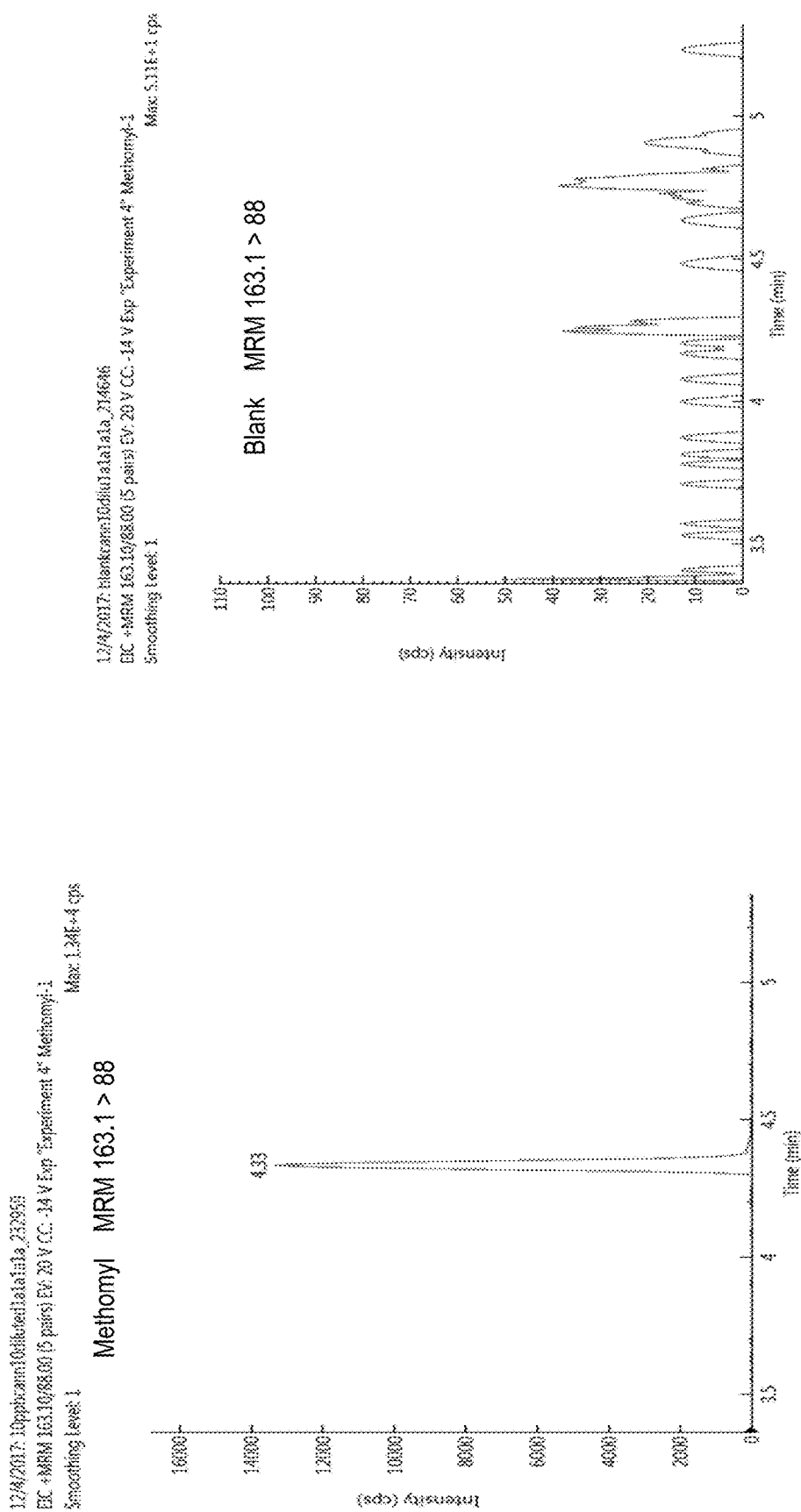
FIGS. 12A-B are chromatograms of *cannabis* samples analyzed for the presence of methomyl using an MRM transition of 163.1>88.
Figure 13B:
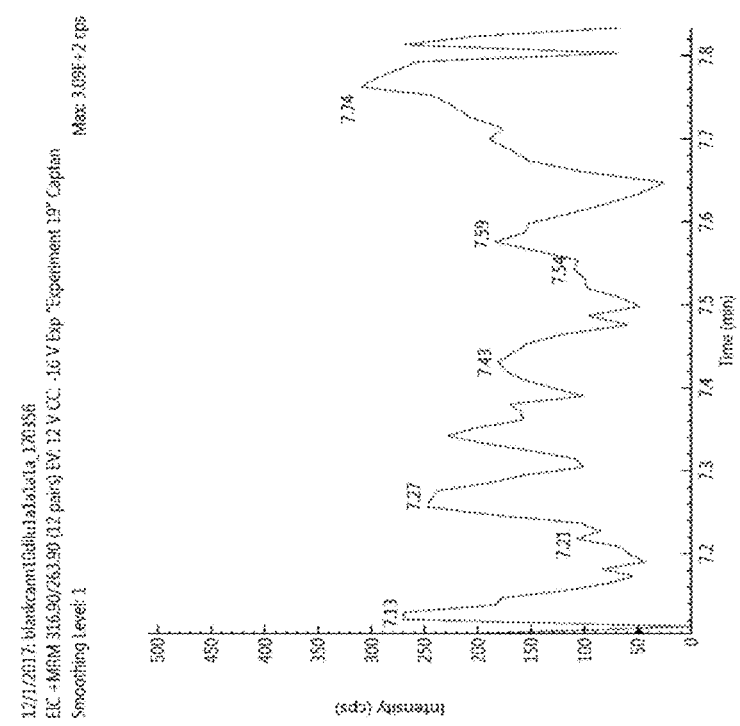
FIGS. 13A-B are chromatograms of *cannabis* samples analyzed for the presence of captan using an MRM transition of 316.9>263.9.
Figure 13A:
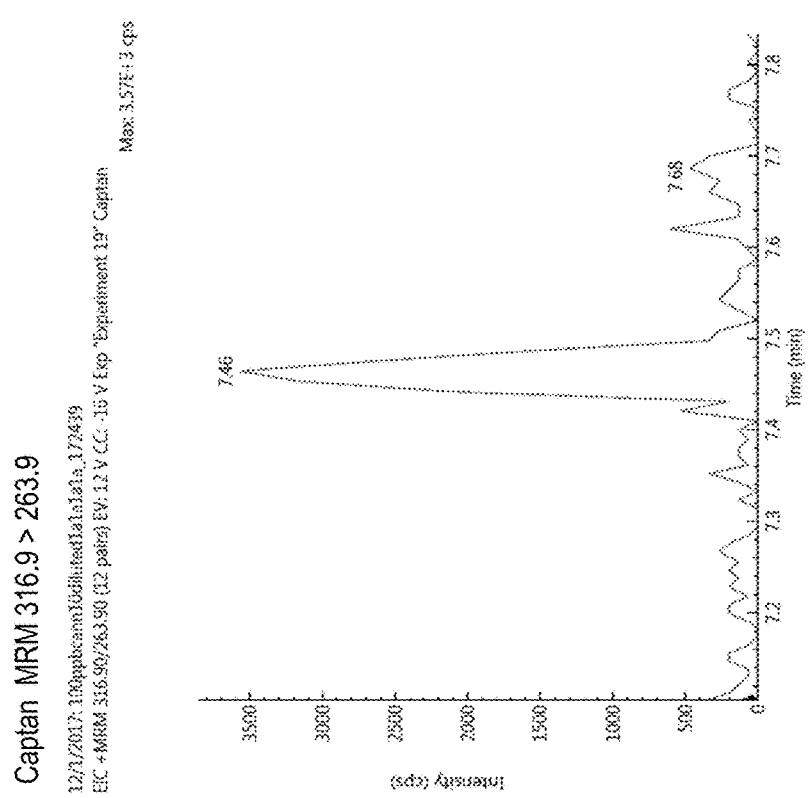

FIGS. 22A-B and 100A-B compare intensities of two different MRM transitions associated with cinerin I for *cannabis* samples comprising 1000 ppb cinerin I and blank *cannabis* samples. Using the MRM transition of 317.2>149 (FIGS. 22A, 22B), the S/N ratio was 180. Using the MRM transition of 317.2>107 MRM transition (FIGS. 100A, 11B), the S/N ratio was 38. The LOQ was approximately 10 ppb.

Example 9. Cinerin II

The six MRM transitions for cinerin II shown in Table 8 were evaluated for matrix interference.

TABLE 8

Signal for Six MRM transitions of cinerin II in blank *cannabis* extract and at a spiked value of 40 ppb in neat solvent and in *cannabis* matrix

| MRM transition | Signal in Solvent | Blank Signal in *Cannabis* | Signal in *Cannabis* matrix |
| --- | --- | --- | --- |
| 375.2 > 77 (1) | 2.29e4 | 7.7e4 | 1.01e5 |
| 375.2 > 79 (2) | 1.92e4 | 6.35e4 | 7.98e4 |
| 375.2 > 107.1 (3) | 2.89e4 | 3.01e4 | 3.99e4 |
| 375.2 > 121.1 (4) | 5.17e3 | 1.44e4 | 1.86e4 |
| 375.2 > 149.1 (5) | 3.18e4 | 2e3 | 1.5e4 |
| 375.2 > 213.1 (6) | 4.3e3 | 5e2 | 1.8e3 |

Conventionally, MRM transitions yielding the highest signal amplitudes for the solvent samples ("Signal in Solvent" column), in this case MRM 3, would be used to detect and/or quantify cinerin II. Despite MRM 6 having lowest signal in solvent, MRM 6 (375.2>213.1) reduces matrix interference, as does MRM 5 (375.2>149.1).

Figure 21B:
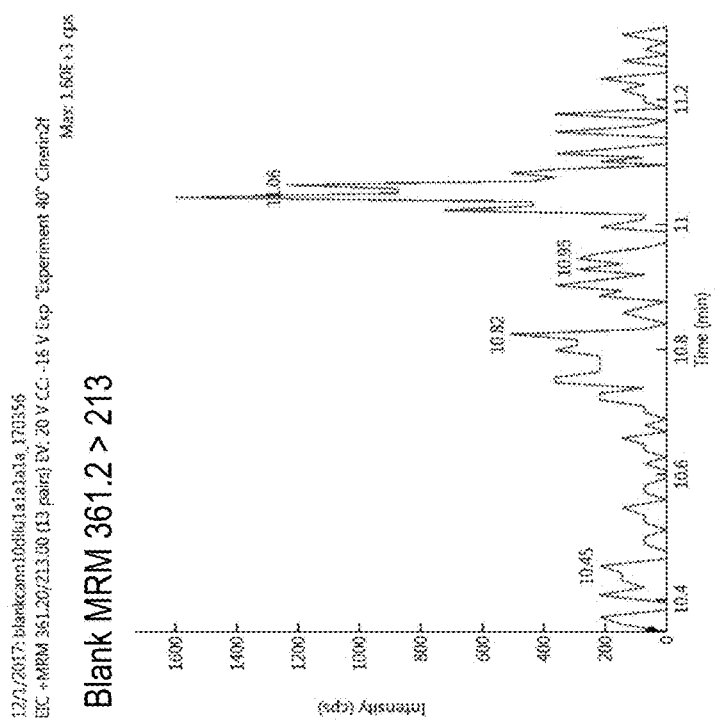
Figure 21A:
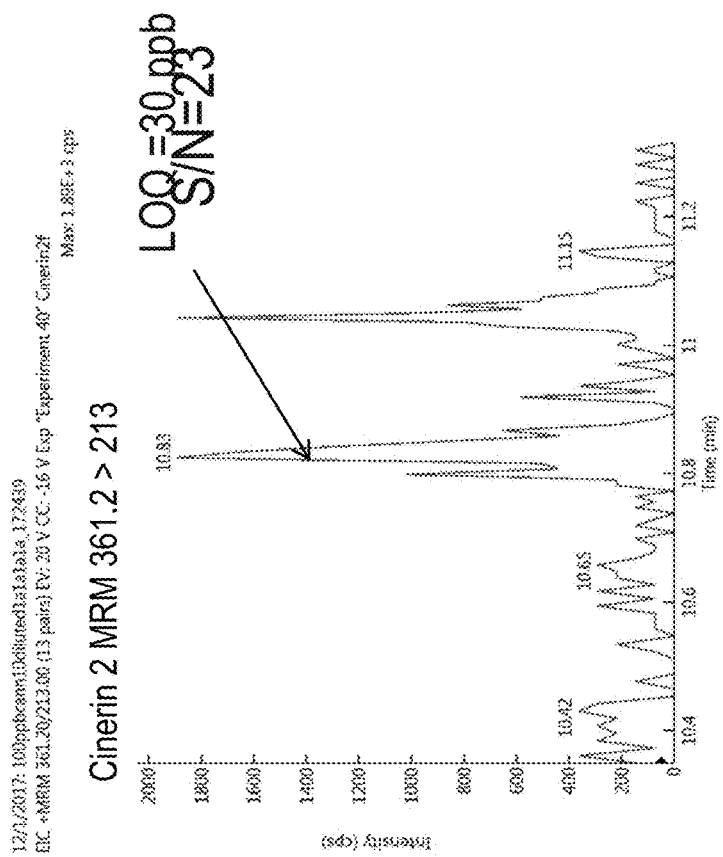
Figures 22A, 22B:
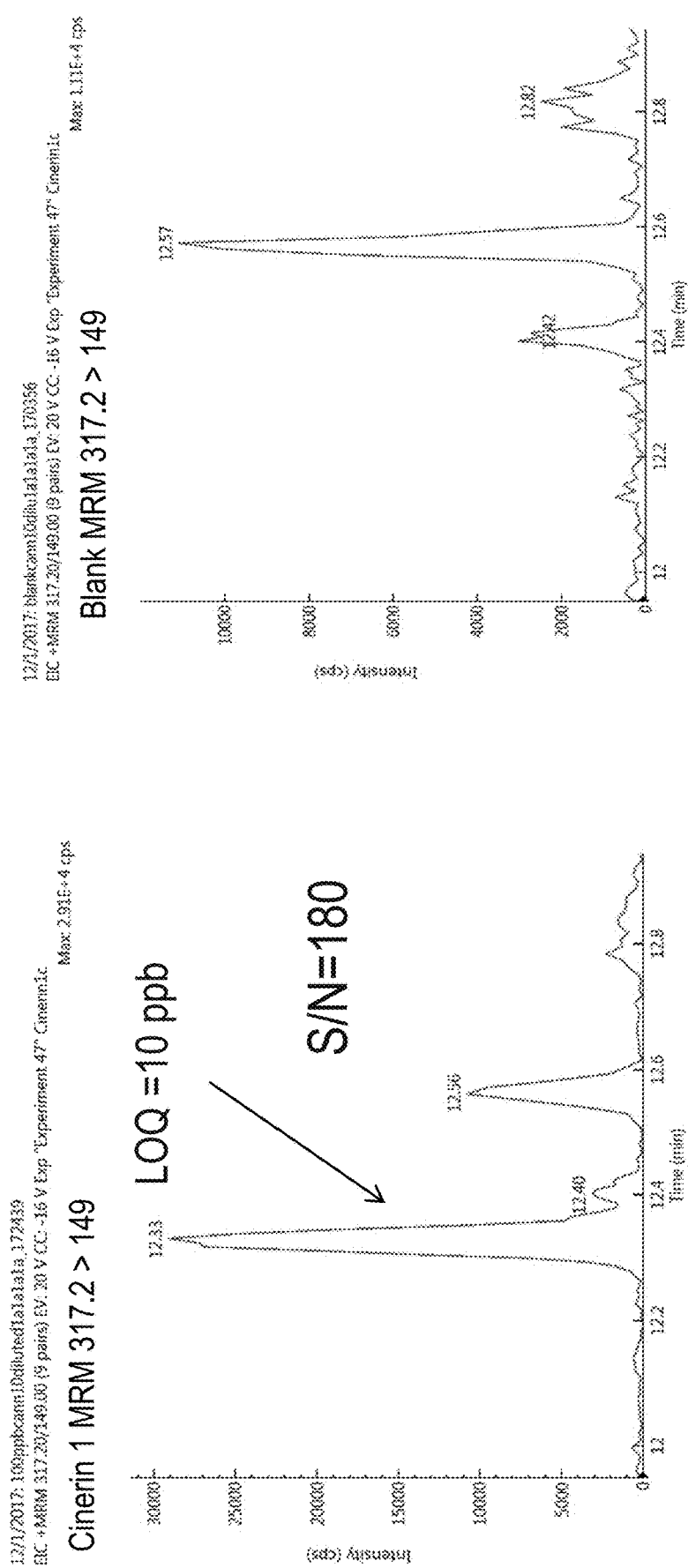
FIGS. 22A-B are chromatograms of *cannabis* samples analyzed for the presence of cinerin I using MRM transition 317.2>149.
Figures 23A, 23B:
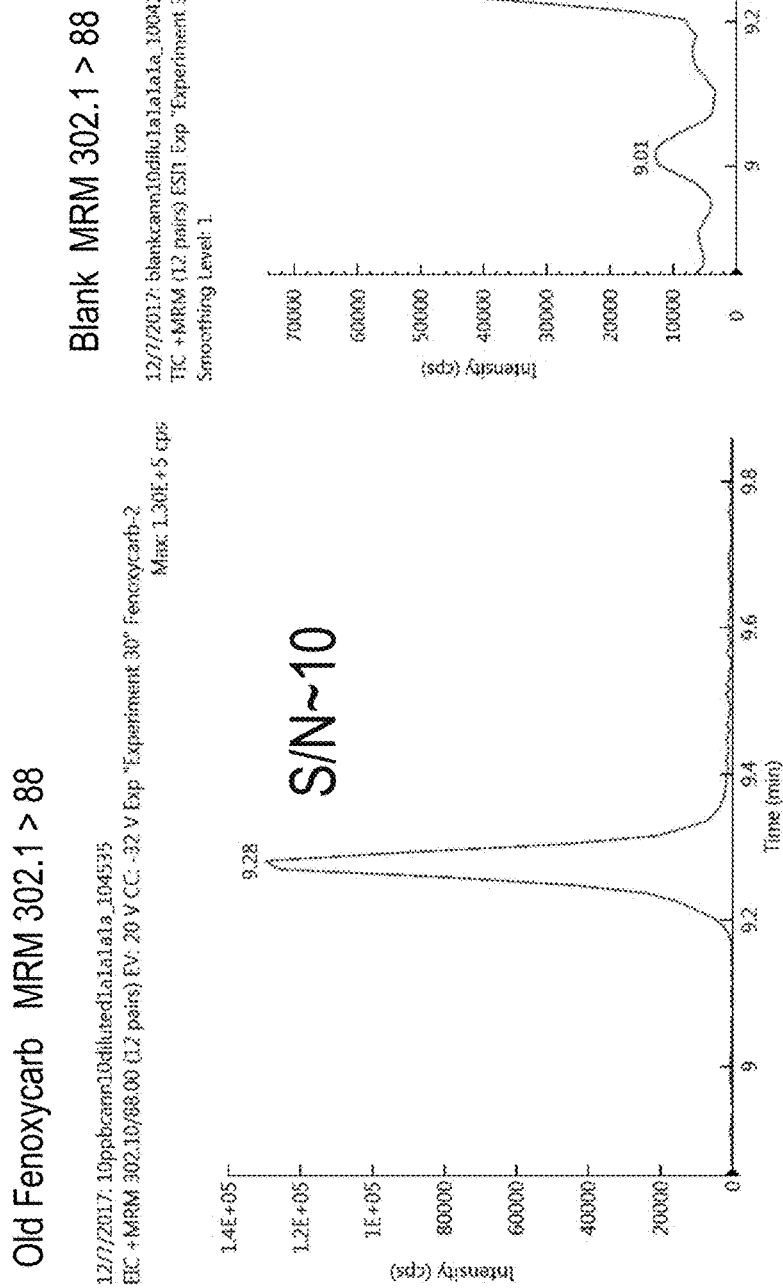
FIGS. 23A-F are chromatograms of *cannabis* samples analyzed for the presence of fenoxycarb using MRM transitions 302.1>88 (FIGS. 23A, 23B), 302.1>256 (FIGS. 23C, 23D), and 302.1>116 (FIGS. 23E, 23F).
Figure 23D:
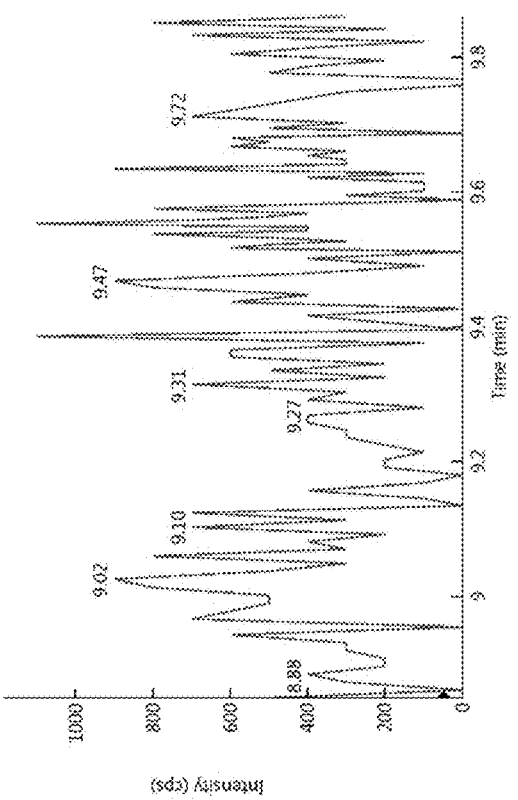
Figure 23C:
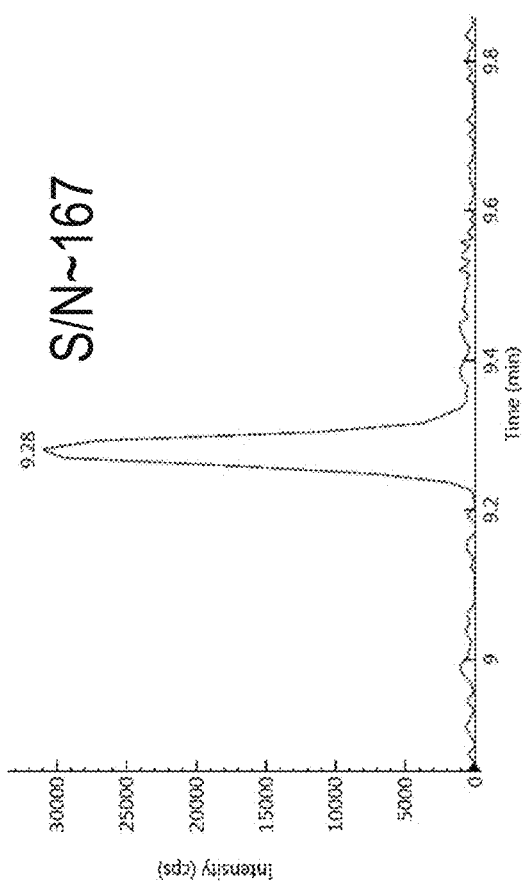
Figure 23F:
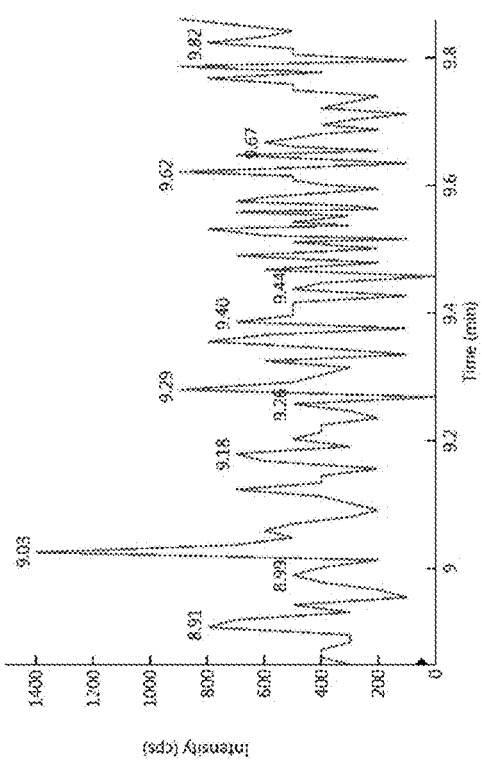
Figure 23E:
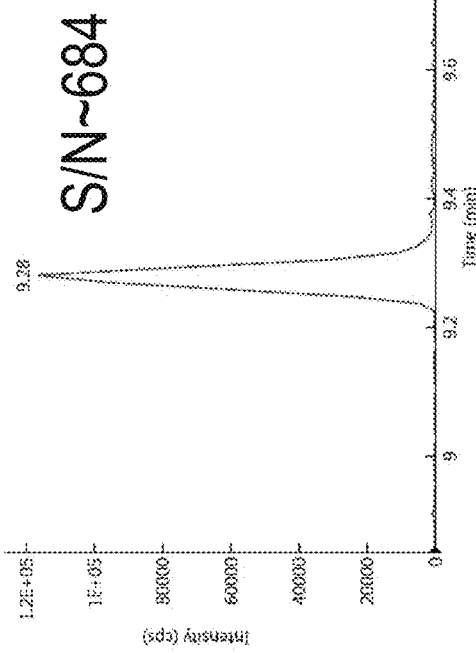

FIGS. 21A-B and 96A-B compare intensities of two different MRM transitions associated with cinerin II for *cannabis* samples comprising 1000 ppb cinerin II and blank *cannabis* samples. The S/N ratio for the 361.2>213 MRM transition was 23 (FIGS. 21A, 21B). The S/N ratio for the 361.2>149 MRM transition was 36 (FIGS. 96A, 96B). A LOQ was approximately 30 ppb.

FIG. 21E and FIG. 21F show challenges matrix interference effects present for certain transitions. FIG. 21E and FIG. 21F plot intensities of a 361.2>107 MRM transition for *cannabis* samples comprising 1000 ppb cinerin II and blank *cannabis* samples, respectively. The two intensity plots are nearly indistinguishable, indicating that this transition is dominated by matrix interference from the *cannabis* matrix. Accordingly, this transition cannot be used for low level analysis of cinerin II in *cannabis* samples.

Example 10. Cyfluthrin

FIGS. 116A-F are chromatograms obtained using various MRM transitions associated with cyfluthrin. FIG. 116A and FIG. 116B show intensity measurements for various MRM transitions that are associated with cyfluthrin but suffer from matrix interference. FIG. 116A plots intensity of a 451>434 MRM transition for a pesticide sample comprising 1000 ppb cyfluthrin and a blank *cannabis* sample. FIG. 116B plots intensity of a 453>436 MRM transition for a pesticide sample comprising 1000 ppb cyfluthrin and a blank *cannabis* sample. These MRM transitions suffer from matrix interference (i.e., peaks present in the pesticide sample measurements are also present in the blank *cannabis* sample measurements). The 451>434 MRM transition provided an S/N ratio of 10. The LOQ was approximately 1000 ppb.

FIG. 116C and FIG. 116D show intensity measurements for two MRM transitions that are associated with cyfluthrin and avoid matrix interferences, but provide low signal amplitude. FIG. 116C plots intensity of a 451>127 MRM transition for a pesticide sample comprising 1000 ppb cyfluthrin and a blank *cannabis* sample. FIG. 116D plots intensity of a 451>206 MRM transition for a pesticide sample comprising 1000 ppb cyfluthrin and a blank *cannabis* sample. These MRM transitions provide lower amplitude peaks than the 451>191 and 453>193, but still avoid matrix interference (the intensities for the blank *cannabis* sample measurements are relatively flat). The 451>127 MRM transition provided an S/N ratio of 25 and the 451>206 MRM transition provided an S/N ratio of 16. The LOQ was approximately 400 ppb.

FIG. 116E plots intensity of a 451>191 MRM transition for a pesticide sample comprising 1000 ppb cyfluthrin and a blank *cannabis* sample. FIG. 116F plots intensity of a 453>193 MRM transition for a pesticide sample comprising 1000 ppb cyfluthrin and a blank *cannabis* sample. For both of these MRM transitions, peaks are observed in the pesticide sample measurements, while the intensities for the blank *cannabis* sample measurements are relatively flat. The 451>191 MRM transition provided an S/N ratio of 66 and the 453>193 MRM transition provided an S/N ratio of 33. The LOQ was approximately 150 ppb was obtained via these MRM transitions.

Figures 90A, 90B, 90C, 90D:
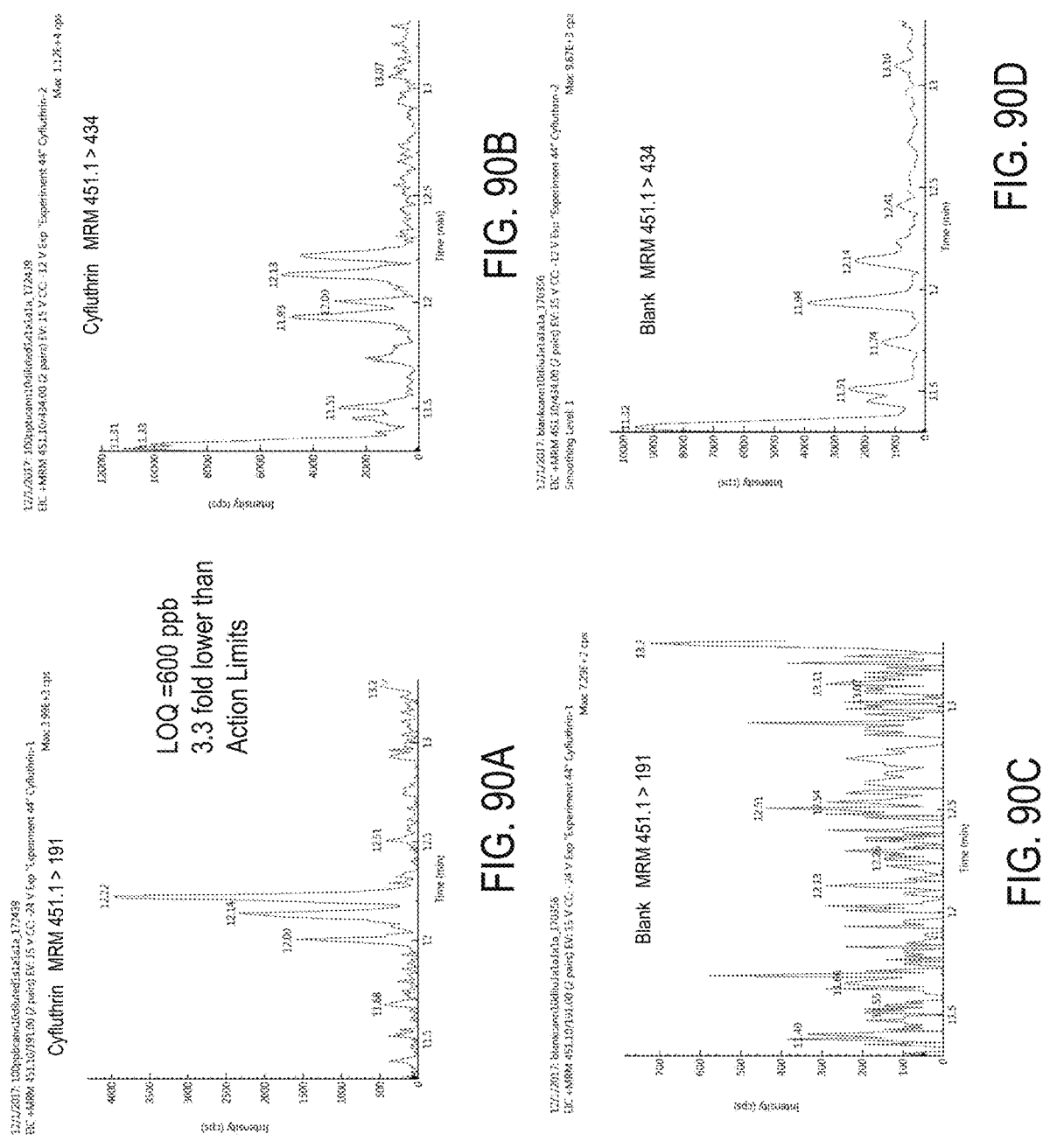

FIGS. 90A-D also compare MRM transition intensities for *cannabis* samples comprising 1000 ppb cyfluthrin with blank *cannabis* sample measurements. FIGS. 90A and 90C compare intensities of the 451.1>191 MRM transition, and FIGS. 90B and 90D compare intensities of the 451.1>434 MRM transition. The LOQ was approximately 600 ppb.

Example 11. Cypermethrin

FIGS. 94A-D compare MRM transition intensities for *cannabis* samples comprising 1000 ppb cypermethrin with blank *cannabis* sample measurements. FIGS. 94A and 94C compare intensities of a 433.1>127 MRM transition for a pesticide sample comprising 1000 ppb cypermethrin and a blank *cannabis* sample, respectively. FIGS. 94B and 94D compare intensities of a 433.1>191.1 MRM transition for a pesticide sample comprising 1000 ppb cypermethrin and a blank *cannabis* sample, respectively. The LOQ was approximately 150 ppb.

FIGS. 117A-D plot intensities of MRM transitions associated with cypermethrin measured for blank *cannabis* samples and *cannabis* samples comprising 100 ppb cypermethrin. The MRM transitions shown in FIGS. 117A-D avoid matrix interference from *cannabis* matrix components and provide an LOQ of 100 ppb. FIG. 117A plots intensities of a 435.1>193.1 MRM transition, which provided an S/N ratio of 105. FIG. 117B plots intensities of a 433.1>191.1 MRM transition, which provided an S/N ratio of 100. FIG. 117C plots intensities of a 433.1>127 MRM transition, which provided an S/N ratio of 110. FIG. 117D plots intensities of a 435.1>127 MRM transition, which provided an S/N ratio of 39. FIG. 117E plots intensities of a 433.1>91 MRM transition and a pesticide sample comprising cypermethrin at 1000 ppb concentration. The 433.1>91 MRM transition suffers from matrix interference and provided an S/N ratio of 20. The LOQ for this transition was 500 ppb.

Example 12. Daminozide

Figures 17A, 17B:
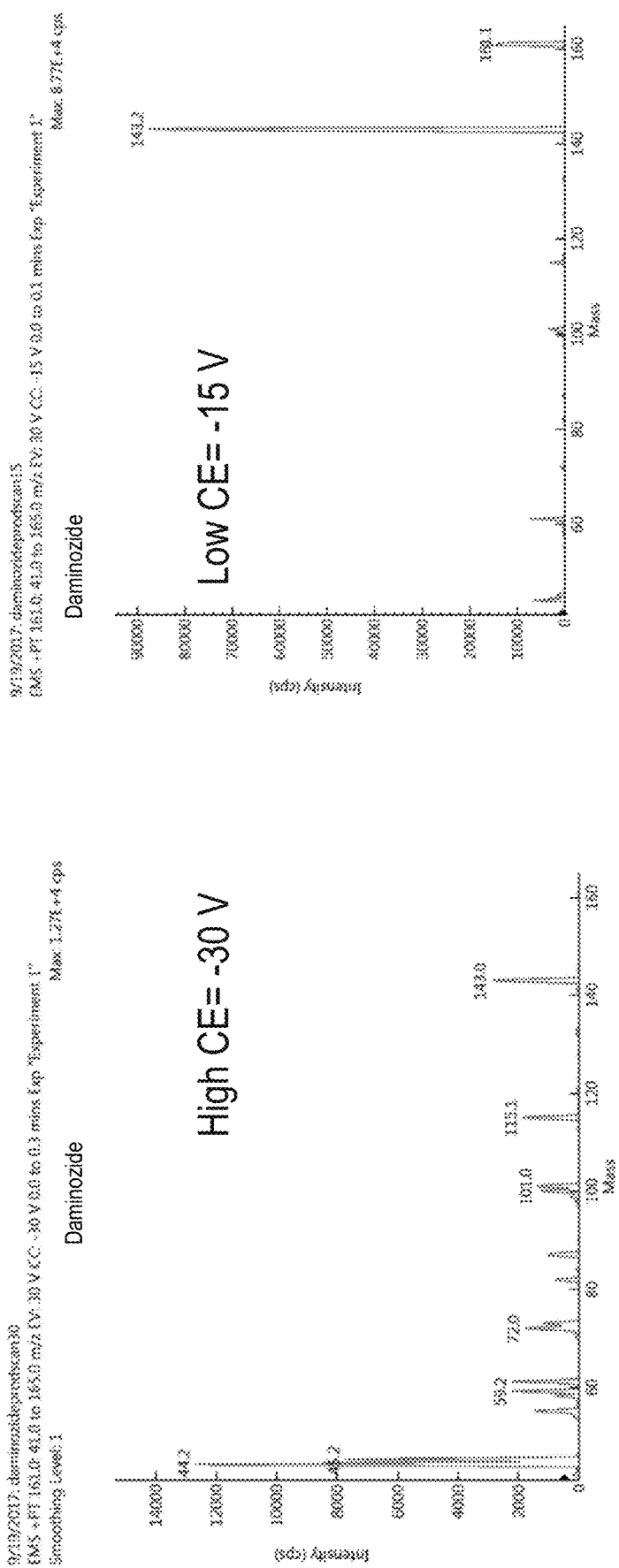
FIGS. 17A and 17B are graphs showing product ion scans for daminozide.

FIGS. 17A-B are product ion scans for daminozide with a precursor (parent) ion mass of approximately 161. FIG. 17A shows a product ion scan for a high collision energy (CE) of −30V. FIG. 17B shows a product ion scan for a low CE of −15V.

Figure 17D:
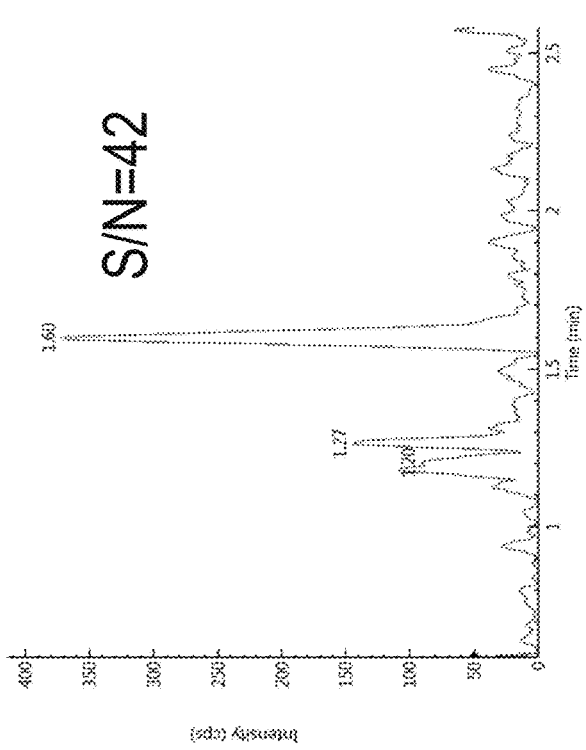
FIGS. 17C-E are chromatograms of *cannabis* samples comprising 100 ppb of daminozide and analyzed for the presence of daminozide using MRM transitions of 161.1>44 (FIG. 17C), 161.1>101 (FIG. 17D), and 161.1>143 (FIG. 17E).
Figure 17C:
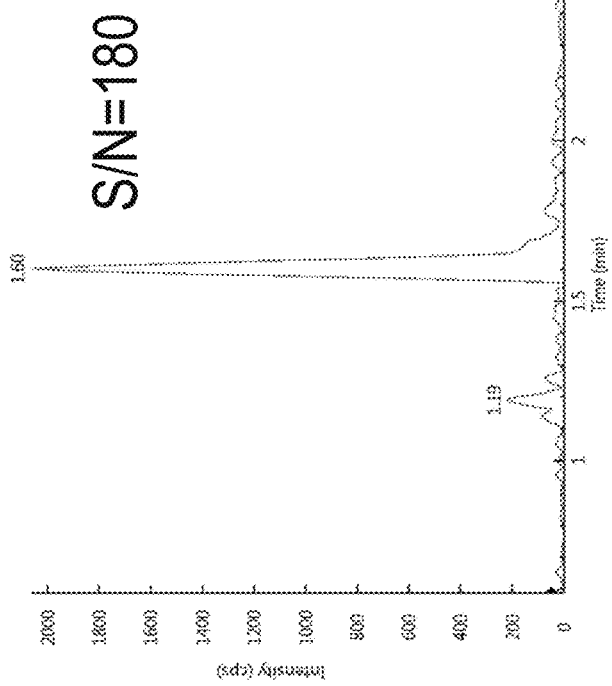
Figure 17E:
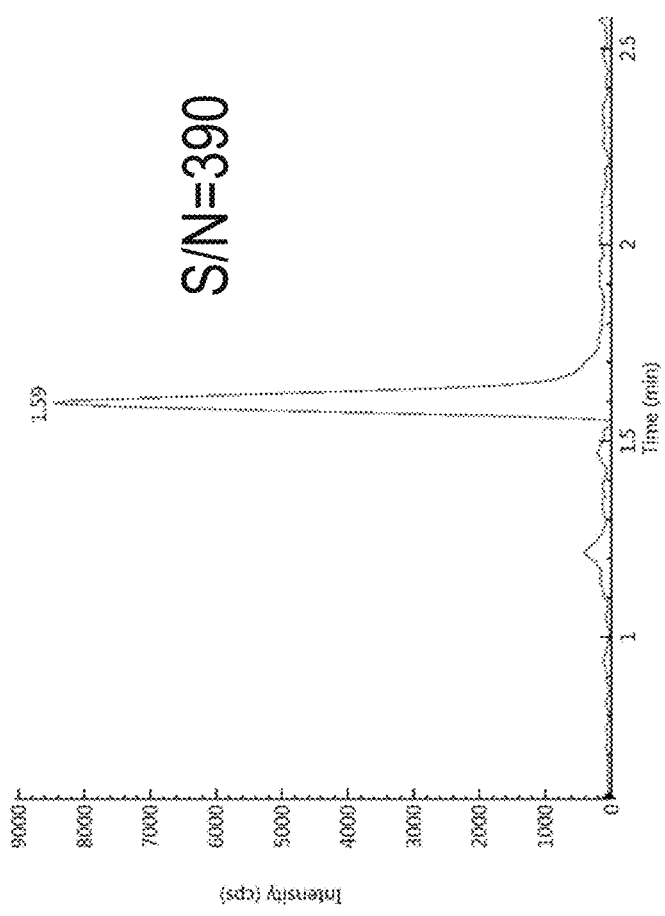
Figures 18A, 18B:
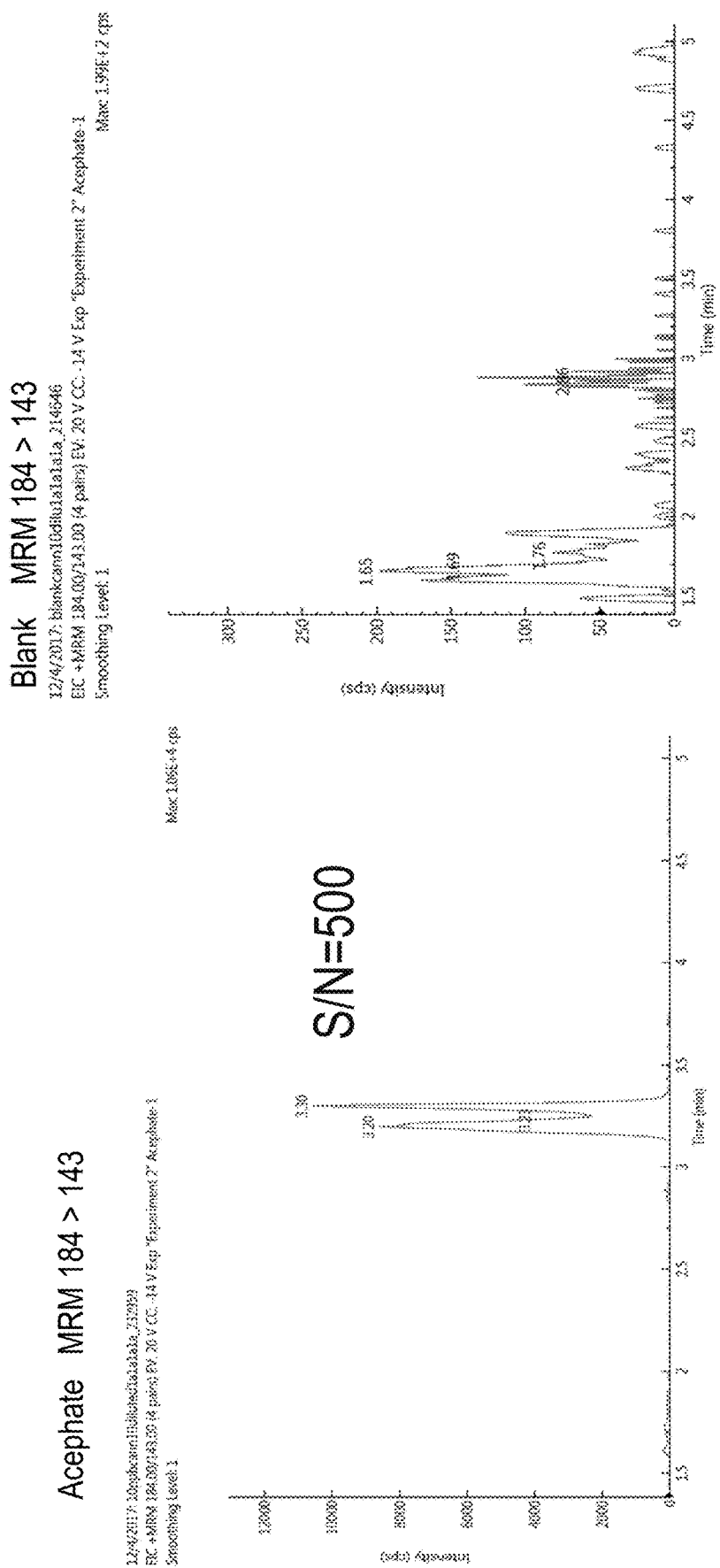
FIGS. 18A-B are chromatograms of *cannabis* samples analyzed for the presence of acephate using MRM transition 184>143.
Figure 19B:
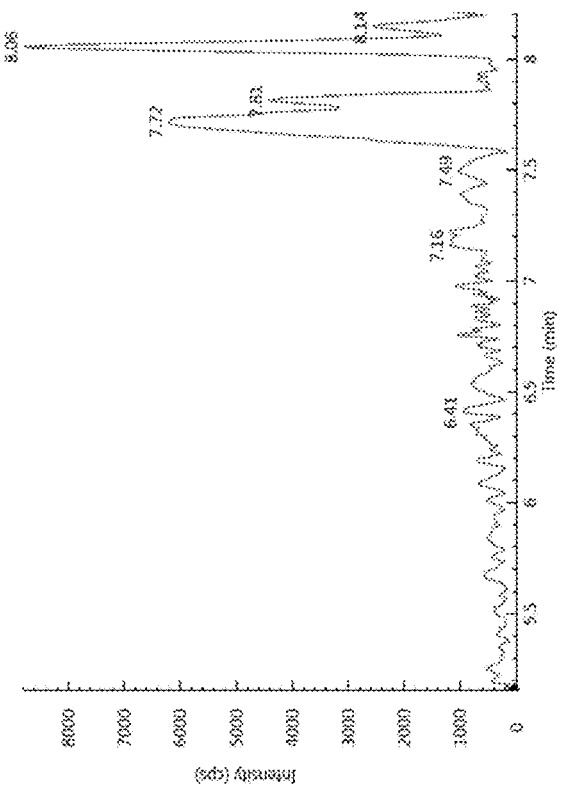
FIGS. 19A-B are chromatograms of *cannabis* samples analyzed for the presence of imazalil using MRM transitions 297>41.
Figure 19A:
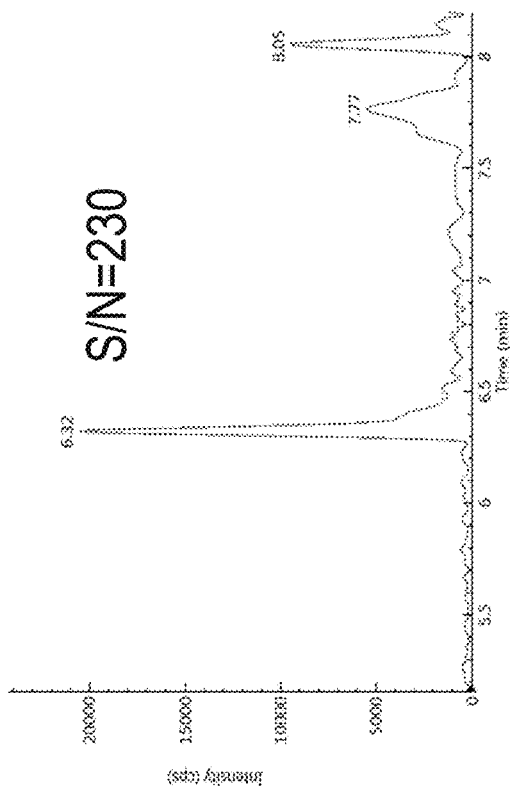

FIGS. 17C-E plot intensities of three different MRM transitions for *cannabis* samples comprising 100 ppb daminozide (100 ppb concentration). FIG. 17C plots an intensity of a 161.1>44 MRM transition, for which the determined S/N was 180. FIG. 17D plots an intensity of a 161.1>101 MRM transition, for which the determined S/N was 42. FIG. 17E plots an intensity of a 161.1>143 MRM transition, for which the determined S/N was 390. Accordingly, sensitivity of measurements for daminozide can be improved by a factor of 4 via use of appropriate MRM transitions. Determined LOQs were as low as 11 ppb.

FIGS. 41A-D compare MRM transition intensities for *cannabis* samples comprising 100 ppb daminozide with blank *cannabis* sample measurements. FIGS. 41A and 41C compare intensities of a 161.1>143 MRM transition for a pesticide sample comprising 100 ppb daminozide and a blank *cannabis* sample, respectively. FIGS. 41B and 41D compare intensities of a 161.1>44 MRM transition for a pesticide sample comprising 100 ppb daminozide and a blank *cannabis* sample, respectively. The LOQ was approximately 10.8 ppb.

Example 13. Dimethomorph

Figure 24B:
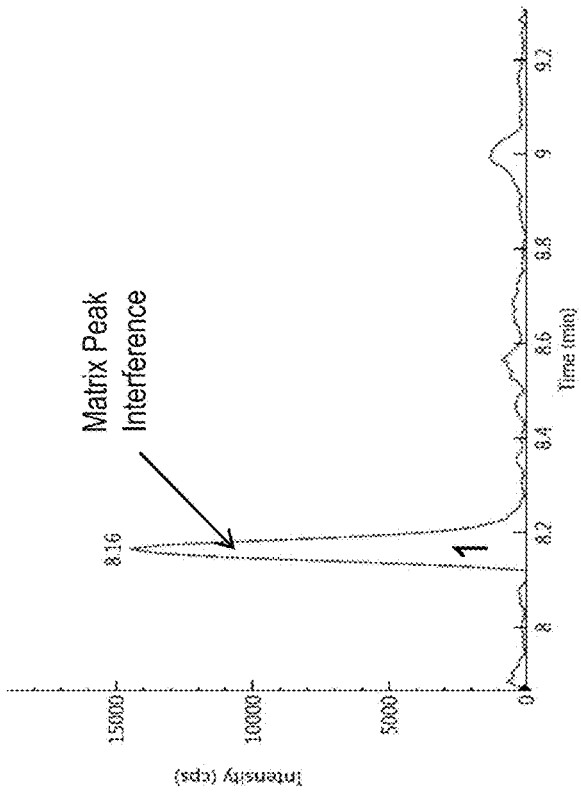
FIGS. 24A-F are chromatograms of *cannabis* samples analyzed for the presence of dimethomorph using MRM transitions 388.1>165 (FIGS. 24A, 24B), 388.1>273 (FIGS. 24C, 24D), and 388.1>301 (FIGS. 24E, 24F).
Figure 24A:
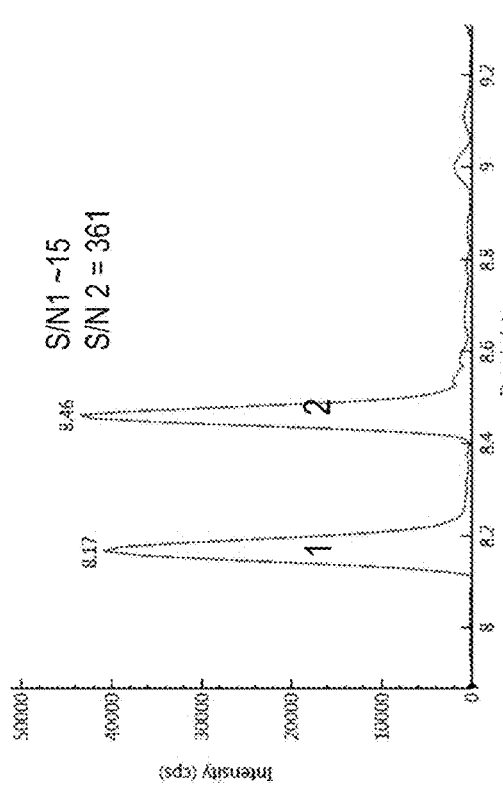
Figure 24D:
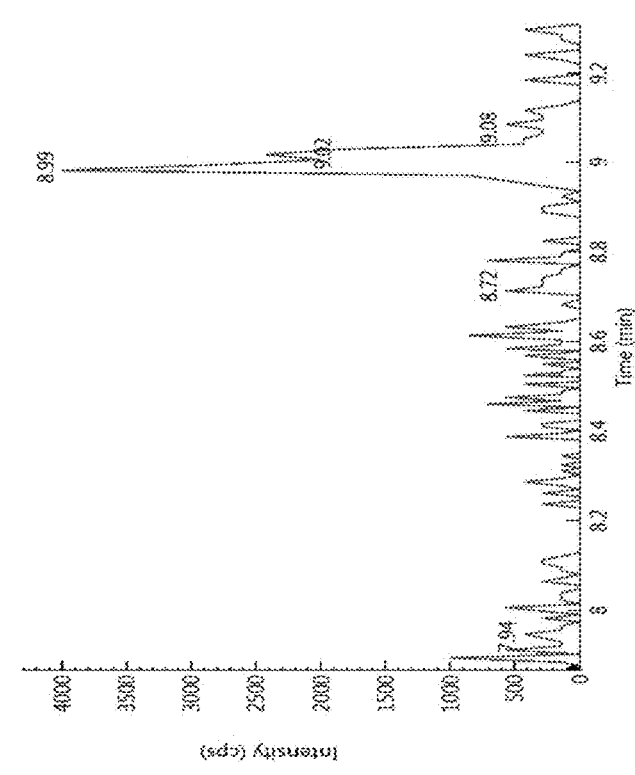
Figure 24C:
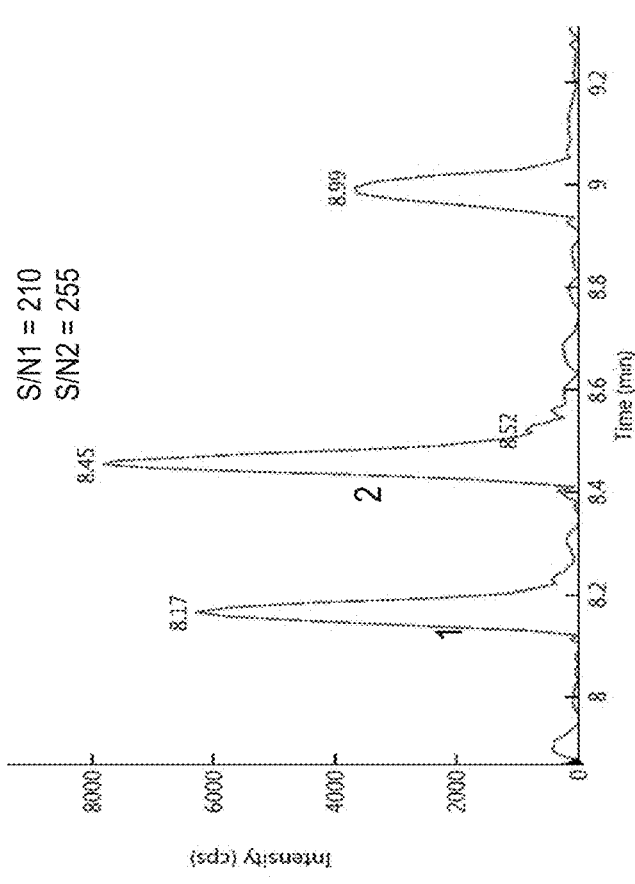
Figures 24E, 24F:
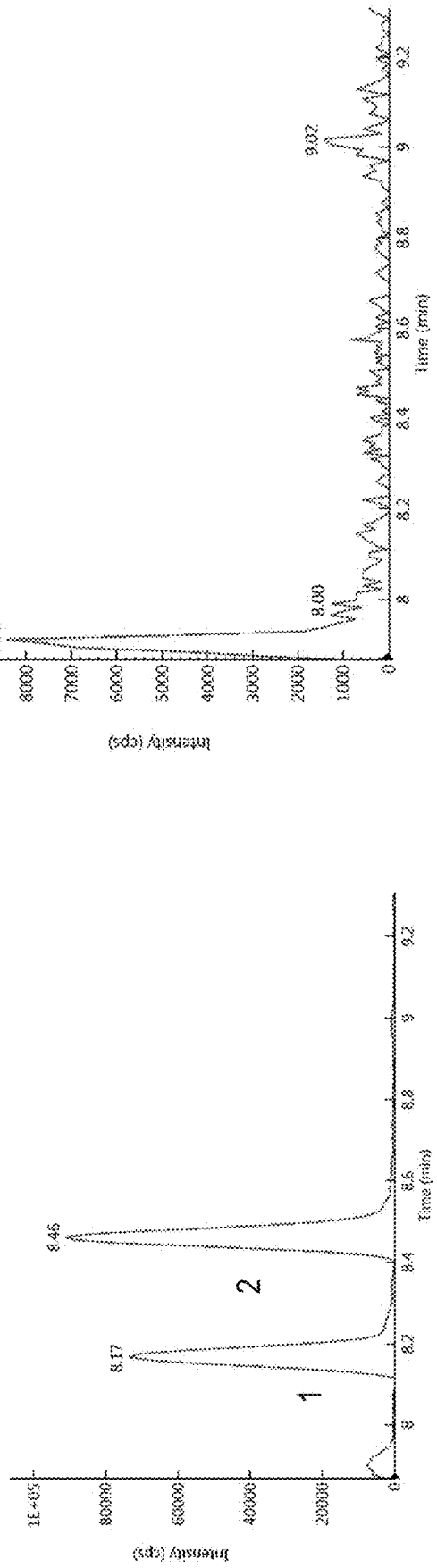
Figure 25B:
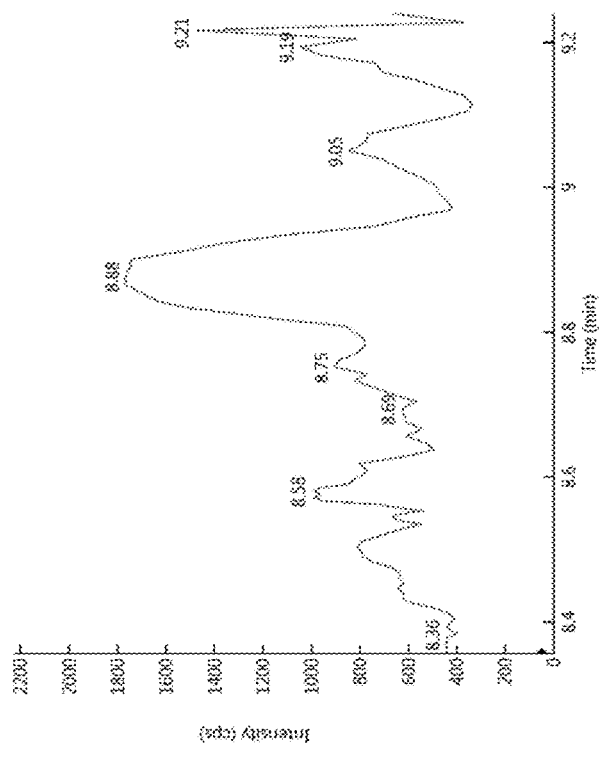
FIGS. 25A-B are chromatograms of *cannabis* samples analyzed for the presence of fenhexamid using MRM transition 302.1>55.
Figure 25A:
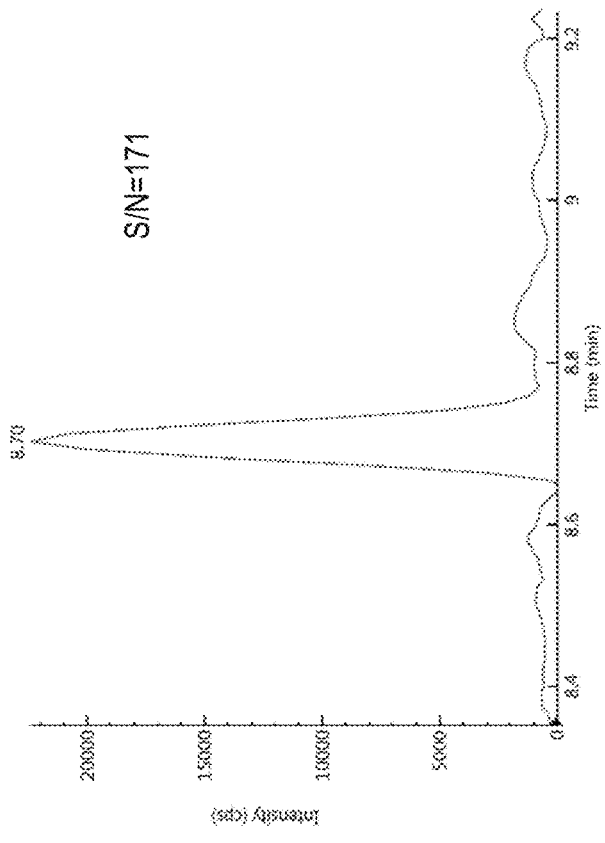
Figures 26A, 26B:
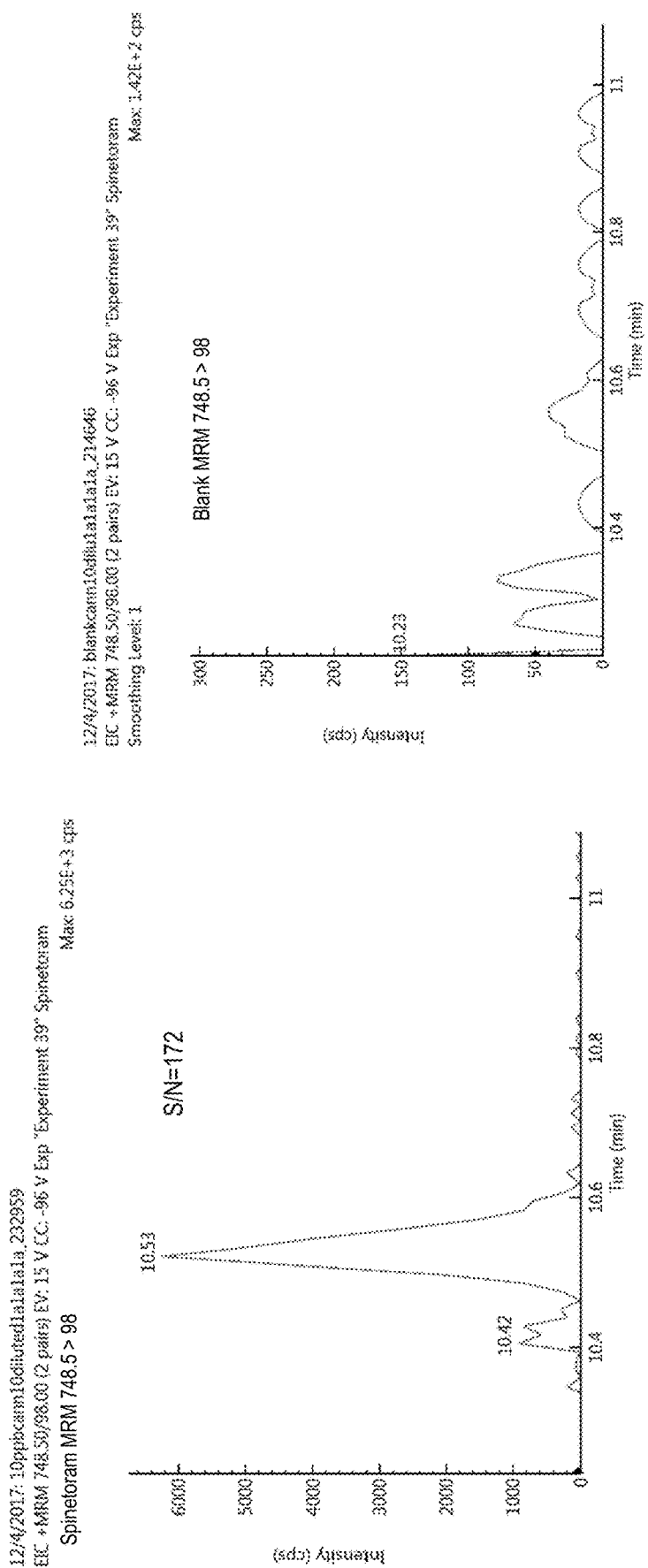
FIGS. 26A-B are chromatograms of *cannabis* samples analyzed for the presence of spinetoram using MRM transition 748.5>98.

The chromatograms shown in FIGS. 24A-F and FIGS. 72A-D compare intensities of different MRM transitions associated with dimethomorph for *cannabis* samples comprising 100 ppb dimethomorph (100 ppb concentration) and blank *cannabis* samples. For each of the transitions, two peaks are observed in the intensity plots for the *cannabis* samples comprising 100 ppb dimethomorph (FIGS. 24A-C, FIGS. 72A, B). FIGS. 24A and 24D plot intensities of a 388.1>165 MRM transition for a sample comprising dimethomorph and a blank *cannabis* sample, respectively. The first, earlier occurring peak suffers from matrix interference (i.e., a corresponding peak at around the same time is present in the intensity plot for the blank *cannabis* sample; FIG. 24D) and provides a lower S/N ratio (approximately 15) than the second, later occurring peak, which provided an S/N ratio of 361.

FIGS. 24B and 24E and FIGS. 72A and 72C plot intensities of a 388.1>273 MRM transition for a pesticide sample comprising dimethomorph and a blank *cannabis* sample, respectively. Neither peak suffers from matrix interference. For the first (earlier occurring) peak, the determined S/N was 210 and for the second (later occurring) peak, the S/N was 255.

FIGS. 24C and 24F and FIGS. 72B and 72D plot intensities of a 388.1>301 MRM transition for a pesticide sample comprising dimethomorph and a blank *cannabis* sample, respectively. Neither peak suffers from matrix interference. For the first (earlier occurring) peak, the S/N ratio was 807 and for the second (later occurring) peak, the S/N ratio was 1251. Through use of appropriate MRM transitions, detection limits for dimethomorph were improved by a factor of 10, to an LOQ of 10 ppb.

Example 14. Naled ("Dibrom")

Figure 16A:
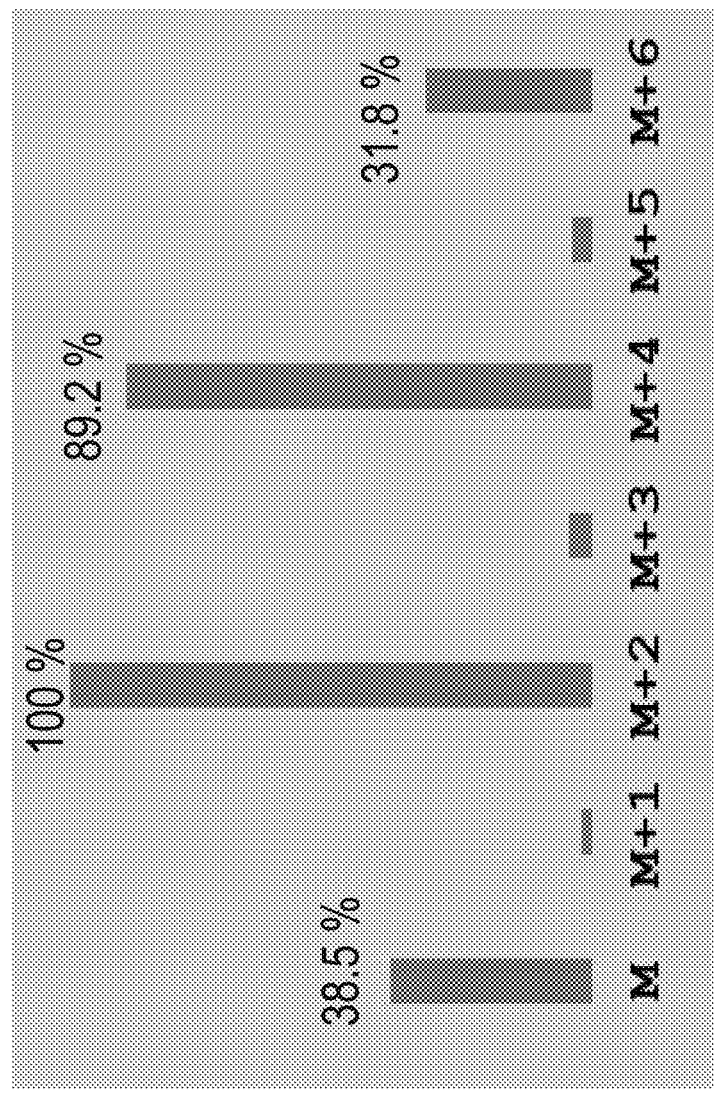
FIG. 16A is a graph showing an isotope distribution of naled (also referred to as "dibrom" or "DiBrom").

FIG. 16A is a graph showing a calculated isotope distribution of naled, whose structure is shown below:

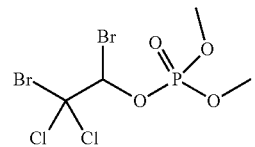

Figure 16B:
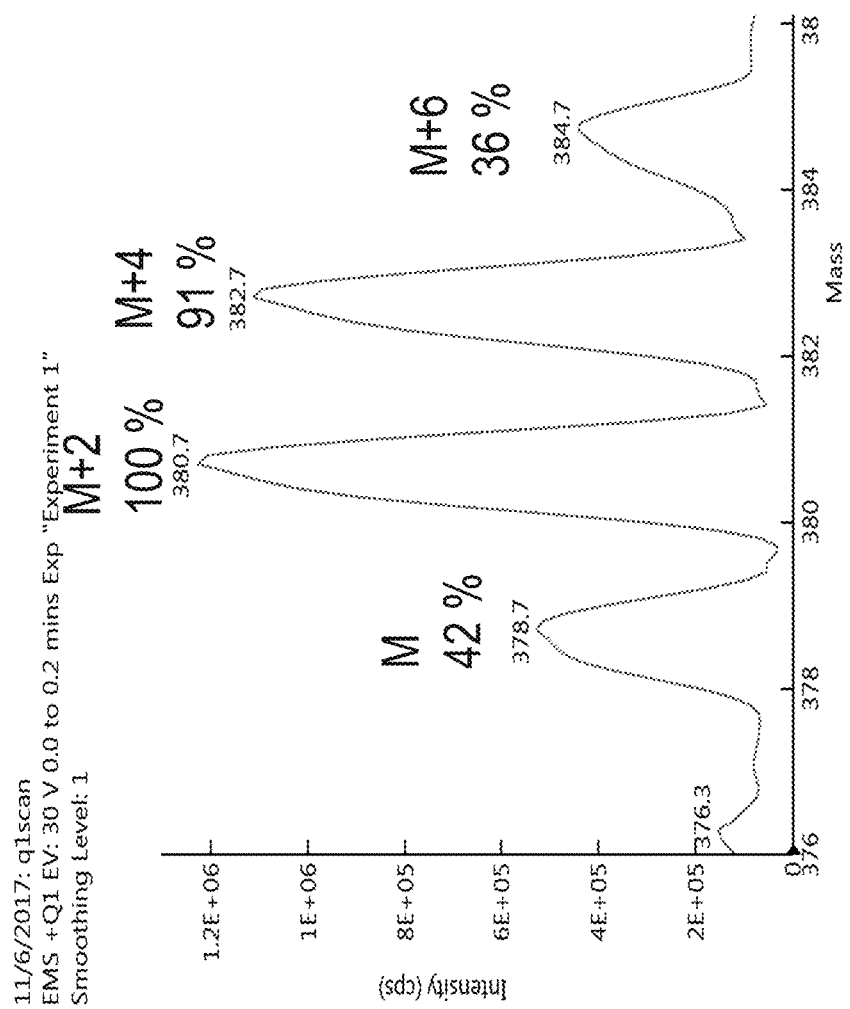
FIG. 16B is a precursor (parent) mass scan for a sample comprising naled.
Figure 16C:
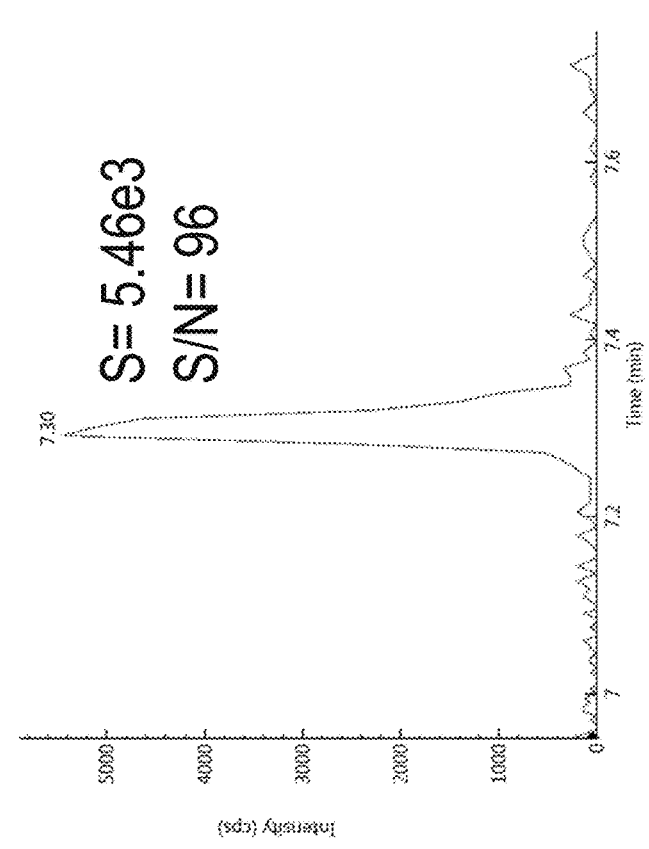
Figure 16D:
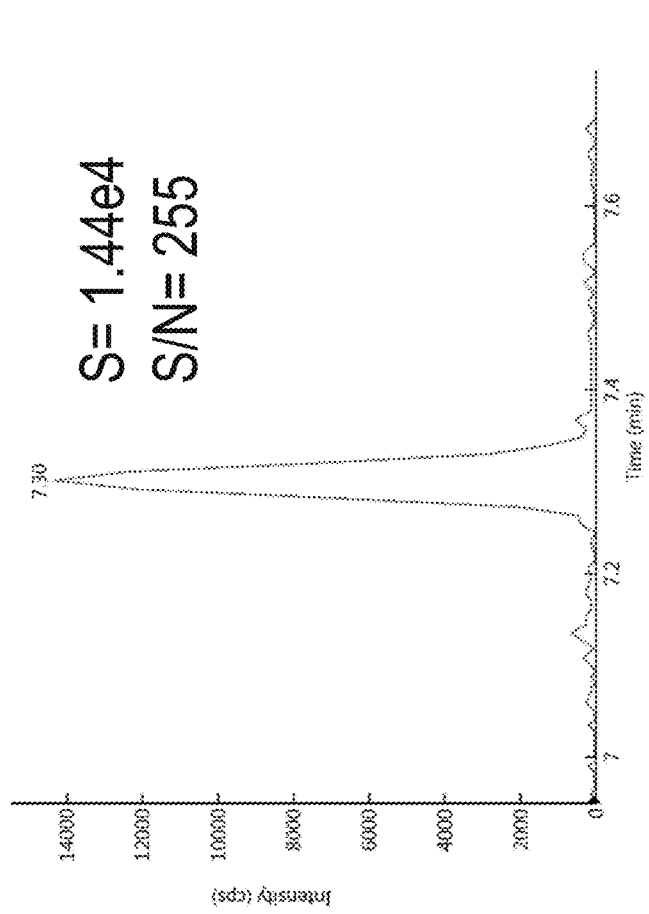

FIG. 16B is a precursor (parent) mass scan for a sample comprising naled. In FIG. 16B, the relative abundances of M (378.7 peak), M+2 (380.7 peak), M+4 (382.7 peak) and M+6 (384.7 peak) ions are 42%, 100%, 91%, and 36%, respectively.

FIGS. 16C-F and FIG. 113 are chromatograms obtained using different MRM transitions associated with naled for *cannabis* samples comprising 100 ppb naled. An MRM transition of 380.8>127 (FIG. 16C) provides a signal (peak) amplitude of $1.44 \times 10^4$ and an S/N ratio of 255. An MRM transition of 378.8>127 (FIG. 16D) provides a signal amplitude of $5.46 \times 10^3$ and a S/N ratio of 96. Using an MRM transition of 380.8>109 (FIG. 16E) provides a signal amplitude of $3.57 \times 10^3$ and a S/N ratio of 60. An MRM transition of 382.8>127 (FIG. 113) provides a signal of $1.38 \times 10^4$ and a S/N ratio of 300. An MRM transition of 378.8>109 (FIG. 16F) provides a signal of $1.6 \times 10^3$ and a S/N ratio of 1230.

FIGS. 60A and 60C compare intensities of the 380.8>109 MRM transition for a pesticide sample comprising naled (100 ppb concentration) and a blank *cannabis* sample, respectively. FIGS. 60B and 60D compare intensities of the 380.8>127 MRM transition for a *cannabis* samples comprising 100 ppb naled and a blank *cannabis* sample, respectively.

The LOQs were as low as approximately 23 ppb.

Example 15. N-Octyl Bicycloheptene Dicarboximide ("MGK-264")

Figure 20A:
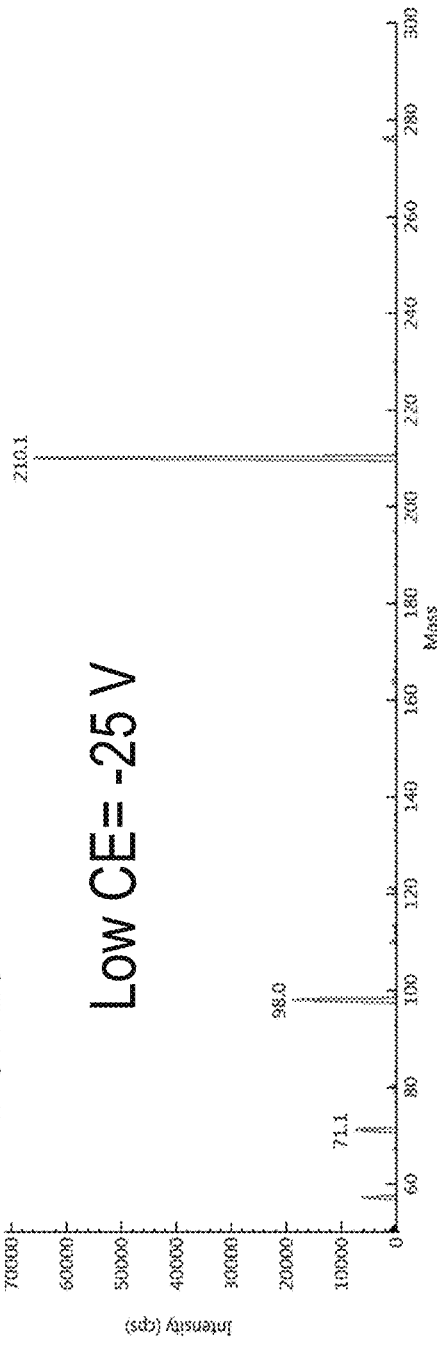
FIG. 20A and FIG. 20B are product ion scans for N-octyl bicycloheptene dicarboximide (MGK-264).
Figure 20B:
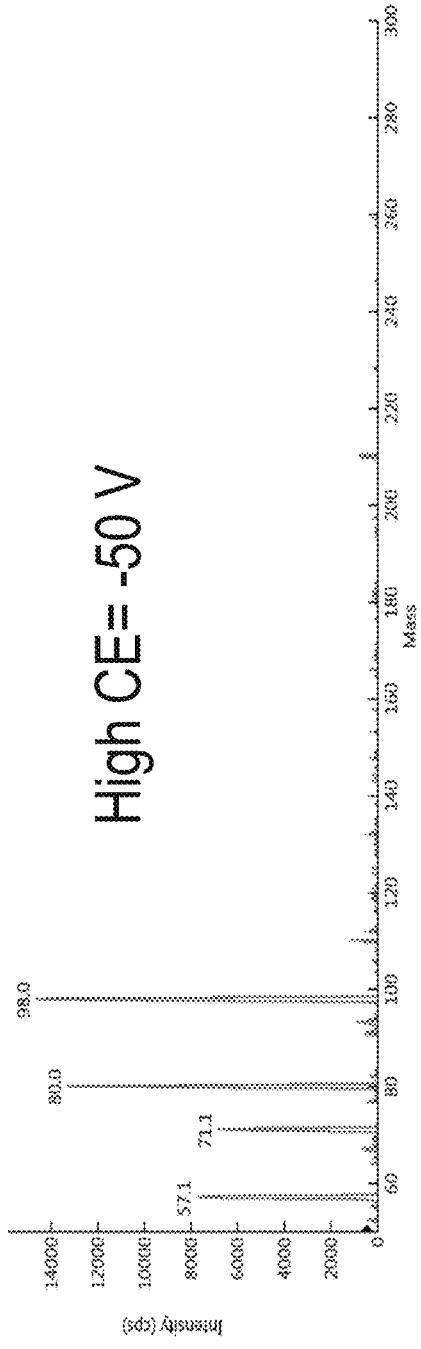
Figures 20C, 20D:
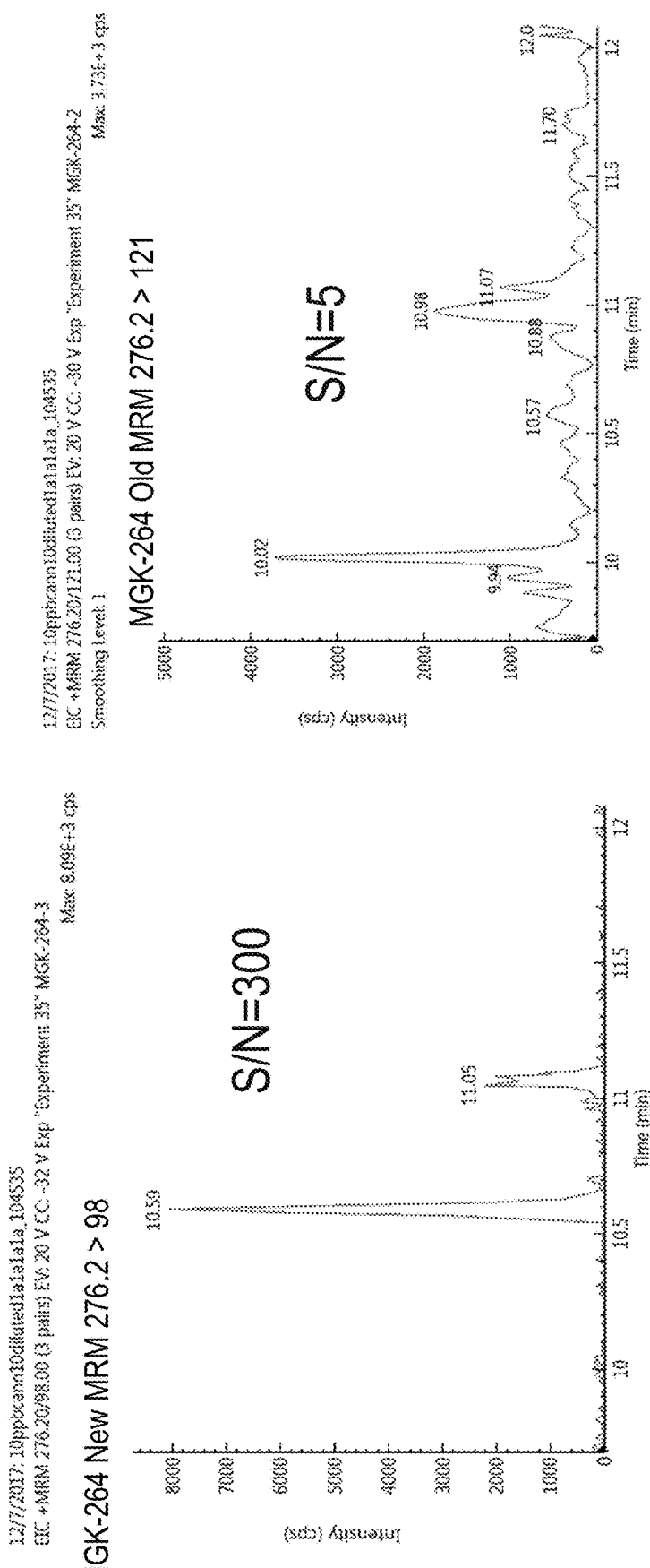
FIGS. 20C-E are chromatograms of *cannabis* samples comprising 100 ppb of MGK-264 and analyzed for the presence of MGK-264 using MRM transitions 276.2>98 (FIG. 20C), 276.2>121 (FIG. 20D), and 276.2>210 (FIG. 20E).
Figure 20E:
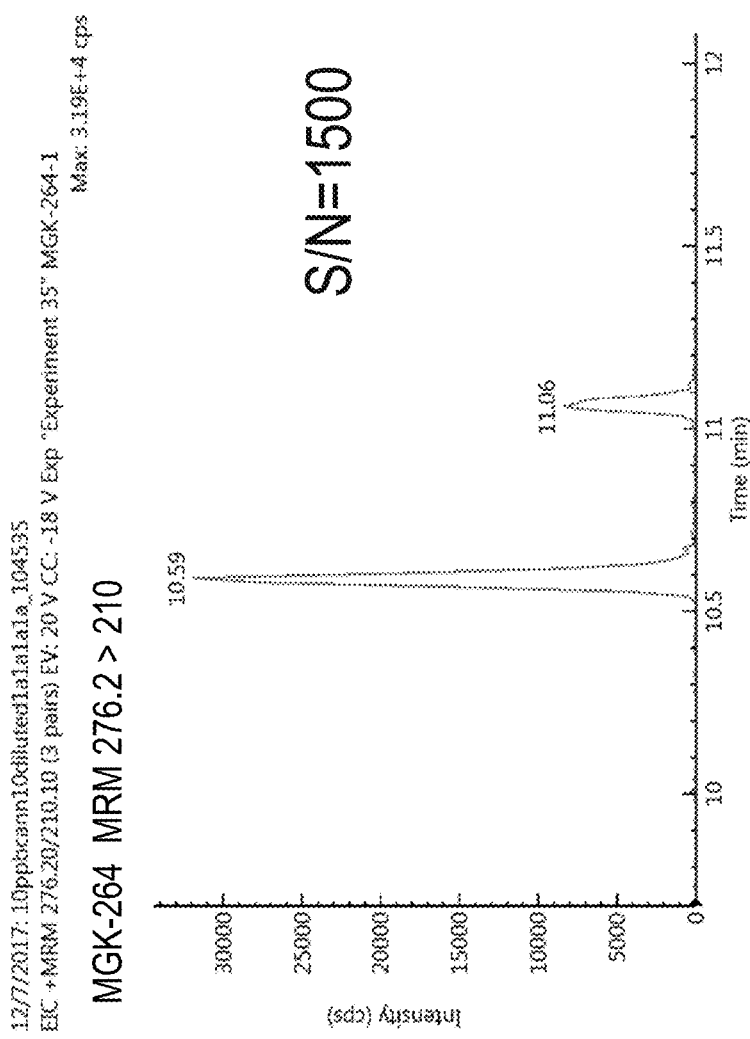

FIG. 20A and FIG. 20B are product ion scans for MGK-264. FIG. 20A shows a product ion scan for a low collision energy of −25V. FIG. 20B shows a product ion scan for a high collision energy of −50V. Major fragment ions at mass 210.1 and mass 98 were observed. FIGS. 20C-E plot intensities of three different MRM transitions for *cannabis* samples comprising 100 ppb MGK-264. Using an MRM transition of 276.2>98 (FIG. 20C) provides a S/N ratio of 300. Using an MRM transition of 276.2>121 (FIG. 20D) provides a S/N ratio of 5. Using an MRM transition of 276.2>210 (FIG. 20E) provides a S/N ratio of 1500. Accordingly, improvements in S/N of factors of 10 or more may be obtained through use of appropriate MRM transitions.

FIGS. 85A-D compare MRM transition intensities for *cannabis* samples comprising 100 ppb MGK-264 with blank *cannabis* sample measurements. FIGS. 85A and 85C compare intensities of a 276.2>98 MRM transition, and FIGS. 85B and 85D compare intensities of a 276.2>210.1 MRM transition. The LOQ was approximately 10 ppb.

Example 16. Propiconazole

Some *cannabis* plant extracts have lower levels of matrix interference than others with MRM transitions based on nominal Q1 mass of about 342 Da. These example provides MRM transitions useful for detecting propiconazole in both types of extracts.

FIGS. 87A-D compare MRM transition intensities for *cannabis* samples having relatively low matrix interference comprising 100 ppb propiconazole with blank *cannabis* sample measurements. FIGS. 87A and 87C compare intensities of a 342.1>69 MRM transition, and FIGS. 87B and 87D compare intensities of a 342.1>159 MRM transition. The LOQ was approximately 19 ppb, which is 5.3-fold lower than the lowest California action limit of 100 ppb.

FIGS. 114A-D are four graphs that compare intensities of two different MRM transitions measured for *cannabis* samples having higher matrix interference with MRM transitions based on nominal Q1 mass of 342 and comprising 10 ppb propiconazole with measurements from blank *cannabis* samples. FIG. 114A plots intensity of a 342>69 MRM transition, FIG. 114B plots intensity of a 342>159 MRM transition, and FIG. 114D plots intensity of the 342>69 MRM transition for a blank *cannabis* sample. For both the 342>69 and the 342>159 MRM transitions, matrix interference peaks were present in the blank *cannabis* sample measurements, as shown in FIG. 114C and FIG. 114D.

FIGS. 114E-H (10 ppb propiconazole) show intensities of two MRM transitions, 344>69 and 344>161, that do not suffer from matrix interference. FIG. 114E and FIG. 114F plot intensities of a 344>69 MRM transition, and FIGS. 114G and 114H plot intensities of a 344>161 MRM transitions. Intensity peaks present in the pesticide sample measurements (FIG. 114E and FIG. 114F) were not observed in the corresponding blank *cannabis* sample measurements (FIG. 114G and FIG. 114H). The LOQ was approximately 10 ppb.

FIGS. 114I-L compare four MRM transition intensity measurements for *cannabis* samples comprising 100 ppb propiconazole with blank *cannabis* sample measurements. Each of FIGS. 114I-L plots intensity measurements for a particular MRM transition. In particular, measurements of a 342>69, a 342>159, a 344>69, and a 344>161 MRM transition are shown in FIG. 114I, FIG. 114J, FIG. 114K, and FIG. 114L, respectively. In each of FIGS. 114I-L, a first trace plots intensity of the MRM transition measured for a pesticide sample comprising 100 ppb propiconazole and a second trace plots intensity of the MRM transition. As shown in FIG. 114I and FIG. 114J, for the 342>69 and 342>159 MRM transitions suffer from matrix interference, as intensity peaks present in the pesticide sample measurements are also present for the blank *cannabis* sample. In contrast, the 344>69 and 344>161 MRM transitions do not suffer from matrix interference. As shown in FIG. 114K and FIG. 114L, large signal peaks are observed in the pesticide sample measurements, whereas the blank *cannabis* sample intensity varies minimally in comparison.

Example 17. APCI Method for Quintozene (PCNB) and Chlordane

Two very hydrophobic and chlorinated pesticides (quintozene and chlordane) are traditionally analyzed by GC-MS because they do not ionize sufficiently by LC-MS with an ESI source. This example describes the use of an APCI source to ionize quintozene and chlordane. This method also can be used to ionize chlorfenapyr.

The structure of quintozene is shown below.

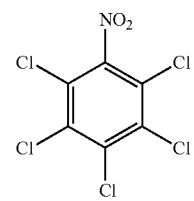 [SMILES: O=[N+]([O-])c1c(Cl)c(Cl)c(Cl)c(Cl)c1Cl]

Quintozene does not comprise any hydrogen atoms and is therefore difficult to ionize using LC-MS-compatible techniques, in which protons are either gained or lost to form ions. Quintozene also does not form adducts and cannot gain or lose a proton. Instead, conventional approaches rely on GCMS with electron ionization (EI) for detection and/or quantification of quintozene.

Chlordane is highly chlorinated and has very low protein affinity. Two forms of chlordane exist: a cis form and a trans form. Chemical structures of these two forms of chlordane are shown below.

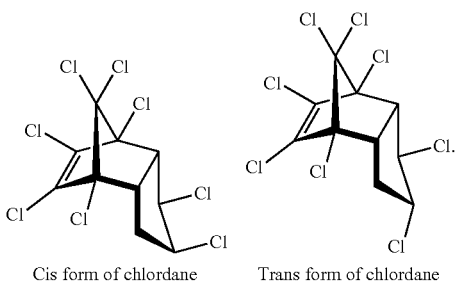

Cis form of chlordane    Trans form of chlordane

In this example, quintozene and chlordane were ionized using an APCI source with air as a nebulizing gas. It is also possible, however, to use air and/or other gases, such as nitrogen, argon, and carbon dioxide.

Using a fast 6 minute LC-MS/MS method with short LC gradient and the APCI source of the QSight LC-MS/MS system, the LOQs of quintozene and chlordane in *cannabis* samples comprising 100 ppb of either pesticide were 10 and 33 ppg, respectively.

Figure 33A:
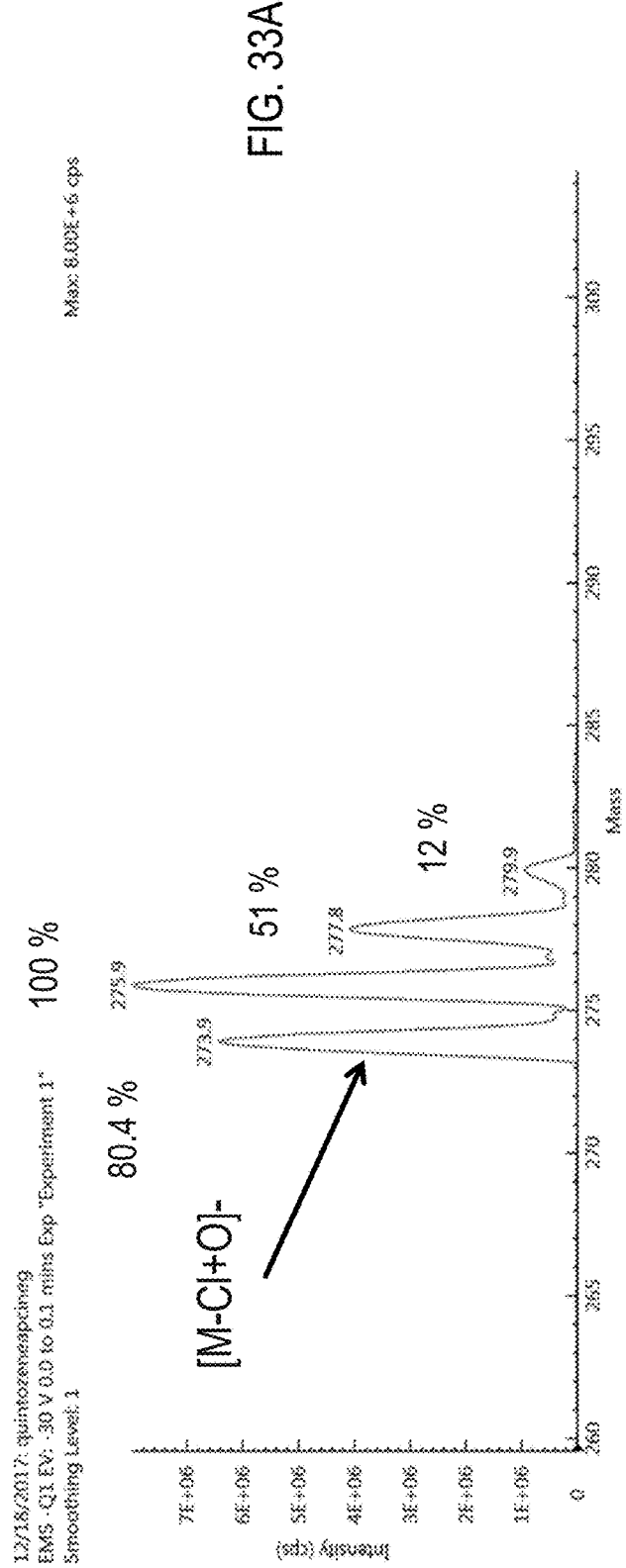
FIG. 33A is a precursor (parent) mass scan for pentachloronitrobenzene (PCNB; quintozene).
Figure 33B:
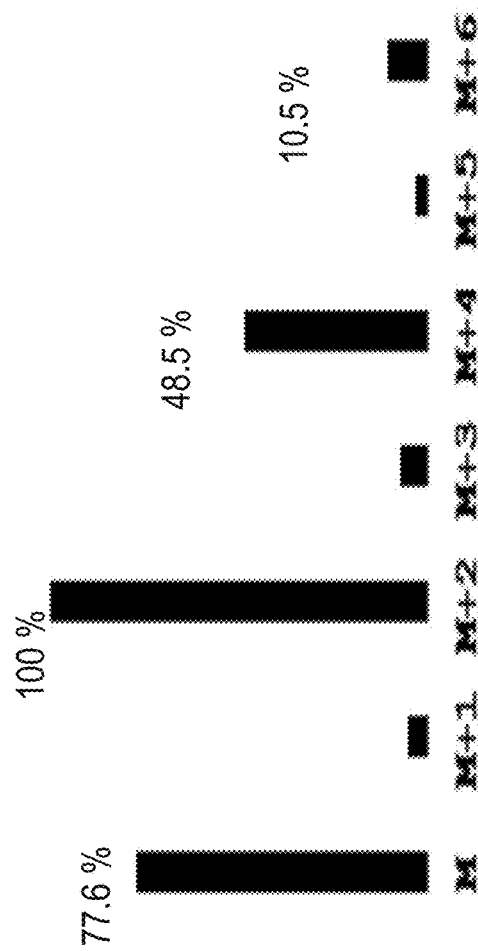
FIG. 33B is a graph showing an isotope distribution for quintozene.

FIG. 33A and FIG. 33B show isotope distributions for quintozene ions formed via APCI. FIG. 33A shows a precursor (parent) mass scan for qunozene obtaiend via APCI in negative mode. In FIG. 33A, the lowest mass (273.9) peak corresponds to [M-Cl+O]—. The relative abundances of ions corresponding to the 273.9 peak, 275.9 peak, 277.8 peak and 279.9 peak are 80.4%, 100%, 51%, and 12%, respectively. FIG. 33B shows the calculated isotope distribution.

Figure 34A:
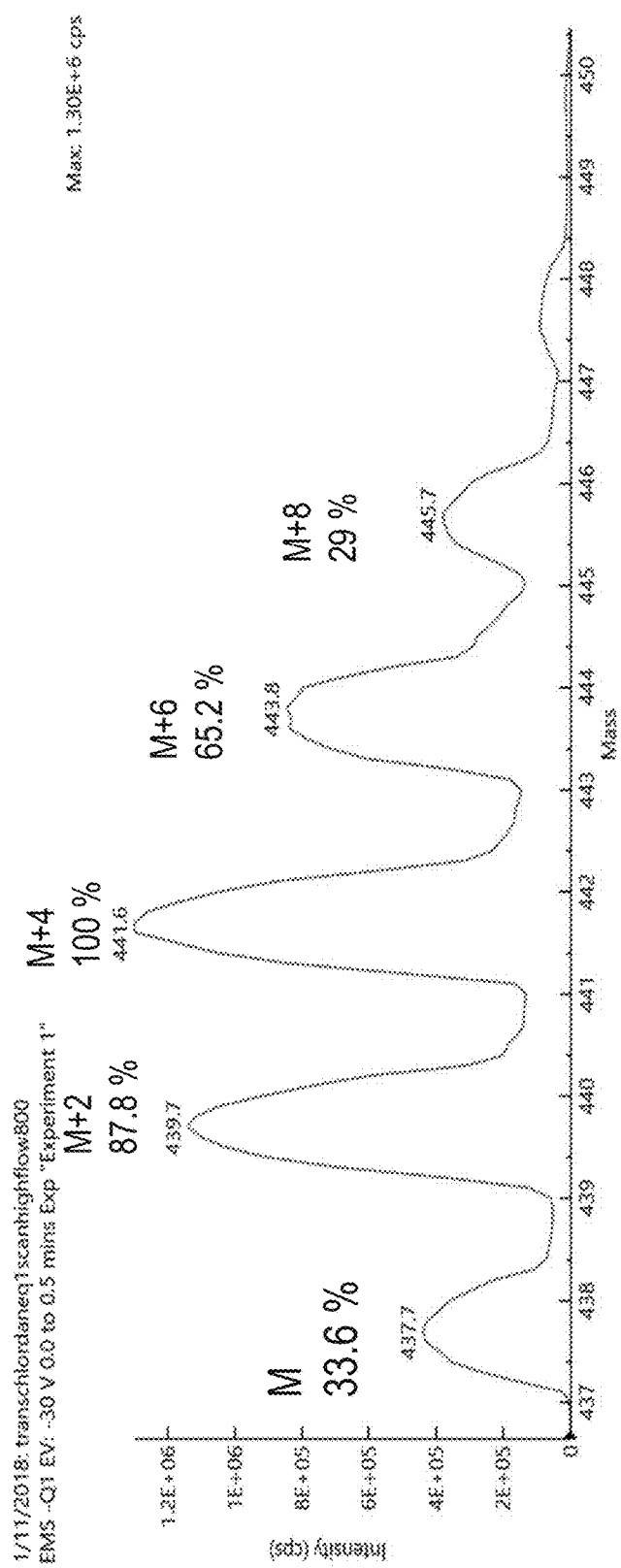
FIG. 34A is a precursor (parent) mass scan for chlordane.
Figure 34B:
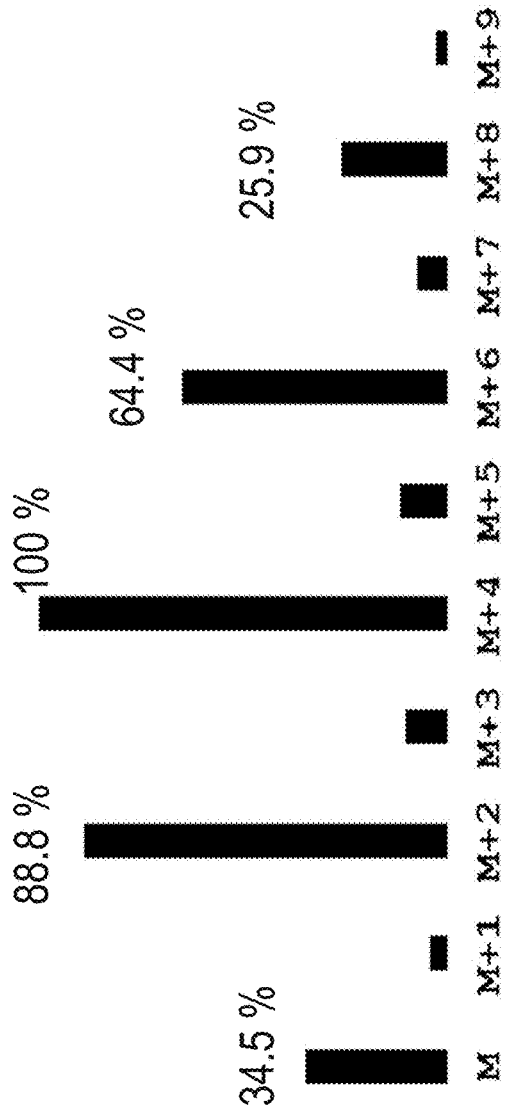
FIG. 34B is a graph showing an isotope distribution for chlordane.

FIG. 34A and FIG. 34B show isotope distributions for chlordane ions formed via APCI. FIG. 34A shows a precursor (parent) mass scan for chlordane obtaiend via APCI. In FIG. 34A, the relative abundances of the ions corresponding to the 437.7 peak (M), 439.7 peak (M+2), 441.6 peak (M+4), 443.8 peak (M+6), and 445.7 peak (M+8) are 34.5%, 88.8%, 100%, 64.4%, and 25.9%, respectively. FIG. 34B shows a calculated distribution.

Figure 35A:
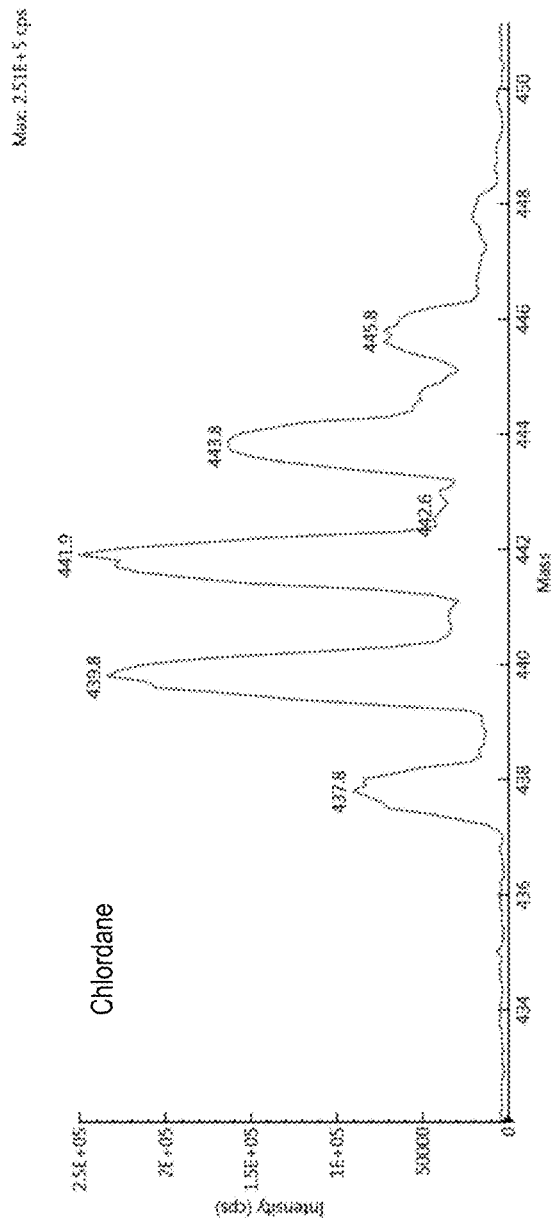
FIG. 35A is a precursor (parent) mass scan for a sample comprising chlordane and processed using a LC method that employs mobile phases without additives.
Figure 35B:
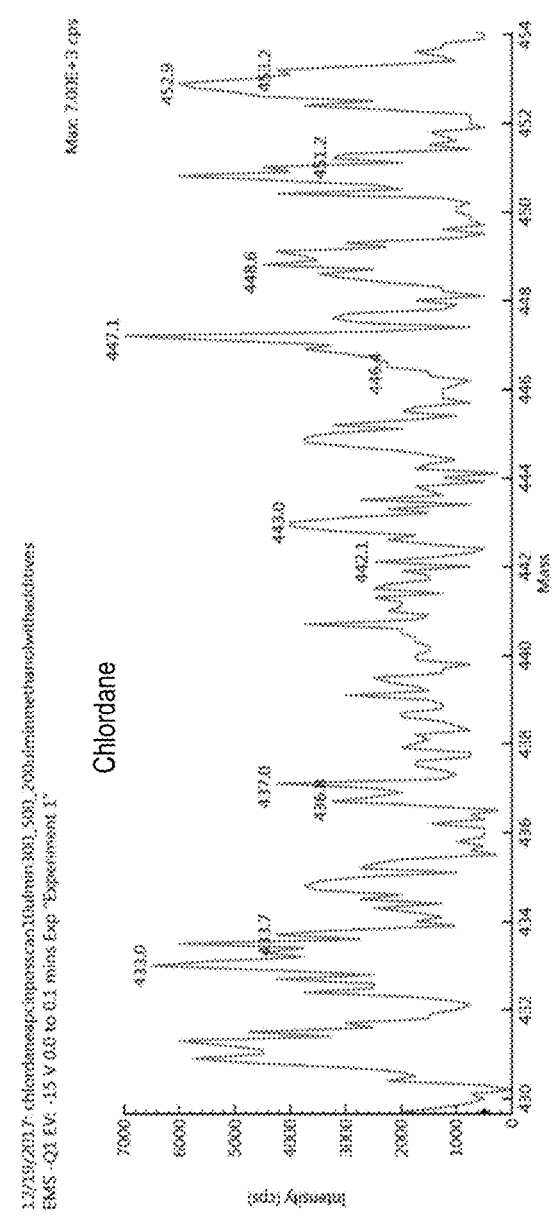
FIG. 35B is a precursor (parent) mass scan for a sample comprising chlordane and processed using a LC method that employs a mobile phase with formic acid.

As described herein, presence of additives in mobile phases used by LC methods can influence signal levels obtained for molecules ionized via the disclosed APCI technique. In this example, the influence of presence of additives in LC methods is shown for chlordane in FIG. 35A and FIG. 35B. FIG. 35A plots a precursor (parent) mass scan for a sample comprising chlordane that was separated using a LC method that employed mobile phases without additives. FIG. 35B plots a precursor (parent) mass scan for a sample comprising chlordane that was separated using a LC method that employed mobile phases with formic acid. Good signal is observed for the LC method without additives (FIG. 35A), while no signal was observed for chlordane for the LC method with additives (FIG. 35B).

Figure 36:
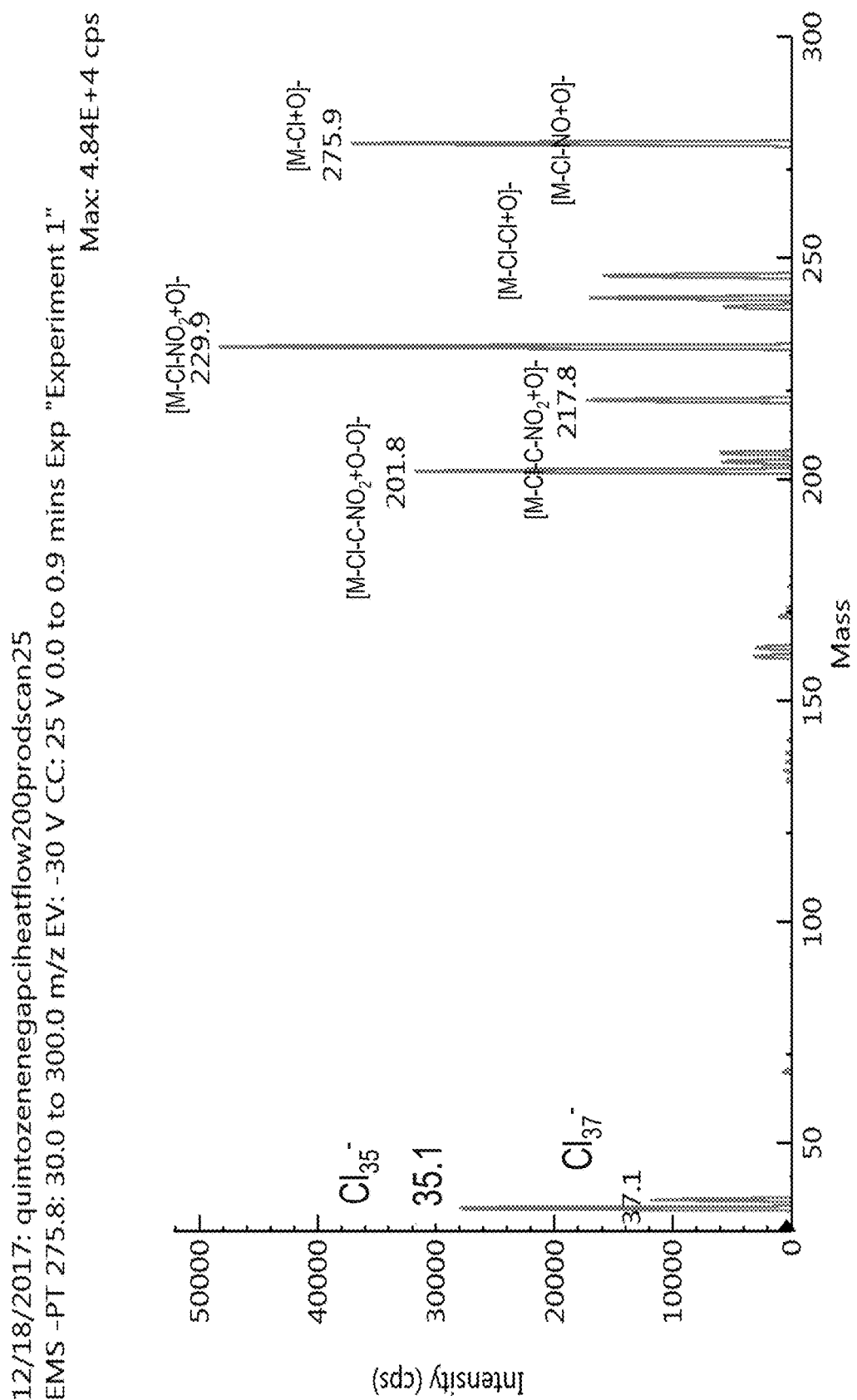
FIG. 36 is a product ion scan for quintozene obtained using an APCI source in a negative ion mode.

FIG. 36 is a graph showing a product ion scan for quintozene. The various peaks in the graph correspond to the following ions (relevant peak listed in parentheses): Cl35- (35.1), Cl37- (37.1), [M—Cl—C—NO$_2$+O]$^-$ (201.8), [M—Cl—C—NO$_2$+O]$^-$ (271.8), [M—Cl—NO$_2$+O]$^-$ (229.9), [M—Cl—Cl+O]$^-$ (240.9), [M—Cl—NO+O]$^-$ (245.9), [M—Cl+O]$^-$ (275.9), where M represents quintozene (pentachloronitrobenzene).

Figure 39:
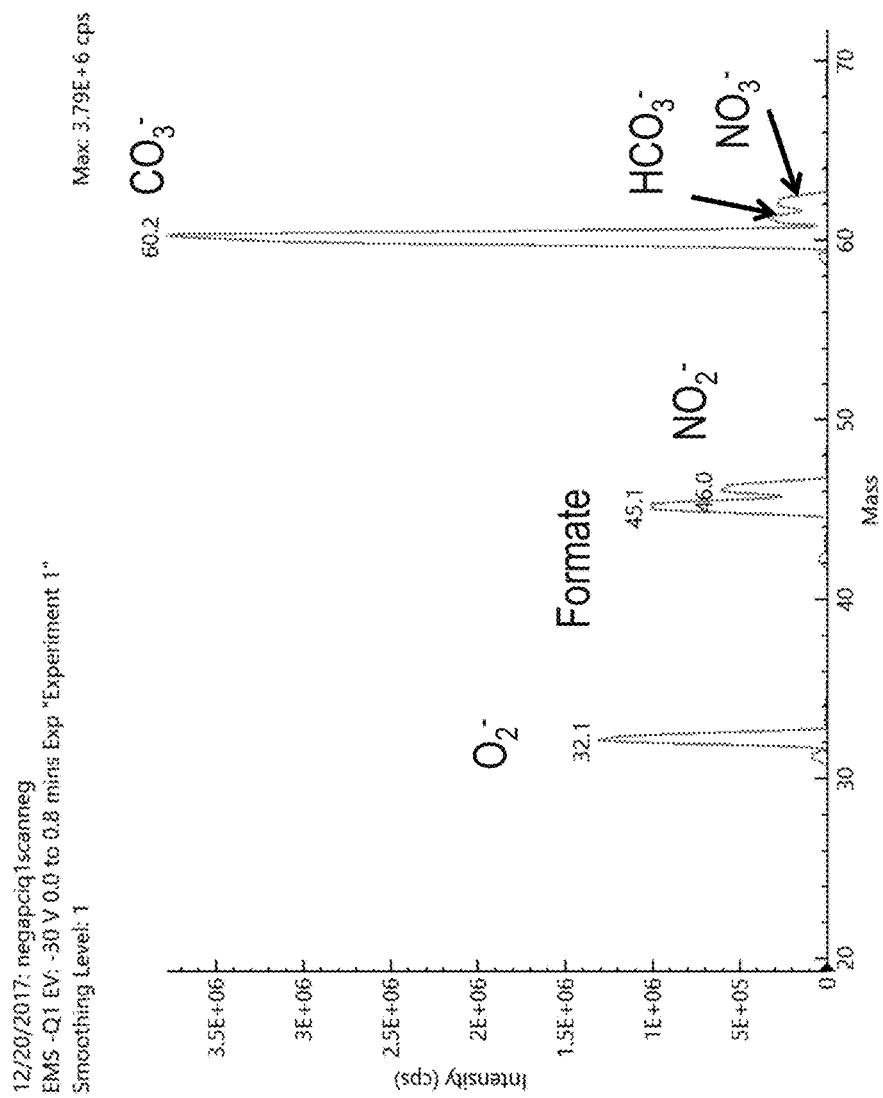
FIG. 39 is a graph showing background spectra obtained using an APCI source in a negative ion mode.

FIG. 39 is a graph showing background spectra for mobile phase entering into an APCI source in a negative ion mode over low mass range of 15-100.

Without wishing to be bound to any particular theory, it is believed that the mechanism of quintozene ionization with an APCI source is as follows:

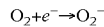

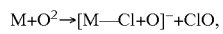

where M represents quintozene.

Without wishing to be bound to any particular theory, it is believed that the mechanism of chlordane ionization with an APCI source is as follows:

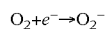

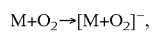

where M represents chlordane.

FIGS. 37A-B are chromatograms of *cannabis* samples analyzed for the presence of quintozene using MRM transitions 275.8>35.1 (FIGS. 37A, 37C) and 273.8>35.1 (FIGS. 37B, 37D). FIGS. 37A and 37B are *cannabis* samples comprising 100 ppb quintozene. FIGS. 37C and 37D are blank *cannabis* samples.

Figure 38A:
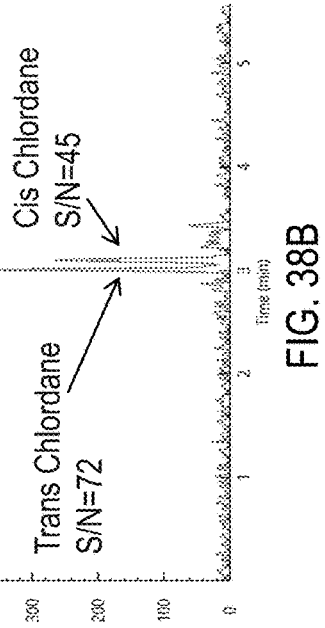
FIG. 38A-D are chromatograms of *cannabis* samples analyzed for the presence of chlordane using MRM transitions 439.8>35.1 (FIGS. 38A, 38C) and 441.8>35.1 (FIGS. 38B, 38D).
Figure 38C:
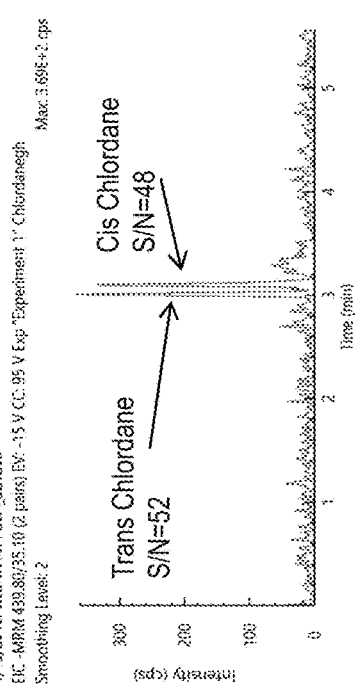
Figure 38B:
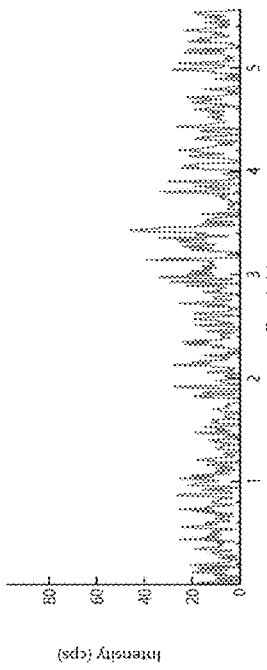
Figure 38D:
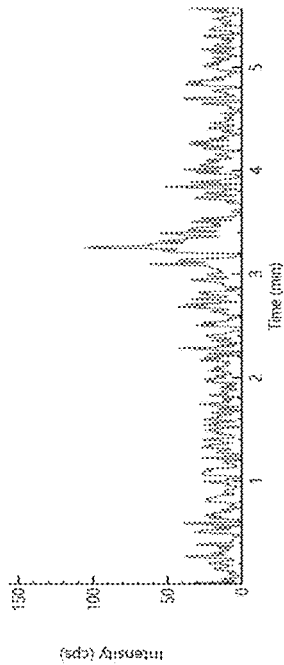

FIG. 38A-B are chromatograms of *cannabis* samples analyzed for the presence of chlordane using MRM transitions 275.8>35 (FIGS. 38A, 38C; qualifier) and 273.8>35 (FIGS. 38B, 38D, quantifier). FIGS. 38A and 38B are *cannabis* samples comprising 100 ppb chlordane. FIGS. 38C and 38D are blank *cannabis* samples.

Example 18. Long Term Stability

Long term stability data for pesticide and mycotoxin analysis in *cannabis* was collected using a triple quadrupole mass spectrometer fitted with dual electrospray ionization source and atmospheric chemical ionization source (APCI) and combined with a heated and self-cleaning stay clean source with laminar flow interface.

FIG. 120 shows long term response (1 week) for a *cannabis* extract comprising 100 ng/ml of diazinon. Long term stability data for pesticide analysis in *cannabis* showed that response RSD over 1 week for majority of pesticides and mycotoxins was between 1.5 to 20%. These results demonstrate that the heated self-cleaning stay clean source in a LC-MS/MS system reduce maintenance needs of the LC-MS/MS based method for pesticide and mycotoxins analysis in dirty matrices such as *cannabis*. Most of LC-MS/MS methods published in literature with other LCMS systems on the market either do not show long term stability data or state that they had to clean electrospray source every day or after a batch to maintain sensitivity of mass spectrometer (Geis-Asteggiante et al., J. Chromatogr. A, 1258, 43-54, 2012). Also, they divert LC flow away from the MS for the first few minutes and after the last peak elutes out to reduce MS contamination from un-retained and late eluting matrix compounds from LC column. In this study, excellent long term stability data was obtained without diverting the LC flow from MS in the first few minutes and at the end of run and periodical cleaning of ion source.

Example 19. Recovery Studies with Solvent Extraction

QuEChERS is a method for extraction of low levels of contaminants such as pesticides from fruit and vegetable matrices with higher water content (Anastassiades et al., J. AOAC Int. 86(2), 412-31, 2003). It works for extraction for broad range of pesticides from these food matrices with effective removal of sugars and other compounds in fruits and vegetables (Chung & Chan, J. Chromatogr. A, 1217, 4815-24, 2010; Cunha et al., J. Sep. Sci. 30(4), 620-26, 2007; Sapozhinikova, J. Agric. Food Chem. 62, 3684-89, 2014; Wang & Cheung, J. AOAC Int. 99(2), 539-57, 2016; Villar-Pulido et al., Talanta 85, 1419-27, 2011). It is not suitable for very polar pesticides such as daminozide which is included in California and other states monitoring list for *cannabis* daminozide is too polar to be extracted efficiently with QuEChERS extraction procedure since it remains in the aqueous phase and does not partition into the organic solvent during salting out step. The recovery of daminozide from *cannabis* matrix with QuEChERS extraction has been reported to be less than 10% (Stenerson & Oden, Cann. Sci. & Tech. 1(1), 48-53, 2018). Moreover, *cannabis* matrix contains mostly hydrophobic compounds such as cannabinoids and terpenes, therefore QuEChERS extraction method does not remove much of matrix compounds during salting out step. Different groups have tried to develop advanced QuEChERS methods with d-SPE step which utilizes PSA and other adsorbents to remove matrix from *cannabis* extract (e.g., Kowlaski et al., LCGC 35(5) 8-22, 2017; Wang et al., LCGC 34(10), 20-7, 2016). These compounds bind to PSA adsorbent in the d-SPE step, and thus they have poor recoveries.

Due to above shortcomings of QuEChERS method for extraction of pesticides from *cannabis* matrix, we used a simple acetonitrile based solvent extraction method for extraction of pesticides from *cannabis* matrix. Fortified *cannabis* flower samples were produced to determine pesticides and aflatoxins recovery. The *cannabis* flower samples were tested to confirm the absence of pesticides before spiking with them. Five *cannabis* flower samples were spiked at 2 levels (low and high) of all pesticides (0.1 and 1 μg/g) and mycotoxins (0.02 and 0.1 μg/g) standard. These two levels were chosen based on regulatory limits, for pesticides and mycotoxins in *cannabis*, from California and other states. Table 9, 10, and 11 show that absolute recoveries of all 66 pesticides and 5 mycotoxins at 2 different levels was within acceptable range of 70-120% with RSD less than 20% for 5 *cannabis* flower samples. For 3 pesticides, the recovery values were not reported at low spiked value because it was below their LOQ value.

TABLE 9

Recovery of Category II pesticides at 2 different levels from *cannabis* with acetonitrile solvent extraction method

| Pesticide | Low Level 0.1 µg/g | | High Level 1 µg/g | |
|---|---|---|---|---|
| | Recovery/% | RSD/% (n = 5) | Recovery/% | RSD/% (n = 5) |
| Abamectin | 85 | 10 | 89 | 9 |
| Acephate | 93 | 16 | 91 | 9 |
| Acequinocyl | 90 | 11 | 86 | 6 |
| Acetamiprid | 87 | 13 | 95 | 9 |
| Azoxystrobin | 87 | 12 | 92 | 8 |
| Bifenazate | 88 | 8 | 88 | 7 |
| Bifenthrin | 84 | 13 | 94 | 7 |
| Boscalid | 87 | 10 | 89 | 5 |
| Captan | NA | NA | 70 | 15 |
| Carbaryl | 84 | 12 | 92 | 10 |
| Chlorantraniliprole | 88 | 13 | 90 | 8 |
| Clofentezine | 87 | 13 | 91 | 12 |
| Cyfluthrin | NA | NA | 97 | 17 |
| Cypermethrin | 98 | 18 | 85 | 13 |
| Diazinon | 96 | 10 | 95 | 10 |
| Dimethomorph | 87 | 15 | 90 | 7 |
| Etoxazole | 89 | 10 | 92 | 10 |
| Fenhexamid | 87 | 12 | 87 | 7 |
| Fenpyroximate | 87 | 9 | 93 | 8 |
| Flonicamid | 93 | 15 | 92 | 12 |
| Fludioxonil | 94 | 13 | 93 | 8 |
| Hexythiazox | 86 | 11 | 93 | 7 |
| Imidacloprid | 89 | 11 | 91 | 9 |
| Kresoxim-methyl | 91 | 10 | 95 | 8 |
| Malathion | 90 | 12 | 91 | 7 |
| Metalaxyl | 86 | 10 | 92 | 8 |
| Methomyl | 89 | 10 | 90 | 9 |
| Myclobutanil | 84 | 10 | 93 | 7 |
| Naled | 87 | 10 | 91 | 7 |
| Oxamyl | 93 | 16 | 94 | 9 |
| Pentachloronitrobenzene | 80 | 16 | 88 | 8 |
| Permethrin | 87 | 17 | 92 | 9 |
| Phosmet | 86 | 11 | 91 | 7 |
| Piperonylbutoxide | 91 | 8 | 94 | 8 |
| Prallethrin | 88 | 15 | 94 | 8 |
| Propiconazole | 90 | 14 | 95 | 11 |
| Pyrethrins | 89 | 12 | 93 | 9 |
| Pyridaben | 84 | 13 | 92 | 9 |
| Spinetoram | 93 | 13 | 94 | 9 |
| Spinosad | 88 | 14 | 90 | 10 |
| Spiromesifen | 90 | 8 | 92 | 5 |
| Spirotetramat | 97 | 10 | 90 | 7 |
| Tebuconazole | 94 | 12 | 91 | 7 |
| Thiamethoxam | 90 | 10 | 95 | 10 |
| Trifloxystrobin | 86 | 12 | 93 | 9 |

TABLE 10

Recovery of Category II mycotoxins at 2 different levels from *cannabis* with acetonitrile solvent extraction method

| Mycotoxin | Low Level 0.02 µg/g | | High Level 0.1 µg/g | |
|---|---|---|---|---|
| | Recovery/% | RSD/% (n = 5) | Recovery/% | RSD/% (n = 5) |
| Aflatoxin B1 | 75 | 15 | 84 | 9 |
| Aflatoxin B2 | 78 | 14 | 82 | 9 |
| Aflatoxin G1 | 76 | 12 | 85 | 7 |
| Aflatoxin G2 | 79 | 12 | 84 | 6 |

TABLE 11

Recovery of Category I pesticides at 2 different levels from *cannabis* with acetonitrile solvent extraction method

| Pesticide | Low Level 0.1 µg/g | | High Level 1 µg/g | |
|---|---|---|---|---|
| | Recovery/% | RSD/% (n = 5) | Recovery/% | RSD/% (n = 5) |
| Aldicarb | 87 | 11 | 94 | 11 |
| Carbofuran | 86 | 11 | 91 | 9 |
| Chlordane | 87 | 19 | 92 | 10 |
| Chlorfenapyr | NA | NA | 99 | 10 |
| Chlorpyrifos | 94 | 8 | 92 | 8 |
| Coumaphos | 90 | 12 | 95 | 10 |
| daminozide | 82 | 15 | 80 | 14 |
| DDVP (Dichlorvos) | 94 | 14 | 91 | 11 |
| Dimethoate | 89 | 11 | 96 | 9 |
| Ethoprop(hos) | 92 | 9 | 94 | 7 |
| Etofenprox | 88 | 13 | 93 | 8 |
| Fenoxycarb | 91 | 11 | 93 | 7 |
| Fipronil | 89 | 9 | 95 | 8 |
| Imazalil | 86 | 10 | 89 | 10 |
| Methiocarb | 81 | 9 | 93 | 6 |
| Methyl parathion | 89 | 14 | 96 | 11 |
| Mevinphos | 86 | 10 | 95 | 10 |
| Paclobutrazol | 79 | 13 | 90 | 6 |
| Propoxur | 91 | 13 | 93 | 9 |
| Spiroxamine | 88 | 9 | 89 | 9 |
| Thiacloprid | 89 | 13 | 95 | 10 |

Example 20. Quantification

Figure 31:
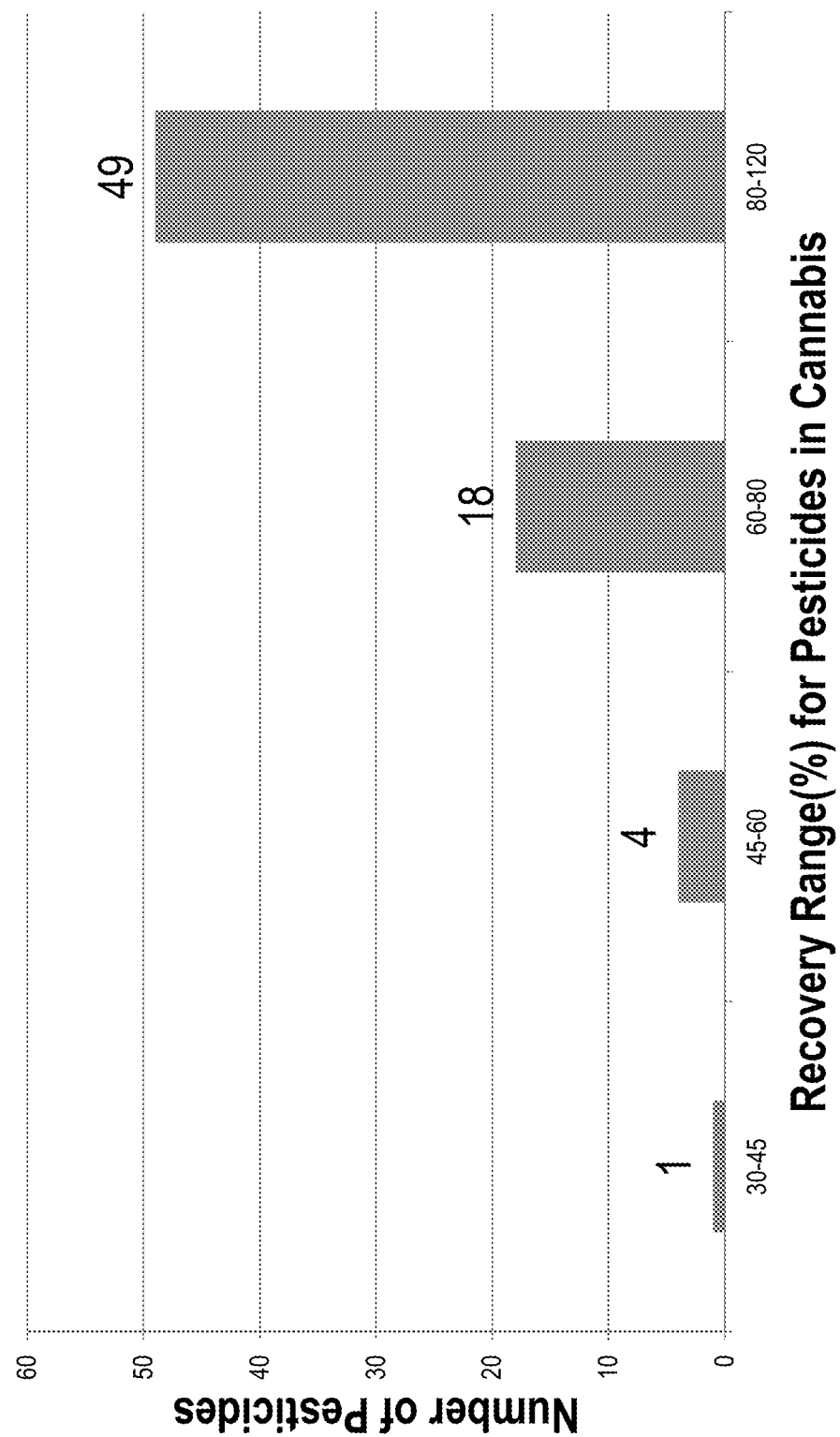
FIG. 31 is a graph showing overall pesticide recovery in a *cannabis* sample.
Figure 32A:
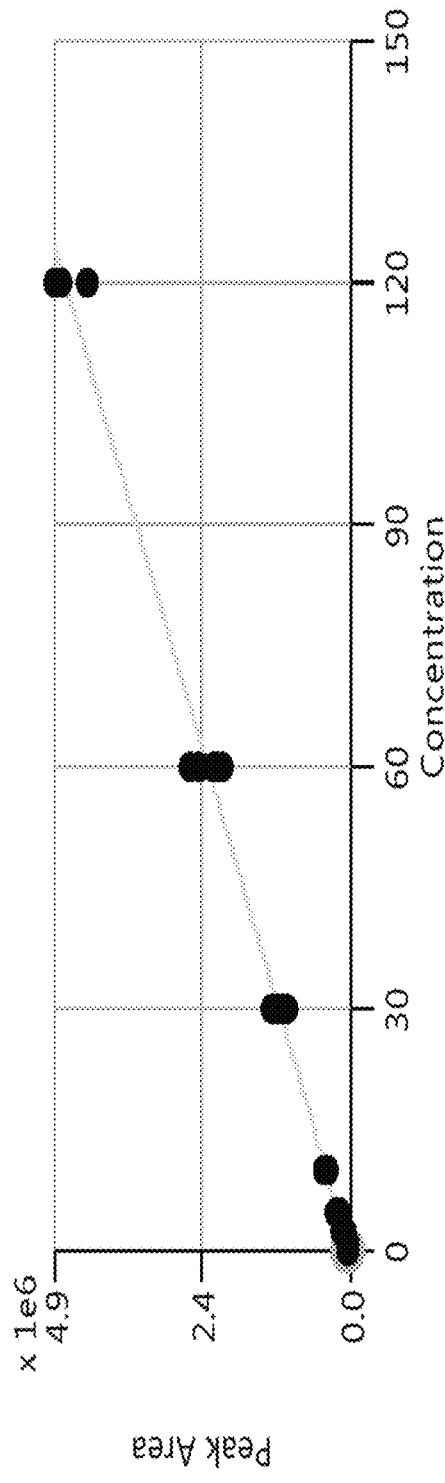
FIGS. 32A-B are calibration curves for azoxystrobin in a *cannabis* matrix (FIG. 32A) and in solvent (FIG. 32B).
Figure 32B:
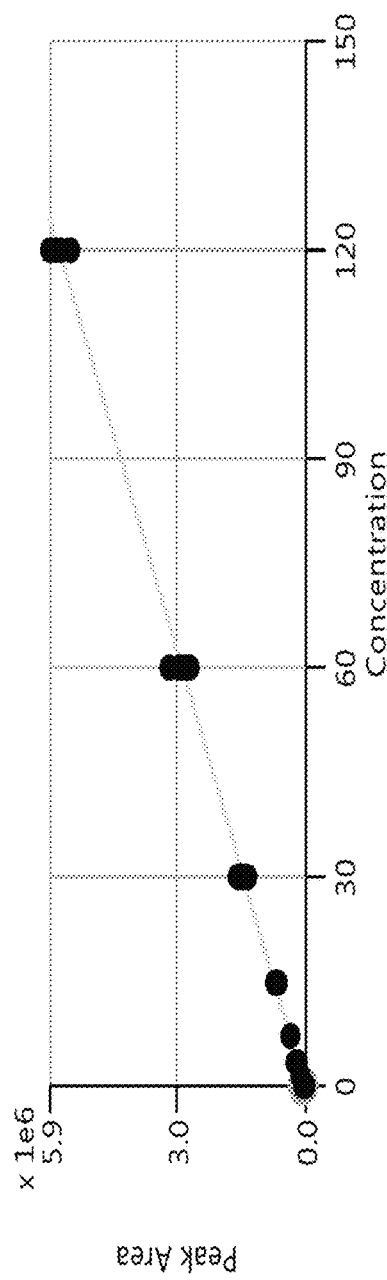

FIG. 31 is a bar graph showing overall recovery ranges for analyzed pesticides. As shown, overall recovery values for 93% of the pesticides ranged from 80% to 120% (overall recovery values for 49 of 72 pesticides ranged from 80% to 120% and overall recovery values for 18 of 72 pesticides ranged from 60% to 80%). These calculations were based on use of mixture of only 10 internal standards. The use of the internal standards mixture disclosed in this specification has the potential to improve recoveries for the remaining 5 pesticides (those having overall recovery values below 60%) to values ranging from 60% to 120%. For example, FIG. 32A and FIG. 32B show calibration curves for azoxystrobin at concentrations ranging from 0.1-120 ppb in (i) samples comprising *cannabis* plant material (*cannabis* matrix) and (ii) solvent (without *cannabis* plant material), respectively.

Figure 40A:
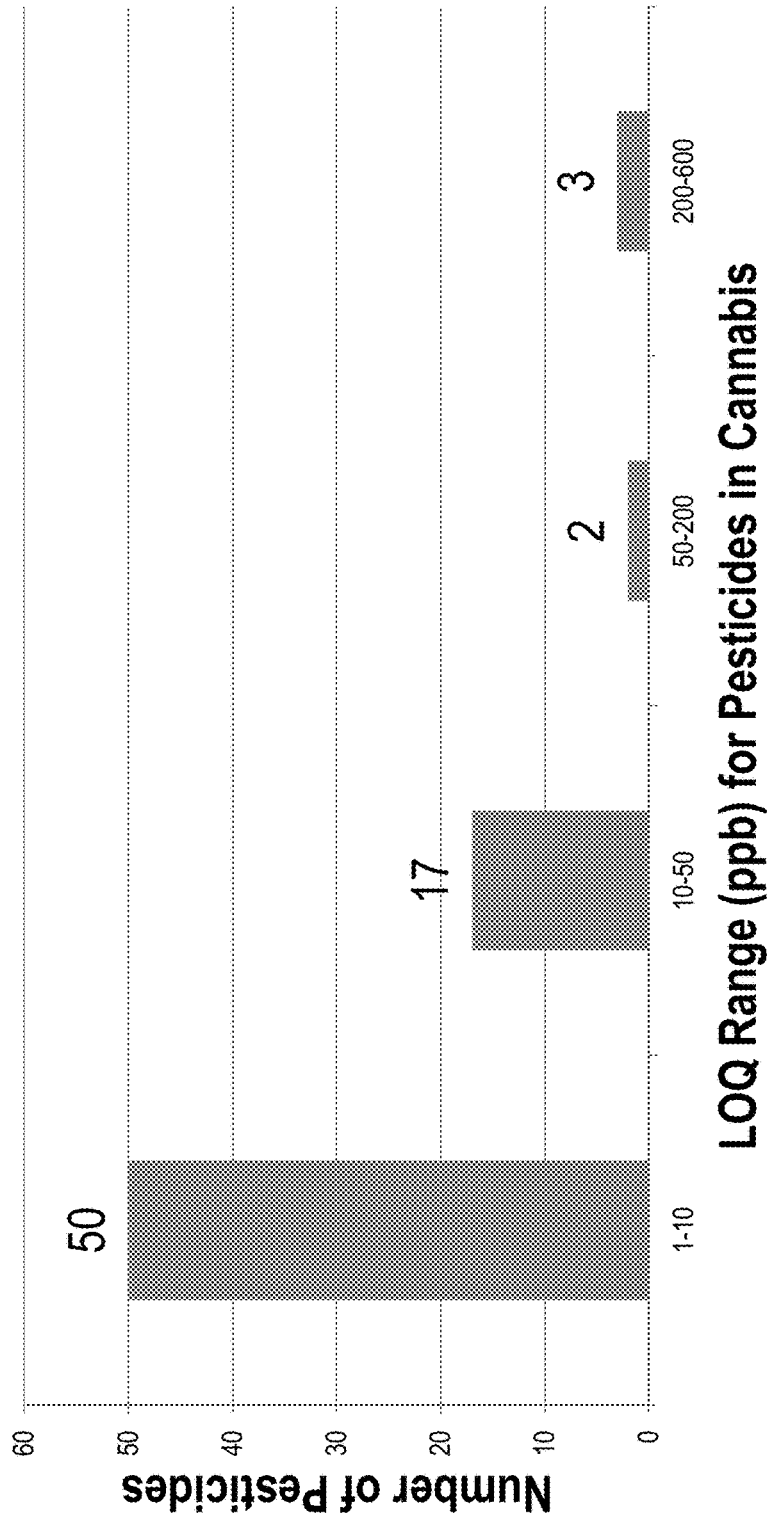
FIG. 40A is a graph showing limits of quantitation (LOQs) calculated based on the sensitivity of both quantifier/qualifier MRM transitions for 72 pesticides.
Figure 40B:
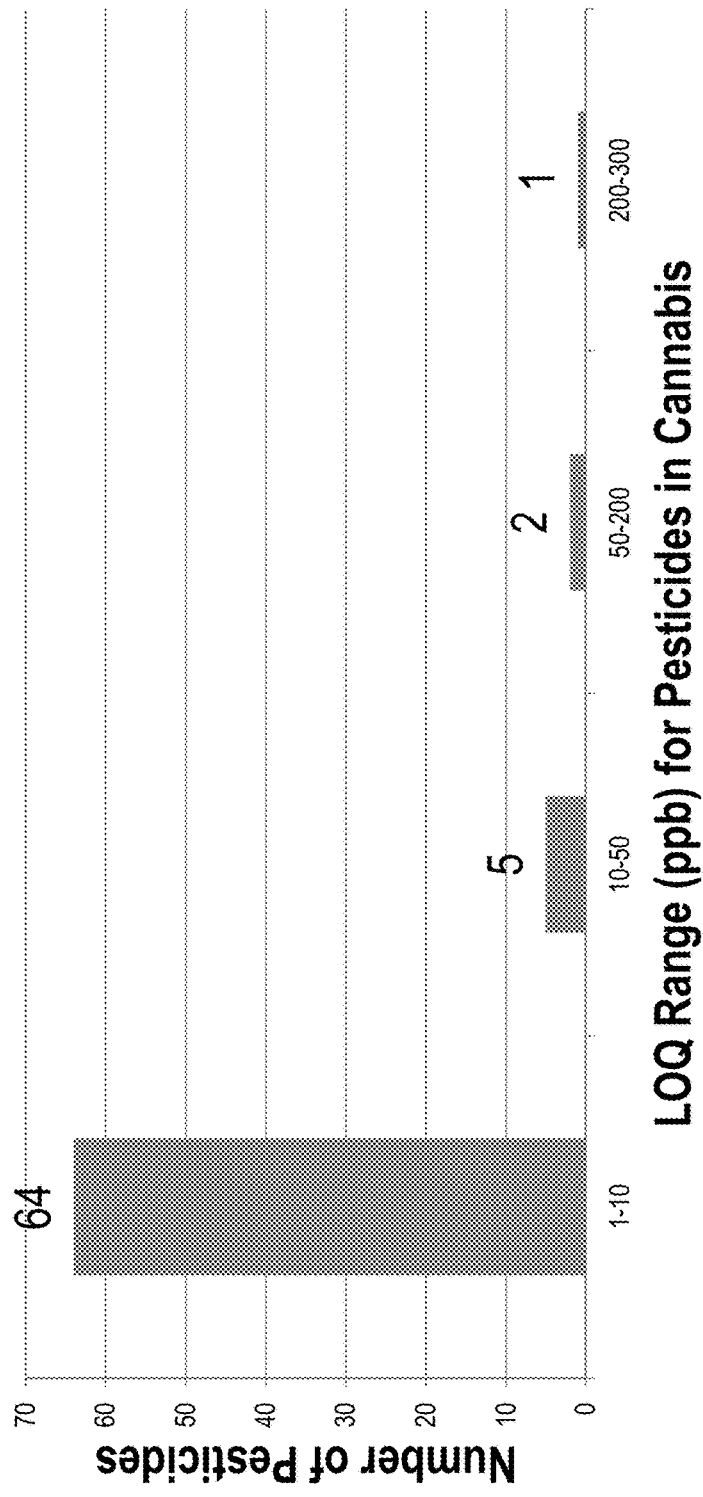
FIG. 40B is a graph showing LOQs calculated based only on sensitivity of a quantifier MRM transition for the 72 pesticides.
Figure 44A:
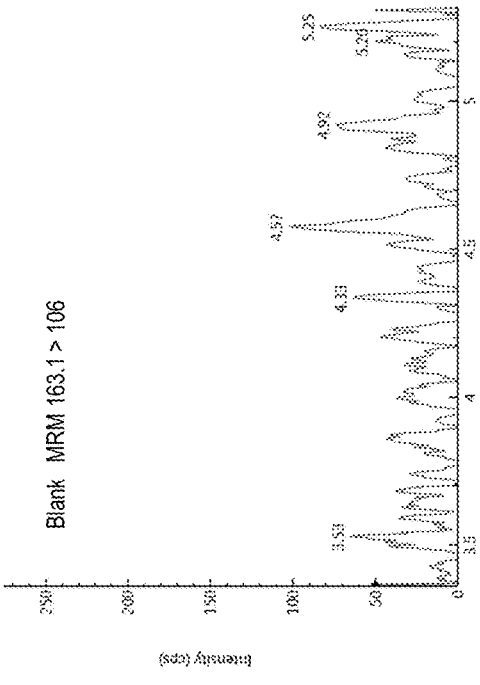
FIGS. 44A-B are chromatograms of *cannabis* samples analyzed for the presence of acephate using MRM transition 184>49.
Figure 44B:
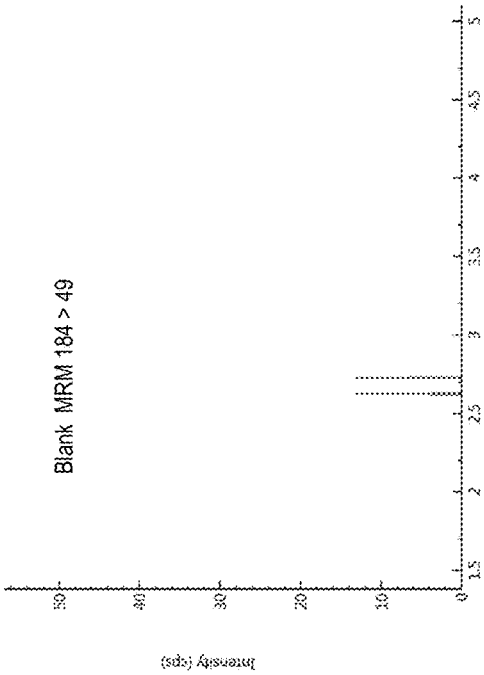
Figure 45A:
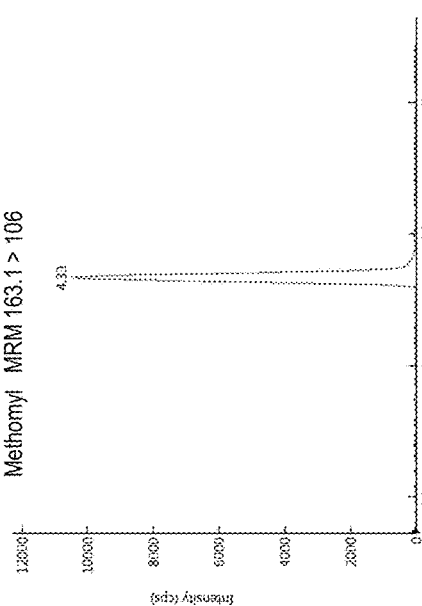
FIGS. 45A-B are chromatograms of *cannabis* samples analyzed for the presence of methomyl using MRM transition 163.1>106.
Figure 45B:
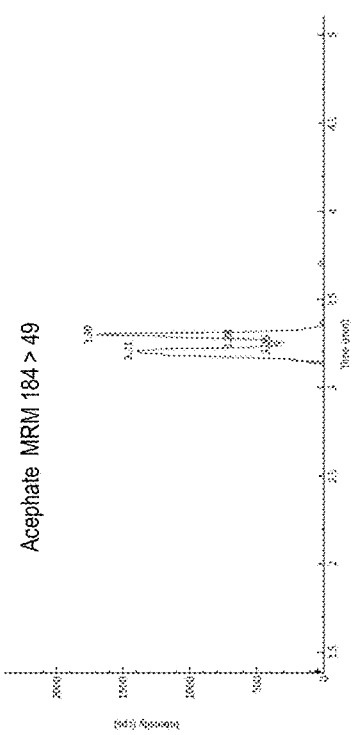
Figure 50A:
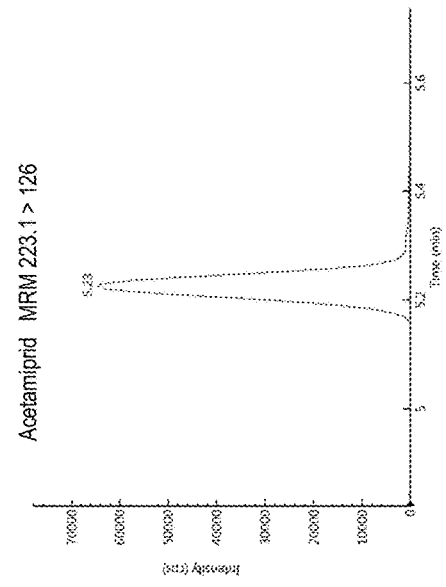
FIGS. 50A-D are chromatograms of *cannabis* samples analyzed for the presence of acetamiprid using MRM transitions 223.1>99 (FIGS. 50A, 50C) and 223.1>126 (FIGS. 50B, 50D).
Figure 50B:
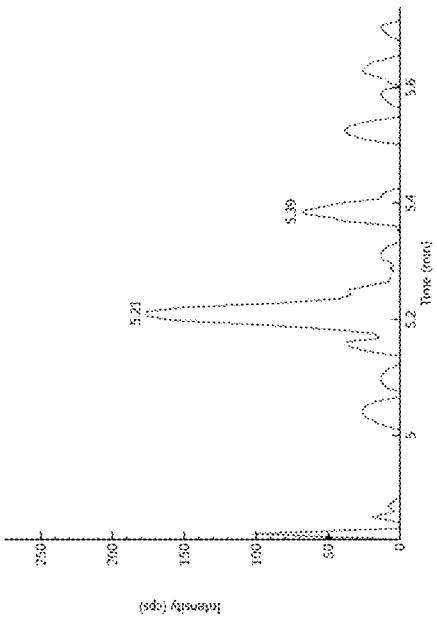
Figure 50C:
Figure 50D:
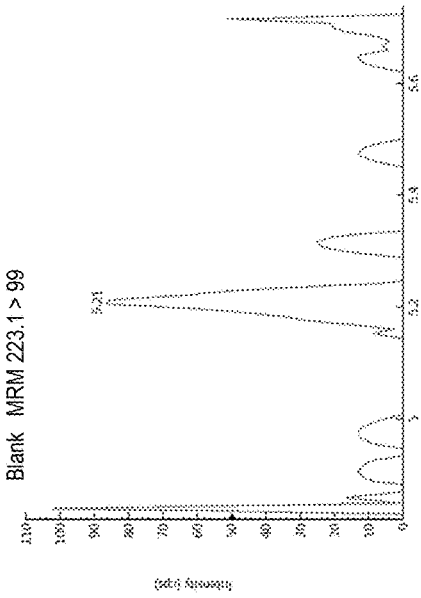
Figures 52A, 52B:
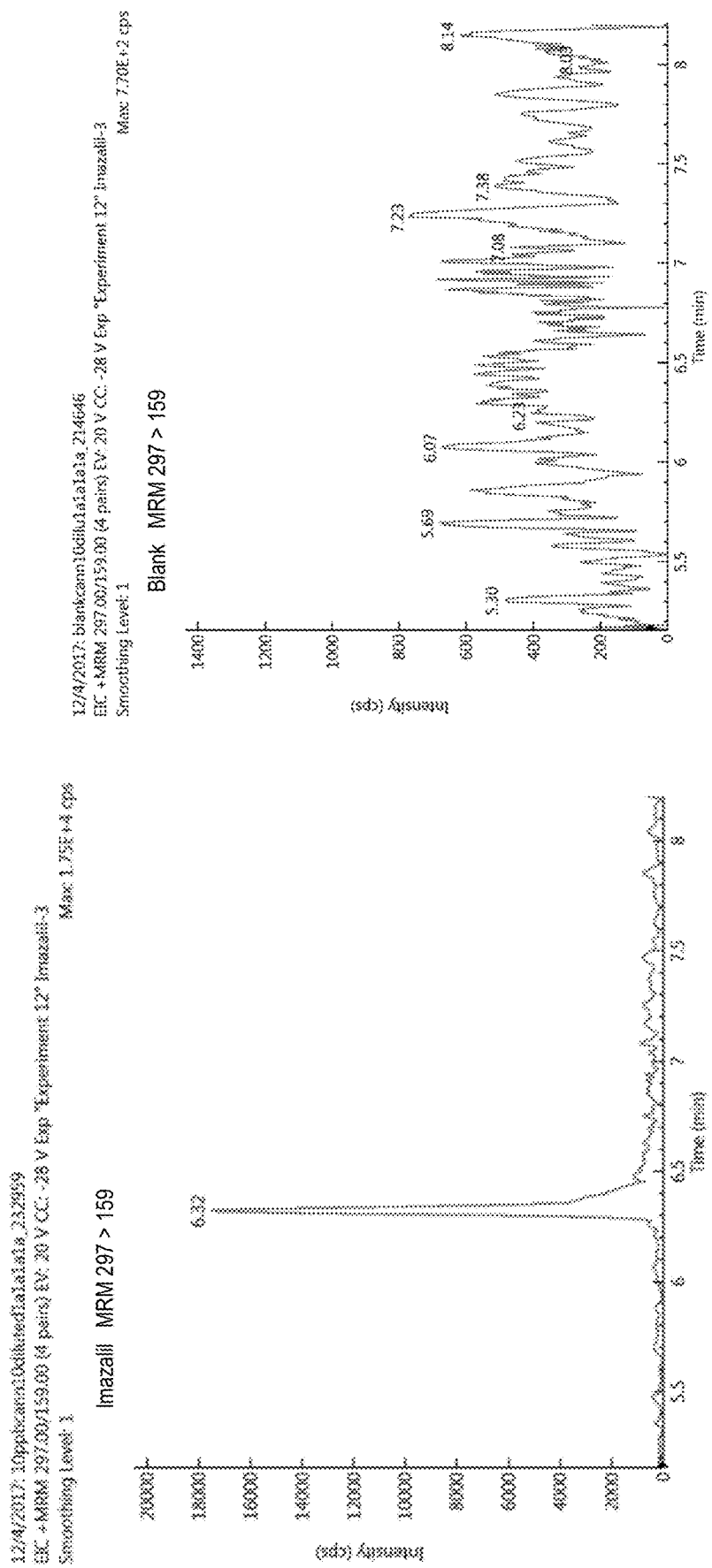
FIGS. 52A-B are chromatograms of *cannabis* samples analyzed for the presence of imazalil using MRM transition 297>159.
Figure 53A:
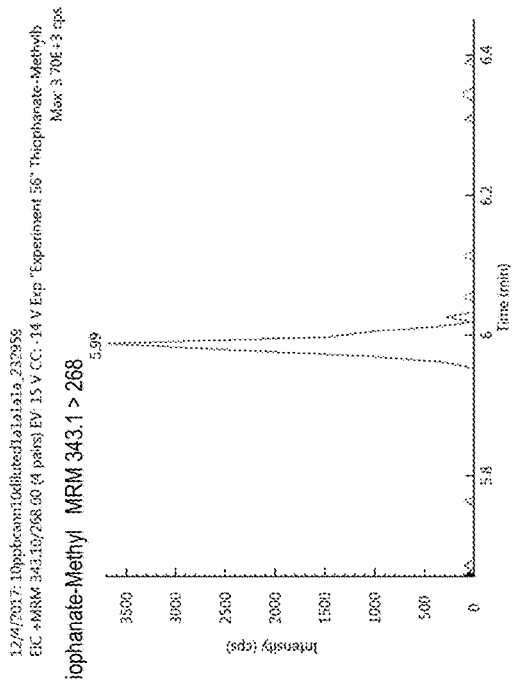
FIGS. 53A-D are chromatograms of *cannabis* samples analyzed for the presence of thiophanate-methyl using MRM transitions 343.1>151 (FIGS. 53A, 53C) and 343.1>268 (FIGS. 53B, 53D).
Figure 53B:
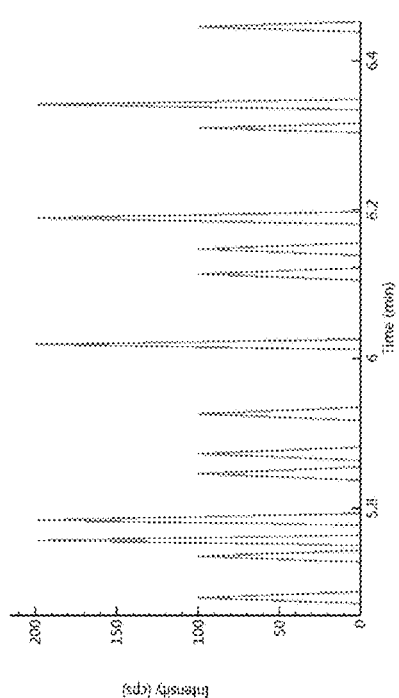
Figure 53C:
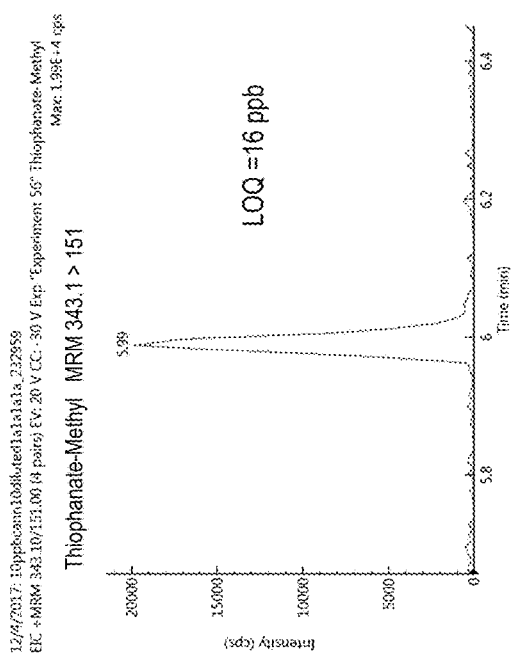
Figure 53D:
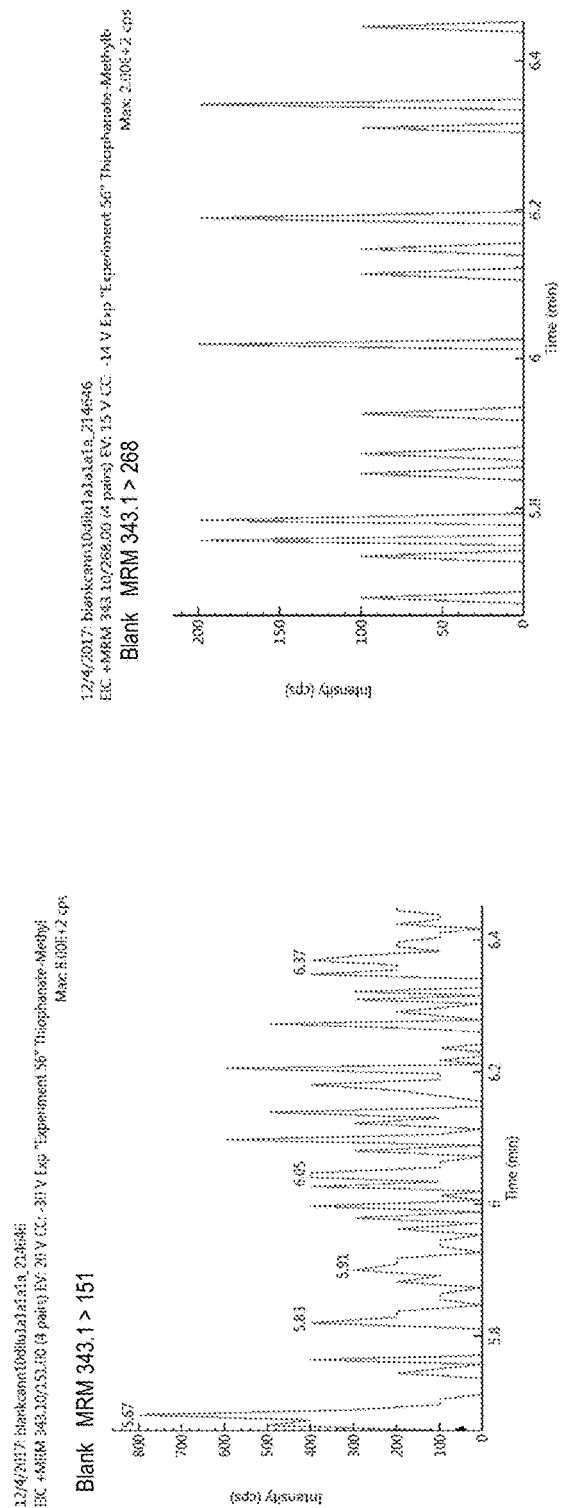
Figure 55A:
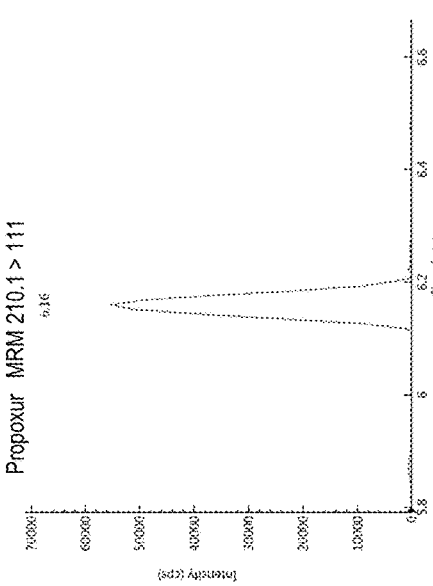
FIGS. 55A-D are chromatograms of *cannabis* samples analyzed for the presence of propoxur using MRM transitions 210.1>168 (FIGS. 55A, 55C) and 210.1>111 (FIGS. 55B, 55D).
Figure 55B:
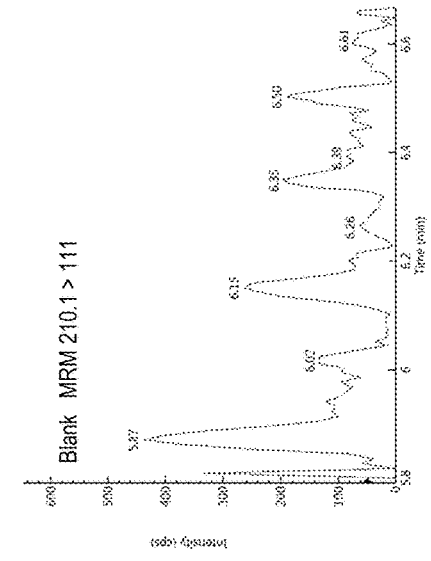
Figure 55C:
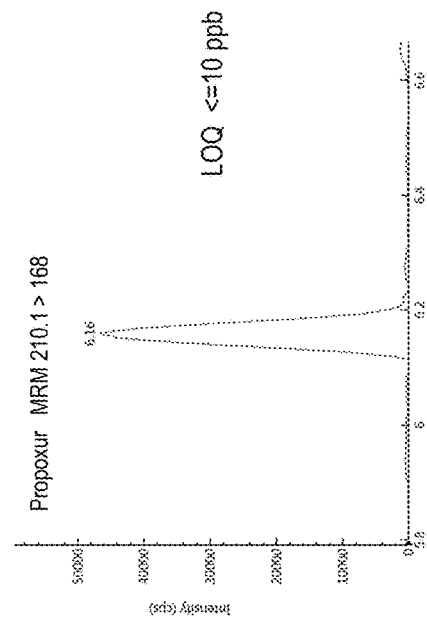
Figure 55D:
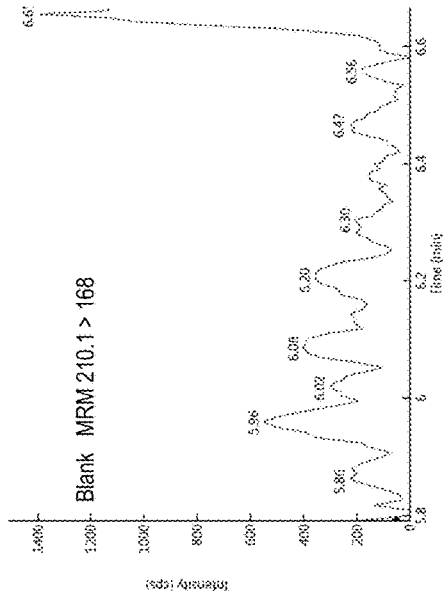
Figure 61A:
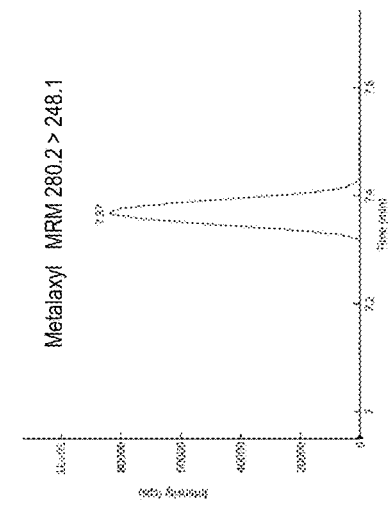
FIGS. 61A-D are chromatograms of *cannabis* samples analyzed for the presence of metalaxyl using MRM transitions 280.2>192.1 (FIGS. 61A, 61C) and 280.2>248.1 (FIGS. 61B, 61D).
Figure 61B:
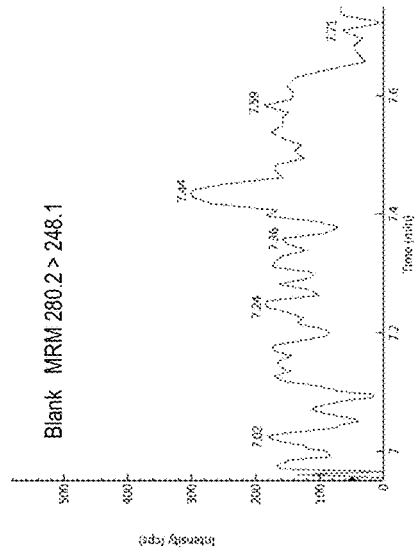
Figure 61C:
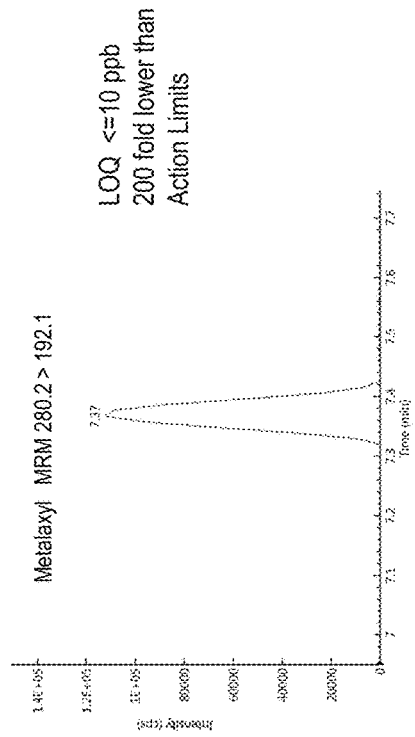
Figure 61D:
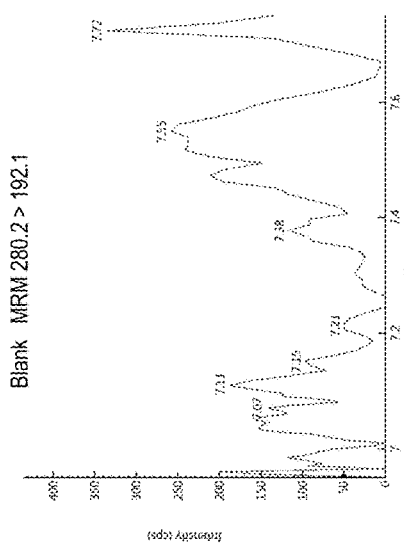
Figure 65A:
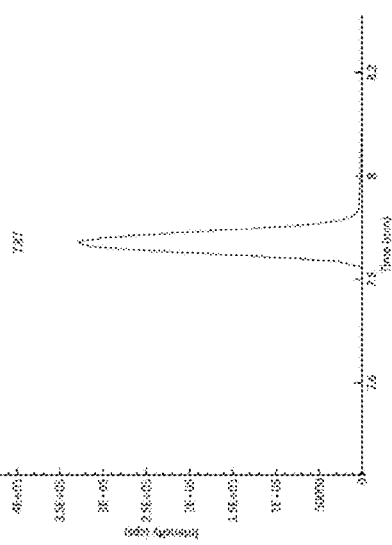
FIGS. 65A-D are chromatograms of *cannabis* samples analyzed for the presence of azoxystrobin using MRM transitions 404.1>344 (FIGS. 65A, 65C) and 404.1>372 (FIGS. 65B, 65D).
Figure 65B:
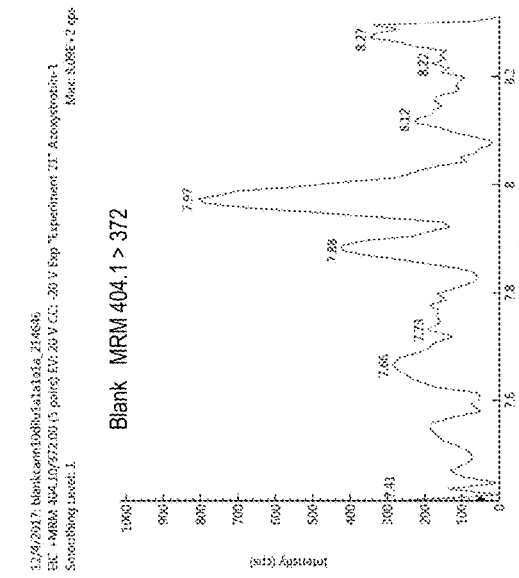
Figure 65C:
Figure 65D:
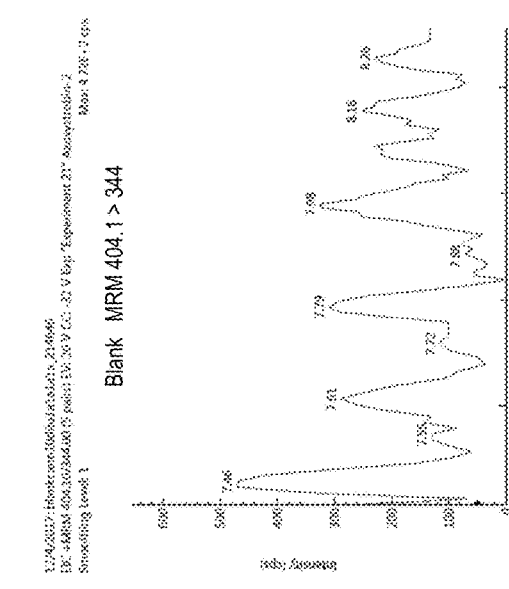
Figures 67A, 67B:
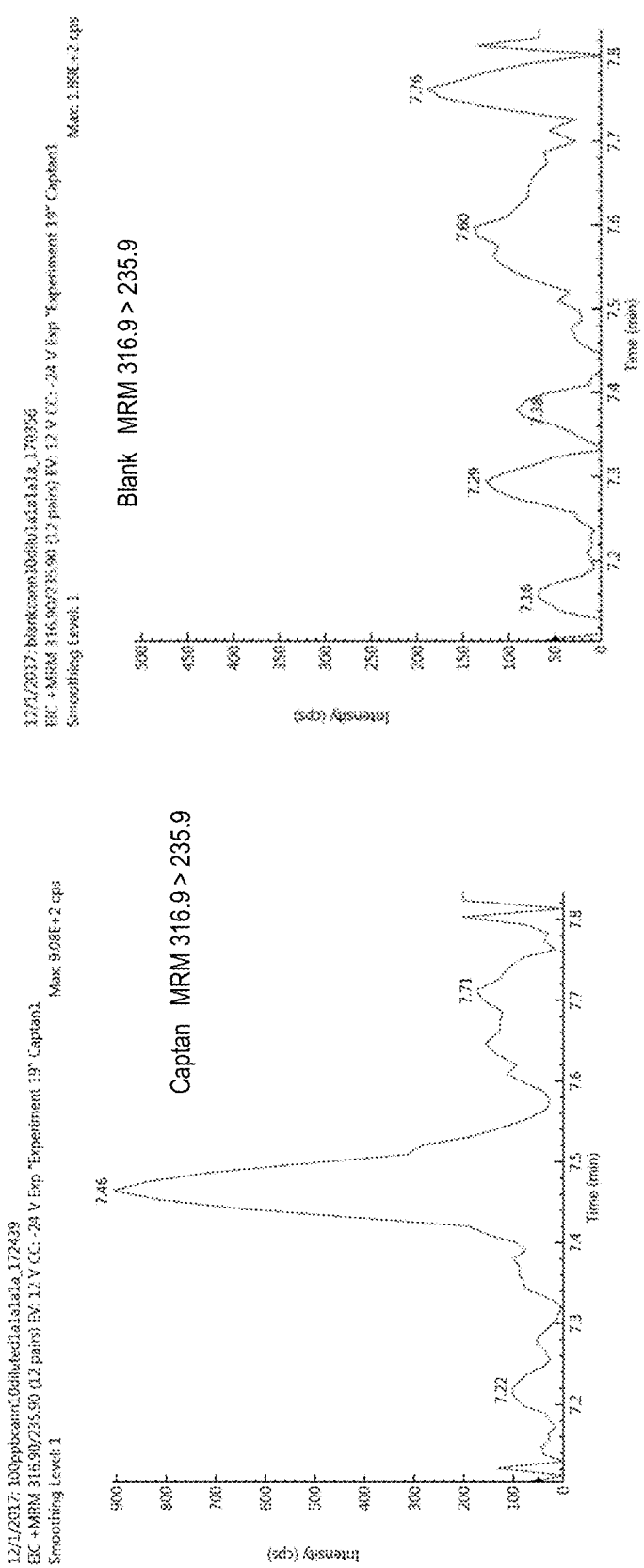
FIGS. 67A-B are chromatograms of *cannabis* samples analyzed for the presence of captan using MRM transition 316.9>235.9.
Figures 75A, 75B:
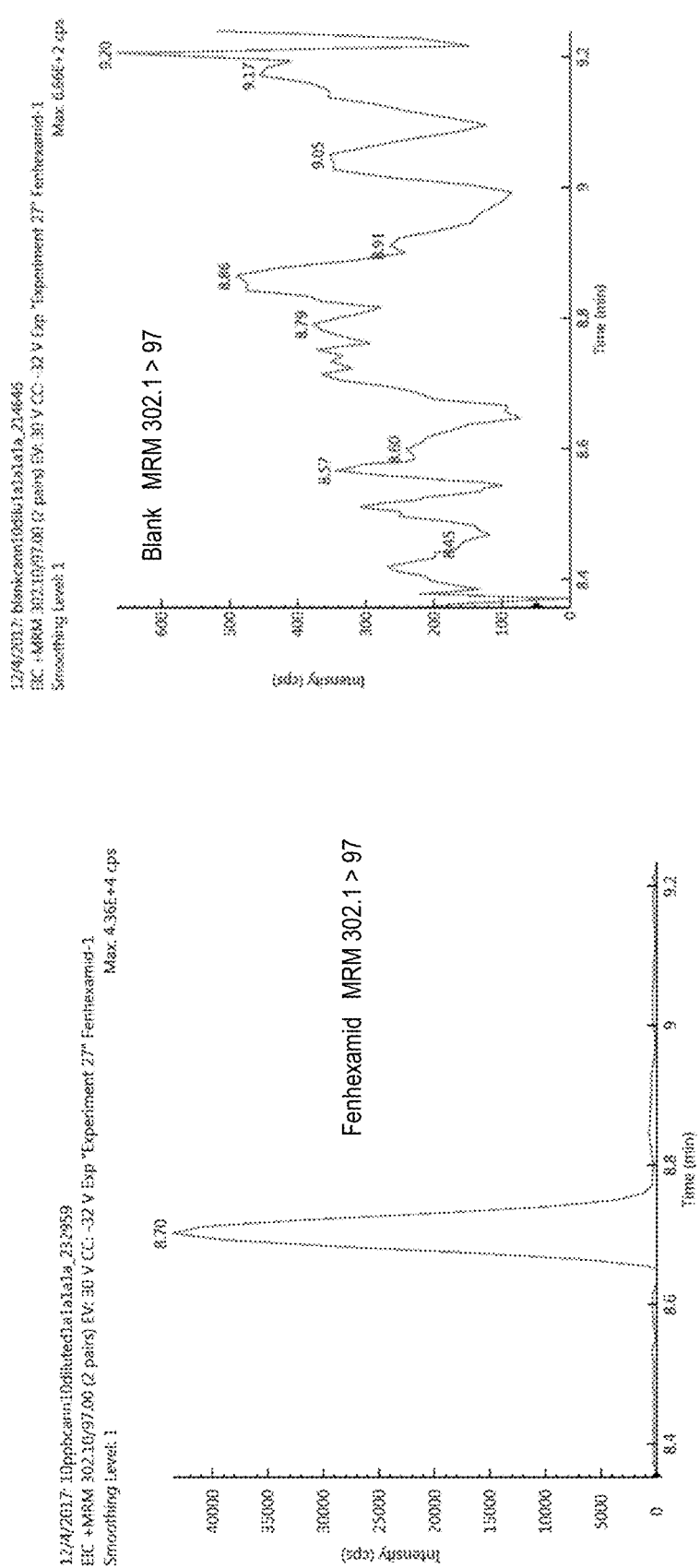
FIGS. 75A-B are chromatograms of *cannabis* samples analyzed for the presence of fenhexamid using MRM transition 302.1>55.
Figures 78A, 78B, 78C, 78D:
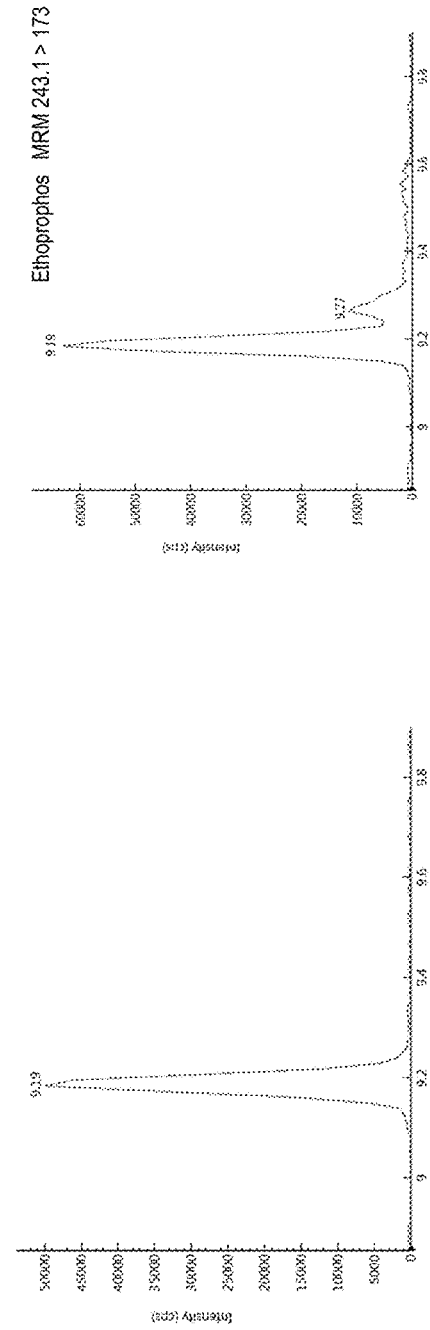
FIGS. 78A-D are chromatograms of *cannabis* samples analyzed for the presence of ethoprophos using MRM transitions 243.1>131 (FIGS. 78A, 78C) and 243.1>173 (FIGS. 78B, 78D).
Figure 89A:
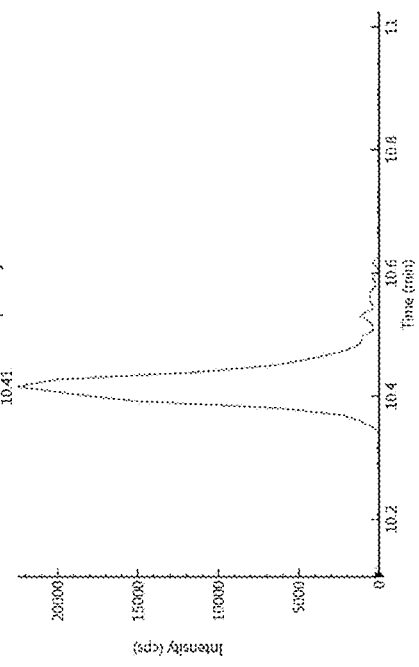
FIGS. 89A-D are chromatograms of *cannabis* samples analyzed for the presence of spinosyn-D using MRM transitions 746.5>98 (FIGS. 89A, 89C) and 746.5>142 (FIGS. 89B, 89D).
Figure 89B:
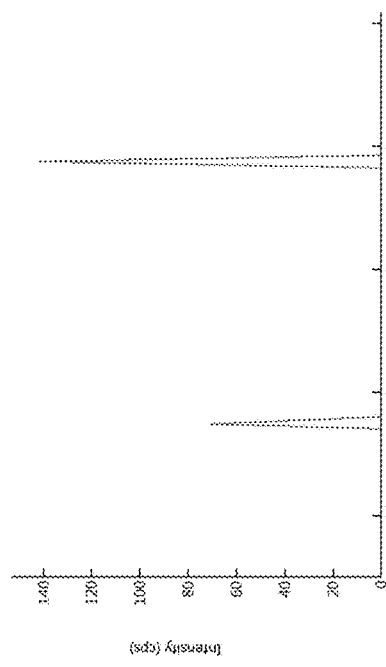
Figure 89C:
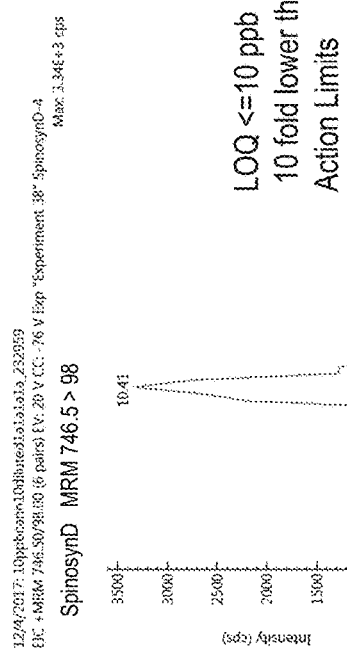
Figure 89D:
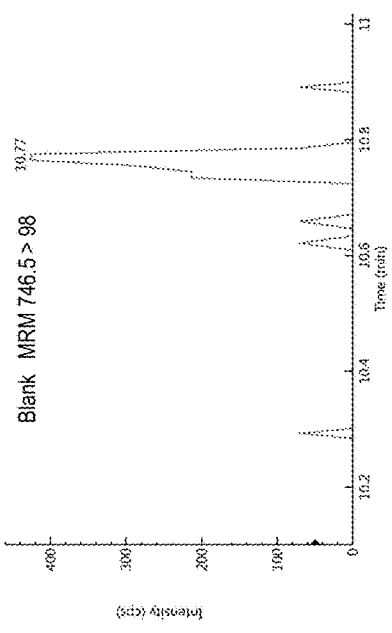

Tables 9-11 above and FIG. 40A and FIG. 40B summarize detection and/or quantification results for pesticides analyzed in this disclosure. FIG. 40A and FIG. 40B plot the various numbers of pesticides for which LOQs within different ranges were obtained. FIG. 40A, the LOQs were determined using both quantifier and qualifier transitions and in FIG. 40B, the LOQs were determined based on the quantifier transitions only.

The limits of quantification (LOQs) and response reproducibility at the LOQ level for each of the EPA category II pesticides (moderately toxic and moderately irritating), EPA category I pesticides (highly toxic and severely irritating), and mycotoxins in *cannabis* extract are summarized in Tables 12, 13, and 14. LOQs were determined by taking into account both the signals of the quantifier and qualifier ions (signal to noise ratio, S/N, >10 for both) and ensuring that the product ion ratios were within the 20% tolerance windows of the expected ratio.

TABLE 12

LOQs for Category II Pesticides.

| Pesticide | LOQ QSight (µg/g) | % CV (n = 7) | California Action Level (µg/g) | Action Level/LOQ QSight |
|---|---|---|---|---|
| Abamectin | 0.025 | 10.6 | 0.1 | 4.0 |
| Acephate | 0.010 | 3.1 | 0.1 | 10.0 |
| Acequinocyl | 0.025 | 13.3 | 0.1 | 10.0 |
| Acetamiprid | 0.010 | 13.1 | 0.1 | 10.0 |
| Azoxystrobin | 0.005 | 5.0 | 0.1 | 20.0 |
| Bifenazate | 0.010 | 10.8 | 0.1 | 10.0 |
| Bifenthrin | 0.010 | 14.4 | 0.5 | 50.0 |
| Boscalid | 0.025 | 12.2 | 0.1 | 4.0 |
| Captan* | 0.25 | 7.0 | 0.7 | 2.8 |
| Carbaryl | 0.010 | 9.5 | 0.5 | 50.0 |
| Chlorantraniliprole | 0.025 | 5.6 | 10.0 | 400.0 |
| Clofentezine | 0.010 | 11.3 | 0.1 | 10.0 |
| Cyfluthrin* | 0.25 | 19.1 | 1.0 | 4 |
| Cypermethrin* | 0.100 | 20 | 1.0 | 10.0 |
| Diazinon | 0.005 | 3.8 | 0.2 | 40.0 |
| Dimethomorph | 0.005 | 1.4 | 2.0 | 400.0 |
| Etoxazole | 0.005 | 13.5 | 0.1 | 20.0 |
| Fenhexamid | 0.010 | 12.5 | 0.1 | 10.0 |
| Fenpyroximate | 0.005 | 6.9 | 0.1 | 20.0 |
| Flonicamid | 0.010 | 10.2 | 0.1 | 10.0 |
| Fludioxonil | 0.050 | 9.5 | 0.1 | 2.0 |
| Hexythiazox | 0.005 | 8.4 | 0.1 | 20.0 |
| Imidacloprid | 0.010 | 10.3 | 3.0 | 300.0 |
| Kresoxim-methyl | 0.025 | 8.1 | 0.1 | 4.0 |
| Malathion | 0.010 | 14.7 | 0.5 | 50.0 |
| Metalaxyl | 0.010 | 8.0 | 2.0 | 200.0 |
| Methomyl | 0.010 | 8.5 | 0.1 | 10.0 |
| Myclobutanil | 0.010 | 10.4 | 0.1 | 10.0 |
| Naled* | 0.010 | 8.4 | 0.1 | 10.0 |
| Oxamyl | 0.010 | 6.7 | 0.2 | 20.0 |
| Pentachloronitrobenzene*† | 0.010 | 13.0 | 0.1 | 10.0 |
| Permethrin* | 0.010 | 16.0 | 0.5 | 50.0 |
| Phosmet | 0.005 | 13.3 | 0.1 | 20.0 |
| Piperonylbutoxide | 0.005 | 3.5 | 3.0 | 600.0 |
| Prallethrin | 0.025 | 7.4 | 0.1 | 4.0 |
| Propiconazole | 0.015 | 8.9 | 0.1 | 6.67 |
| Pyrethrins* | 0.1 | 1.4 | 0.5 | 5.0 |
| Pyridaben | 0.010 | 7.9 | 0.1 | 10.0 |
| Spinetoram | 0.005 | 13.8 | 0.1 | 20.0 |
| Spinosad | 0.005 | 9.3 | 0.1 | 20.0 |
| Spiromesifen | 0.010 | 9.4 | 0.1 | 10.0 |
| Spirotetramat | 0.010 | 8.4 | 0.1 | 10.0 |
| Tebuconazole | 0.005 | 11.0 | 0.1 | 20.0 |
| Thiamethoxam | 0.010 | 3.6 | 4.5 | 450.0 |
| Trifloxystrobin | 0.005 | 8.4 | 0.1 | 20.0 |

*Typically analyzed using GC-MS/MS.
†Analyzed by APCI

TABLE 13

LOQs for Category II Mycotoxins

| Mycotoxin | LOQ QSight (µg/g) | % CV (n = 7) | California Action Level (µg/g) | Action Level/LOQ QSight |
|---|---|---|---|---|
| Ochratoxin A | 0.010 | 18 | 0.020 | 2.0 |
| Aflatoxin B1 | 0.001 | 18 | NA | NA |
| Aflatoxin B2 | 0.0015 | 14 | NA | NA |
| Aflatoxin G1 | 0.010 | 18 | NA | NA |
| Aflatoxin G2 | 0.0015 | 19 | NA | NA |
| Aflatoxin (B1 + B2 + G1 + G2) | 0.005 | NA | 0.020 | 4.0 |

TABLE 14

LOQs for category I Pesticides

| Pesticide | QSight LOQ (µg/g) | % CV (n = 7) | California Action Level (µg/g) |
|---|---|---|---|
| Aldicarb | 0.01 | 10.6 | 0.1 |
| Carbofuran | 0.01 | 3.1 | 0.1 |
| Chlordane*† | 0.033 | 13.3 | 0.1 |
| Chlorfenapyr* | 0.2 | 13.1 | 0.1 |
| Chlorpyrifos | 0.01 | 5.0 | 0.1 |
| Coumaphos | 0.01 | 10.8 | 0.1 |
| daminozide | 0.015 | 14.4 | 0.1 |
| DDVP (Dichlorvos) | 0.025 | 12.2 | 0.1 |
| Dimethoate | 0.01 | 3.8 | 0.1 |
| Ethoprop(hos) | 0.01 | 9.5 | 0.1 |
| Etofenprox | 0.01 | 5.6 | 0.1 |
| Fenoxycarb | 0.01 | 11.3 | 0.1 |
| Fipronil | 0.01 | 19.1 | 0.1 |
| Imazalil | 0.01 | 23.1 | 0.1 |
| Methiocarb | 0.01 | 3.8 | 0.1 |
| Methyl parathion | 0.04 | 1.4 | 0.1 |
| Mevinphos | 0.025 | 13.5 | 0.1 |
| Paclobutrazol | 0.01 | 12.5 | 0.1 |
| Propoxur | 0.01 | 6.9 | 0.1 |
| Spiroxamine | 0.01 | 10.2 | 0.1 |
| Thiacloprid | 0.01 | 9.5 | 0.1 |

*Typically analyzed using GC-MS/MS.
†Analyzed by APCI.

Example 21. Computer System and Network Environment

Figure 4:
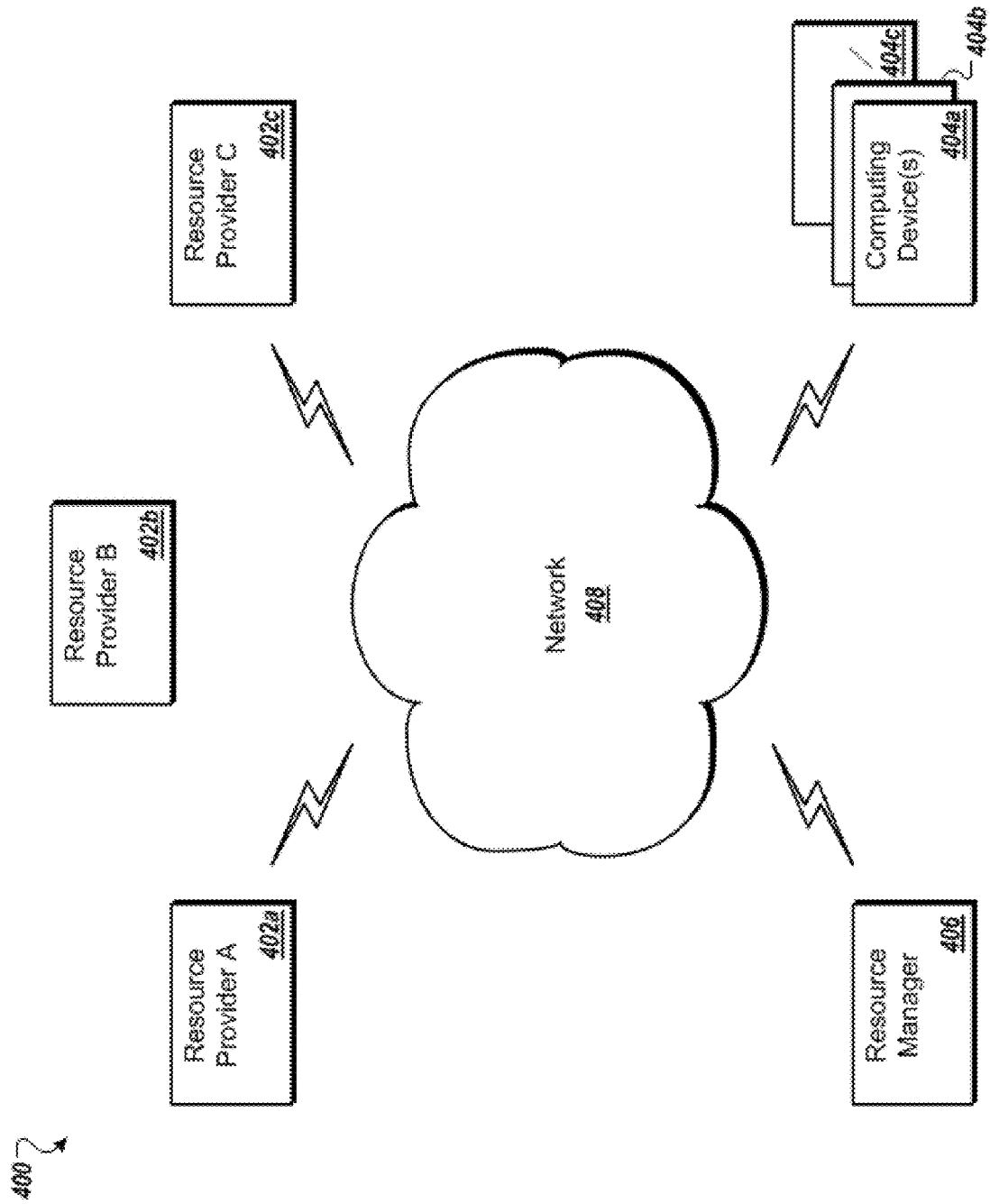
FIG. 4 is a block diagram of an example of a cloud computing environment.

In FIG. 4, an implementation of a network environment 400 for use in providing the systems and methods described herein is shown and described. In brief overview, referring now to FIG. 4, a block diagram of an illustrative cloud computing environment 400 is shown and described. The cloud computing environment 400 may include one or more resource providers 402a, 402b, 402c (collectively, 402). Each resource provider 402 may include computing resources. In some implementations, computing resources may include any hardware and/or software used to process data. For example, computing resources may include hardware and/or software capable of executing algorithms, computer programs, and/or computer applications. In some implementations, illustrative computing resources may include application servers and/or databases with storage and retrieval capabilities. Each resource provider 402 may be connected to any other resource provider 402 in the cloud computing environment 400. In some implementations, the resource providers 402 may be connected over a computer network 408. Each resource provider 402 may be connected to one or more computing device 404a, 404b, 404c (collectively, 404), over the computer network 408.

The cloud computing environment 400 may include a resource manager 406. The resource manager 406 may be connected to the resource providers 402 and the computing devices 404 over the computer network 408. In some implementations, the resource manager 406 may facilitate the provision of computing resources by one or more resource providers 402 to one or more computing devices 404. The resource manager 406 may receive a request for a computing resource from a particular computing device 404. The resource manager 406 may identify one or more resource providers 402 capable of providing the computing resource requested by the computing device 404. The resource manager 406 may select a resource provider 402 to provide the computing resource. The resource manager 406 may facilitate a connection between the resource provider 402 and a particular computing device 404. In some implementations, the resource manager 406 may establish a connection between a particular resource provider 402 and a particular computing device 404. In some implementations, the resource manager 406 may redirect a particular computing device 404 to a particular resource provider 402 with the requested computing resource.

Figure 5:
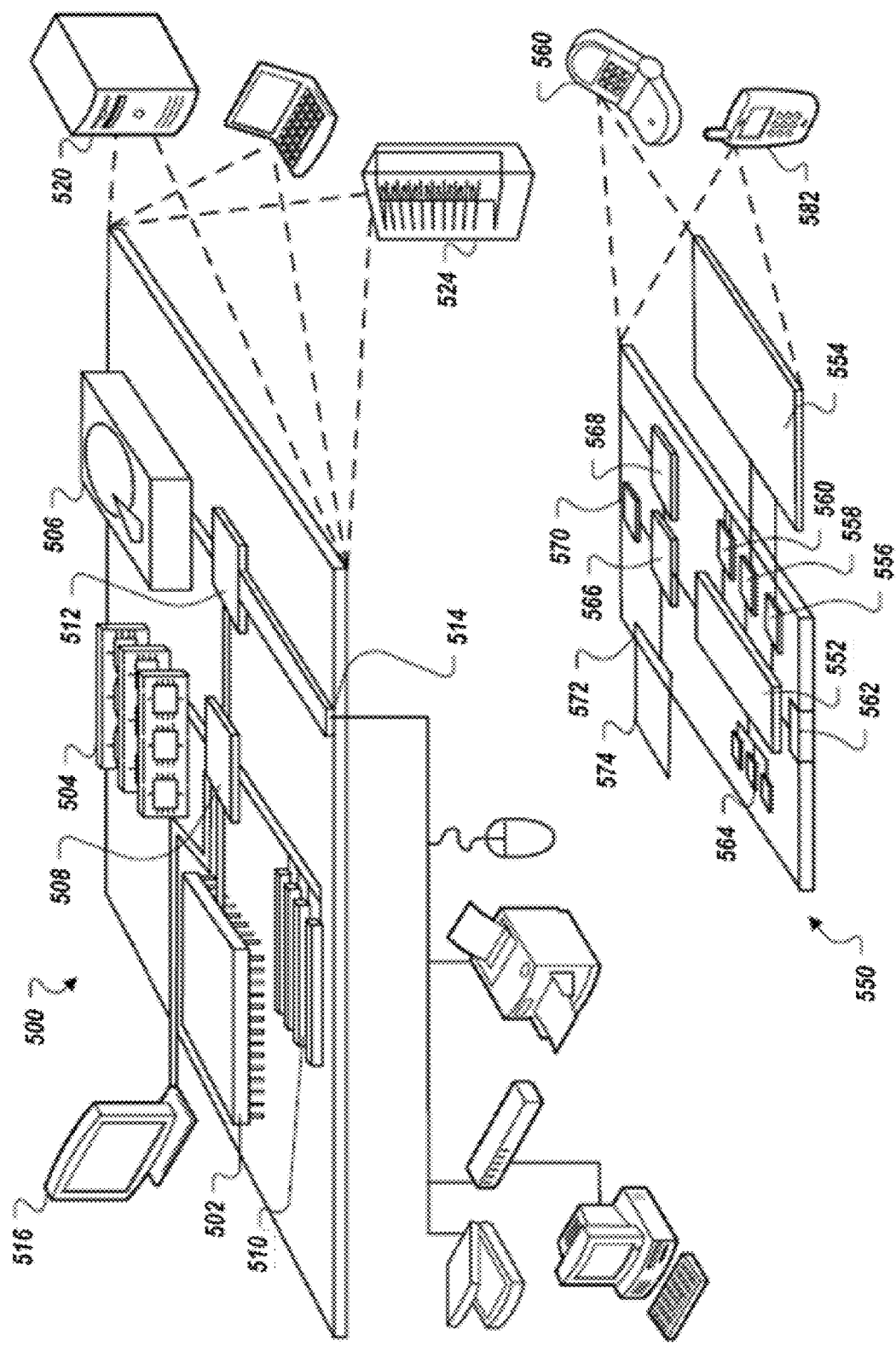
FIG. 5 is a block diagram of an example computing device and an example mobile computing device.

FIG. 5 shows an example of a computing device 500 and a mobile computing device 550 that can be used to implement the techniques described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be illustrative examples only, and are not meant to be limiting.

The computing device 500 may include a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, may be interconnected using various busses, and may be mounted on a common motherboard or in other manners as appropriate. The processor 502 can process instructions for execution within the computing device 500, including instructions stored in the memory 504 or on the storage device 506 to display text and/or graphical information for a graphical user interface (GUI) on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 may manage bandwidth-intensive operations for the computing device 500, while the low-speed interface 512 may manage lower bandwidth-intensive operations. Such allocation of functions is an example only. In some implementations, the high-speed interface 508 may be coupled to the memory 504, the display 516 (e.g., through a graphics processor or accelerator), and to the high-speed expansion ports 510, which may accept various expansion cards (not shown). In some implementations, the low-speed interface 512 may be coupled to the storage device 506 and the low-speed expansion port 514. The low-speed expansion port 514, which may include various communication ports (e.g., USB, BLUETOOTH®, Bluetooth Low Energy, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 may include a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, may be interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, an SD card and/or a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provide as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a BLUETOOTH®, WI-FI™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, various modules can be separated, combined or incorporated into single or combined modules. Any modules depicted in the figures are not intended to limit the systems described herein to the software architectures shown therein.

The invention claimed is:

1. A triple quadrupole mass spectrometer comprising
   (a) an atmospheric chemical ionization (APCI) source; and
   (b) a first ionized sample stream ionized by the APCI source,
   wherein the triple quadrupole mass spectrometer is configured to detect a first MRM transition in the first ionized sample stream, wherein the first MRM transition is selected from the group consisting of 439.8>35.1 (chlordane) and 441.8>35.1 (chlordane).

2. The triple quadrupole mass spectrometer of claim 1, further comprising:
   (c) an electrospray ionization (ESI) source; and
   (d) a second ionized sample stream ionized by the ESI source, and further configured to detect a second MRM transition in the second ionized sample stream.

3. The triple quadrupole mass spectrometer of claim 2, wherein the second MRM transition is an MRM transition of a pesticide, wherein the pesticide is selected from the group consisting of abamectin, acephate, acequinocyl, acetamiprid, aldicarb, atrazine, azoxystrobin, bifenazate, bifenthrin, boscalid, captan, carbaryl, carbofuran, chlorantraniliprole, chlorfenapyr, chlorpyrifos, cinerin-I, cinerin-II, clofentezine, coumaphos, cyfluthrin, cypermethrin, daminozide, diazinon, dichlorvos, dimethoate, dimethomorph, ethoprophos, etofenprox, etoxazole, fenhexamid, fenoxycarb, fenpyroximate, fipronil, flonicamid, fludioxonil, hexythiazox, imazalil, imidacloprid, jasmolin-I, jasmolin-II, kresoxim-methyl, malathion, metalaxyl, methiocarb, methomyl, mevinphos, myclobutanil, naled, n-octyl bicycloheptene dicarboximide (MGK-264), oxamyl, paclobutrazol, parathion methyl, permethrin, phosmet, piperonyl butoxide, prallethrin, propiconazole, propoxur, pyrethrin-I, pyrethrin-II, pyridaben, spinetoram, spinosyn A, spinosyn D, spiromesifen, spirotetramat, spiroxamine, tebuconazole, thiachloprid, thiamethoxam, thiophanate methyl, and trifloxystrobin.

4. The triple quadrupole mass spectrometer of claim 3, further configured to detect a third MRM transition in the second ionized sample stream, wherein the third MRM transition is associated with a mycotoxin selected from the group consisting of mycotoxin B1, mycotoxin B2, mycotoxin G1, mycotoxin G2, and ochratoxin A.

5. The triple quadrupole mass spectrometer of claim 2, further configured to detect a third MRM transition in the second ionized sample stream, wherein the third MRM transition is associated with a mycotoxin selected from the group consisting of mycotoxin B1, mycotoxin B2, mycotoxin G1, mycotoxin G2, and ochratoxin A.

6. The triple quadrupole mass spectrometer of claim 2, wherein the second MRM transition is selected from the group consisting of 402.2>343.1 (acequinocyl) and 402.2>189 (acequinocyl).

7. The triple quadrupole mass spectrometer of claim 2, wherein the second MRM transition is selected from the group consisting of 316.9>263.9 (captan), 316.9>235.9 (captan), 318.9>265.9 (captan), and 318.9>237.9 (captan).

8. The triple quadrupole mass spectrometer of claim 2, wherein the second MRM transition is selected from the group consisting of 407.0>59.1 (chlorfenapyr), 424.0>59.1 (chlorfenapyr), and 426.0>59.1 (chlorfenapyr).

9. The triple quadrupole mass spectrometer of claim 2, wherein the second MRM transition is 361.2>213.0 (cinerin-II).

10. The triple quadrupole mass spectrometer of claim 2, wherein the second MRM transition is 453.1>193.0 (cyfluthrin).

11. The triple quadrupole mass spectrometer of claim 2, wherein the second MRM transition is 435.1>193.1 (cypermethrin).

12. The triple quadrupole mass spectrometer of claim 2, wherein the second MRM transition is selected from the group consisting of 161.1>44.0 (daminozide) and 161.1>45.0 (daminozide).

13. The triple quadrupole mass spectrometer of claim 2, wherein the second MRM transition is 375.2>213.0 (jasmolin II).

14. The triple quadrupole mass spectrometer of claim 2, wherein the second MRM transition is selected from the group consisting of 380.8>127.0 (naled) and 382.8>127.0 (naled).

15. The triple quadrupole mass spectrometer of claim 2, wherein the second MRM transition is selected from the group consisting of 344.1>69.0 (propiconazole) and 344.1>161.0 (propiconazole).

16. The triple quadrupole mass spectrometer of claim 1, wherein the first ionized sample stream is obtained from a *cannabis* sample.

17. The triple quadrupole mass spectrometer of claim 1, further configured to detect a second MRM transition in the first ionized sample stream, which comprises the ESI source and wherein the second MRM transition is selected from the group consisting of 275.8>35.1 (PCNB), 273.8>35.1 (PCNB), and 275.8>201.9 (PCNB).

18. The triple quadrupole mass spectrometer of claim 1, further configured to detect a second MRM transition in the first ionized sample stream, which comprises the ESI source and wherein the second MRM transition is selected from the group consisting of 216.8>35.0 (etridiazole) and 218.8>35.0 (etridiazole).

19. The triple quadrupole mass spectrometer of claim 1, further configured to detect a second MRM transition in the first ionized sample stream, which comprises the ESI source and wherein the second MRM transition is selected from the group consisting of 346.9>79.0 (chlorfenapyr) and 348.9>81.0 (chlorfenapyr).

* * * * *